(12) United States Patent
Lee et al.

(10) Patent No.: US 11,127,904 B2
(45) Date of Patent: Sep. 21, 2021

(54) COMPOUND, COATING COMPOSITION COMPRISING SAME, ORGANIC LIGHT EMITTING DEVICE USING SAME, AND MANUFACTURING METHOD THEREOF

(71) Applicant: LG Chem, Ltd., Seoul (KR)

(72) Inventors: Kilsun Lee, Daejeon (KR); Sungkyoung Kang, Daejeon (KR); Soyoung Yu, Daejeon (KR); Jaesoon Bae, Daejeon (KR); Jaechol Lee, Daejeon (KR); Daeho Kim, Daejeon (KR)

(73) Assignee: LG Chem, Ltd.

( * ) Notice: Subject to any disclaimer, the term of this patent is extended or adjusted under 35 U.S.C. 154(b) by 198 days.

(21) Appl. No.: 16/484,233

(22) PCT Filed: Sep. 11, 2018

(86) PCT No.: PCT/KR2018/010611
§ 371 (c)(1),
(2) Date: Aug. 7, 2019

(87) PCT Pub. No.: WO2019/066306
PCT Pub. Date: Apr. 4, 2019

(65) Prior Publication Data
US 2020/0052220 A1 Feb. 13, 2020

(30) Foreign Application Priority Data
Sep. 29, 2017 (KR) .................. 10-2017-0127207

(51) Int. Cl.
*H01L 51/00* (2006.01)
*H01L 51/50* (2006.01)
(Continued)

(52) U.S. Cl.
CPC ........ *H01L 51/0061* (2013.01); *C07D 209/86* (2013.01); *C09D 4/00* (2013.01);
(Continued)

(58) Field of Classification Search
None
See application file for complete search history.

(56) References Cited

U.S. PATENT DOCUMENTS

2016/0118599 A1 4/2016 Jeong et al.
2017/0174835 A1* 6/2017 Hsieh .................. C08G 65/485
(Continued)

FOREIGN PATENT DOCUMENTS

CN 102329411 A 1/2012
CN 103666455 A 3/2014
(Continued)

OTHER PUBLICATIONS

Search report from International Application No. PCT/KR2018/010611, dated Dec. 20, 2018.

*Primary Examiner* — Vu A Nguyen
(74) *Attorney, Agent, or Firm* — Lerner, David, Littenberg, Krumholz & Mentlik, LLP

(57) ABSTRACT

The present specification relates to a compound of Chemical Formula 1, a coating composition comprising the compound of Chemical Formula 1, an organic light emitting device using the same, and a method for manufacturing the same.

18 Claims, 3 Drawing Sheets

(51) Int. Cl.
*C07D 209/86* (2006.01)
*C09D 4/00* (2006.01)
*C09D 5/24* (2006.01)

(52) U.S. Cl.
CPC .............. *C09D 5/24* (2013.01); *H01L 51/006* (2013.01); *H01L 51/0039* (2013.01); *H01L 51/0003* (2013.01); *H01L 51/0058* (2013.01); *H01L 51/0072* (2013.01); *H01L 51/5056* (2013.01); *H01L 51/5088* (2013.01)

(56) References Cited

U.S. PATENT DOCUMENTS

| | | |
|---|---|---|
| 2017/0222157 A1 | 8/2017 | Jatsch et al. |
| 2018/0337341 A1 | 11/2018 | Heo et al. |

FOREIGN PATENT DOCUMENTS

| | | | |
|---|---|---|---|
| CN | 105884830 A | | 8/2016 |
| EP | 2468725 A1 | | 6/2012 |
| JP | 2019500326 A | | 1/2019 |
| KR | 10-2009-0114716 A | | 11/2009 |
| KR | 10-2014-0132562 A | | 11/2014 |
| KR | 20140132562 A | * | 11/2014 |
| KR | 20150093995 A | * | 8/2015 |
| KR | 10-2016-0041124 A | | 4/2016 |
| TW | 200609331 A | | 3/2006 |
| WO | 2012-015265 A1 | | 2/2012 |
| WO | 2016012075 A1 | | 1/2016 |
| WO | 2017-107117 A1 | | 6/2017 |

\* cited by examiner

[FIG. 1]
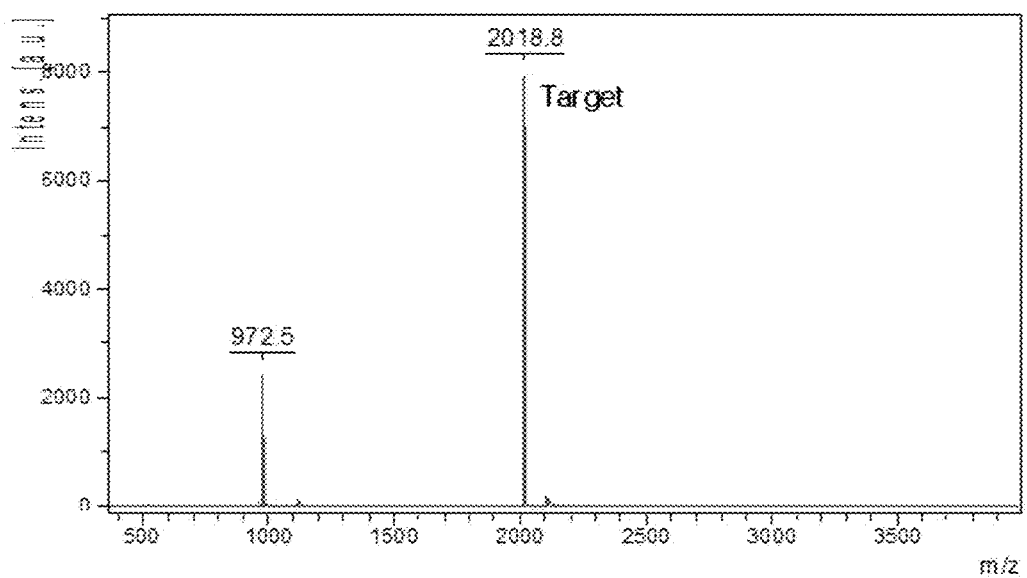
[FIG. 2]

【FIG. 3】
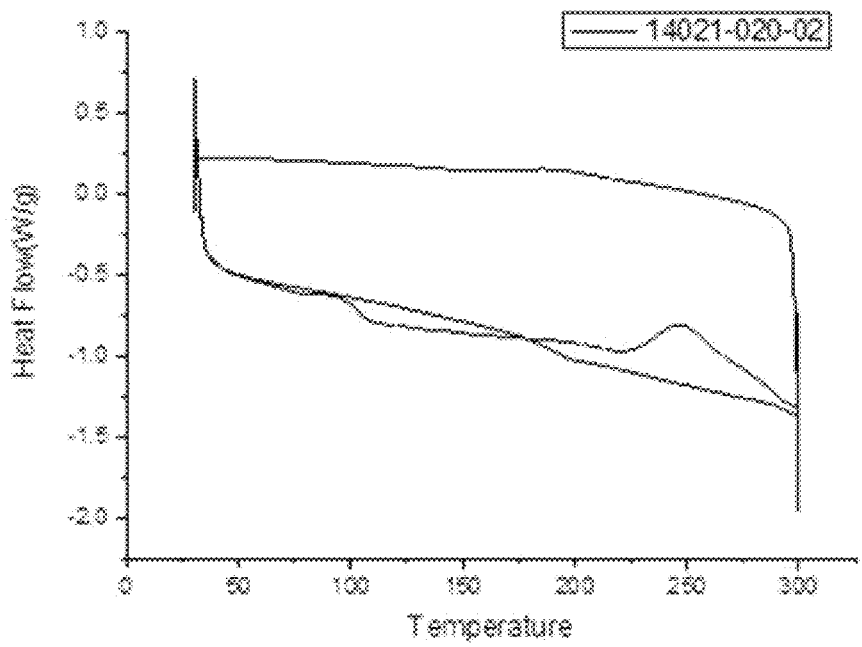
【FIG. 4】
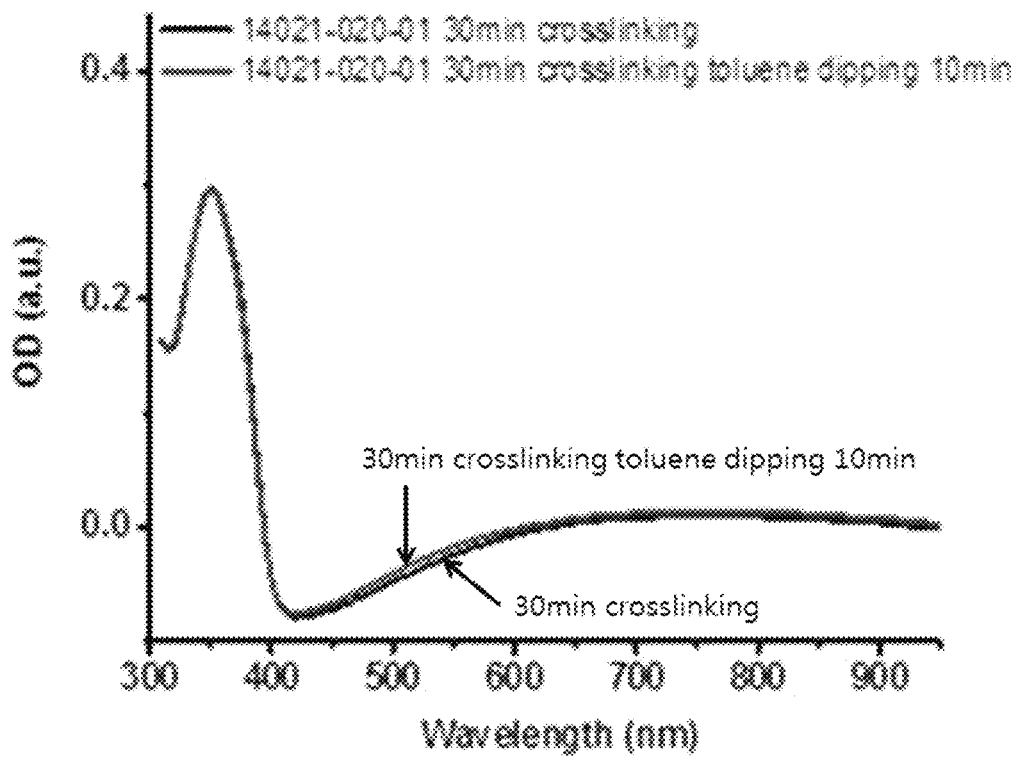

[FIG. 5]
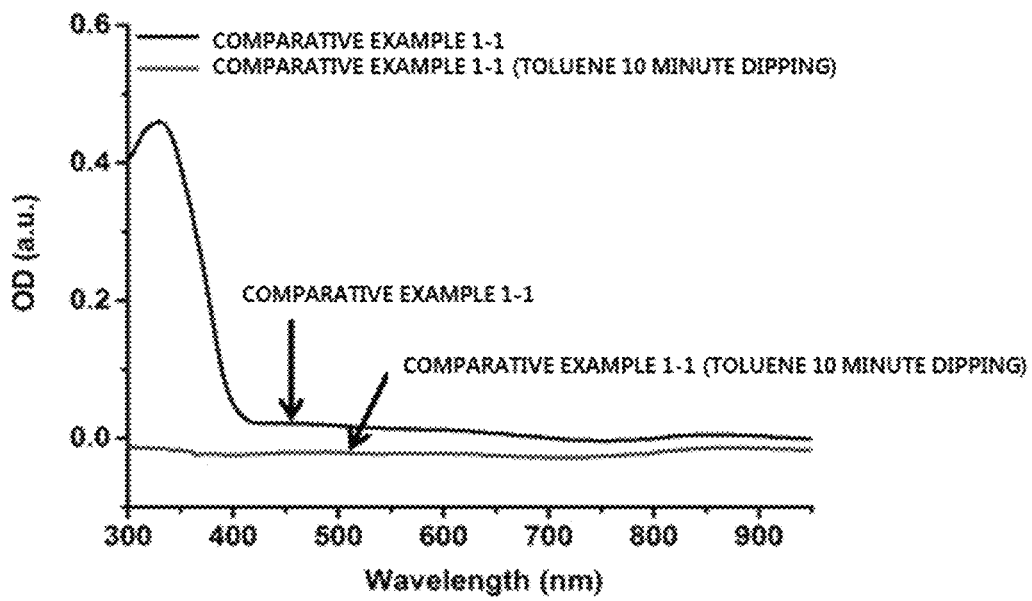
[FIG. 6]
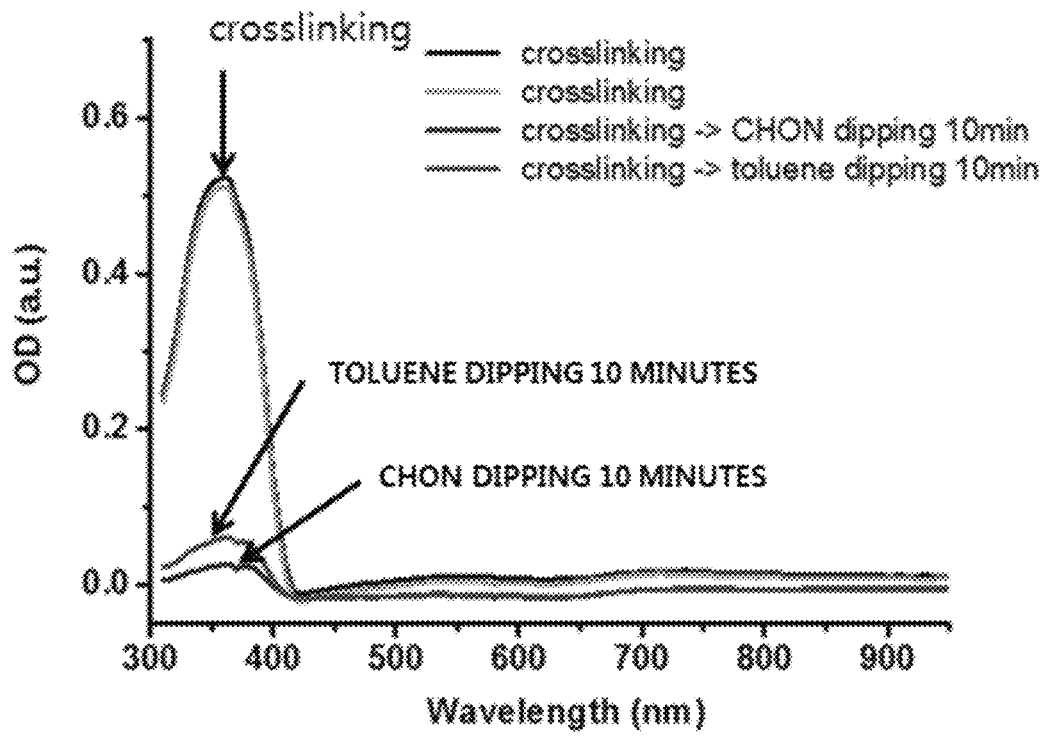

COMPOUND, COATING COMPOSITION COMPRISING SAME, ORGANIC LIGHT EMITTING DEVICE USING SAME, AND MANUFACTURING METHOD THEREOF

CROSS-REFERENCE TO RELATED APPLICATIONS

The present application is a national phase entry under 35 U.S.C. § 371 of International Application No. PCT/KR2018/010611 filed Sep. 11, 2018, which claims priority from Korean Patent Application No. 10-2017-0127207 filed Sep. 29, 2017, all of which are incorporated herein by reference.

TECHNICAL FIELD

The present specification relates to a compound, a coating composition comprising the compound, an organic light emitting device formed using the coating composition, and a method for manufacturing the same.

BACKGROUND ART

An organic light emission phenomenon is one of examples converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

A deposition process has been normally used in the art for manufacturing an organic light emitting device. However, manufacturing an organic light emitting device using a deposition process has a problem of high material loss, and in order to resolve such a problem, technologies for manufacturing a device through a solution process capable of increasing production efficiency with low material loss have been developed, and development of materials usable in a solution process has been required.

Materials used in an organic light emitting device for a solution process need to have properties as follows.

First, a storable homogeneous solution needs to be formed. Commercialized materials for a deposition process have favorable crystallinity, and are not well-dissolved in a solution, or crystals are readily caught even when forming a solution. Therefore, a concentration gradient of the solution may change depending on the storage time or possibility of forming a defective device is high.

Second, materials used in the solution process need to have excellent coatability when forming a thin film so that a thin film with a uniform thickness is formed without causing holes or aggregation.

Third, layers going through the solution process need to have tolerance for solvents and materials used in the process forming other layers. For this, a curing group needs to be introduced to form a self-crosslinked polymer on a substrate through heat treatment or UV irradiation after solution coating so that sufficient tolerance is obtained for solvents and materials used in the next process, or materials capable of having tolerance for solvents by themselves need to be used. Generally, arylamine-based monomers used in an organic light emitting device do not have tolerance for solvents of the next process by themselves, and therefore, development of arylamine-based monomer compounds having a curing group introduced thereto so as to be used in an organic light emitting device for a solution process has been required.

PRIOR ART DOCUMENTS

Patent Documents (Patent Document 1) Korean Patent Application Laid-Open Publication No. 2009-114716

DISCLOSURE

Technical Problem

The present specification is directed to providing a compound usable in an organic light emitting device for a solution process, and an organic light emitting device comprising the same.

Technical Solution

One embodiment of the present specification provides a compound represented by the following Chemical Formula 1.

[Chemical Formula 1]

In Chemical Formula 1,

R1 to R3 and R5 to R7 are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, R4 and R8 are the same as or different from each other, and each independently a functional group crosslinkable by heat or light, Ar1 and Ar2 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group, L1 and L2 are the same as or different from each other, and each independently a direct bond; a substituted or unsubstituted divalent alkyl group; a substituted or unsubstituted divalent aryl group; or a substituted or unsubstituted divalent heteroaryl group, L11 and L12 are the same as or different from each other, and each independently a direct bond; or a substituted or unsubstituted divalent aryl group, L is a substituted or unsubstituted divalent or trivalent aryl group; a substituted or unsubstituted divalent or trivalent heteroaryl group; or a substituted or unsubstituted divalent or trivalent arylamine group, m1 and m2 are each an integer of 0 to 12, n1 and n5 are each an integer of 0 to 5, n2 and n6 are each an integer of 0 to 4, n3 and n7 are each an integer of 0 to 3, p1 and p2 are each an integer of 1 to 4, q is 1 or 2, when n1 to n3, n5 to n7, p1 and p2 are each 2 or greater, substituents in the parentheses are the same as or different from each other, and when q is 2, substituents in the parentheses are the same as or different from each other.

One embodiment of the present specification provides a coating composition comprising the compound.

In addition, one embodiment of the present specification provides an organic light emitting device comprising a first electrode; a second electrode; and one or more organic material layers provided between the first electrode and the second electrode, wherein one or more layers of the organic material layers comprise a cured material of the coating composition, and the cured material of the coating composition is in a cured state by heat treating or light treating the coating composition.

Lastly, one embodiment of the present specification provides a method for manufacturing an organic light emitting device comprising preparing a substrate; forming a first electrode on the substrate; forming one or more organic material layers on the first electrode; and forming a second electrode on the organic material layer, wherein the forming of organic material layers comprises forming one or more organic material layers using the coating composition.

Advantageous Effects

A compound according to one embodiment of the present disclosure can be used in a solution process, and therefore, large area devices can be manufactured. The compound can be used as a material of an organic material layer of an organic light emitting device, and provides low driving voltage, high light emission efficiency and long lifetime properties. In addition thereto, the organic material layer comprising the compound has tolerance for solvents and materials used in the process forming other layers in the organic light emitting device.

In addition, the compound according to one embodiment of the present disclosure has advantages of controlling a glass transition temperature and a melting point by a fluorene structure and an aryl group directly bonding to number 9 carbon of the fluorene and an alkyl group, a linker between a curing group and the fluorene, inhibiting interactions between the molecules, and, by the linear-type alkyl group, lowering a curing temperature by increasing mobility of the curing group or reducing steric hindrance around the curing group.

DESCRIPTION OF DRAWINGS

FIG. 1 illustrates an example of an organic light emitting device according to one embodiment of the present specification.

101: Substrate

201: Anode

301: Hole Injection Layer

401: Hole Transfer Layer

501: Light Emitting Layer

601: Electron Transfer Layer

701: Cathode

FIG. 2 is a diagram showing an MS graph of Compound 1.

FIG. 3 is a diagram showing a DSC measurement graph of Compound 1.

FIG. 4 is a diagram showing a film retention rate test result of Example 1-1.

FIG. 5 is a diagram showing a film retention rate test result of Comparative Example 1-1.

FIG. 6 is a diagram showing a film retention rate test result of Comparative Example 1-2.

MODE FOR DISCLOSURE

Hereinafter, the present specification will be described in detail.

One embodiment of the present specification provides a compound represented by the following Chemical Formula 1.

[Chemical Formula 1]

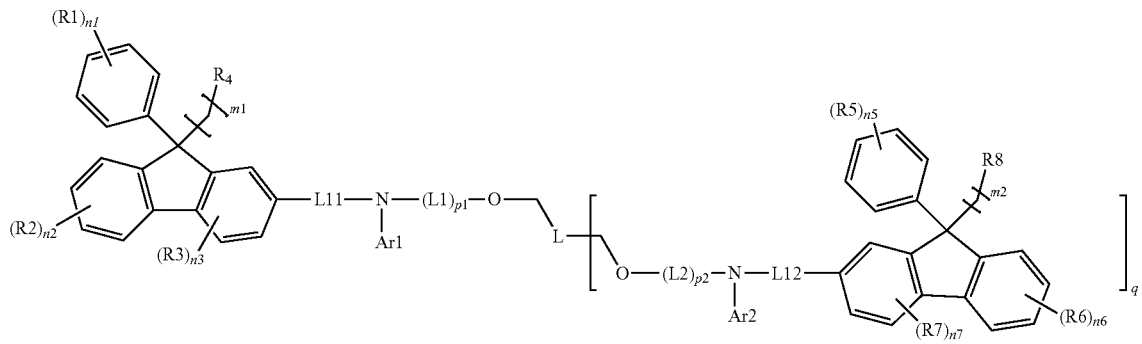

In Chemical Formula 1,

R1 to R3 and R5 to R7 are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, R4 and R8 are the same as or different from each other, and each independently a functional group crosslinkable by heat or light, Ar1 and Ar2 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group, L1 and L2 are the same as or different from each other, and each independently a direct bond; a substituted or unsubstituted divalent alkyl group; a substituted or unsubstituted divalent aryl group; or a substituted or unsubstituted divalent heteroaryl group, L11 and L12 are the same as or different from each other, and each independently a direct bond; or a substituted or unsubstituted divalent aryl group, L is a substituted or unsubstituted divalent or trivalent aryl group; a substituted or unsubstituted divalent or trivalent heteroaryl group; or a substituted or unsubstituted divalent or trivalent arylamine group, m1 and m2 are each an integer of 0 to 12,
n1 and n5 are each an integer of 0 to 5,
n2 and n6 are each an integer of 0 to 4,
n3 and n7 are each an integer of 0 to 3,
p1 and p2 are each an integer of 1 to 4,
q is 1 or 2, when n1 to n3, n5 to n7, p1 and p2 are each 2 or greater, substituents in the parentheses are the same as or different from each other, and when q is 2, substituents in the parentheses are the same as or different from each other.

The compound according to one embodiment of the present disclosure has excellent solubility by the aryl group and alkyl group directly bonding to number 9 carbon of the fluorene, and by maintaining a proper distance between the fluorene and the curing group due to a linker, mobility of the curing group increases or steric hindrance around the curing group is reduced, which helps with a curing reaction, and as a result, an organic light emitting device having excellent tolerance for solvents, and having excellent efficiency and device properties is provided.

In the present specification, a description of a certain member being placed "on" another member comprises not only a case of the one member adjoining the another member but a case of still another member being present between the two members.

In the present specification, a description of a certain part "comprising" certain constituents means capable of further comprising other constituents, and does not exclude other constituents unless particularly stated on the contrary.

In one embodiment of the present specification, the compound of Chemical Formula 1 preferably comprises compounds having solubility for proper organic solvents.

In addition, with the compound according to one embodiment of the present specification, an organic light emitting device may be manufactured using a solution coating method, and therefore, large area devices may be manufactured.

In the present specification, the "functional group crosslinkable by heat or light" may mean a reactive substituent crosslinking compounds by being exposed to heat or light. The crosslinkage may be produced by linking radicals produced while carbon-carbon multiple bonds or cyclic structures are disintegrated by heat treatment or light irradiation.

Hereinafter, substituents of the present specification will be described in detail.

In the present specification, means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of deuterium; a halogen group; a nitrile group; a silyl group; a boron group; an alkyl group; a cycloalkyl group; an alkoxy group; an alkenyl group; an aryl group; and a heterocyclic group, or being unsubstituted, or being substituted with a substituent linking two or more substituents among the substituents illustrated above, or being unsubstituted. For example, "a substituent linking two or more substituents" may comprise a biphenyl group. In other words, a biphenyl group may be an aryl group, or interpreted as a substituent linking two phenyl groups.

In the present specification, the halogen group is fluorine (F), chlorine (Cl), bromine (Br) or iodine (I).

In the present specification, the silyl group may be represented by a chemical formula of —SiR$_a$R$_b$R$_c$, and R$_a$, R$_b$ and R$_c$ may each be hydrogen; a substituted or unsubstituted alkyl group; or a substituted or unsubstituted aryl group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by a chemical formula of —BR$_d$R$_e$, and R$_d$ and R$_e$ may each be hydrogen; a substituted or unsubstituted alkyl group; or a substituted or unsubstituted aryl group. Specific examples of the boron group may comprise a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms may be from 1 to 60, and according to one embodiment, the number of carbon atoms of the alkyl group may be from 1 to 30. According to another embodiment, the number of carbon atoms of the alkyl group is from 1 to 10. Specific examples of the alkyl group may comprise a methyl group, an ethyl group, a propyl group, an isopropyl group, a butyl group, an isobutyl group, a tert-butyl group, a sec-butyl group, a 1-methyl-butyl group, a 1-ethyl-butyl group, a pentyl group, an isopentyl group, a neopentyl group, a tert-pentyl group, a 1-methylpentyl group, a 2-methylpentyl group, a 4-methyl-2-pentyl group, a hexyl group, an isohexyl group, a 4-methylhexyl group, a 5-methylhexyl group, a heptyl group and the like, but are not limited thereto.

In the present specification, the cycloalkyl group is not particularly limited, but may have 3 to 60 carbon atoms, and according to one embodiment, the number of carbon atoms of the cycloalkyl group is from 3 to 40. According to another embodiment, the number of carbon atoms of the cycloalkyl group is from 3 to 20. Specific examples of the cycloalkyl group may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may be linear, branched or cyclic. The number of carbon atoms of the alkoxy group is not particularly limited, but may be from 1 to 20. Specific examples of the alkoxy group may comprise a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, an 2-ethylbutyloxy group, an n-octyloxy group, an n-nonyloxy group, an n-decyloxy group, a benzyloxy group, a p-methylbenzyloxy group and the like, but are not limited thereto.

In the present specification, the alkenyl group may be linear or branched, and although not particularly limited thereto, the number of carbon atoms may be from 2 to 30, and according to one embodiment, the number of carbon atoms of the alkenyl group may be from 2 to 20. Specific examples of the alkenyl group may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl) vinyl-1-yl group, a 2,2-bis(diphenyl-1-yl)vinyl-1-yl group, a stilbenyl group, a styrenyl group and the like, but are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group comprising two or more aryl groups may comprise monocyclic aryl groups, polycyclic aryl groups, or both monocyclic aryl groups and polycyclic aryl groups. For example, the aryl group in the arylamine group may be selected from among the examples of the aryl group described above. Specific examples of the arylamine group may comprise phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, the aryl group is not particularly limited, but may have 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may comprise a phenyl group, a biphenyl group, a terphenyl group and the like, but are not limited thereto. Examples of the polycyclic aryl group may comprise a naphthyl group, an anthracenyl group, a phenanthrenyl group, a pyrenyl group, a perylenyl group, a triphenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted, spirofluorenyl groups such as

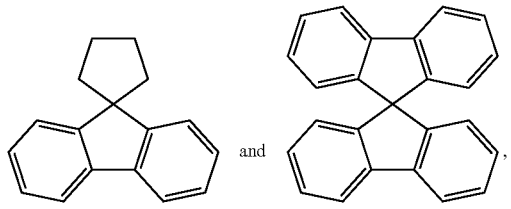

and substituted fluorenyl groups such as

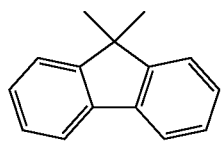

(9,9-dimethylfluorenyl group) and

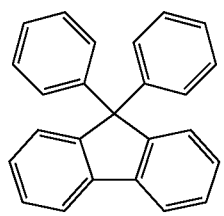 [SMILES: c1ccc(C2(c3ccccc3)c3ccccc3-c3ccccc32)cc1]

(9,9-diphenylfluorenyl group) may be included. However, the structure is not limited thereto.

In the present specification, the heterocyclic group is a heterocyclic group comprising one or more of N, O, P, S, Si and Se as a heteroatom, and although not particularly limited thereto, the number of carbon atoms may be from 2 to 60.

According to one embodiment, the number of carbon atoms of the heterocyclic group is from 2 to 30. According to another embodiment, the number of carbon atoms of the heterocyclic group is from 2 to 20. Examples of the heterocyclic group may comprise a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine or the like, but are not limited thereto.

In the present specification, descriptions on the heterocyclic group provided above may be applied to the heteroaryl group except for being aromatic.

In the present specification, descriptions on the aryl group provided above are applied to the arylene group except for being divalent.

In the present specification, descriptions on the heteroaryl group provided above are applied to the heteroarylene group except for being divalent.

In one embodiment of the present specification, L11 and L12 are the same as or different from each other, and each independently a direct bond; or a substituted or unsubstituted divalent aryl group having 6 to 60 carbon atoms.

According to another embodiment, L11 and L12 are the same as or different from each other, and each independently a direct bond; or a substituted or unsubstituted divalent aryl group having 6 to 30 carbon atoms.

In another embodiment, L11 and L12 are the same as or different from each other, and each independently a direct bond; a substituted or unsubstituted divalent phenyl group; or a substituted or unsubstituted divalent biphenyl group.

In another embodiment, L11 and L12 are the same as or different from each other, and each independently a direct bond; or a divalent phenyl group.

According to one embodiment of the present specification, L11 and L12 are a direct bond.

According to one embodiment of the present specification, L11 and L12 are a divalent phenyl group.

According to one embodiment of the present specification, L1 and L2 are the same as or different from each other, and each independently a direct bond; a substituted or unsubstituted divalent alkyl group having 1 to 60 carbon atoms; a substituted or unsubstituted divalent aryl group having 6 to 60 carbon atoms; or a substituted or unsubstituted divalent heteroaryl group having 2 to 60 carbon atoms.

In another embodiment, L1 and L2 are the same as or different from each other, and each independently a direct bond; a substituted or unsubstituted divalent alkyl group having 1 to 30 carbon atoms; a substituted or unsubstituted divalent aryl group having 6 to 30 carbon atoms; or a substituted or unsubstituted divalent heteroaryl group having 2 to 30 carbon atoms.

According to another embodiment, L1 and L2 are the same as or different from each other, and each independently a direct bond; a substituted or unsubstituted divalent methyl group; a substituted or unsubstituted divalent ethyl group; a substituted or unsubstituted divalent phenyl group; a substituted or unsubstituted divalent biphenyl group; a substituted or unsubstituted divalent terphenyl group; a substituted or unsubstituted divalent naphthyl group; a substituted or unsubstituted divalent fluorenyl group; a substituted or unsubstituted divalent dibenzofuran group; a substituted or unsubstituted divalent dibenzothiophene group; or a substituted or unsubstituted divalent carbazole group.

According to another embodiment, L1 and L2 are the same as or different from each other, and each independently a direct bond; a substituted or unsubstituted divalent methyl group; a substituted or unsubstituted divalent phenyl group; or a substituted or unsubstituted divalent carbazole group.

In another embodiment, L1 and L2 are the same as or different from each other, and each independently a direct bond; a divalent methyl group; a divalent phenyl group; or a divalent carbazole group.

According to one embodiment of the present specification, p1 and p2 are each an integer of 1 to 4.

According to another embodiment, p1 and p2 are 3 or 4.

According to one embodiment of the present specification, Chemical Formula 1 may be represented by the following Chemical Formula 2.

[Chemical Formula 2]

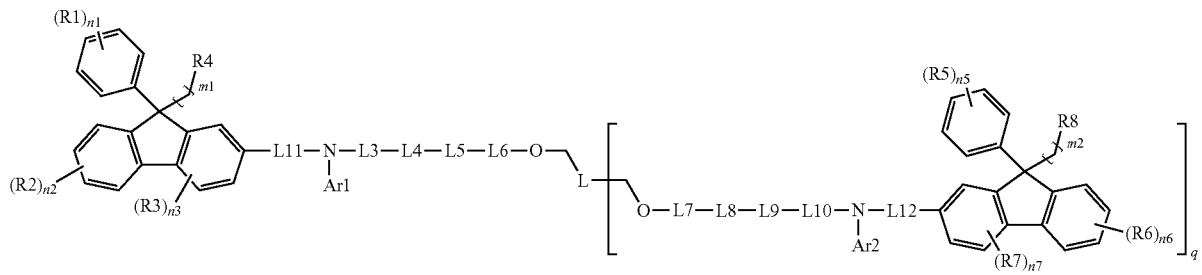

In Chemical Formula 2,

R1 to R8, n1 to n3, n5 to n7, Ar1, Ar2, L, L11, L12, q, m1 and m2 have the same definitions as in Chemical Formula 1, and L3 to L10 are the same as or different from each other, and each independently a direct bond; a substituted or unsubstituted divalent alkyl group; a substituted or unsubstituted divalent aryl group; or a substituted or unsubstituted divalent heteroaryl group.

According to one embodiment of the present specification, L3 to L10 are the same as or different from each other, and each independently a direct bond; a substituted or unsubstituted divalent alkyl group having 1 to 60 carbon atoms; a substituted or unsubstituted divalent aryl group having 6 to carbon atoms; or a substituted or unsubstituted divalent heteroaryl group having 2 to 60 carbon atoms.

According to another embodiment, L3 to L10 are the same as or different from each other, and each independently a direct bond; a substituted or unsubstituted divalent alkyl group having 1 to 30 carbon atoms; a substituted or unsubstituted divalent aryl group having 6 to 30 carbon atoms; or a substituted or unsubstituted divalent heteroaryl group having 2 to 30 carbon atoms.

In another embodiment, L3 to L10 are the same as or different from each other, and each independently a direct bond; a substituted or unsubstituted divalent methyl group; a substituted or unsubstituted divalent ethyl group; a substituted or unsubstituted divalent phenyl group; a substituted or unsubstituted divalent biphenyl group; a substituted or unsubstituted divalent terphenyl group; a substituted or unsubstituted divalent naphthyl group; a substituted or unsubstituted divalent fluorenyl group; a substituted or unsubstituted divalent dibenzofuran group; a substituted or unsubstituted divalent dibenzothiophene group; or a substituted or unsubstituted divalent carbazole group.

According to another embodiment, L3 to L10 are the same as or different from each other, and each independently a direct bond; a substituted or unsubstituted divalent methyl group; a substituted or unsubstituted divalent phenyl group; or a substituted or unsubstituted divalent carbazole group.

In another embodiment, L3 to L10 are the same as or different from each other, and each independently a direct bond; a divalent methyl group; a divalent phenyl group; or a divalent carbazole group.

In one embodiment of the present specification, L3 and L10 are a direct bond, L4 and L9 are a divalent carbazole group, L5 and L8 are a divalent phenyl group, and L6 and L7 are a divalent methyl group.

According to one embodiment of the present specification, L3, L5, L8 and L10 are the same as or different from each other and each independently a substituted or unsubstituted divalent phenyl group, L4 and L9 are the same as or different from each other and each independently a substituted or unsubstituted divalent carbazole group, and L6 and L7 are the same as or different from each other and each independently a substituted or unsubstituted divalent methyl group.

According to another embodiment, L3, L5, L8 and L10 are a divalent phenyl group, L4 and L9 are a divalent carbazole group, and L6 and L7 are a divalent methyl group.

In one embodiment of the present specification, Ar1 and Ar2 are the same as or different from each other, and each independently hydrogen; deuterium; a substituted or unsubstituted aryl group; or a substituted or unsubstituted heterocyclic group.

According to another embodiment, Ar1 and Ar2 are the same as or different from each other, and each independently hydrogen; deuterium; a substituted or unsubstituted aryl group having 6 to 60 carbon atoms; or a substituted or unsubstituted heterocyclic group having 2 to 60 carbon atoms.

In another embodiment, Ar1 and Ar2 are the same as or different from each other, and each independently hydrogen; deuterium; a substituted or unsubstituted aryl group having 6 to 30 carbon atoms; or a substituted or unsubstituted heterocyclic group having 2 to 30 carbon atoms.

According to another embodiment, Ar1 and Ar2 are the same as or different from each other, and each independently hydrogen; deuterium; an aryl group having 6 to 30 carbon atoms unsubstituted or substituted with one or more selected from the group consisting of an alkyl group having 1 to 20 carbon atoms and an aryl group having 6 to 30 carbon atoms; or a heterocyclic group having 2 to 30 carbon atoms unsubstituted or substituted with one or more selected from the group consisting of an alkyl group having 1 to 20 carbon atoms and an aryl group having 6 to 30 carbon atoms.

In another embodiment, Ar1 and Ar2 are the same as or different from each other, and each independently hydrogen; deuterium; an aryl group having 6 to 30 carbon atoms unsubstituted or substituted with one or more selected from the group consisting of a methyl group, an ethyl group, a propyl group, an isopropyl group, a butyl group, a tert-butyl group, a pentyl group, a hexyl group and a phenyl group; or a heterocyclic group having 2 to 30 carbon atoms unsubstituted or substituted with one or more selected from the group consisting of a methyl group, an ethyl group, a propyl group, an isopropyl group, a butyl group, a tert-butyl group, a pentyl group, a hexyl group and a phenyl group.

According to another embodiment, Ar1 and Ar2 are the same as or different from each other, and each independently a phenyl group unsubstituted or substituted with one or more selected from the group consisting of an alkyl group having 1 to 20 carbon atoms and an aryl group having 6 to 30 carbon atoms; a biphenyl group unsubstituted or substituted with one or more selected from the group consisting of an alkyl group having 1 to 20 carbon atoms and an aryl group having 6 to 30 carbon atoms; a naphthyl group unsubstituted or substituted with one or more selected from the group consisting of an alkyl group having 1 to 20 carbon atoms and an aryl group having 6 to 30 carbon atoms; a fluorenyl group unsubstituted or substituted with one or more selected from the group consisting of an alkyl group having 1 to 20 carbon atoms and an aryl group having 6 to carbon atoms; or a carbazole group unsubstituted or substituted with one or more selected from the group consisting of an alkyl group having 1 to 20 carbon atoms and an aryl group having 6 to 30 carbon atoms.

According to another embodiment, Ar1 and Ar2 are the same as or different from each other, and each independently a phenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a biphenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a naphthyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a fluorenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; or a carbazole group unsubstituted or substituted with one or more selected from the group consisting of a methyl group, an ethyl group, a propyl group, an isopropyl group, a butyl group, a tert-butyl group, a pentyl group, a hexyl group and a phenyl group.

According to one embodiment of the present specification, q is 1 or 2.

According to one embodiment of the present specification, L is a substituted or unsubstituted divalent or trivalent aryl group; a substituted or unsubstituted divalent or trivalent heteroaryl group; or a substituted or unsubstituted divalent or trivalent arylamine group.

In one embodiment of the present specification, when q is 1, L is a substituted or unsubstituted divalent aryl group; a substituted or unsubstituted divalent heteroaryl group; or a substituted or unsubstituted divalent arylamine group.

According to another embodiment, when q is 1, L is a substituted or unsubstituted divalent aryl group having 6 to 60 carbon atoms; or a substituted or unsubstituted divalent heteroaryl group having 2 to 60 carbon atoms.

In another embodiment, when q is 1, L is a substituted or unsubstituted divalent aryl group having 6 to 30 carbon atoms; or a substituted or unsubstituted divalent heteroaryl group having 2 to 30 carbon atoms.

According to another embodiment, when q is 1, L is a substituted or unsubstituted divalent aryl group having 6 to 30 carbon atoms.

According to another embodiment, when q is 1, L is a substituted or unsubstituted divalent phenyl group; a substituted or unsubstituted divalent biphenyl group; or a substituted or unsubstituted divalent fluorenyl group.

In another embodiment, when q is 1, L is a divalent phenyl group unsubstituted or substituted with an alkyl group having 1 to 10 carbon atoms; a divalent biphenyl group unsubstituted or substituted with an alkyl group having 1 to 10 carbon atoms; or a divalent fluorenyl group unsubstituted or substituted with an alkyl group having 1 to 10 carbon atoms.

According to another embodiment, when q is 1, L is a divalent phenyl group unsubstituted or substituted with a methyl group or a hexyl group; a divalent biphenyl group unsubstituted or substituted with a methyl group or a hexyl group; or a divalent fluorenyl group unsubstituted or substituted with a methyl group or a hexyl group.

In another embodiment, when q is 1, L is a divalent phenyl group; a divalent 9,9-dimethylfluorenyl group; or a divalent 9,9-dihexylfluorenyl group.

In one embodiment of the present specification, when q is 2, L is a substituted or unsubstituted trivalent aryl group; a substituted or unsubstituted trivalent heteroaryl group; or a substituted or unsubstituted trivalent arylamine group.

According to another embodiment, when q is 2, L is a substituted or unsubstituted trivalent aryl group having 6 to 60 carbon atoms; or a substituted or unsubstituted trivalent arylamine group.

According to another embodiment, when q is 2, L is a substituted or unsubstituted trivalent phenyl group; or a substituted or unsubstituted trivalent triphenylamine group.

According to one embodiment of the present specification, L may be any one of the following structures.

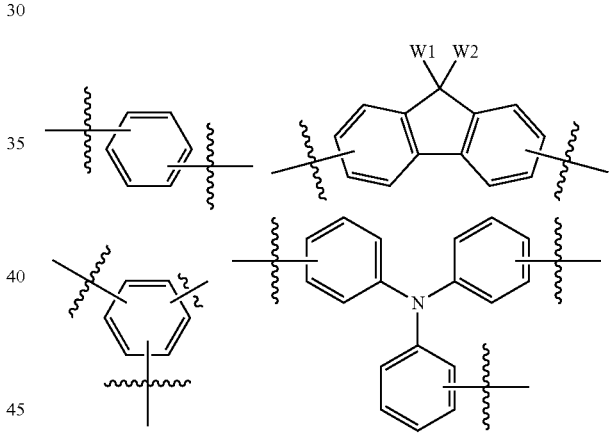

In the structures,

W1 and W2 are the same as or different from each other, and each independently hydrogen; or a substituted or unsubstituted alkyl group, and the structures may be further substituted.

According to one embodiment of the present specification, W1 and W2 are the same as or different from each other, and each independently hydrogen; or a substituted or unsubstituted alkyl group having 1 to 20 carbon atoms.

According to another embodiment, W1 and W2 are the same as or different from each other, and each independently hydrogen; or a substituted or unsubstituted alkyl group having 1 to 10 carbon atoms.

In another embodiment, W1 and W2 are the same as or different from each other, and each independently a substituted or unsubstituted methyl group; a substituted or unsubstituted ethyl group; a substituted or unsubstituted propyl group; a substituted or unsubstituted butyl group; a substituted or unsubstituted pentyl group; or a substituted or unsubstituted hexyl group.

According to another embodiment, W1 and W2 are the same as or different from each other, and each independently a methyl group; an ethyl group; a propyl group; a butyl group; a pentyl group; or a hexyl group.

In another embodiment, W1 and W2 are a methyl group.

According to another embodiment, W1 and W2 are a hexyl group.

According to one embodiment of the present specification, Chemical Formula 1 may be represented by any one of the following Chemical Formula 3 to Chemical Formula 6.

[Chemical Formula 3]

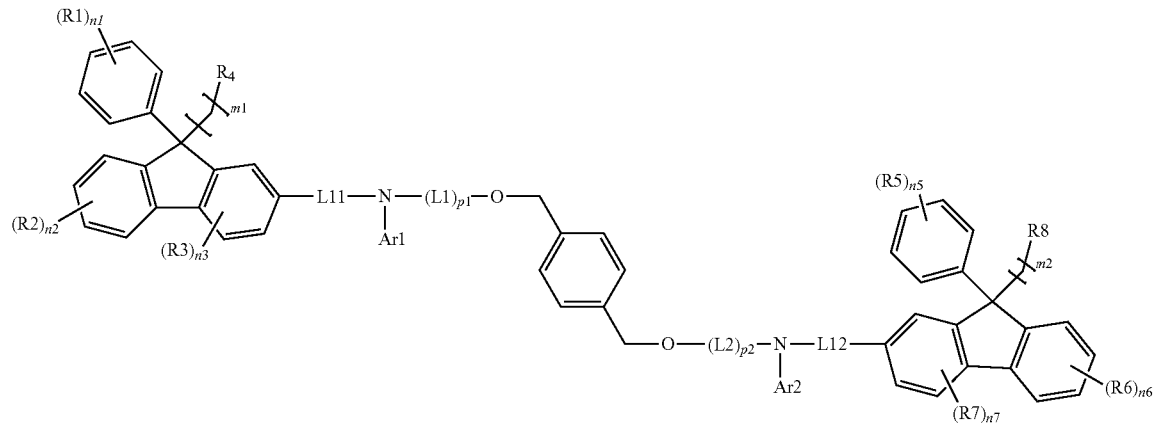

[Chemical Formula 4]

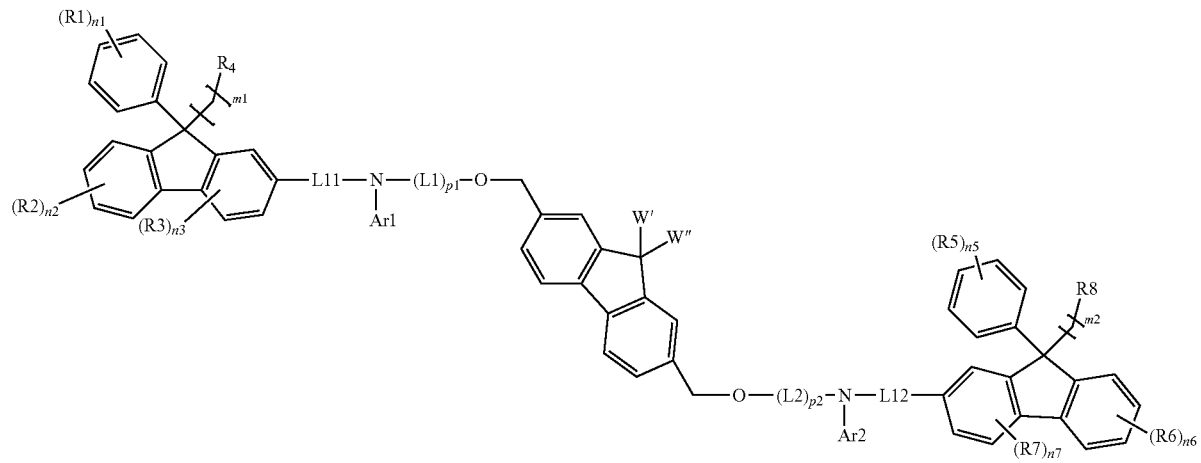

[Chemical Formula 5]
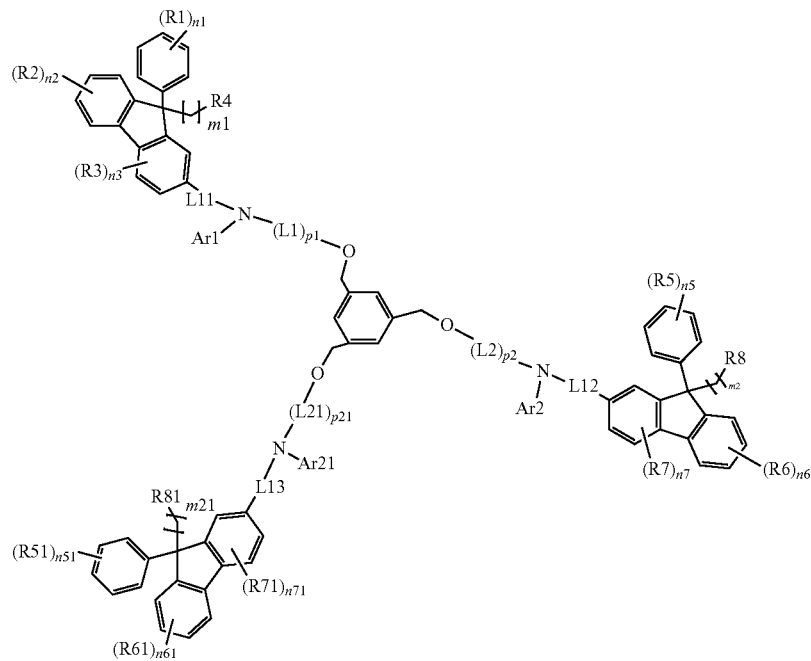
[Chemical Formula 6]
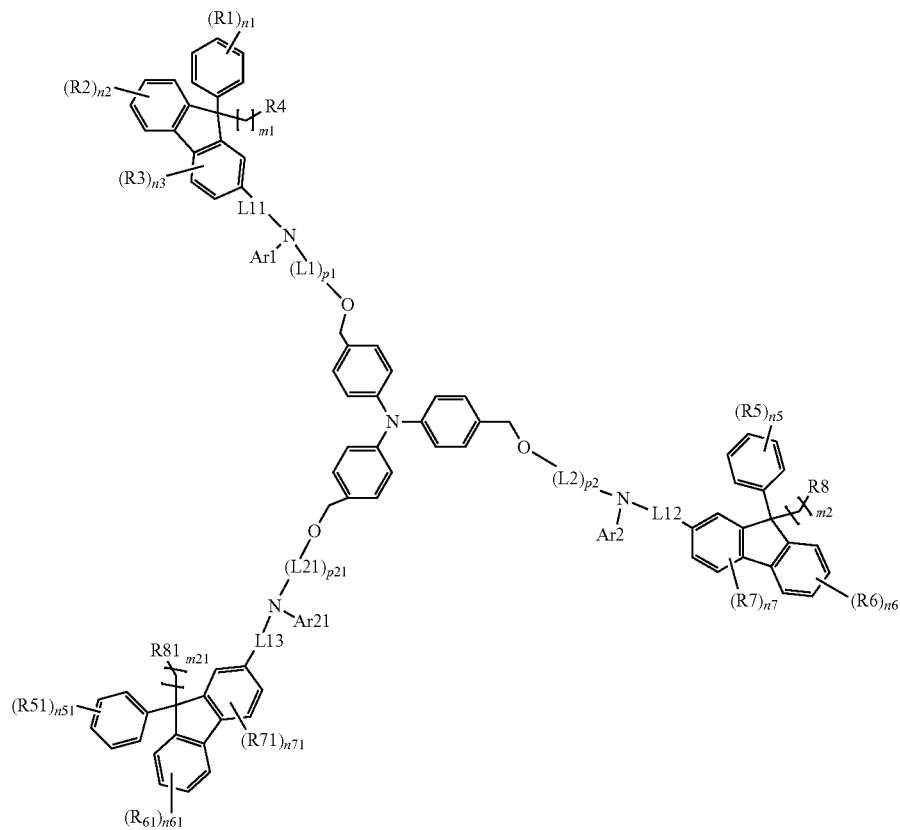

In Chemical Formulae 3 to 6,

R1 to R8, m1, m2, n1 to n3, n5 to n7, L1, L2, L11, L12, p1, p2, Ar1 and Ar2 have the same definitions as in Chemical Formula 1, L13 is a direct bond; or a substituted or unsubstituted divalent aryl group, L21 is a direct bond; a substituted or unsubstituted divalent alkyl group; a substituted or unsubstituted divalent aryl group; or a substituted or unsubstituted divalent heteroaryl group, Ar21 is hydrogen; deuterium; a substituted or unsubstituted alkyl group; a substituted or unsubstituted cycloalkyl group; a substituted or unsubstituted aryl group; or a substituted or unsubstituted heterocyclic group, R51, R61 and R71 are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, R81 is a functional group crosslinkable by heat or light, m21 is an integer of 0 to 12, p21 is an integer of 1 to 4, n51 is an integer of 0 to 5, n61 is an integer of 0 to 4, n71 is an integer of 0 to 3, and when p21, n51, n61 and n71 are each 2 or greater, substituents in the parentheses are the same as or different from each other.

According to one embodiment of the present specification, W' and W" are the same as or different from each other, and each independently hydrogen; or a substituted or unsubstituted alkyl group having 1 to 20 carbon atoms.

According to another embodiment, W' and W" are the same as or different from each other, and each independently hydrogen; or a substituted or unsubstituted alkyl group having 1 to 10 carbon atoms.

In another embodiment, W' and W" are the same as or different from each other, and each independently a substituted or unsubstituted methyl group; a substituted or unsubstituted ethyl group; a substituted or unsubstituted propyl group; a substituted or unsubstituted butyl group; a substituted or unsubstituted pentyl group; or a substituted or unsubstituted hexyl group.

According to another embodiment, W' and W" are the same as or different from each other, and each independently a methyl group; an ethyl group; a propyl group; a butyl group; a pentyl group; or a hexyl group.

In another embodiment, W' and W" are a methyl group.

According to another embodiment, W' and W" are a hexyl group.

In one embodiment of the present specification, L13 is a direct bond; or a substituted or unsubstituted divalent aryl group having 6 to 60 carbon atoms.

According to another embodiment, L13 is a direct bond; or a substituted or unsubstituted divalent aryl group having 6 to 30 carbon atoms.

In another embodiment, L13 is a direct bond; a substituted or unsubstituted divalent phenyl group; or a substituted or unsubstituted divalent biphenyl group.

In another embodiment, L13 is a direct bond; or a divalent phenyl group.

According to one embodiment of the present specification, L21 is a direct bond; a substituted or unsubstituted divalent alkyl group having 1 to 20 carbon atoms; a substituted or unsubstituted divalent aryl group having 6 to 60 carbon atoms; or a substituted or unsubstituted divalent heteroaryl group having 2 to 60 carbon atoms.

According to another embodiment, L21 is a direct bond; a substituted or unsubstituted divalent alkyl group having 1 to 10 carbon atoms; a substituted or unsubstituted divalent aryl group having 6 to 30 carbon atoms; or a substituted or unsubstituted divalent heteroaryl group having 2 to 30 carbon atoms.

According to another embodiment, L21 is a direct bond; a substituted or unsubstituted divalent methyl group; a substituted or unsubstituted divalent ethyl group; a substituted or unsubstituted divalent phenyl group; a substituted or unsubstituted divalent biphenyl group; a substituted or unsubstituted divalent terphenyl group; a substituted or unsubstituted divalent naphthyl group; a substituted or unsubstituted divalent fluorenyl group; a substituted or unsubstituted divalent dibenzofuran group; a substituted or unsubstituted divalent dibenzothiophene group; or a substituted or unsubstituted divalent carbazole group.

According to another embodiment, L21 is a direct bond; a substituted or unsubstituted divalent methyl group; a substituted or unsubstituted divalent phenyl group; or a substituted or unsubstituted divalent carbazole group.

In another embodiment, L21 is a direct bond; a divalent methyl group; a divalent phenyl group; or a divalent carbazole group.

According to one embodiment of the present specification, p21 is an integer of 1 to 4.

According to another embodiment, p21 is 3 or 4.

In one embodiment of the present specification, Ar21s are the same as or different from each other, and each independently hydrogen; deuterium; a substituted or unsubstituted aryl group; or a substituted or unsubstituted heterocyclic group.

According to another embodiment, Ar21s are the same as or different from each other, and each independently hydrogen; deuterium; a substituted or unsubstituted aryl group having 6 to 60 carbon atoms; or a substituted or unsubstituted heterocyclic group having 2 to 60 carbon atoms.

In another embodiment, Ar21s are the same as or different from each other, and each independently hydrogen; deuterium; a substituted or unsubstituted aryl group having 6 to 30 carbon atoms; or a substituted or unsubstituted heterocyclic group having 2 to 30 carbon atoms.

According to another embodiment, Ar21s are the same as or different from each other, and each independently hydrogen; deuterium; an aryl group having 6 to 30 carbon atoms unsubstituted or substituted with one or more selected from the group consisting of an alkyl group having 1 to 20 carbon atoms and an aryl group having 6 to 30 carbon atoms; or a heterocyclic group having 2 to 30 carbon atoms unsubstituted or substituted with one or more selected from the group consisting of an alkyl group having 1 to 20 carbon atoms and an aryl group having 6 to 30 carbon atoms.

In another embodiment, Ar21s are the same as or different from each other, and each independently hydrogen; deuterium; an aryl group having 6 to 30 carbon atoms unsubstituted or substituted with one or more selected from the group consisting of a methyl group, an ethyl group, a propyl group, an isopropyl group, a butyl group, a tert-butyl group, a pentyl group, a hexyl group and a phenyl group; or a heterocyclic group having 2 to 30 carbon atoms unsubstituted or substituted with one or more selected from the group consisting of a methyl group, an ethyl group, a propyl group, an isopropyl group, a butyl group, a tert-butyl group, a pentyl group, a hexyl group and a phenyl group.

According to another embodiment, Ar21s are the same as or different from each other, and each independently a phenyl group unsubstituted or substituted with one or more selected from the group consisting of an alkyl group having 1 to 20 carbon atoms and an aryl group having 6 to 30 carbon atoms; a biphenyl group unsubstituted or substituted with one or more selected from the group consisting of an alkyl group having 1 to 20 carbon atoms and an aryl group having 6 to 30 carbon atoms; a naphthyl group unsubstituted or substituted with one or more selected from the group consisting of an alkyl group having 1 to 20 carbon atoms and an aryl group having 6 to 30 carbon atoms; a fluorenyl group unsubstituted or substituted with one or more selected from the group consisting of an alkyl group having 1 to 20 carbon atoms and an aryl group having 6 to carbon atoms; or a carbazole group unsubstituted or substituted with one or more selected from the group consisting of an alkyl group having 1 to 20 carbon atoms and an aryl group having 6 to 30 carbon atoms.

According to another embodiment, Ar21s are the same as or different from each other, and each independently a phenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a biphenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a naphthyl group unsubstituted or substituted with one or more selected from the group consisting of a methyl group, an ethyl group, a propyl group, an isopropyl group, a butyl group, a tert-butyl group, a pentyl group, a hexyl group and a phenyl group; a fluorenyl group unsubstituted or substituted with one or more selected from the group consisting of a methyl group, an ethyl group, a propyl group, an isopropyl group, a butyl group, a tert-butyl group, a pentyl group, a hexyl group and a phenyl group; or a carbazole group unsubstituted or substituted with one or more selected from the group consisting of a methyl group, an ethyl group, a propyl group, an isopropyl group, a butyl group, a tert-butyl group, a pentyl group, a hexyl group and a phenyl group.

In one embodiment of the present specification, m1 and m2 are each an integer of 0 to 12.

According to another embodiment, m1 and m2 are each an integer of 0 to 6.

In another embodiment, m1 and m2 are each an integer of 1 to 6, and by m1 and m2 being each an integer of 1 to 6, a proper distance between the fluorene and the curing group is maintained, which lowers a curing point by reducing steric hindrance around the curing group.

According to one embodiment of the present specification, m1 and m2 are 2 or 6.

In one embodiment of the present specification, m21 is an integer of 0 to 12.

According to another embodiment, m21 is an integer of 0 to 6.

According to one embodiment of the present specification, m21 is 2 or 6.

In one embodiment of the present specification, R1 to R3 and R5 to R7 are the same as or different from each other, and each independently hydrogen; a substituted or unsubstituted alkyl group; or a substituted or unsubstituted alkoxy group.

According to another embodiment, R1 to R3 and R5 to R7 are the same as or different from each other, and each independently hydrogen; a substituted or unsubstituted alkyl group having 1 to 20 carbon atoms; or a substituted or unsubstituted alkoxy group having 1 to 20 carbon atoms.

In another embodiment, R1 to R3 and R5 to R7 are the same as or different from each other, and each independently hydrogen; or a substituted or unsubstituted alkyl group having 1 to 20 carbon atoms.

According to another embodiment, R1 to R3 and R5 to R7 are the same as or different from each other, and each independently hydrogen; a substituted or unsubstituted methyl group; a substituted or unsubstituted ethyl group; a substituted or unsubstituted propyl group; a substituted or unsubstituted isopropyl group; a substituted or unsubstituted butyl group; or a substituted or unsubstituted tert-butyl group.

In another embodiment, R1 to R3 and R5 to R7 are the same as or different from each other, and each independently hydrogen; a methyl group; an ethyl group; a propyl group; an isopropyl group; a butyl group; or a tert-butyl group.

In another embodiment, R1 to R3 and R5 to R7 are hydrogen.

In one embodiment of the present specification, R51, R61 and R71 are the same as or different from each other, and each independently hydrogen; a substituted or unsubstituted alkyl group; or a substituted or unsubstituted alkoxy group.

According to another embodiment, R51, R61 and R71 are the same as or different from each other, and each independently hydrogen; a substituted or unsubstituted alkyl group having 1 to 20 carbon atoms; or a substituted or unsubstituted alkoxy group having 1 to 20 carbon atoms.

In another embodiment, R51, R61 and R71 are the same as or different from each other, and each independently hydrogen; or a substituted or unsubstituted alkyl group having 1 to 20 carbon atoms.

According to another embodiment, R51, R61 and R71 are the same as or different from each other, and each independently hydrogen; a substituted or unsubstituted methyl group; a substituted or unsubstituted ethyl group; a substituted or unsubstituted propyl group; a substituted or unsubstituted isopropyl group; a substituted or unsubstituted butyl group; or a substituted or unsubstituted tert-butyl group.

In another embodiment, R51, R61 and R71 are the same as or different from each other, and each independently hydrogen; a methyl group; an ethyl group; a propyl group; an isopropyl group; a butyl group; or a tert-butyl group.

In another embodiment, R51, R61 and R71 are hydrogen.

According to one embodiment of the present specification, n1 to n3, n5 to n7, n51, n61 and n71 are each 0 or 1.

According to one embodiment of the present specification, R4 and R8 are the same as or different from each other, and each independently a functional group crosslinkable by heat or light.

According to another embodiment, R81 is a functional group crosslinkable by heat or light.

In one embodiment of the present specification, the functional group crosslinkable by heat or light may be any one of the following structures.

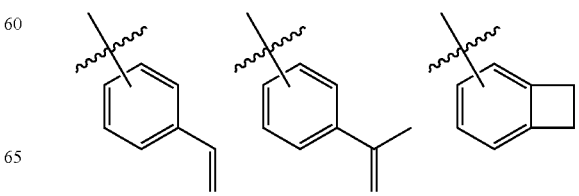

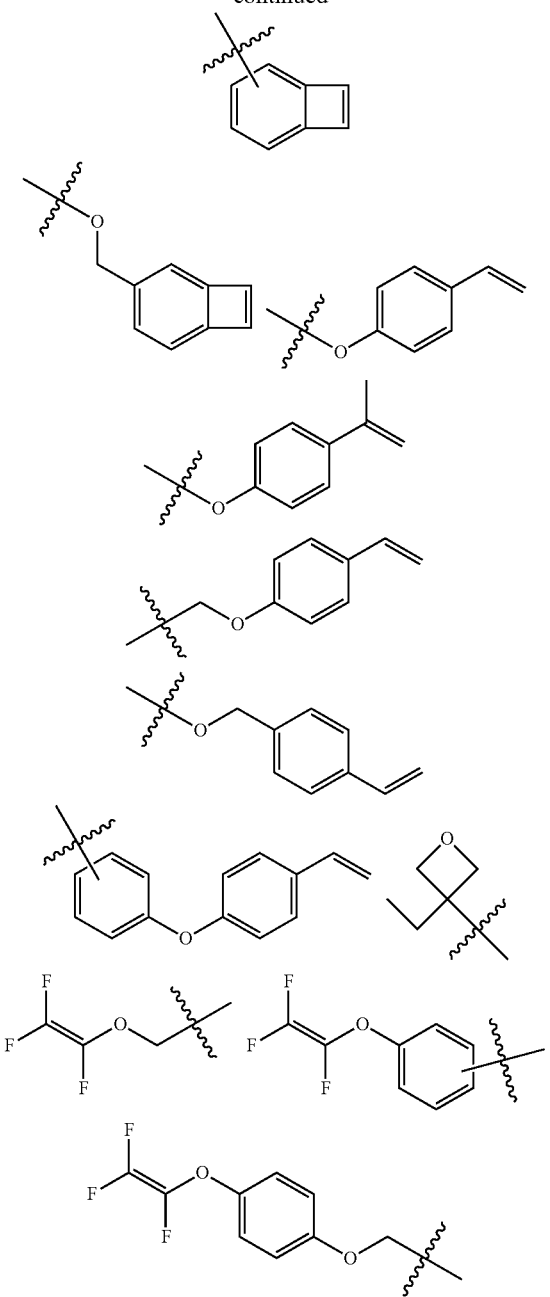
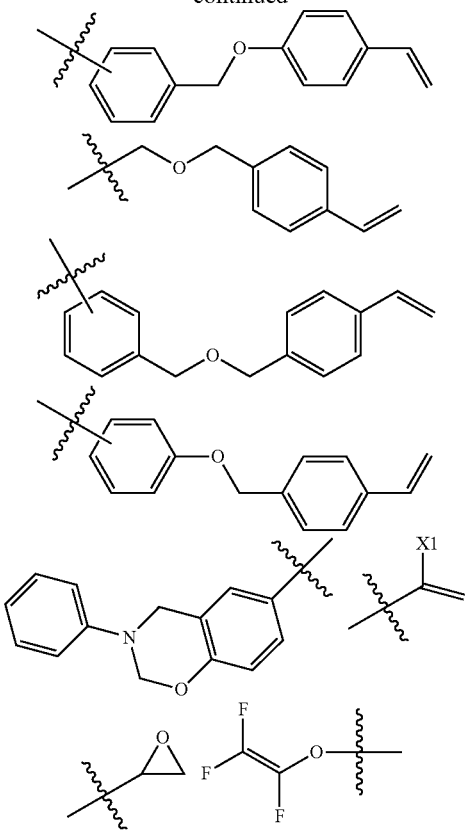

In the structures,

X1 is hydrogen; or a substituted or unsubstituted alkyl group having 1 to 6 carbon atoms.

According to one embodiment of the present specification, X1 is hydrogen; a substituted or unsubstituted methyl group; a substituted or unsubstituted ethyl group; a substituted or unsubstituted propyl group; a substituted or unsubstituted isopropyl group; a substituted or unsubstituted butyl group; a substituted or unsubstituted tert-butyl group; a substituted or unsubstituted pentyl group; or a substituted or unsubstituted hexyl group.

According to another embodiment, X1 is hydrogen; a methyl group; an ethyl group; a propyl group; an isopropyl group; a butyl group; a tert-butyl group; a pentyl group; or a hexyl group.

According to one embodiment of the present specification, Chemical Formula 1 may be represented by any one of the following Compounds 1 to 126.

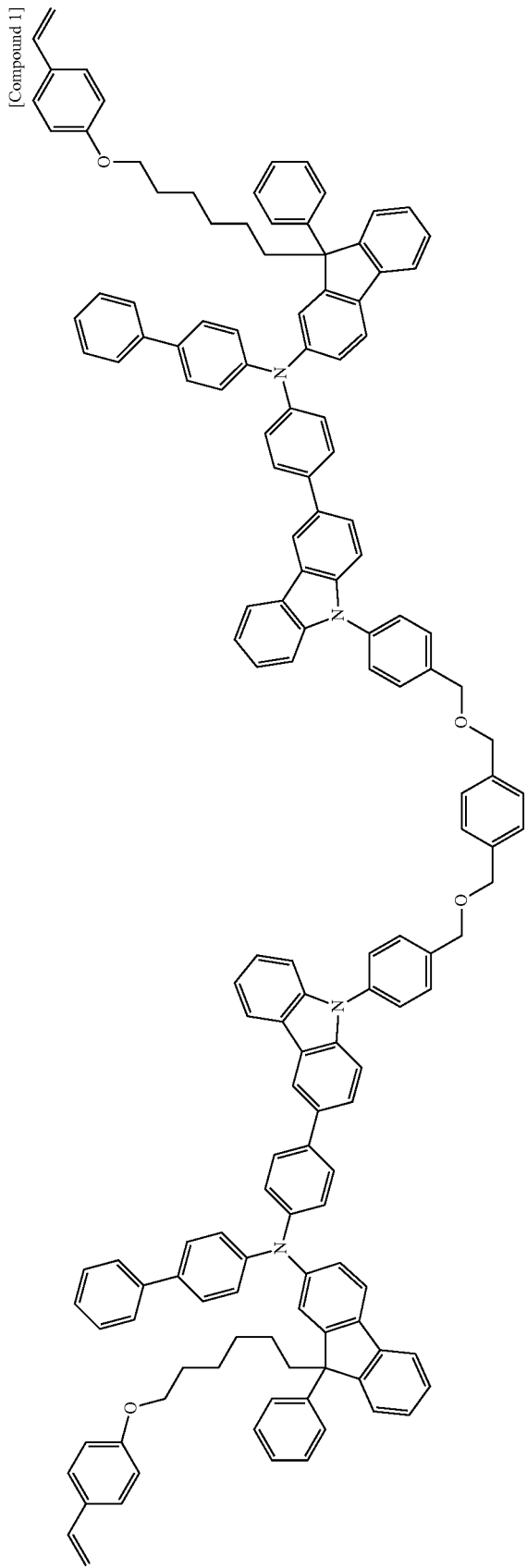
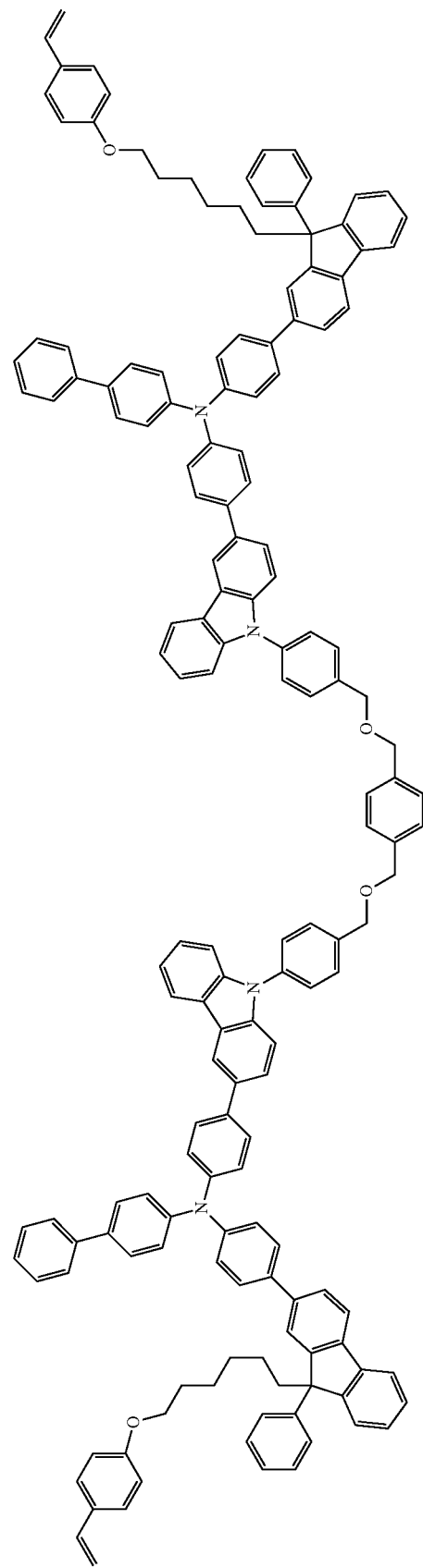

-continued
[Compound 3]
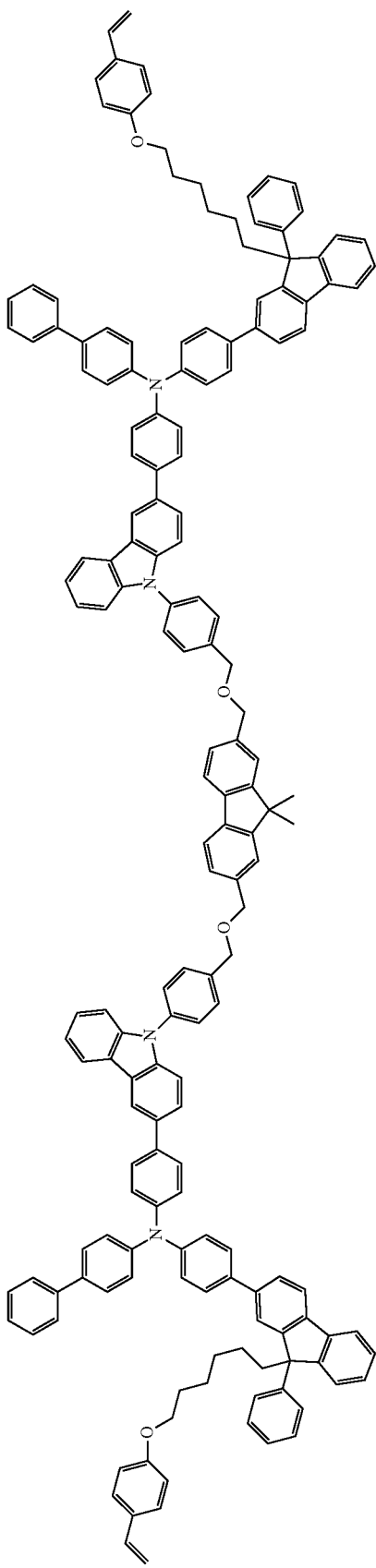
[Compound 4]
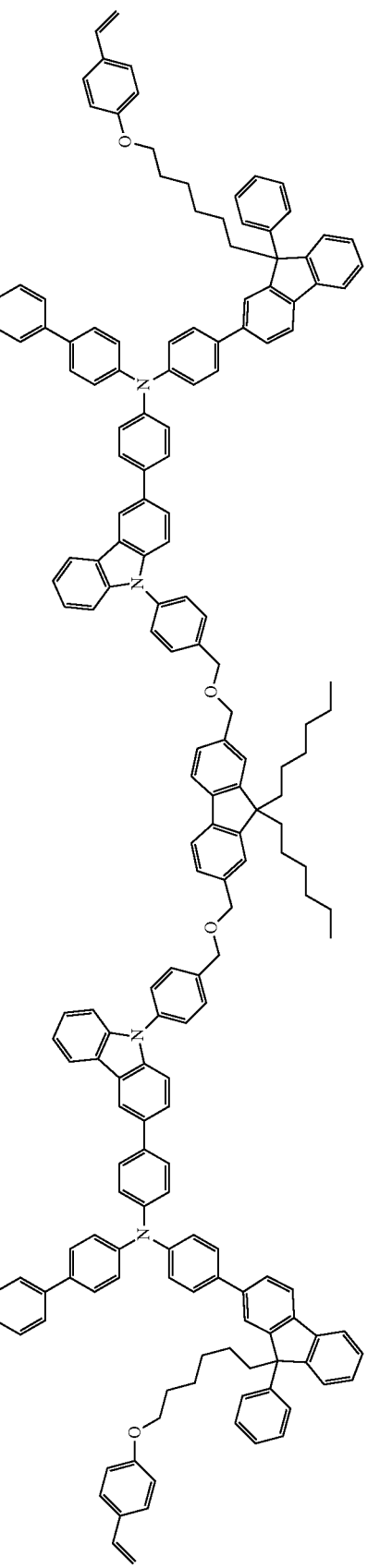

[Compound 5]
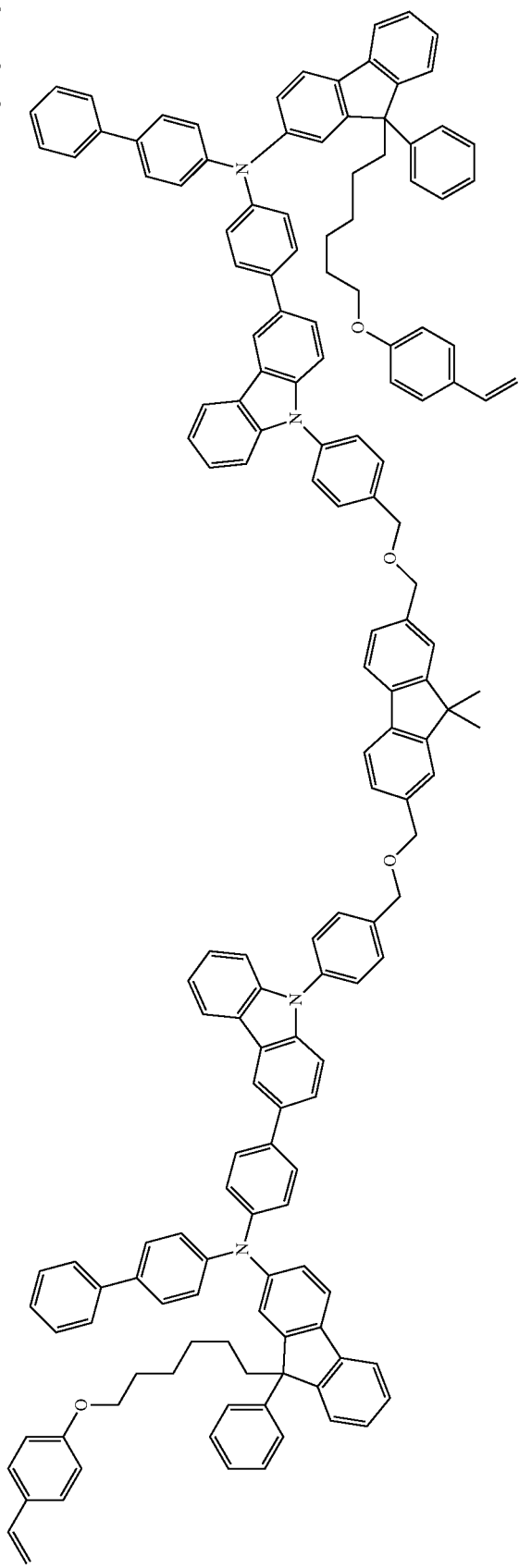

[Compound 6]
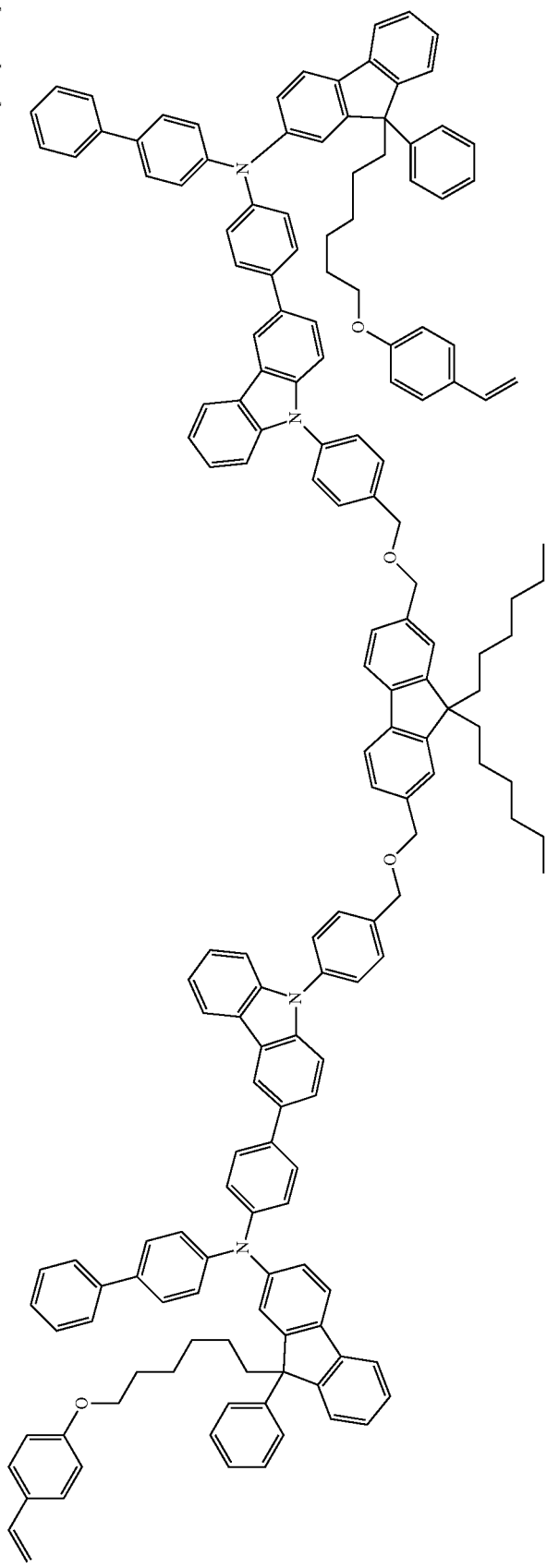

Compound 7
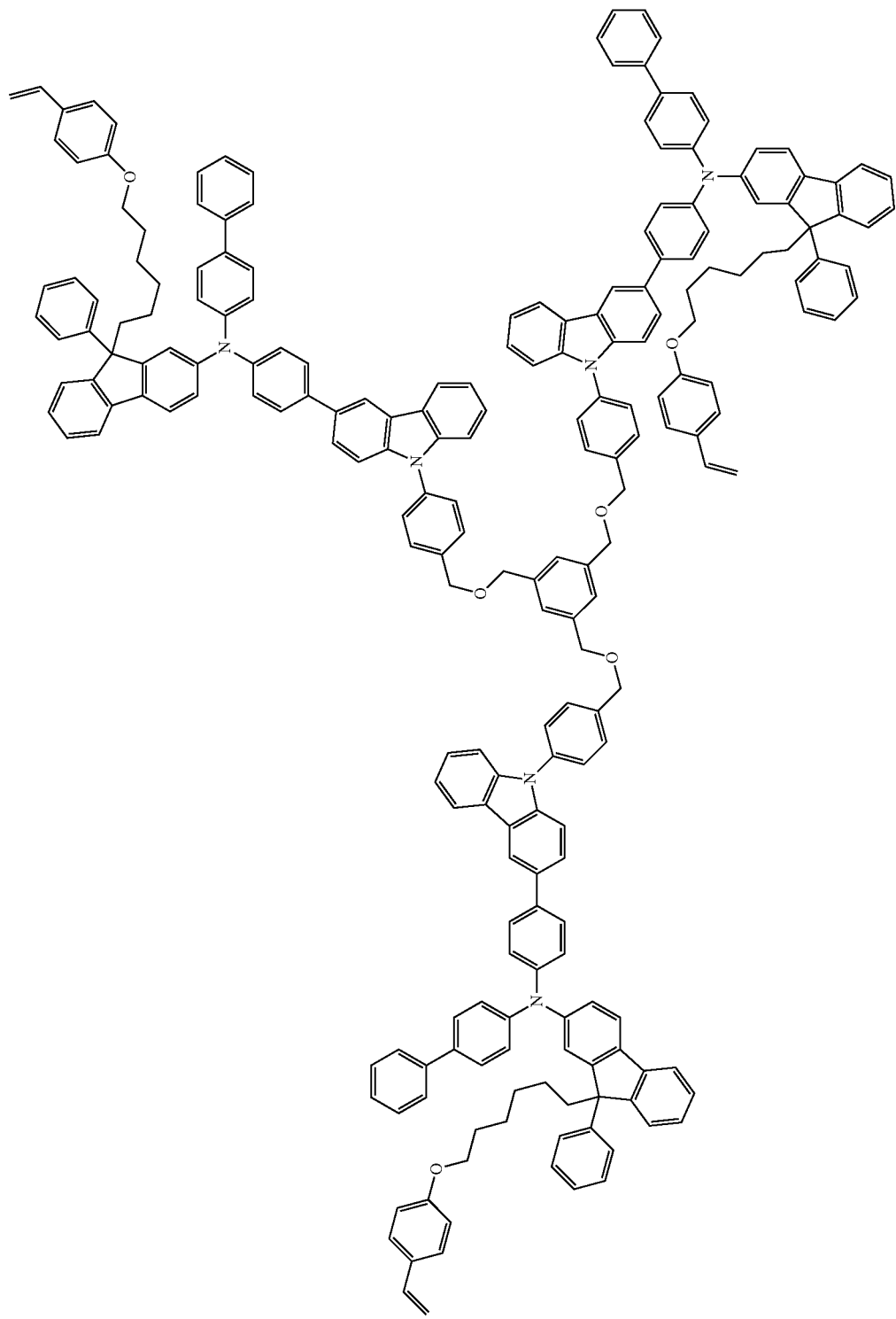

Compound 8
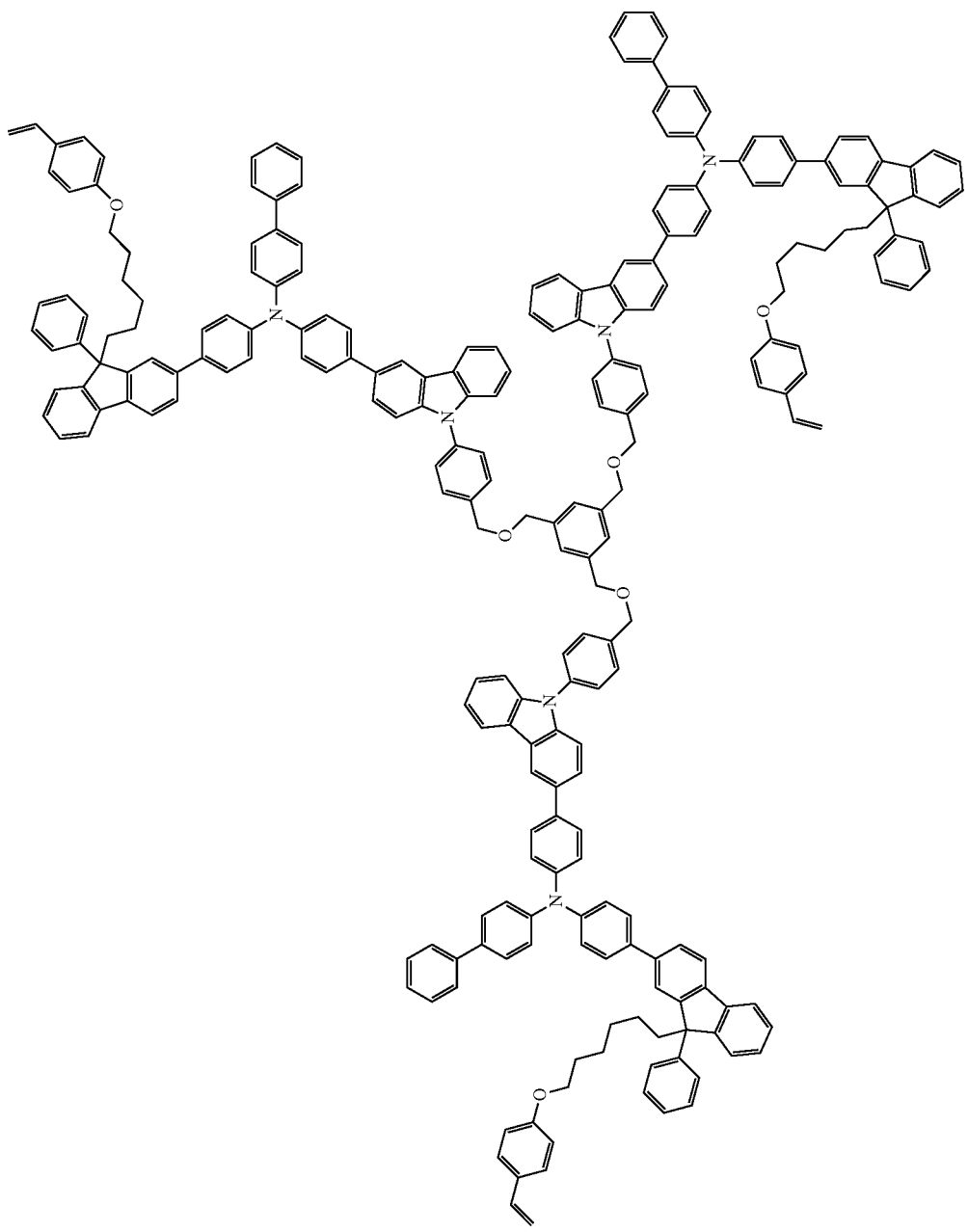

[Compound 9]
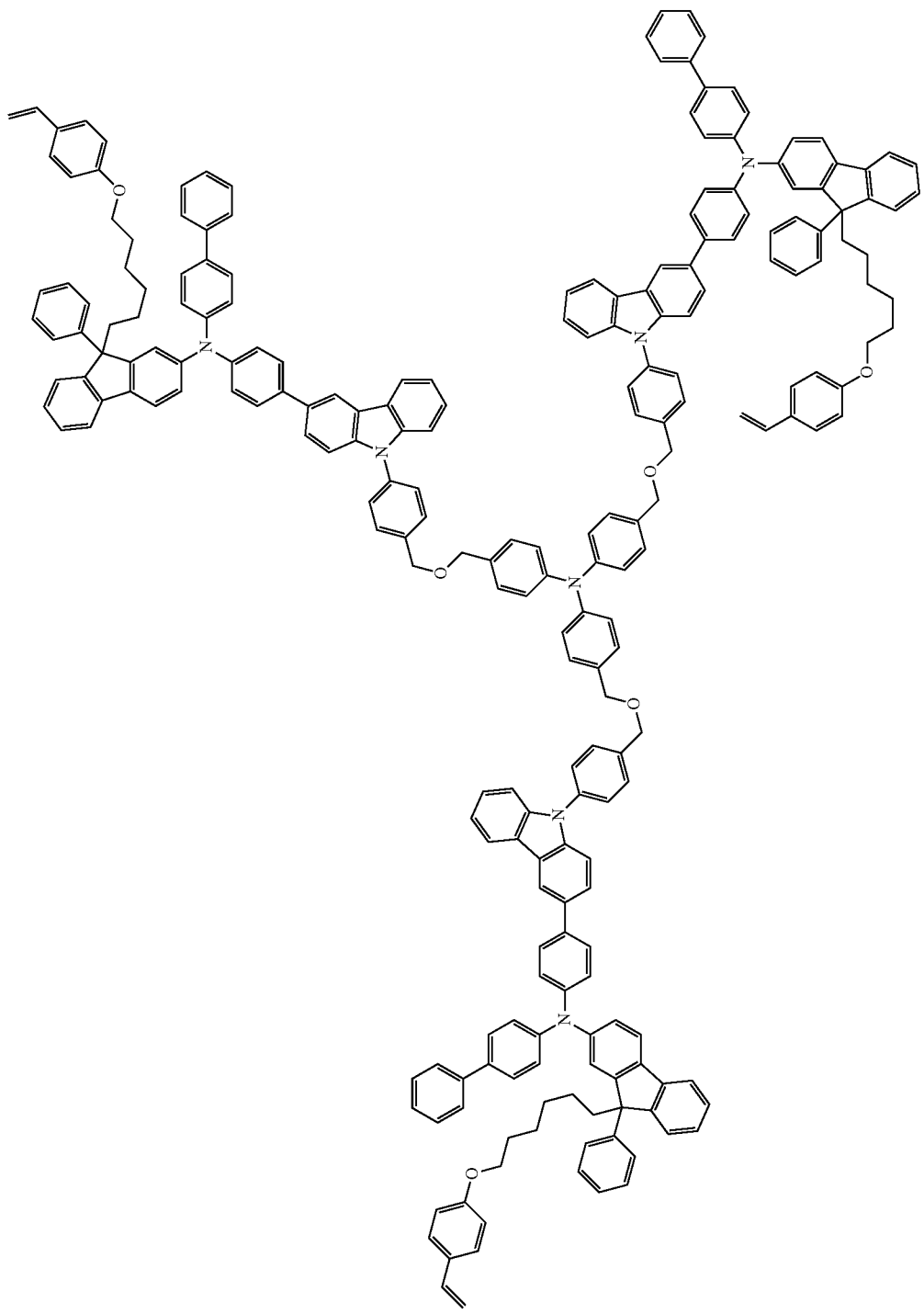

-continued
[Compound 10]
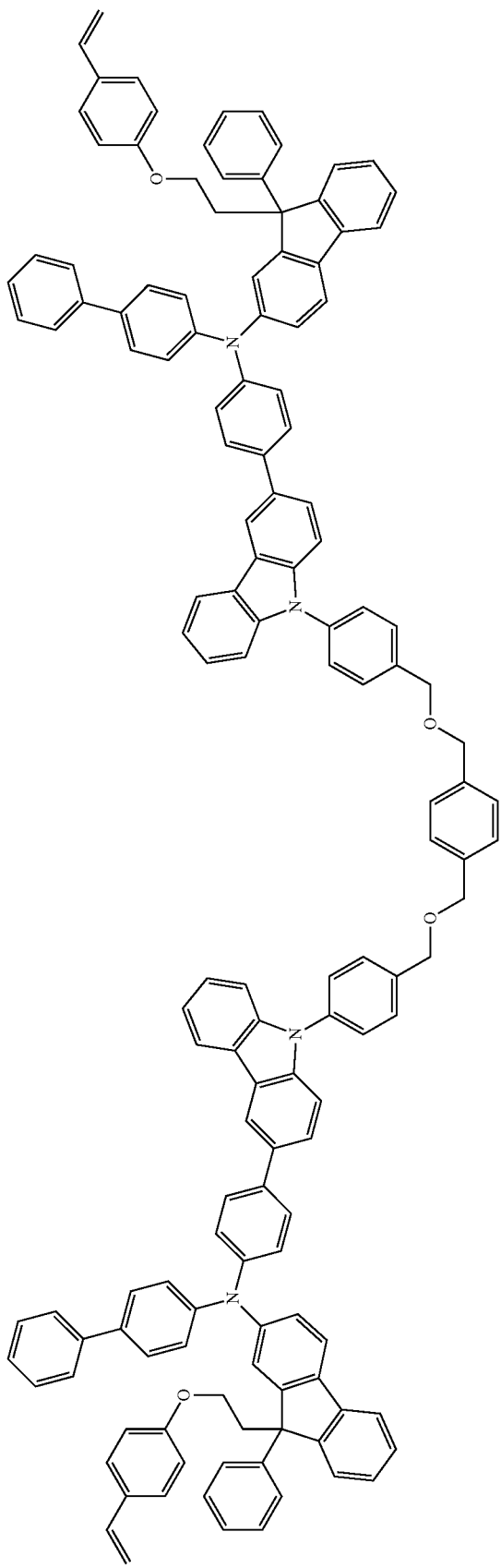
[Compound 11]
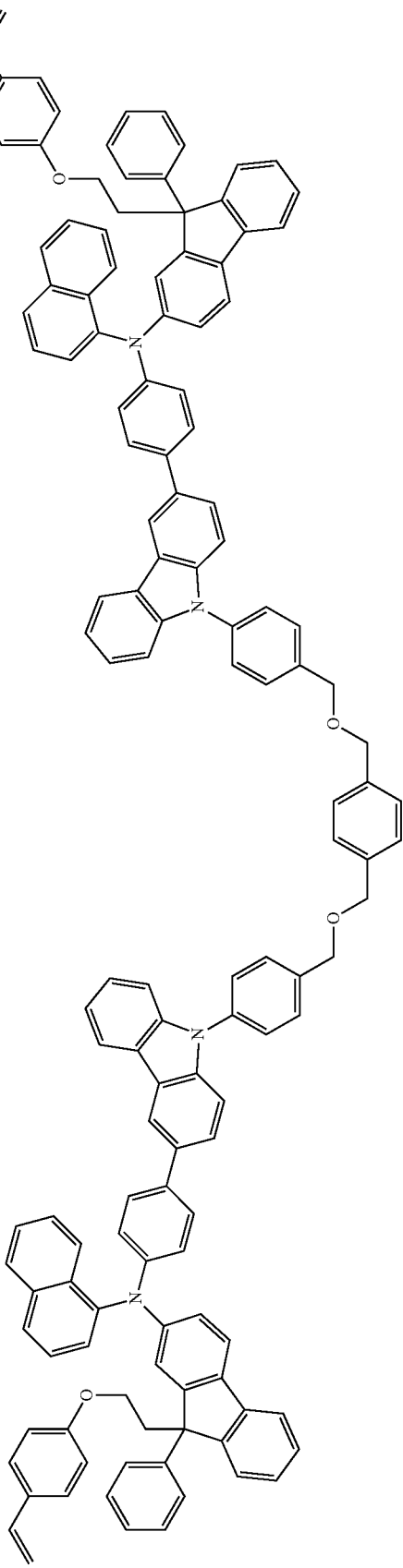

-continued
[Compound 12]
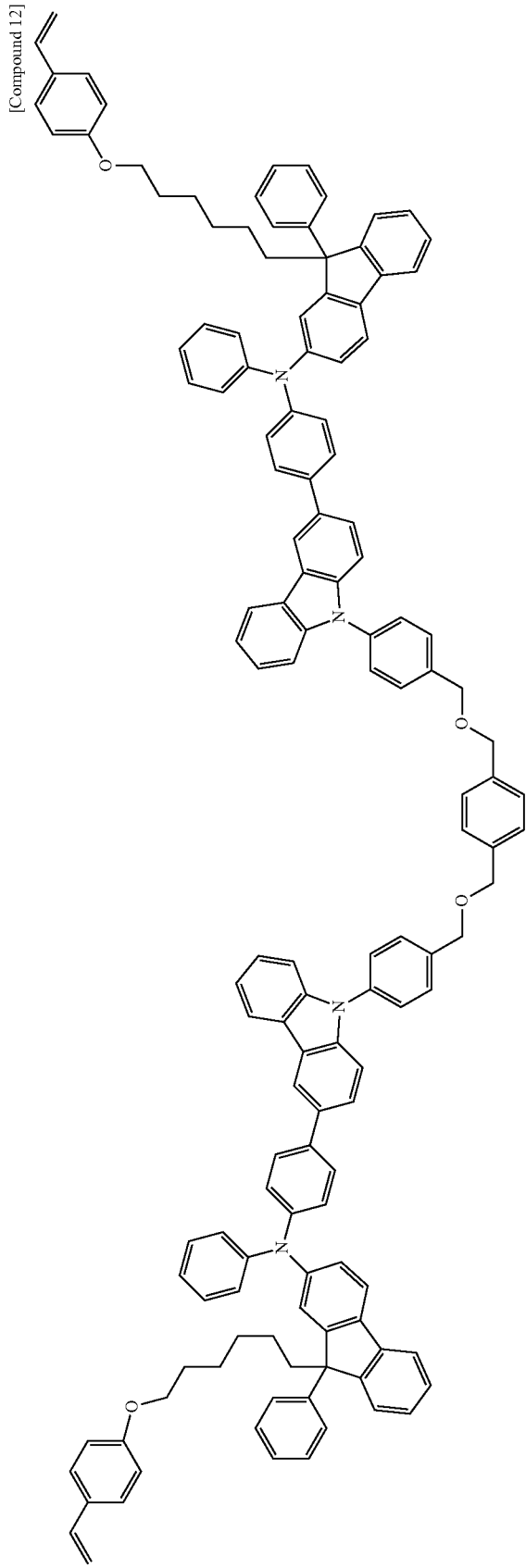
[Compound 13]
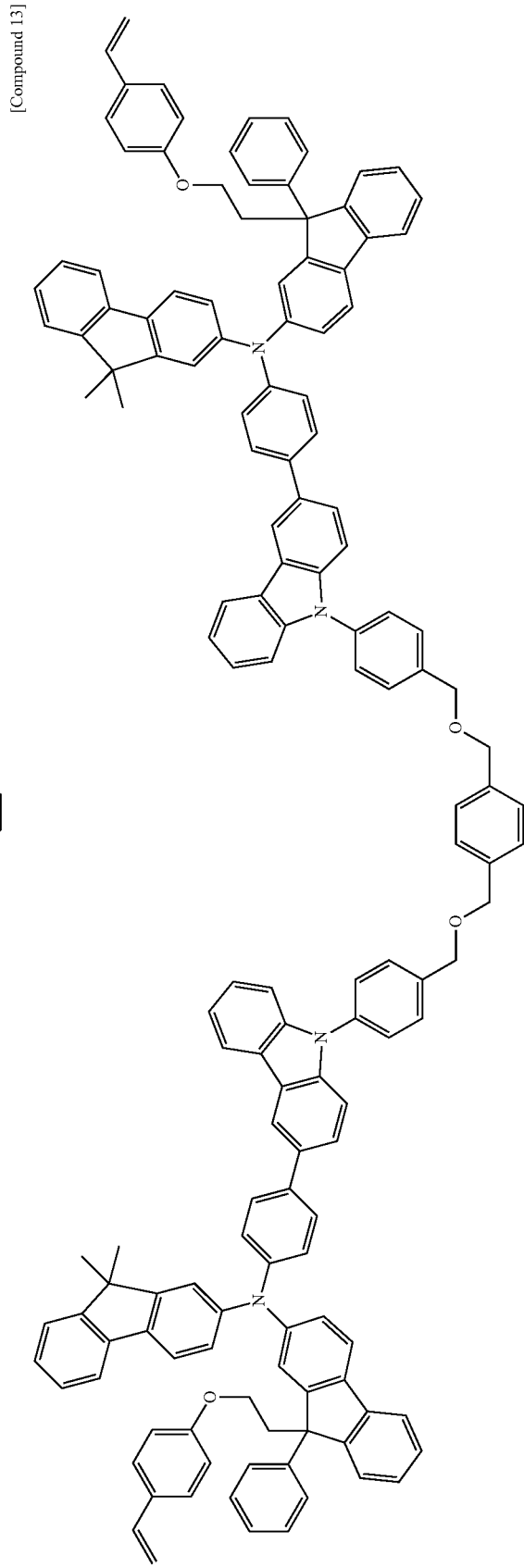

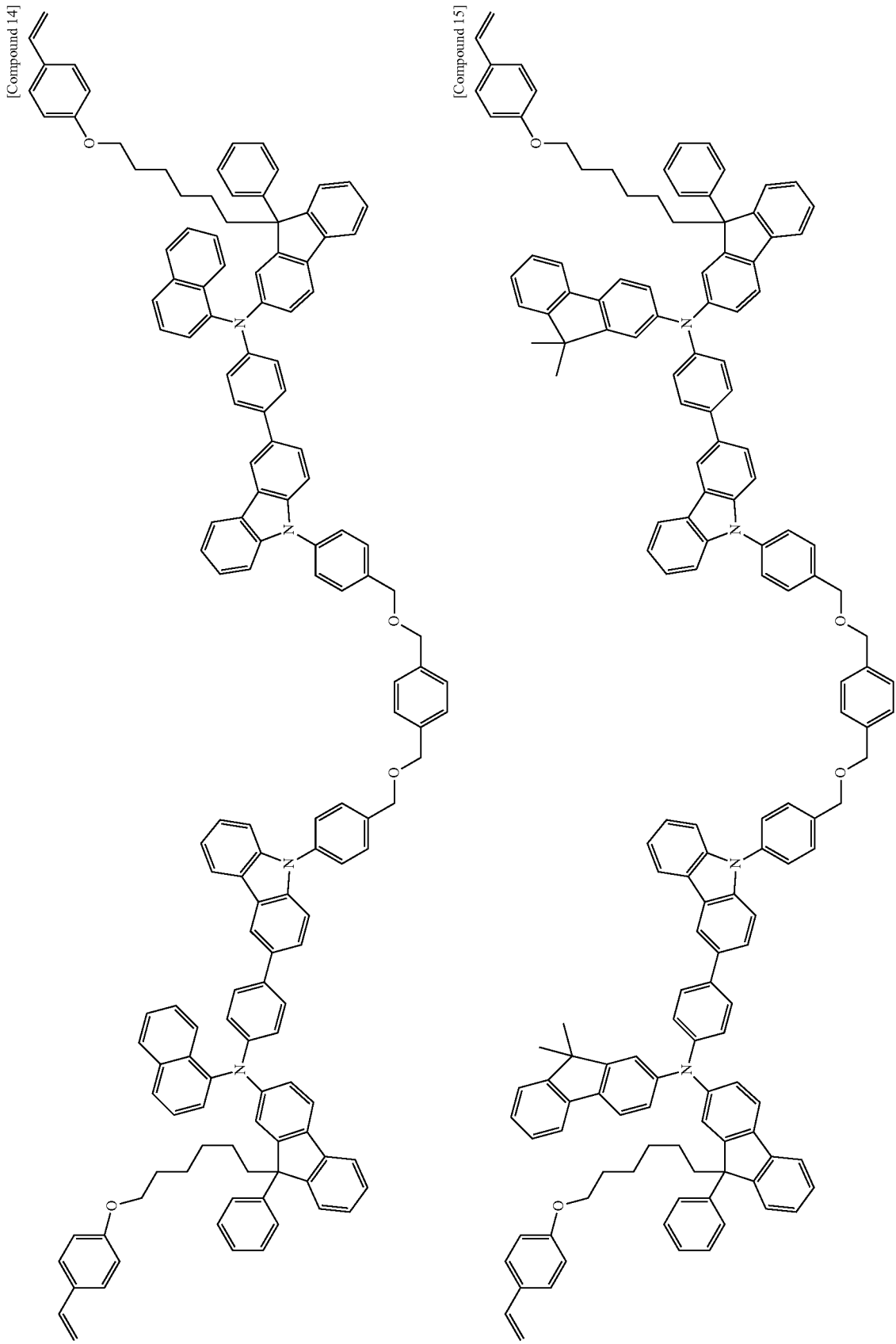

[Compound 16]
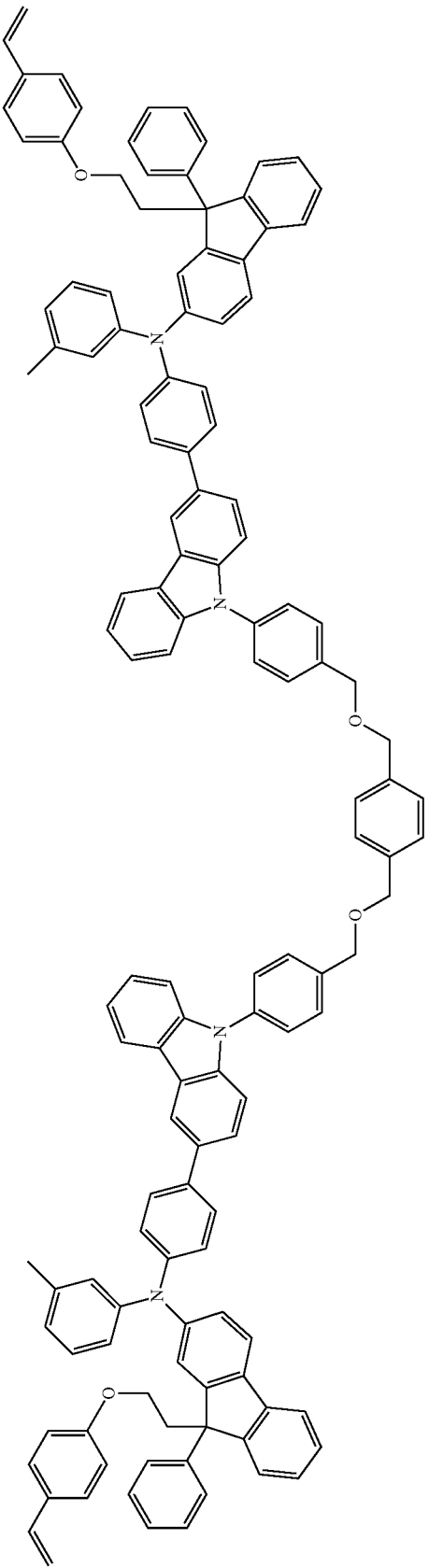
[Compound 17]
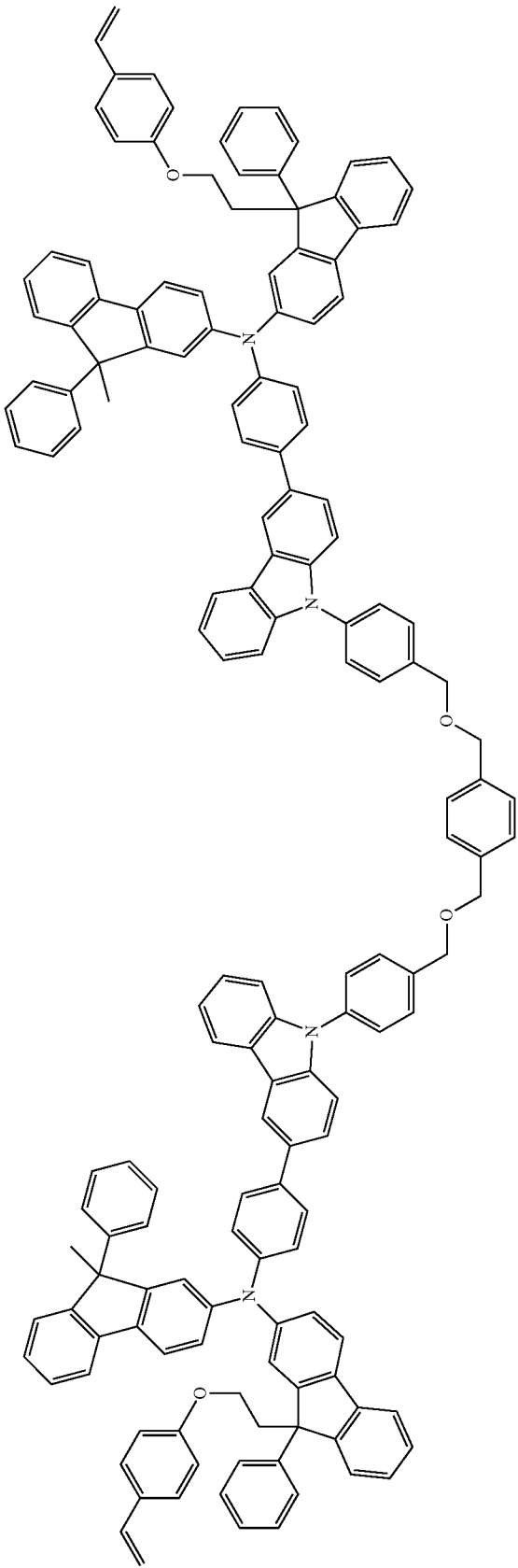

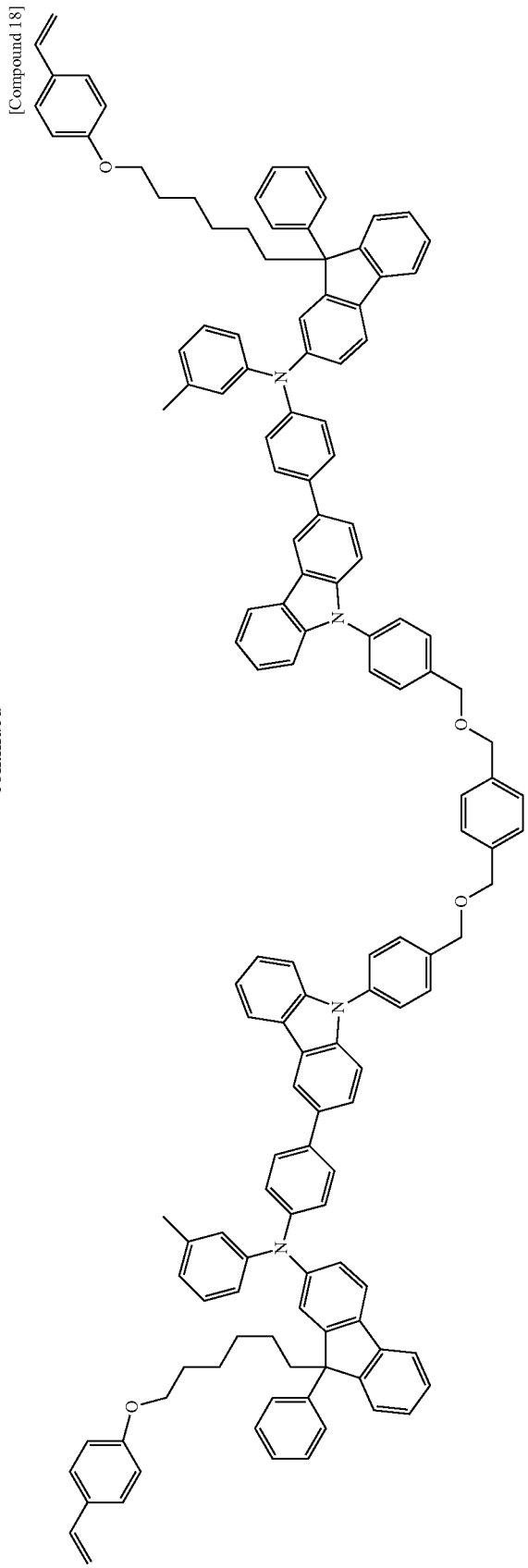

[Compound 20]
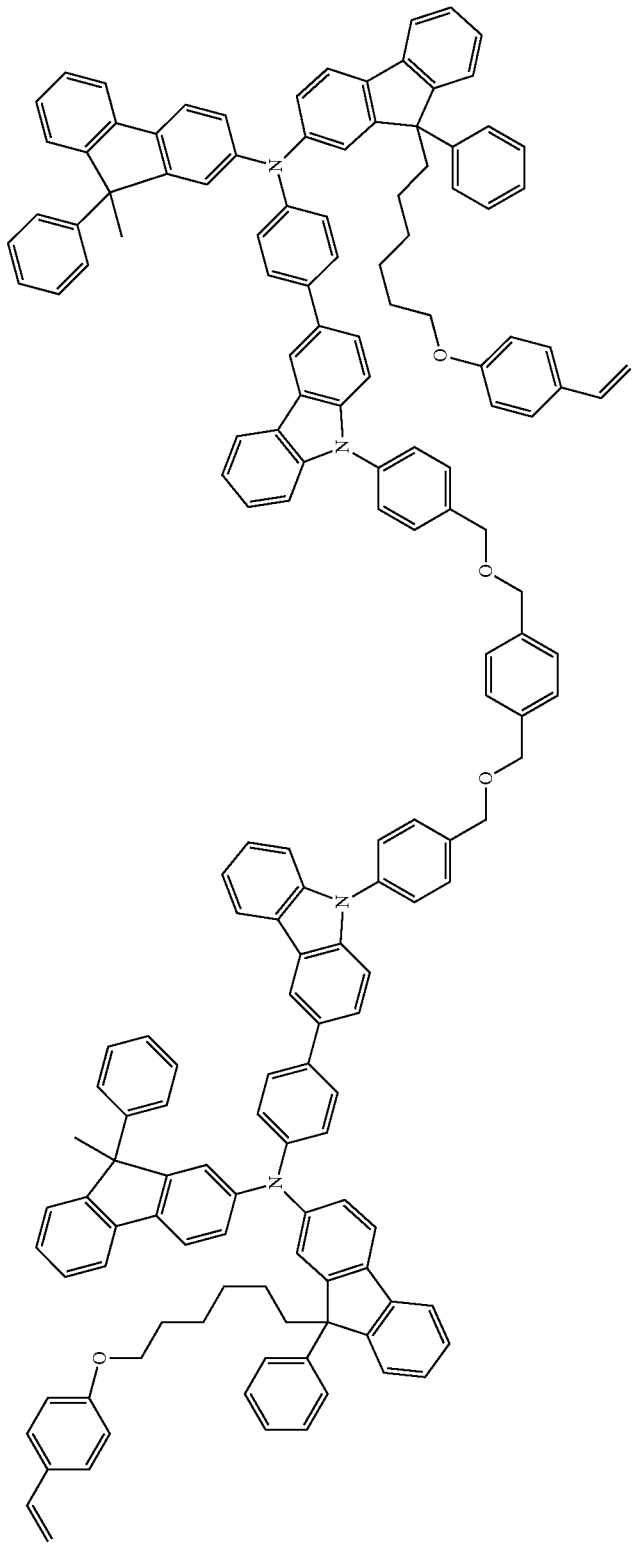
-continued

[Compound 21]
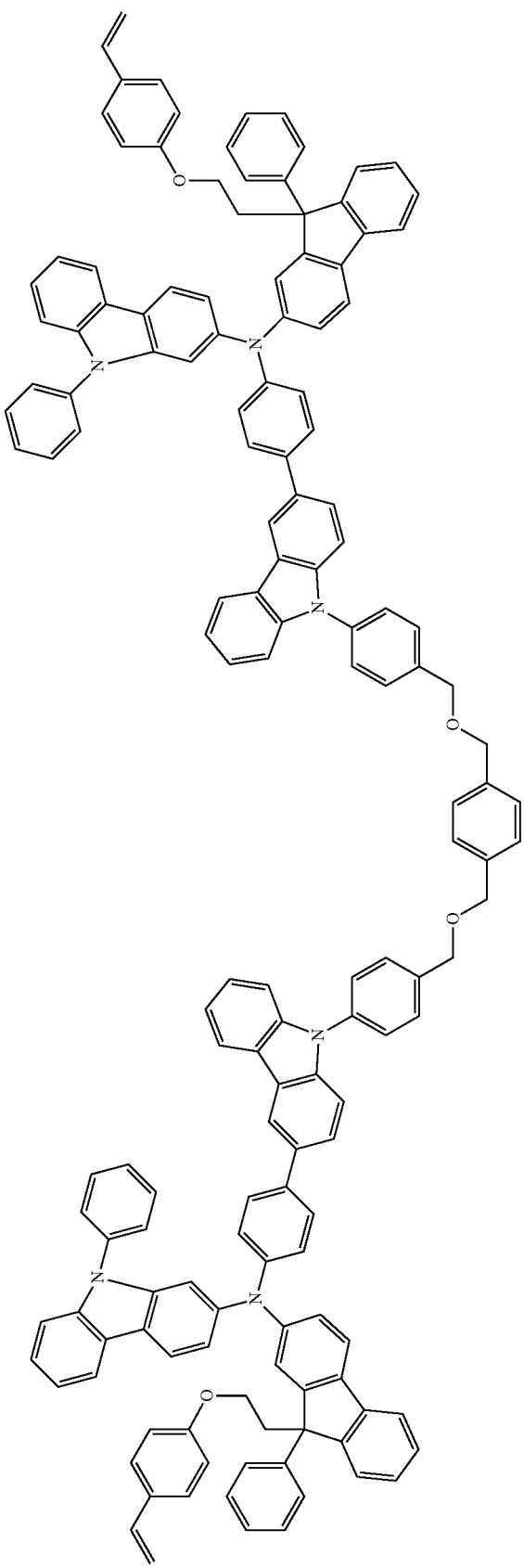

-continued
[Compound 22]
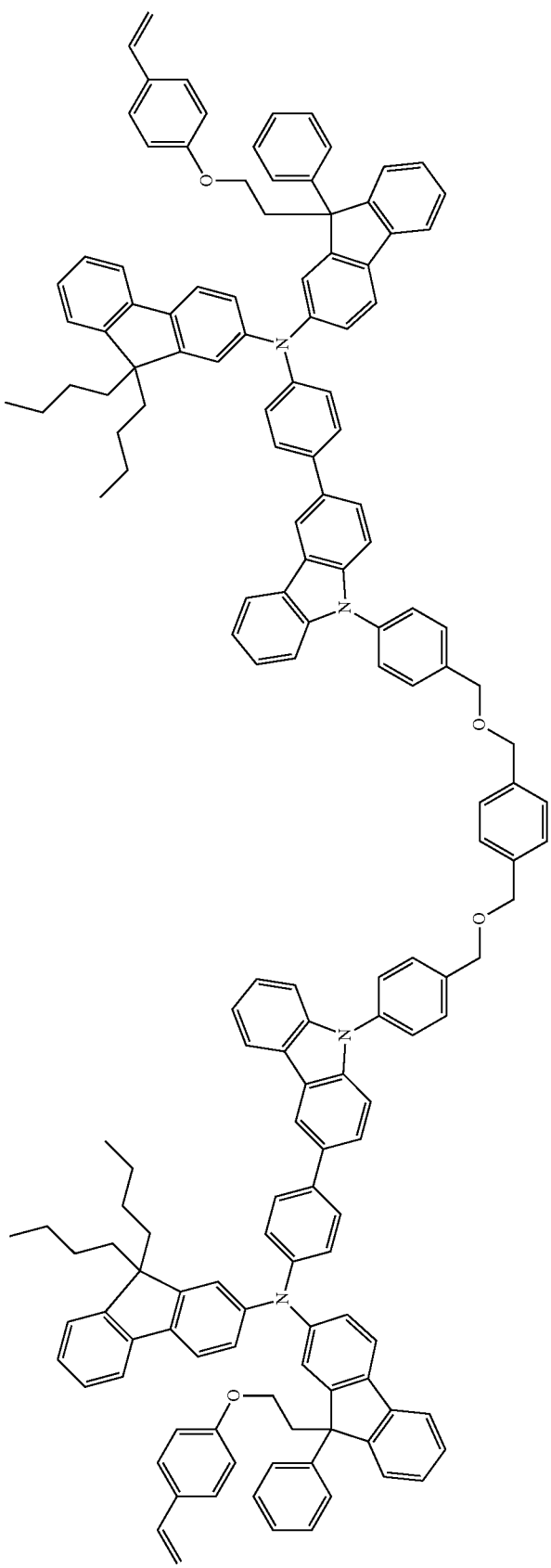

[Compound 23]
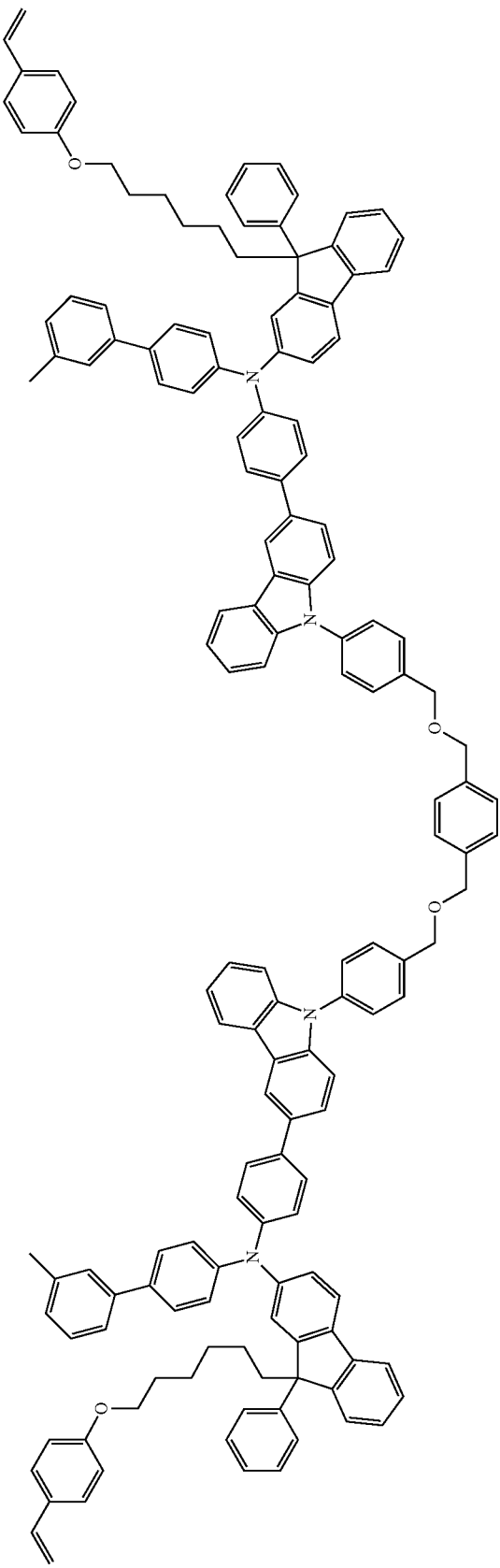

[Compound 24]
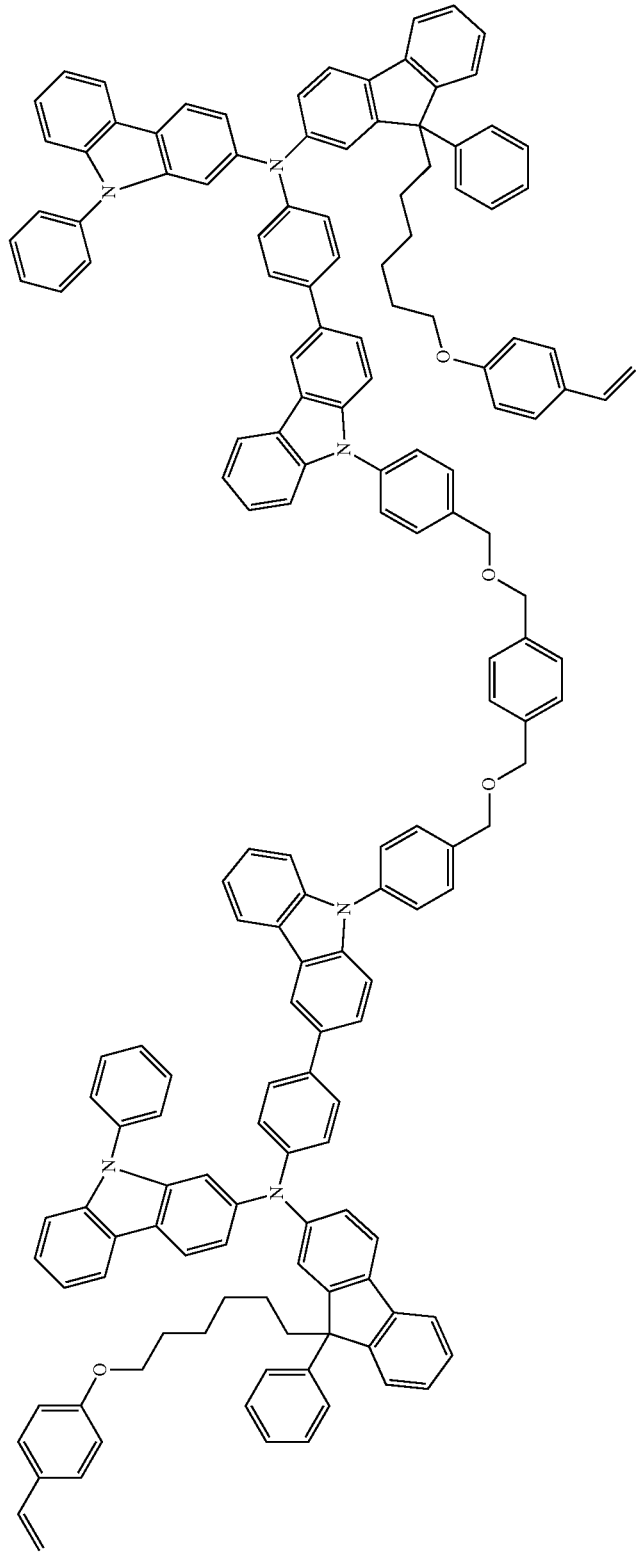

-continued
[Compound 25]
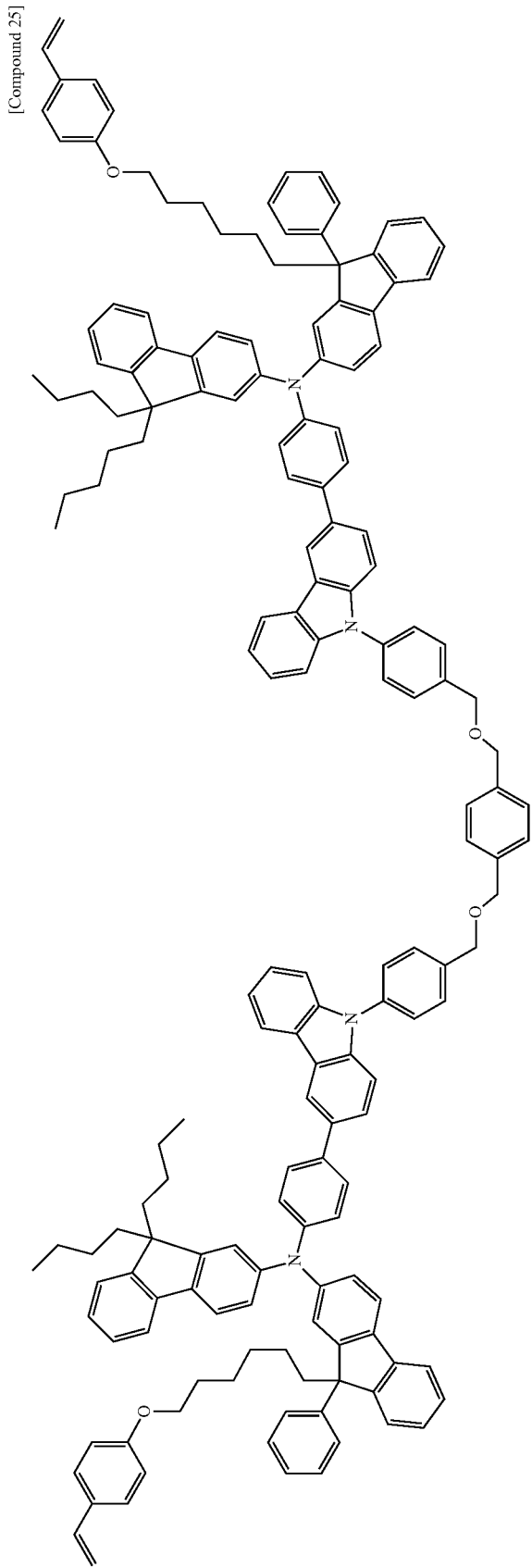
[Compound 26]
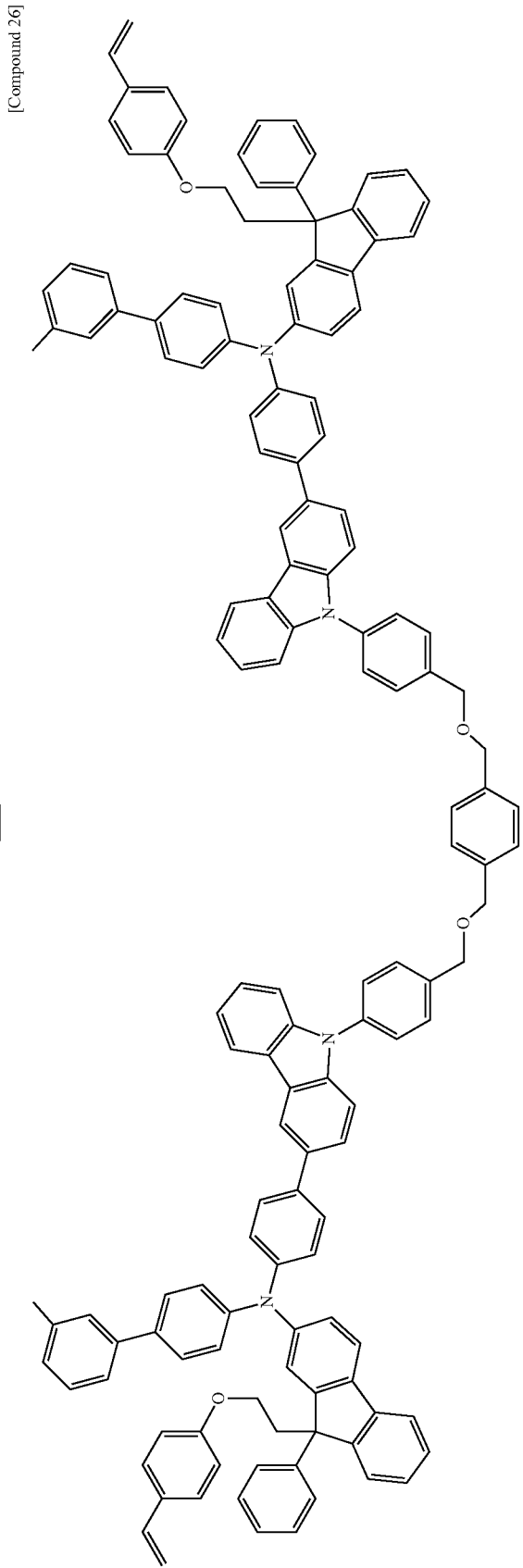

[Compound 27]
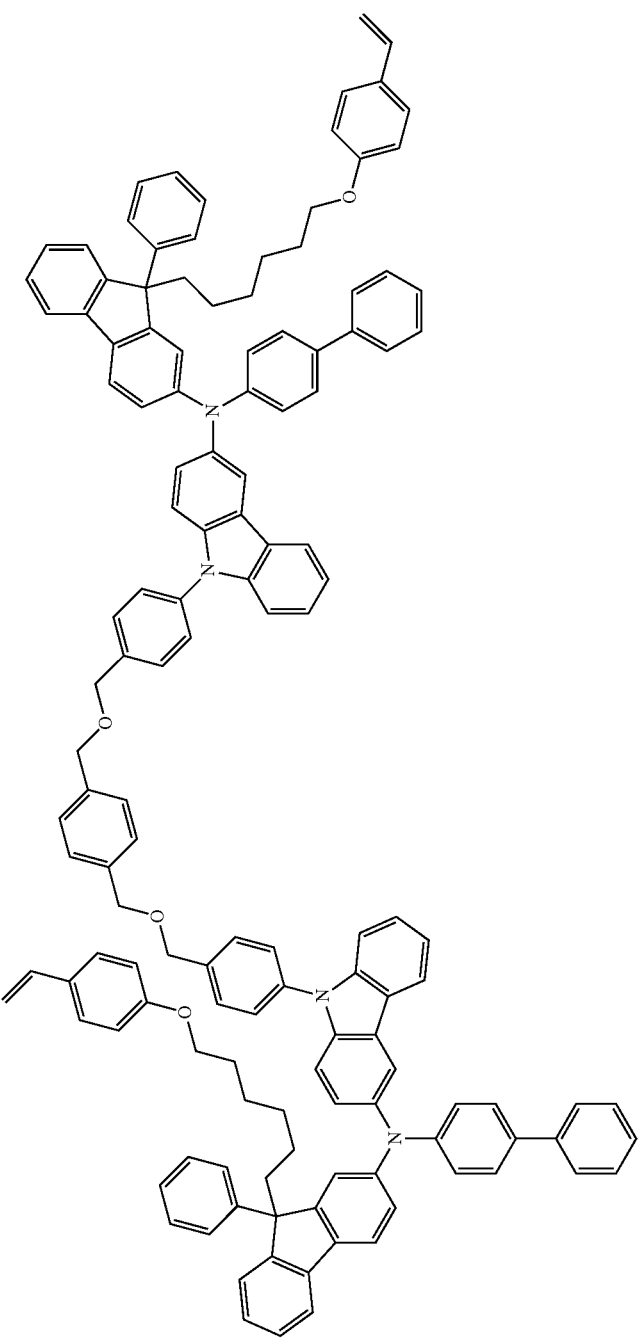

[Compound 28]
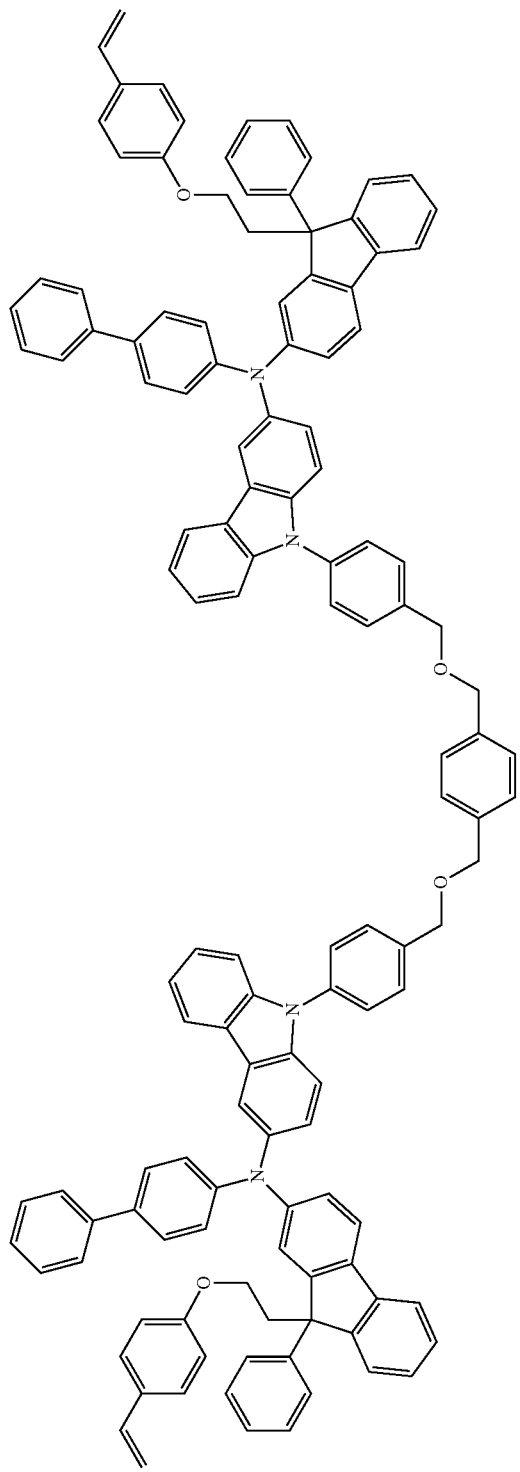
[Compound 29]
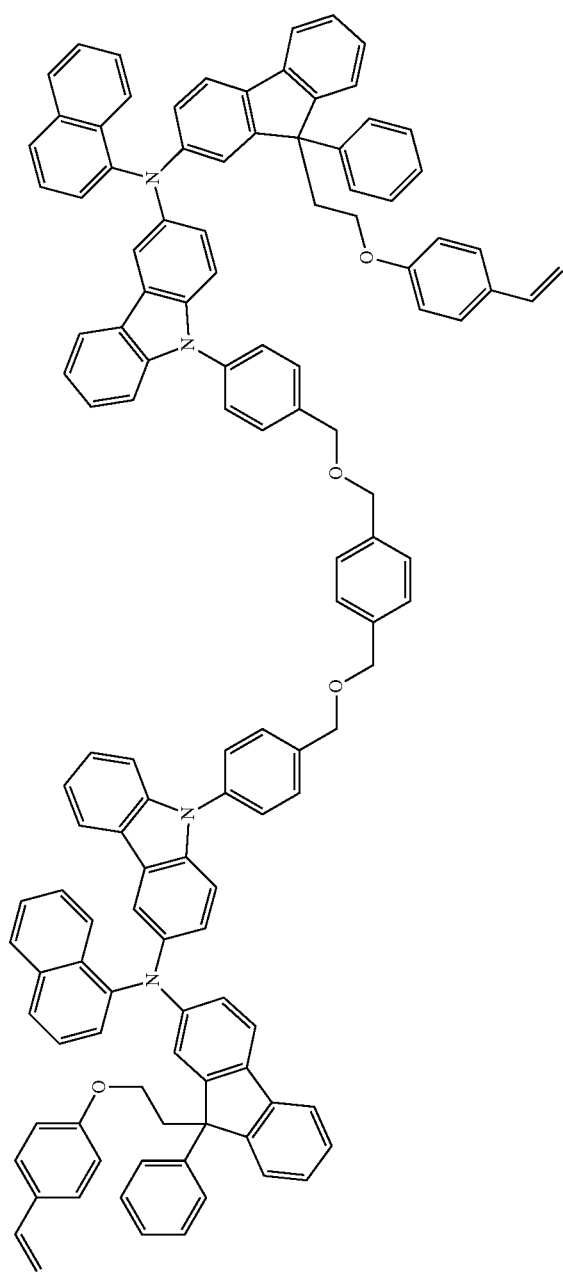

[Compound 30]
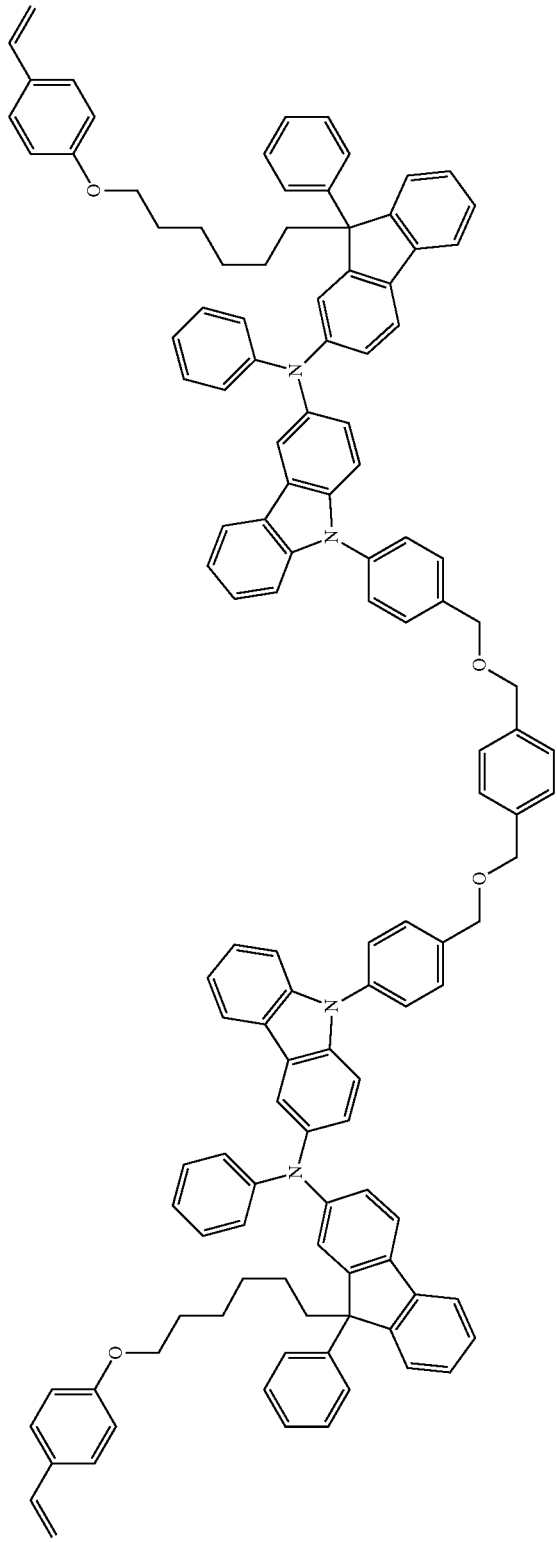
[Compound 31]
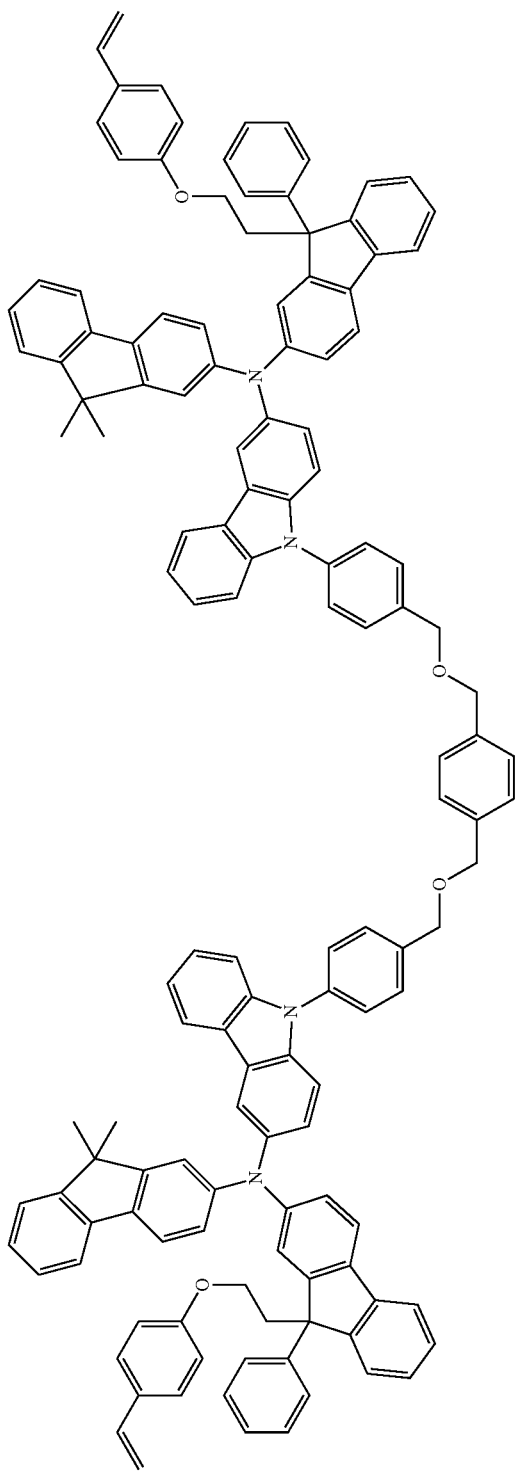

[Compound 32]
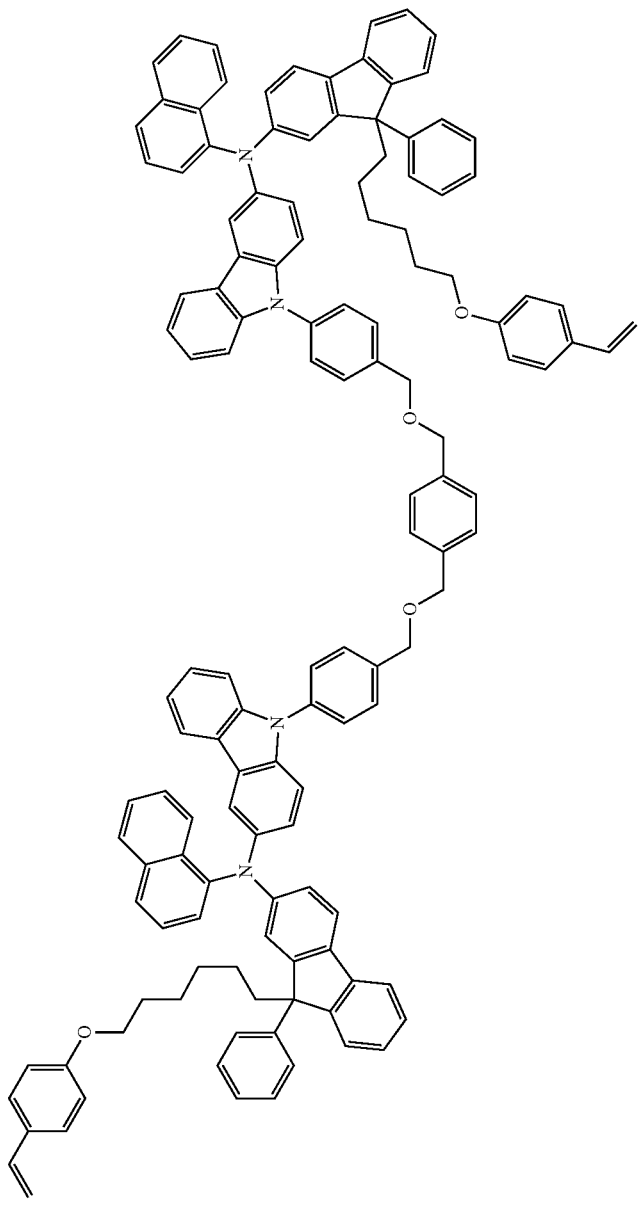

[Compound 33]
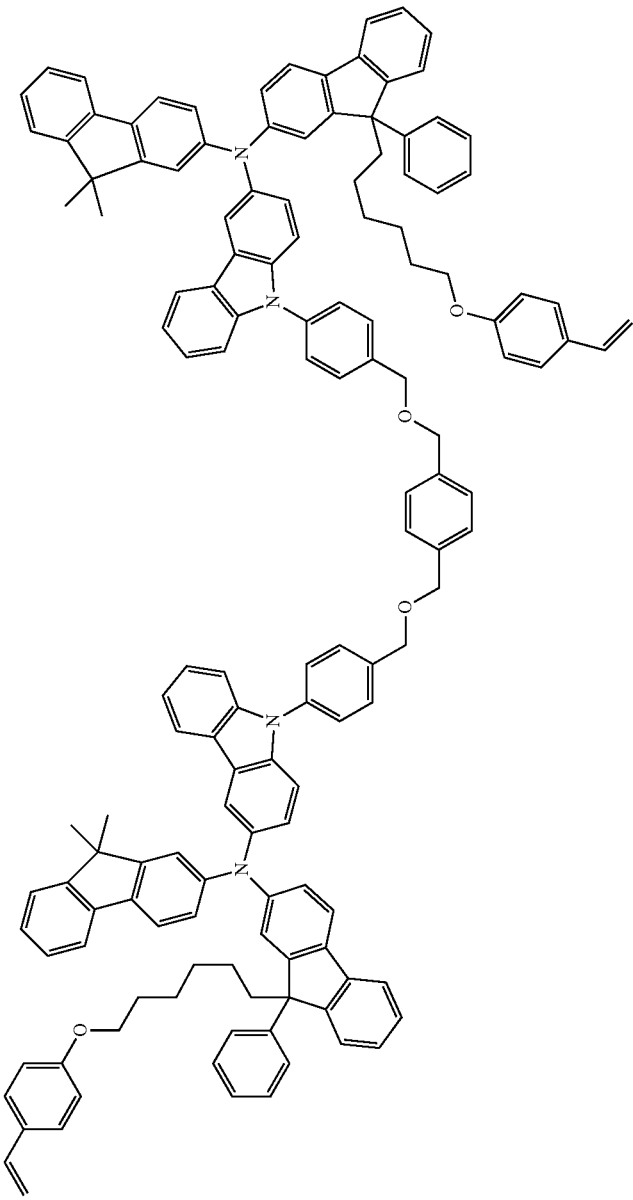
[Compound 34]
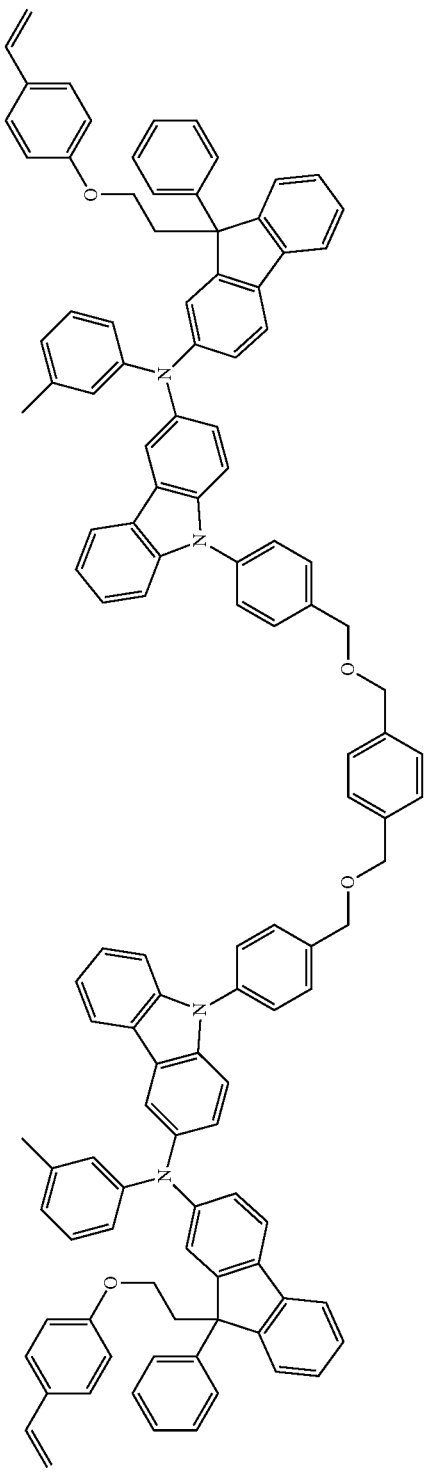

[Compound 35]
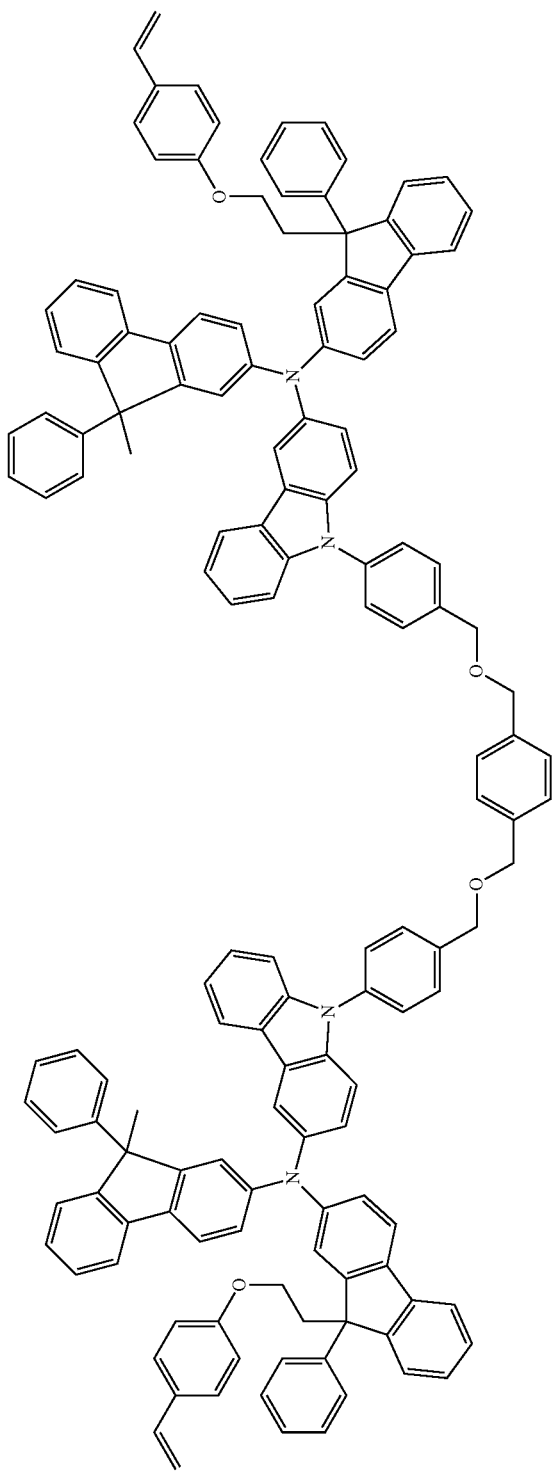
[Compound 36]
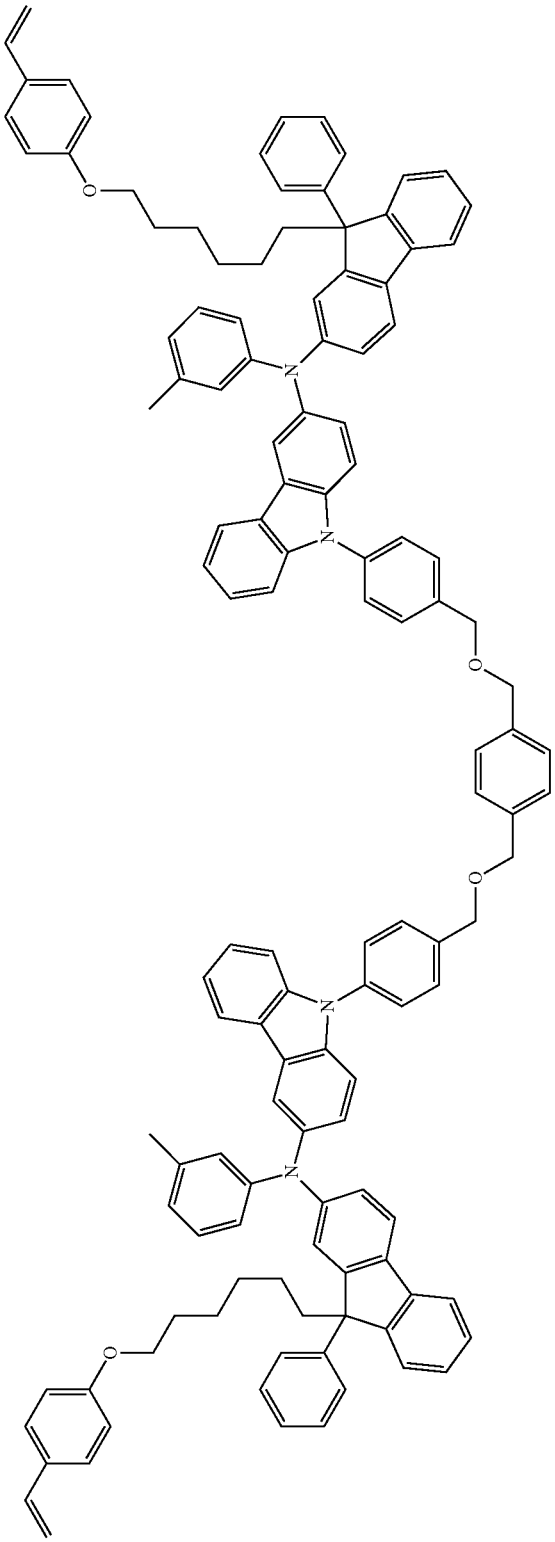

-continued
[Compound 37]
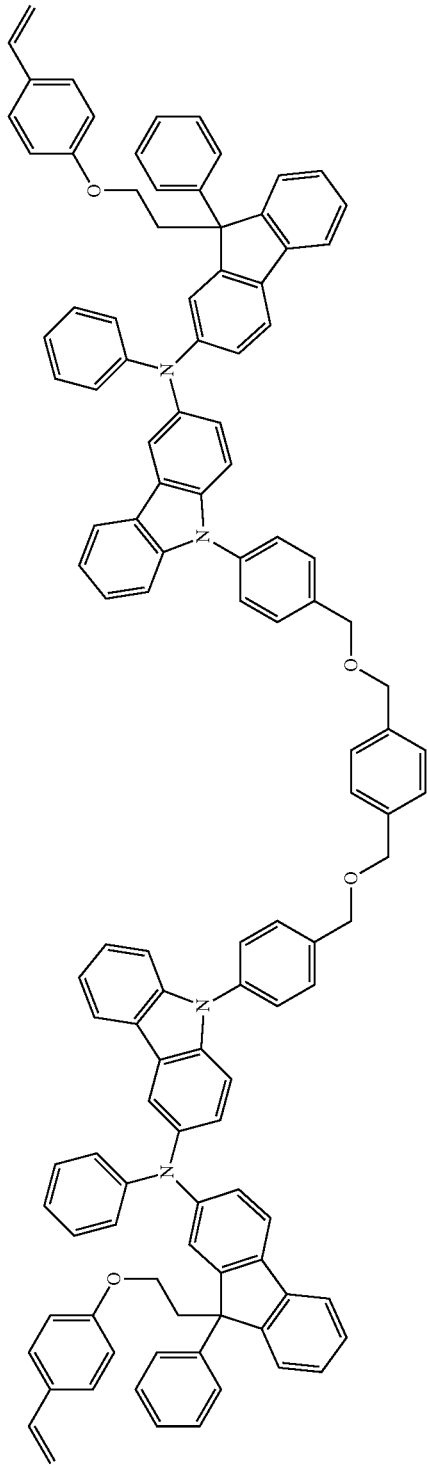
[Compound 38]
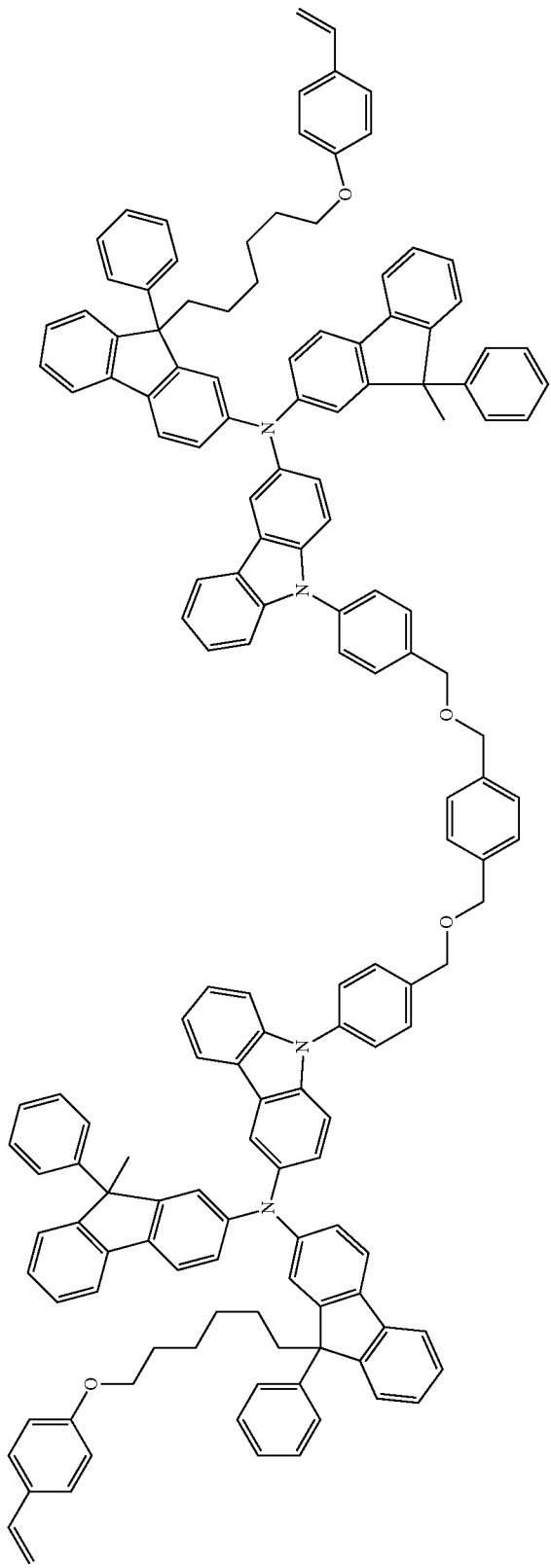

[Compound 39]
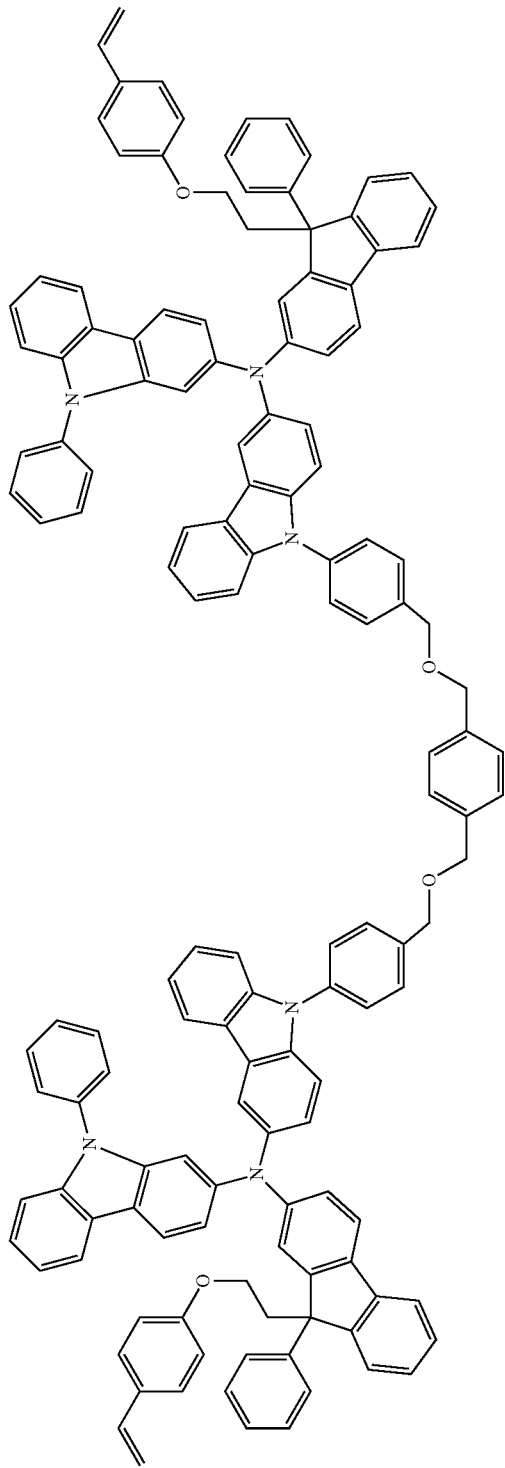
-continued
[Compound 40]
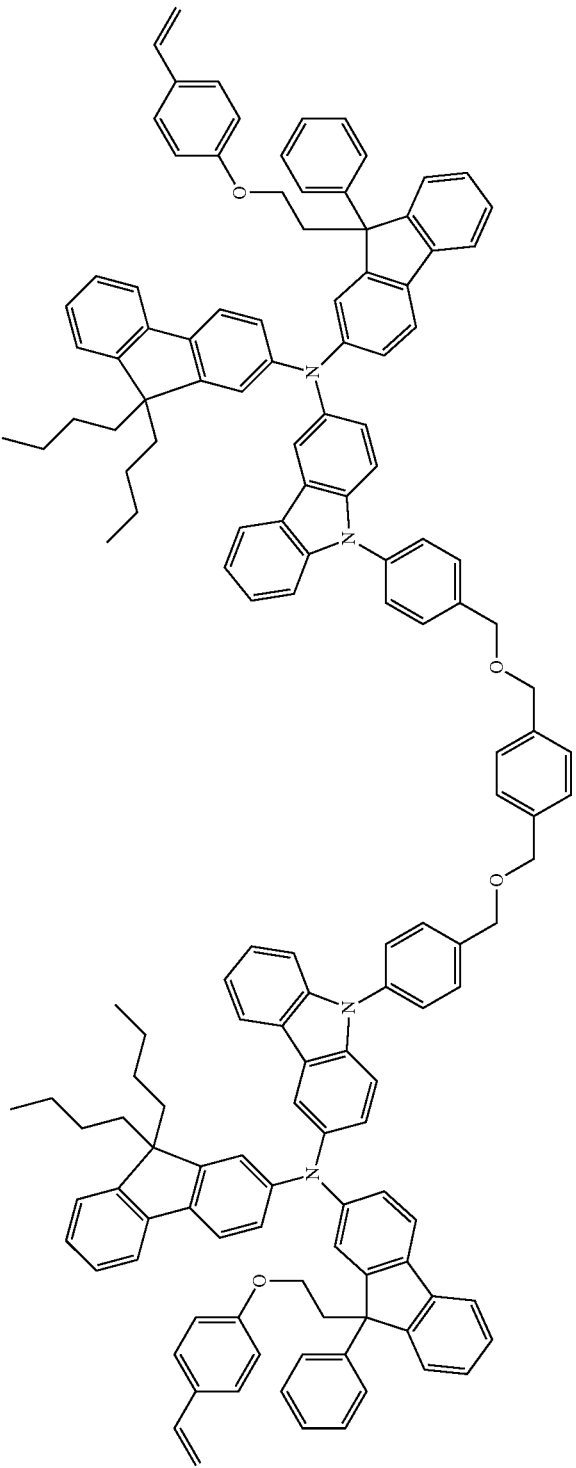

-continued
[Compound 41]
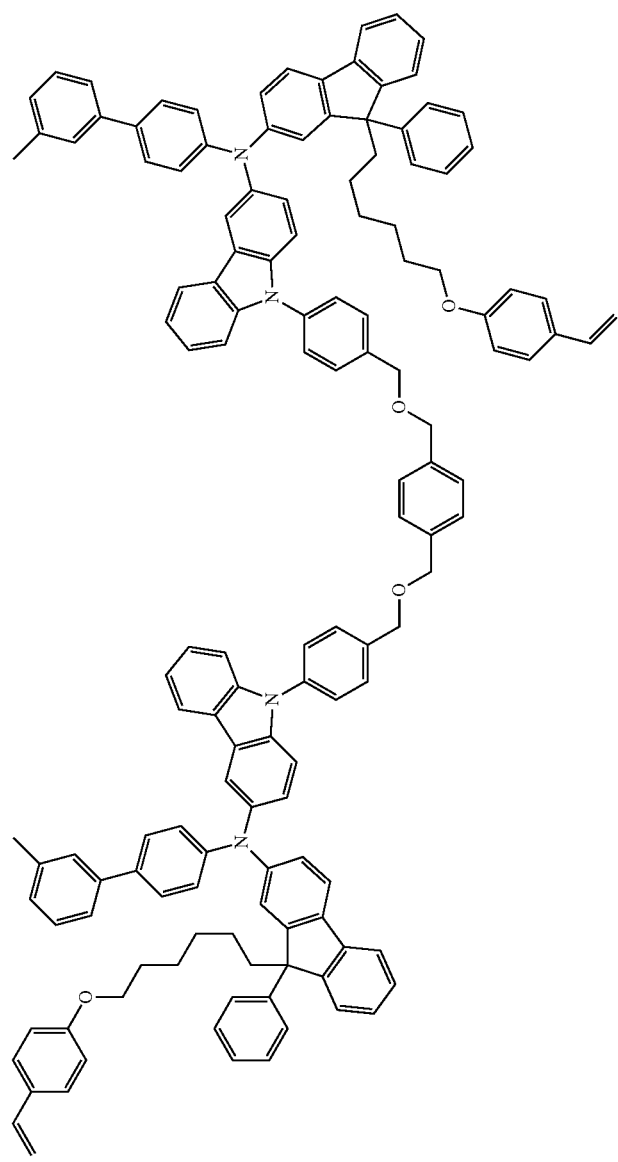

[Compound 42]
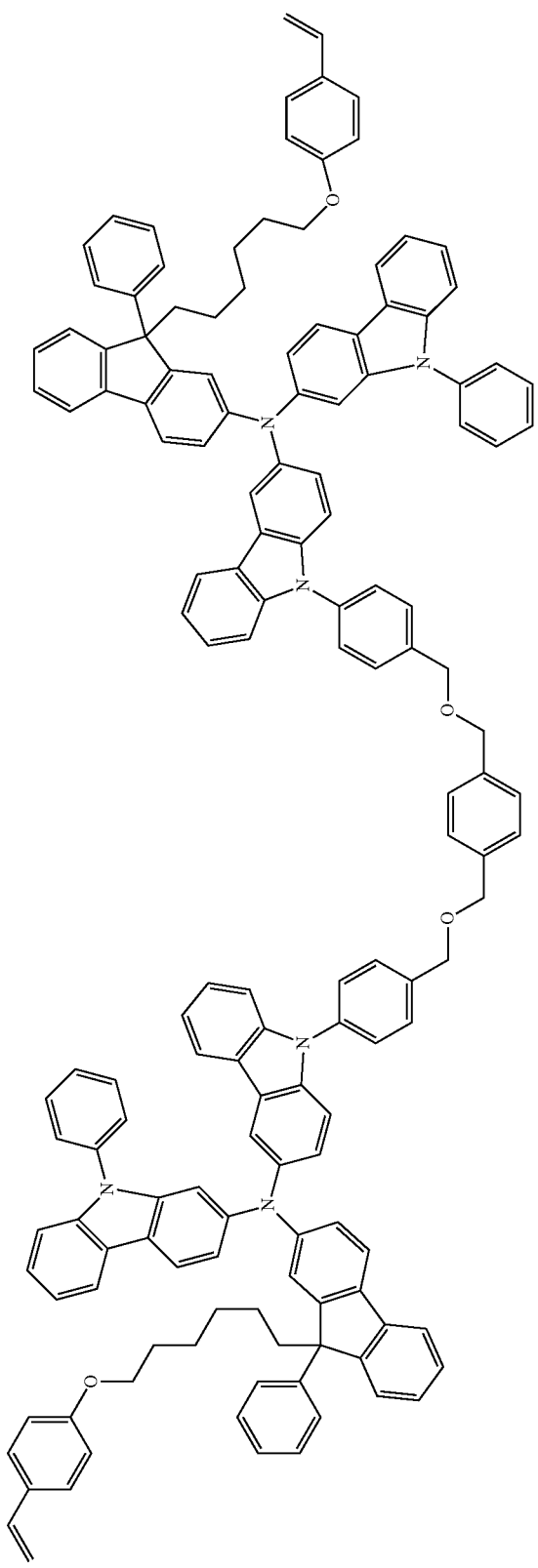

[Compound 43]
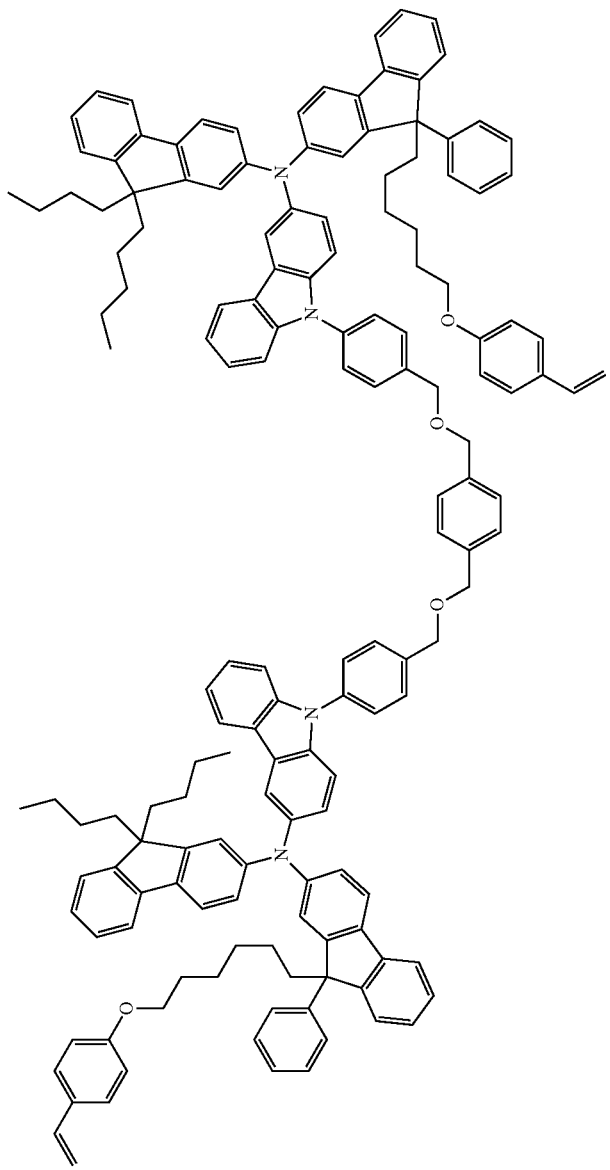

[Compound 44]
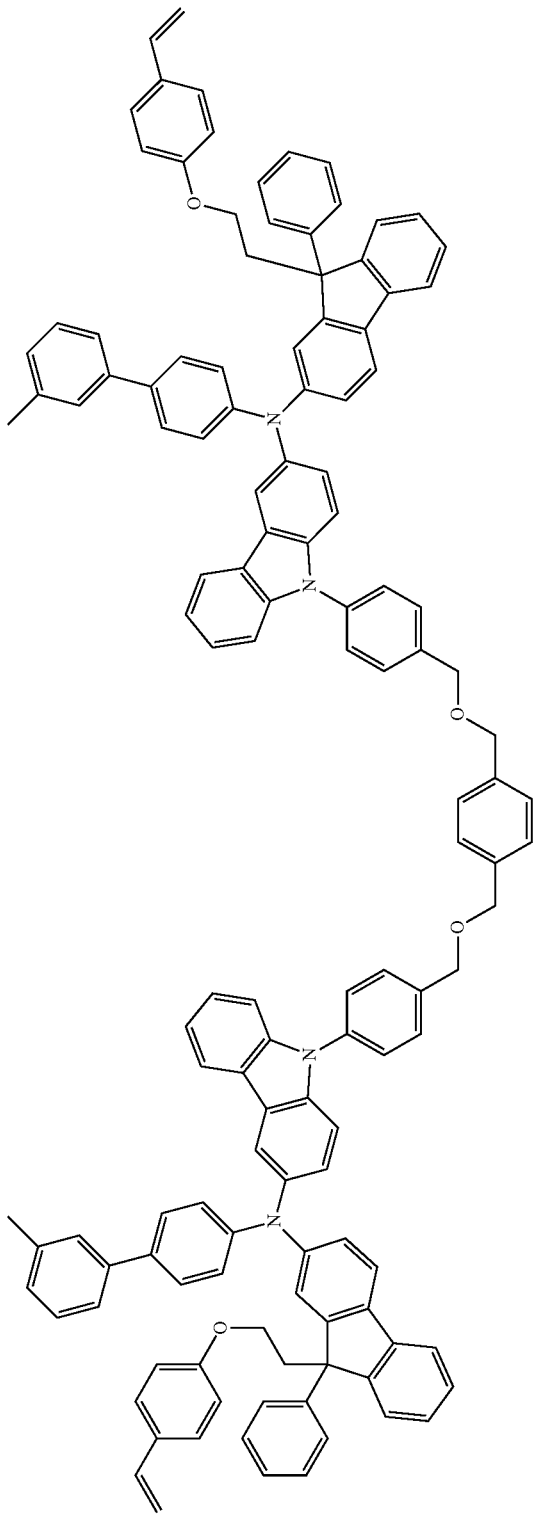
[Compound 45]
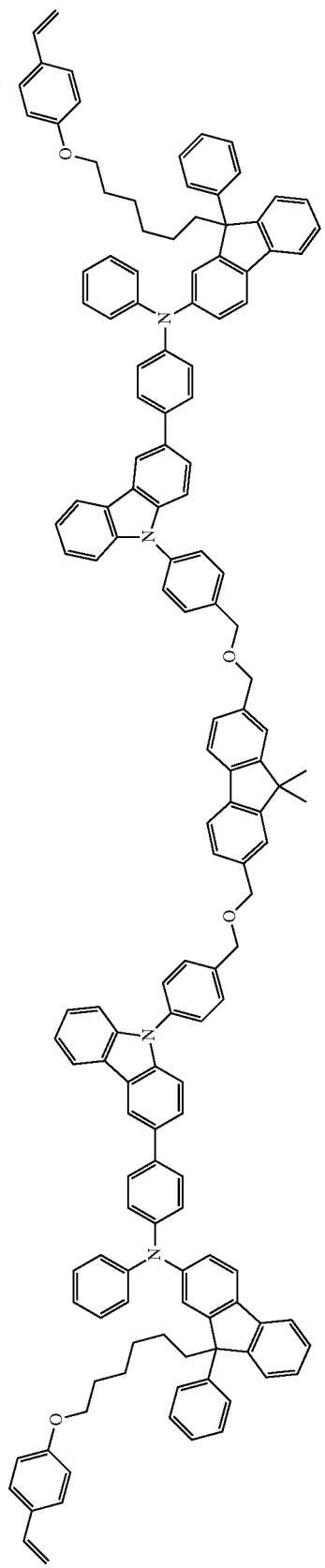

[Compound 46]
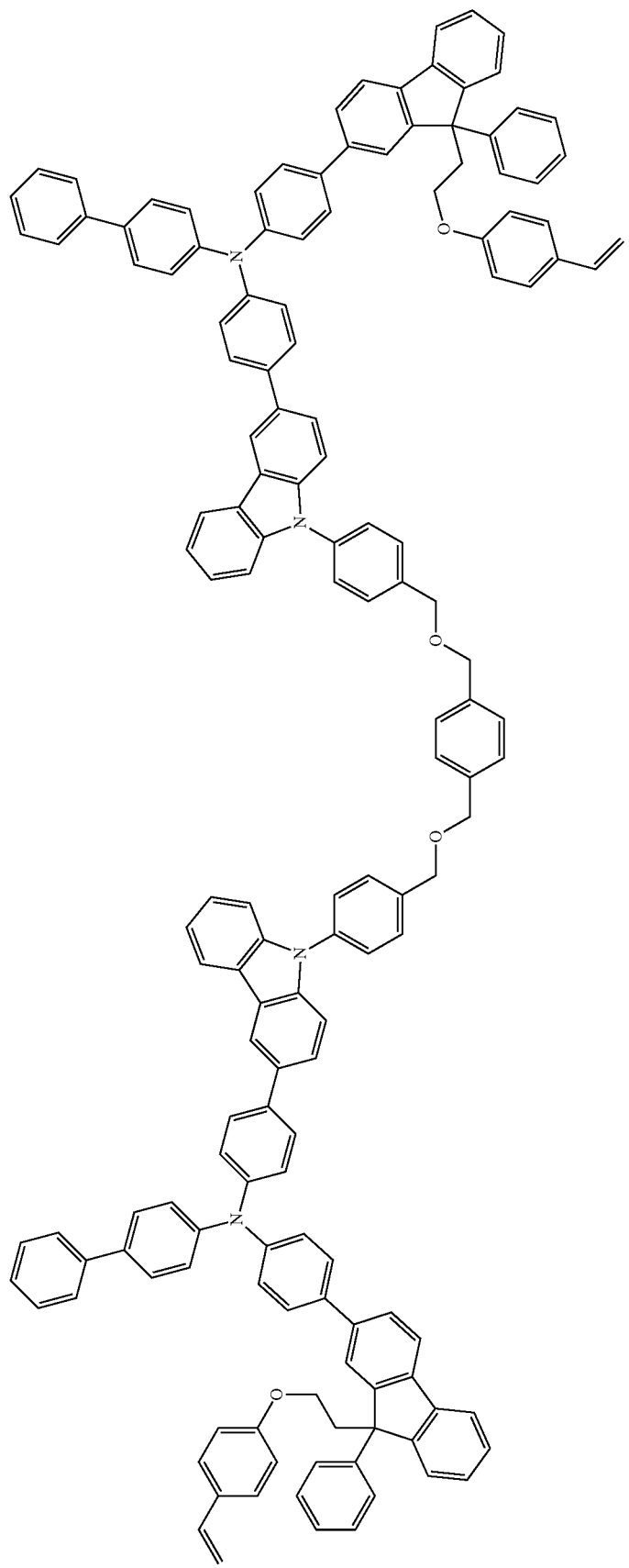

[Compound 47]
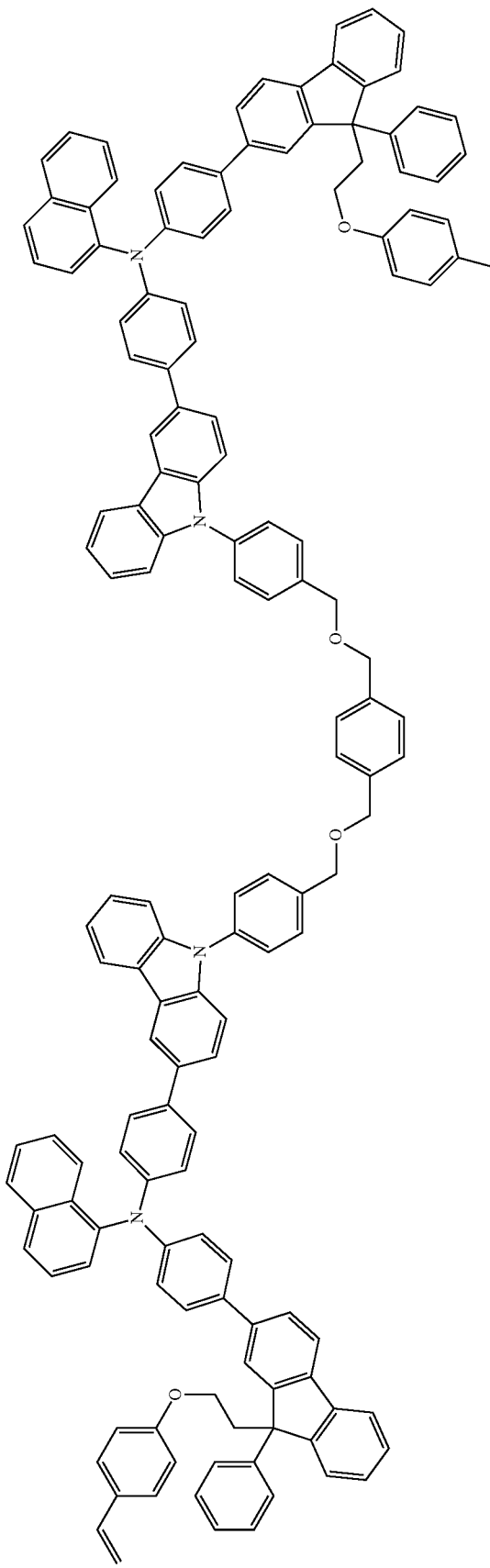
[Compound 48]
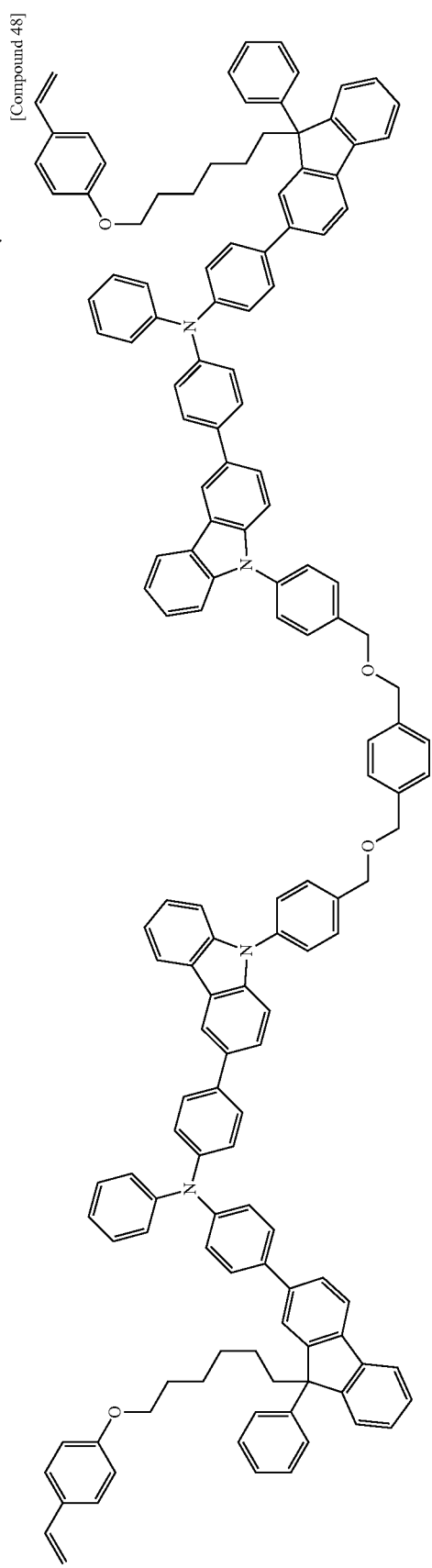

-continued
[Compound 49]
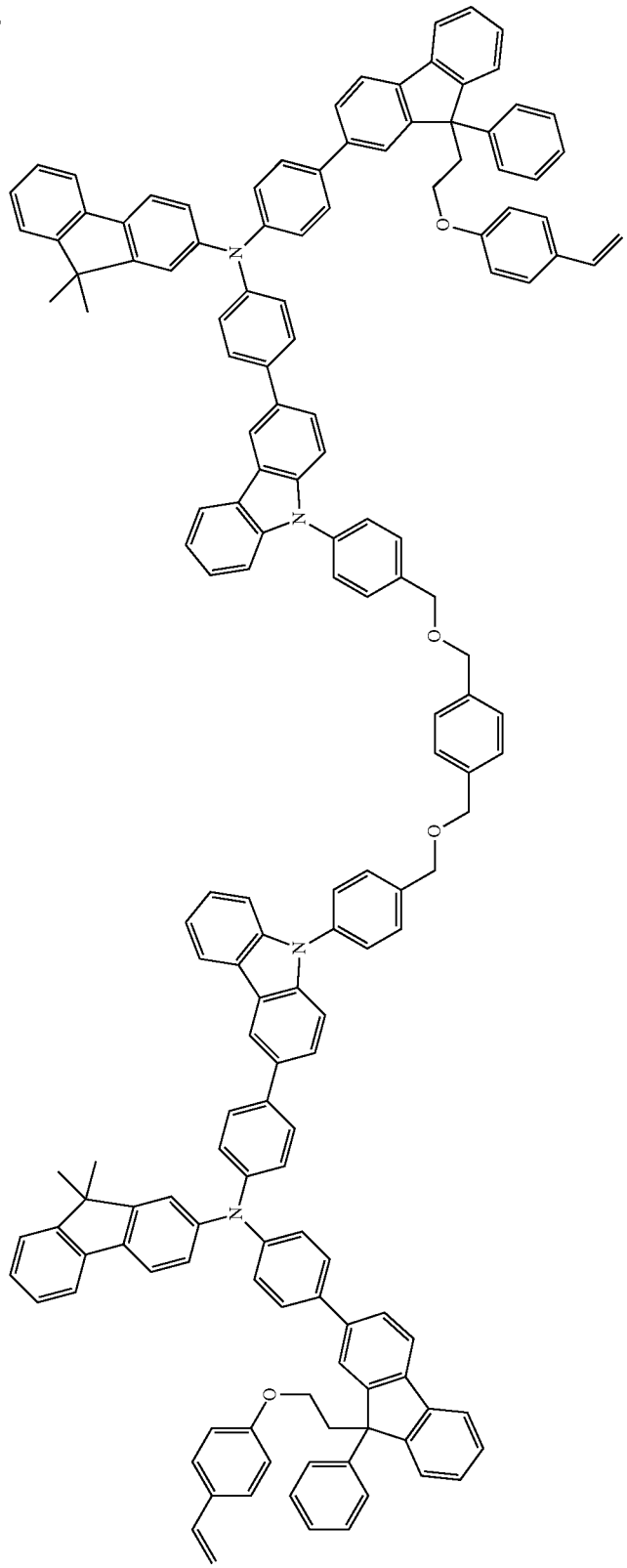
[Compound 50]
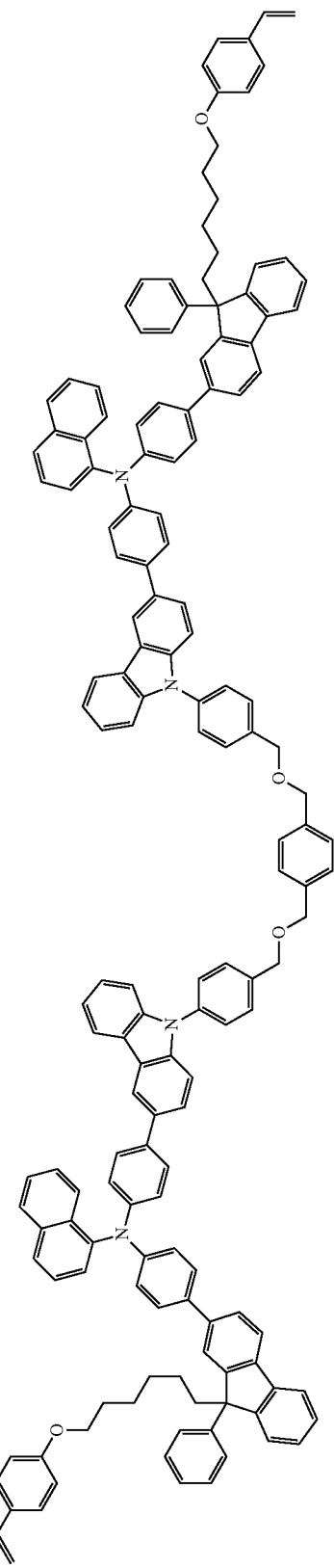

[Compound 51]
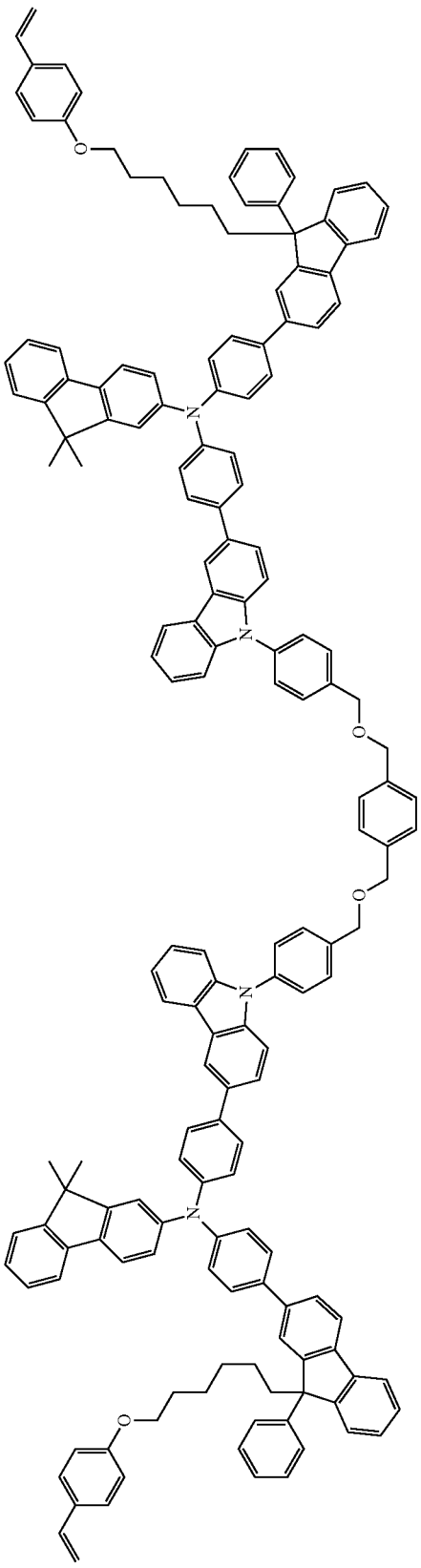
[Compound 52]
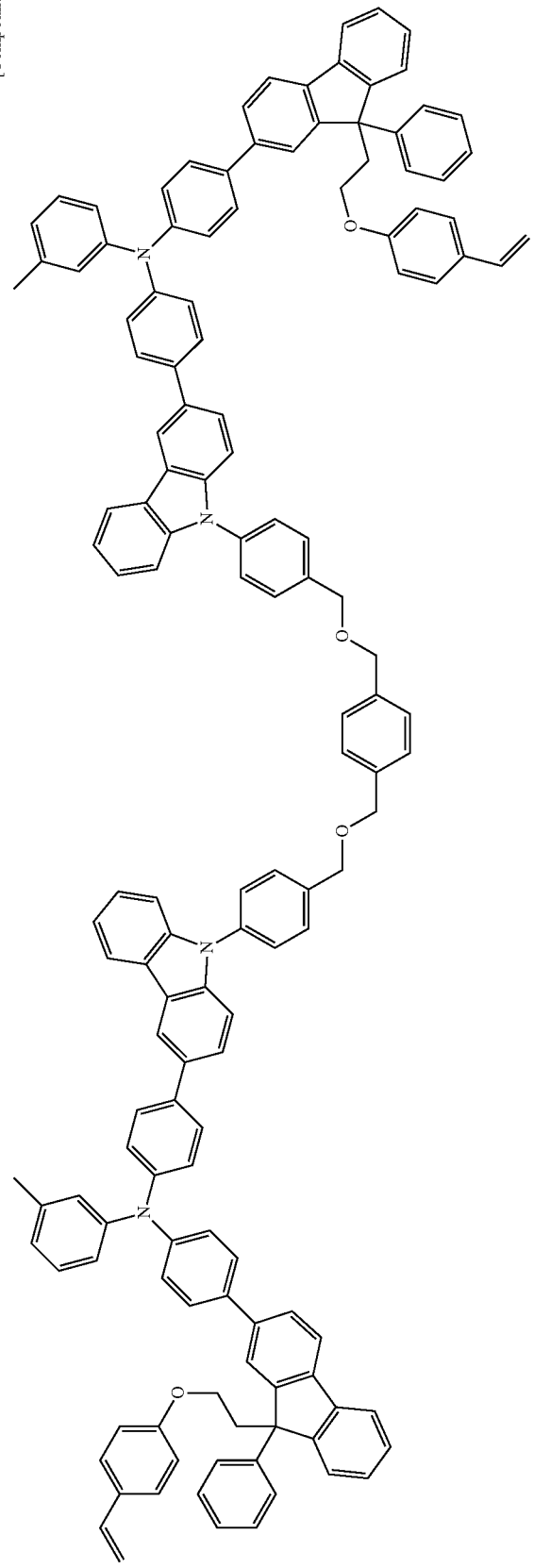

93                                                94
-continued
[Compound 53]
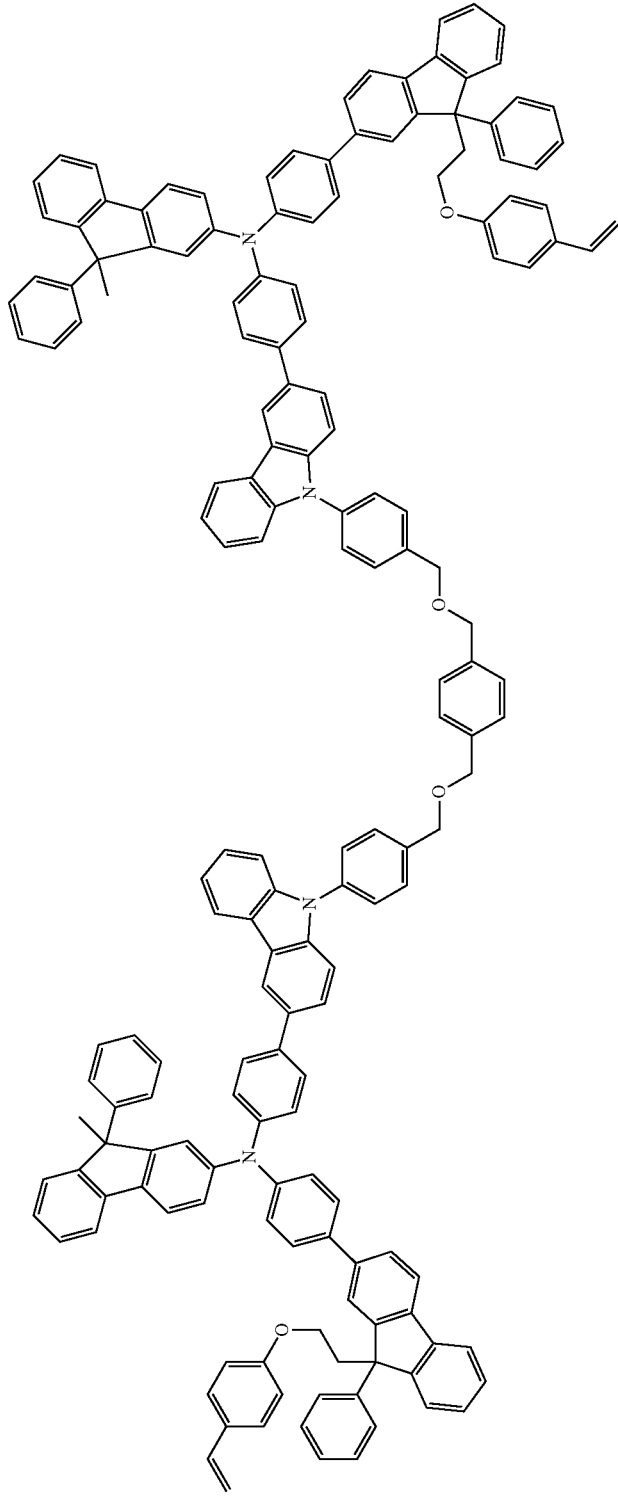
[Compound 54]
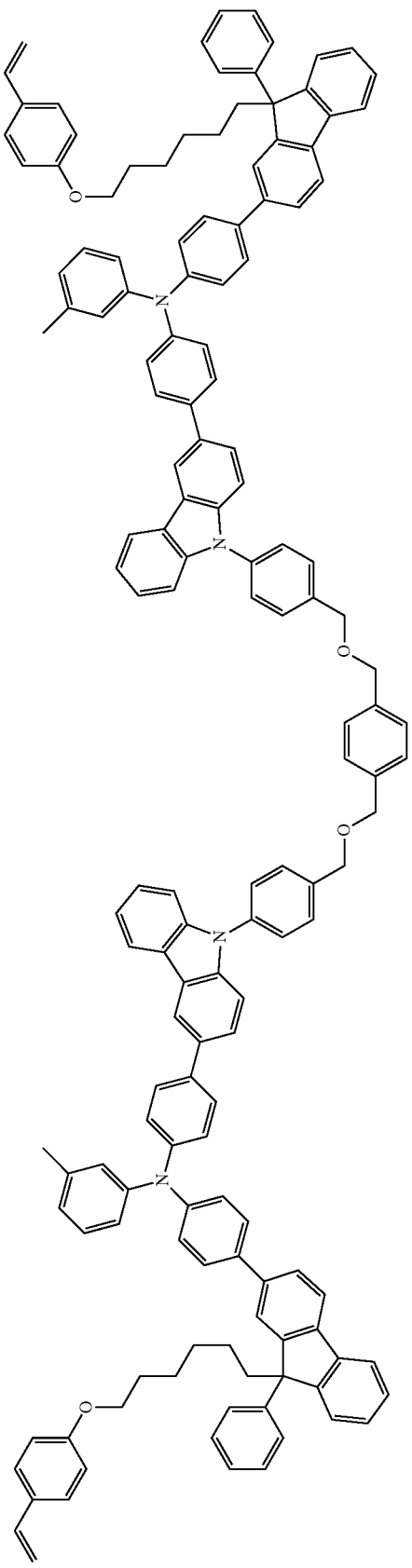

-continued
[Compound 55]
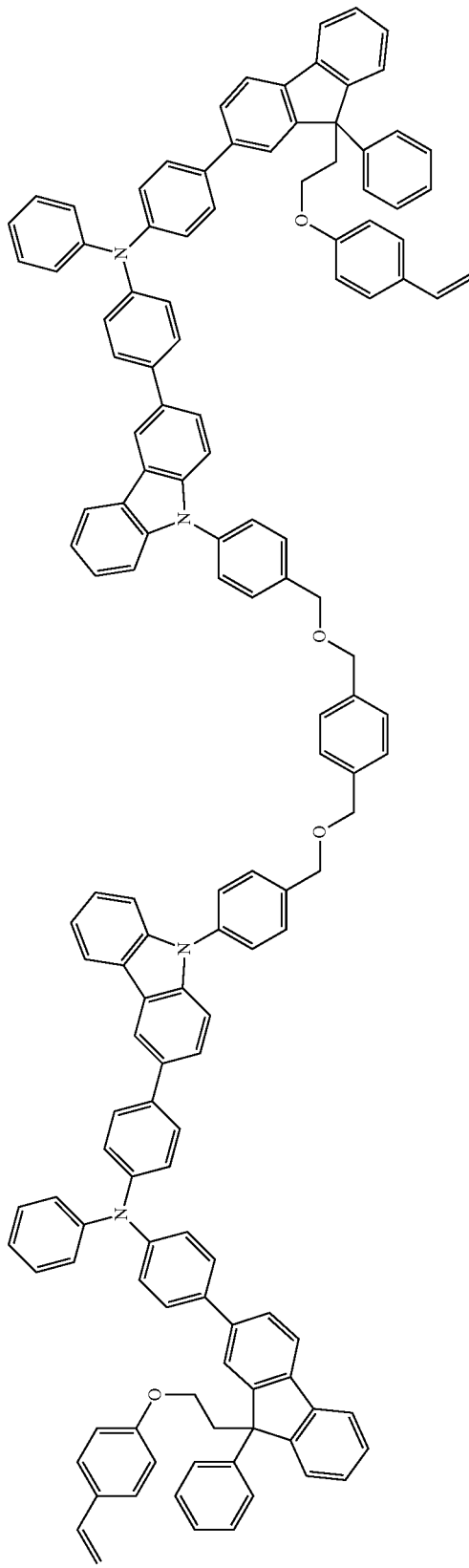
[Compound 56]
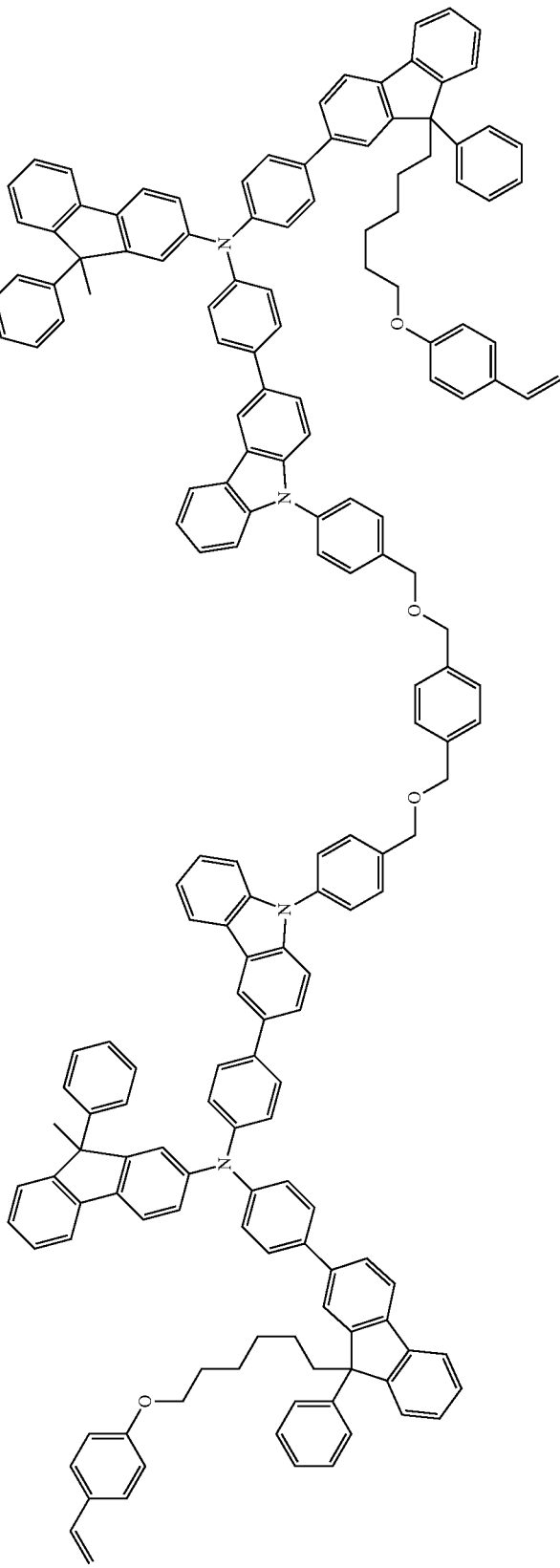

-continued
[Compound 57]
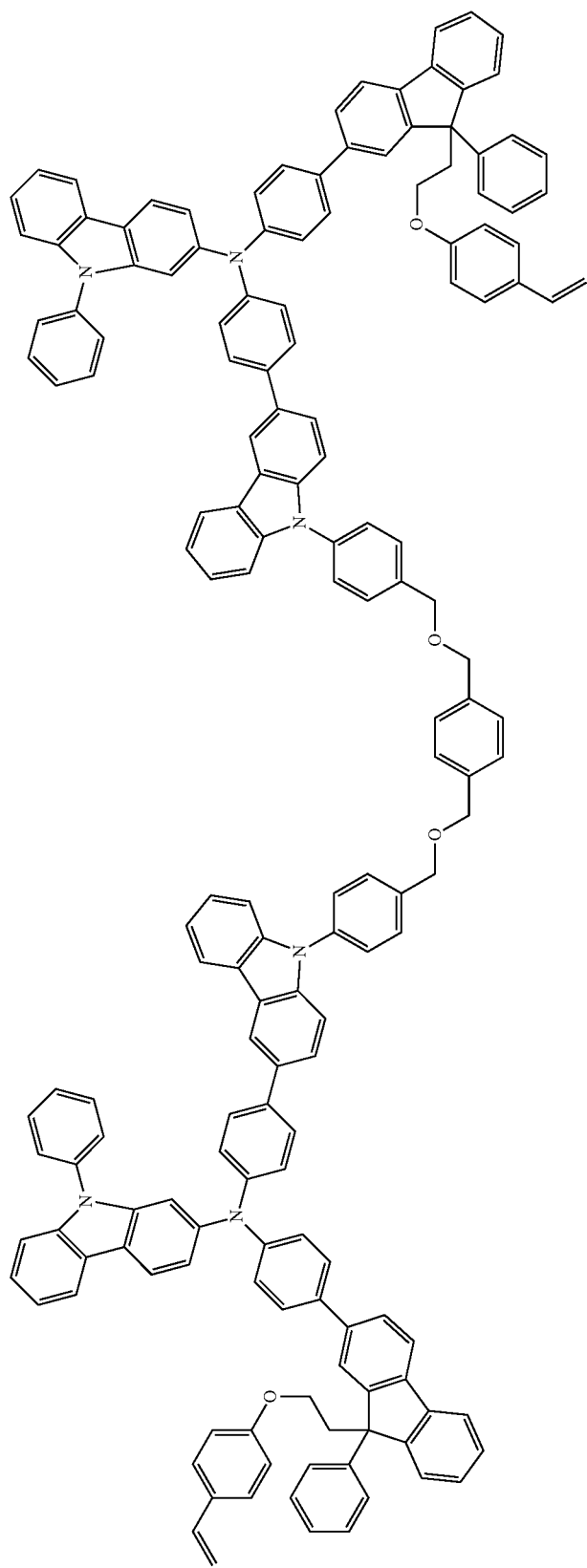

-continued
[Compound 58]
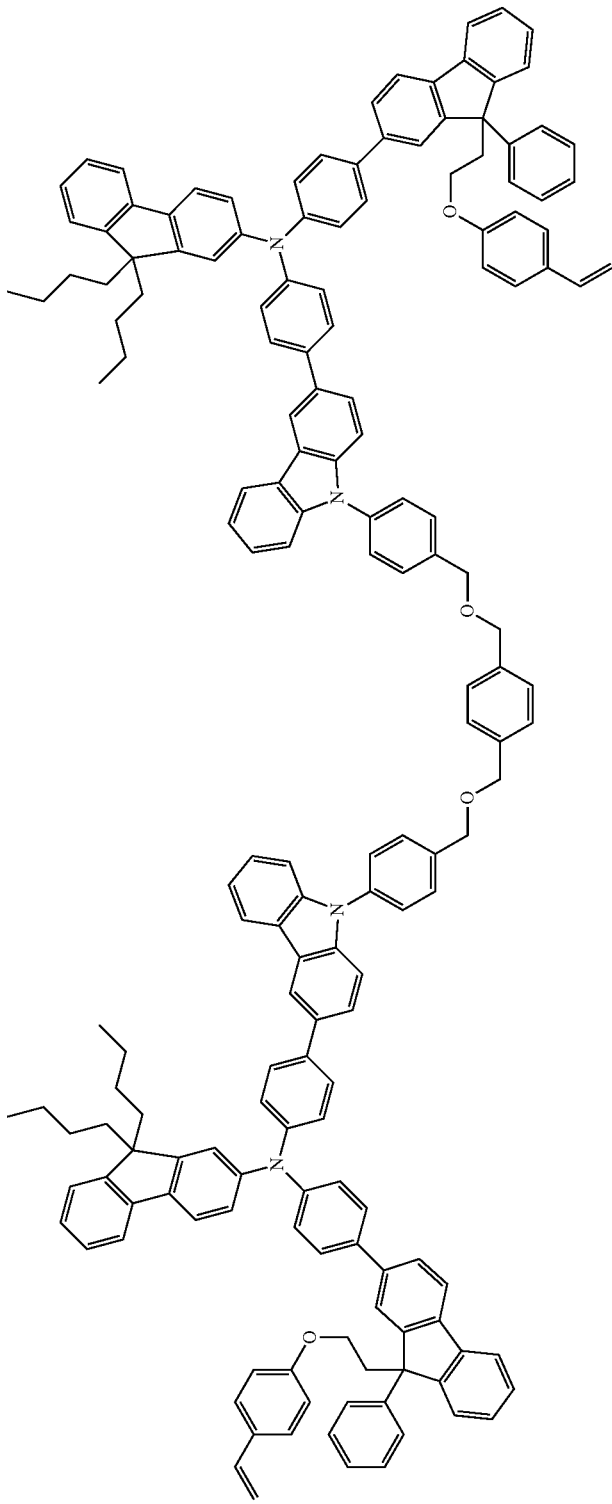
[Compound 59]
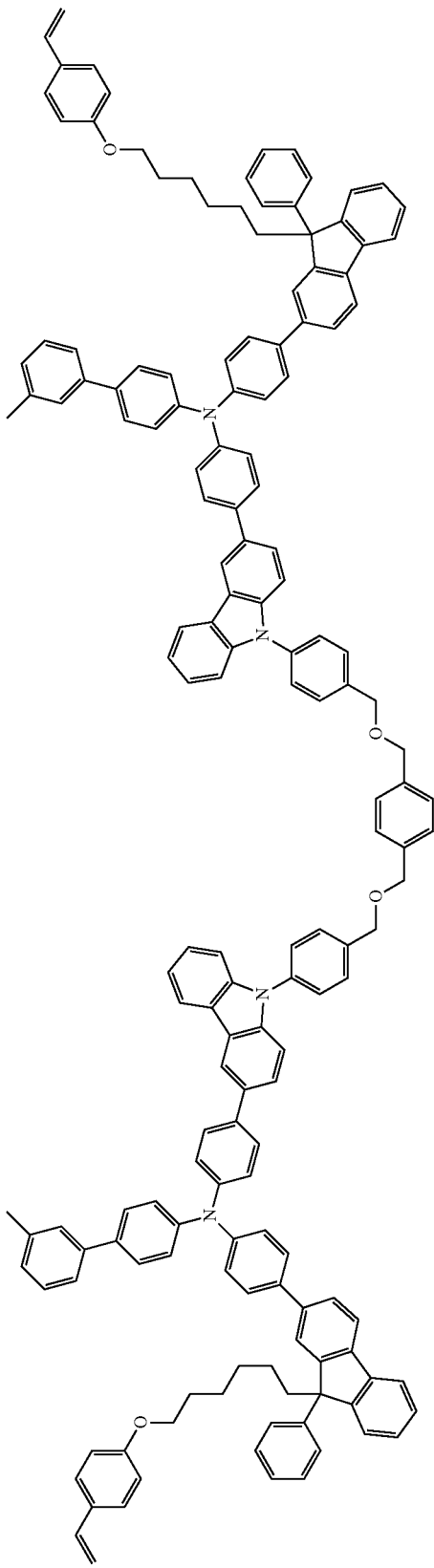

101
[Compound 60]
102
[Compound 61]
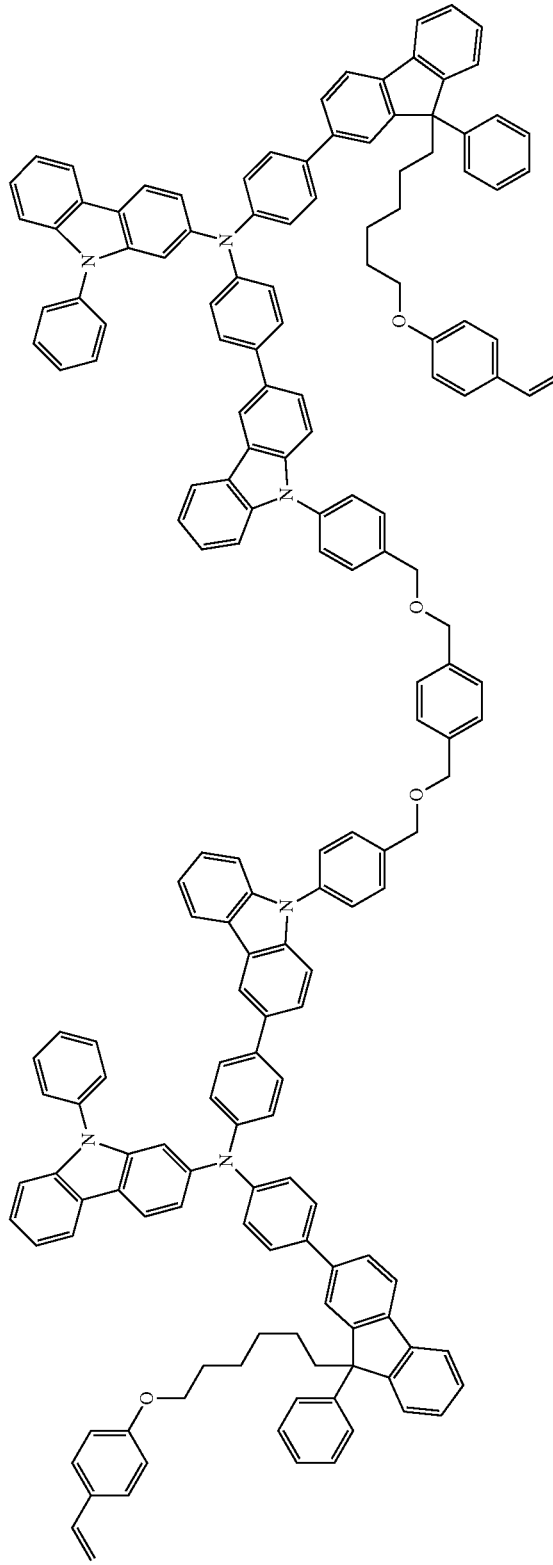
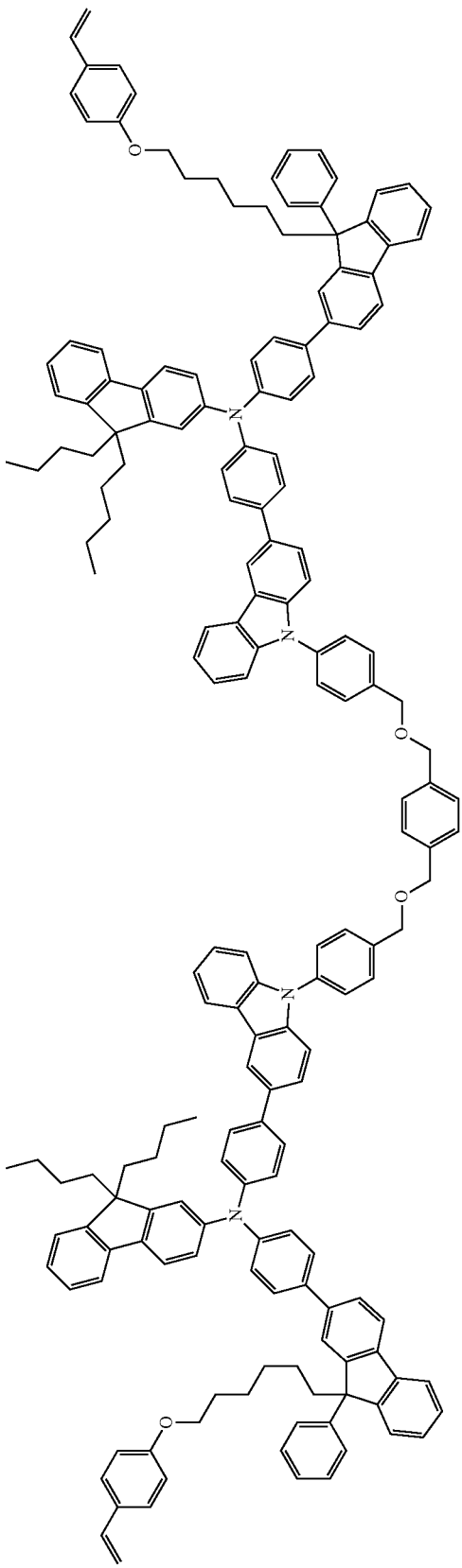

-continued
[Compound 62]
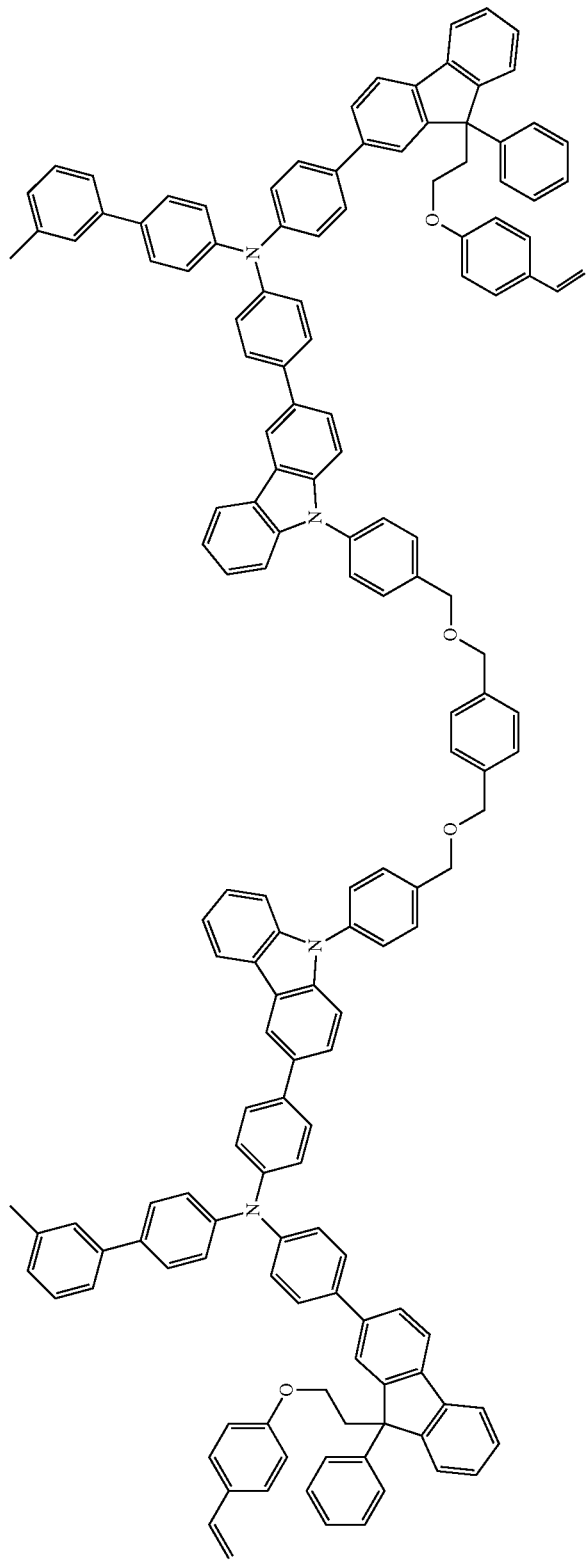
[Compound 63]
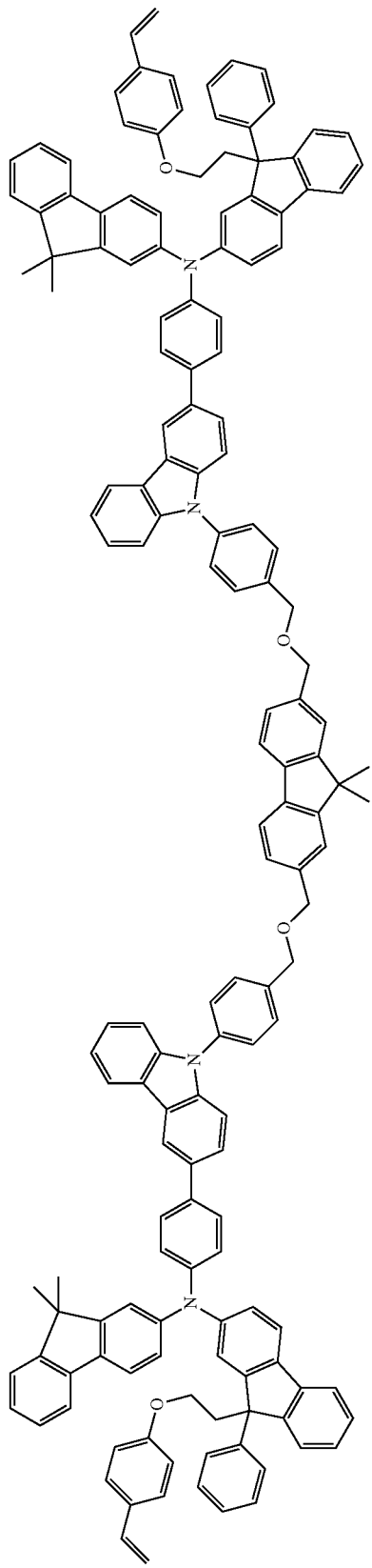

[Compound 64]
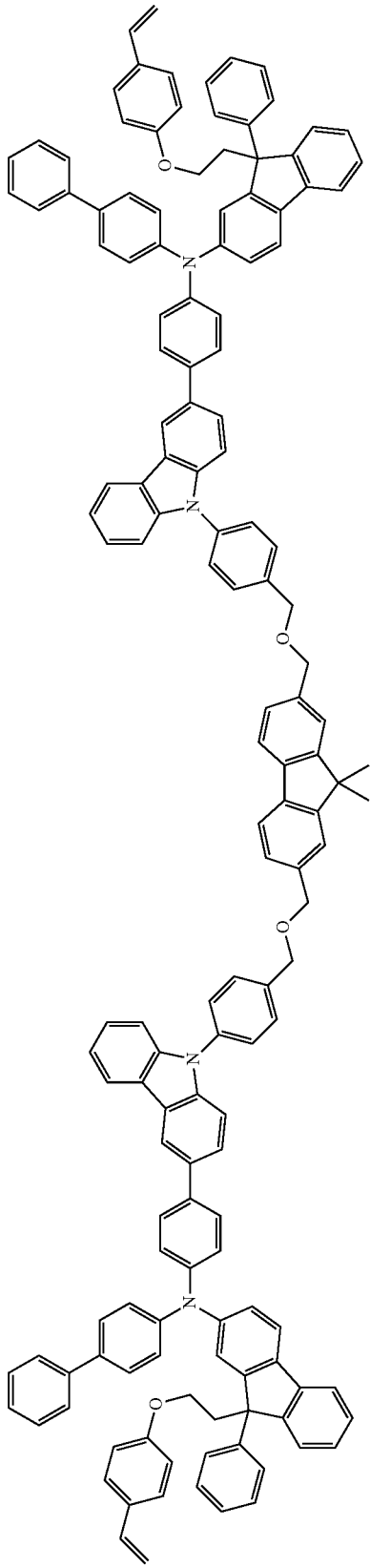
[Compound 65]
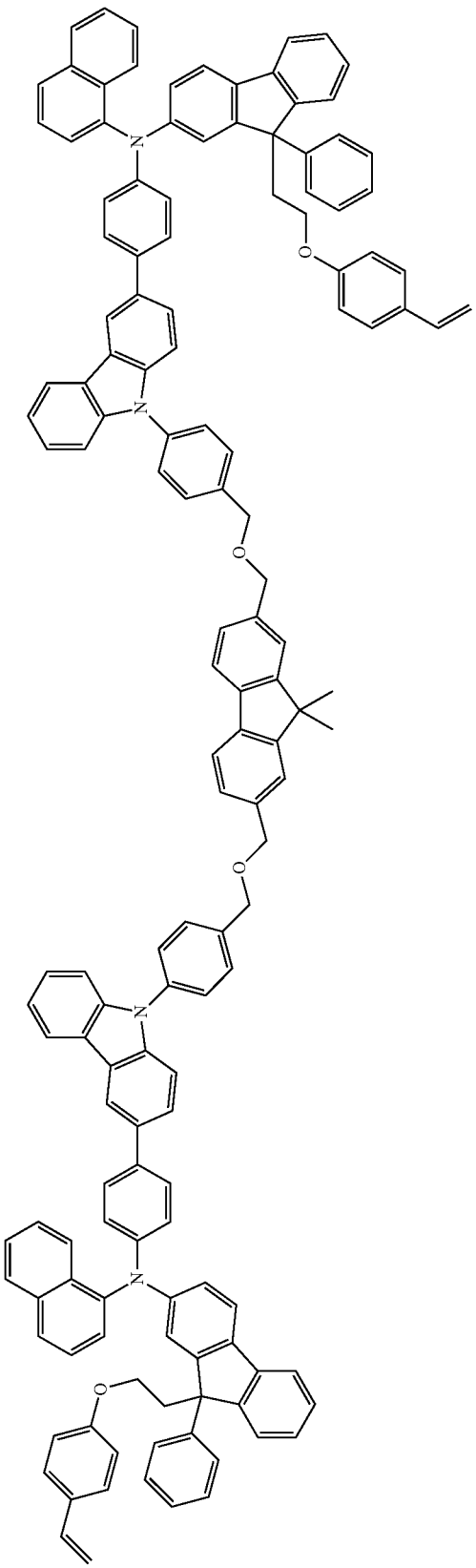

[Compound 66]
[Compound 67]
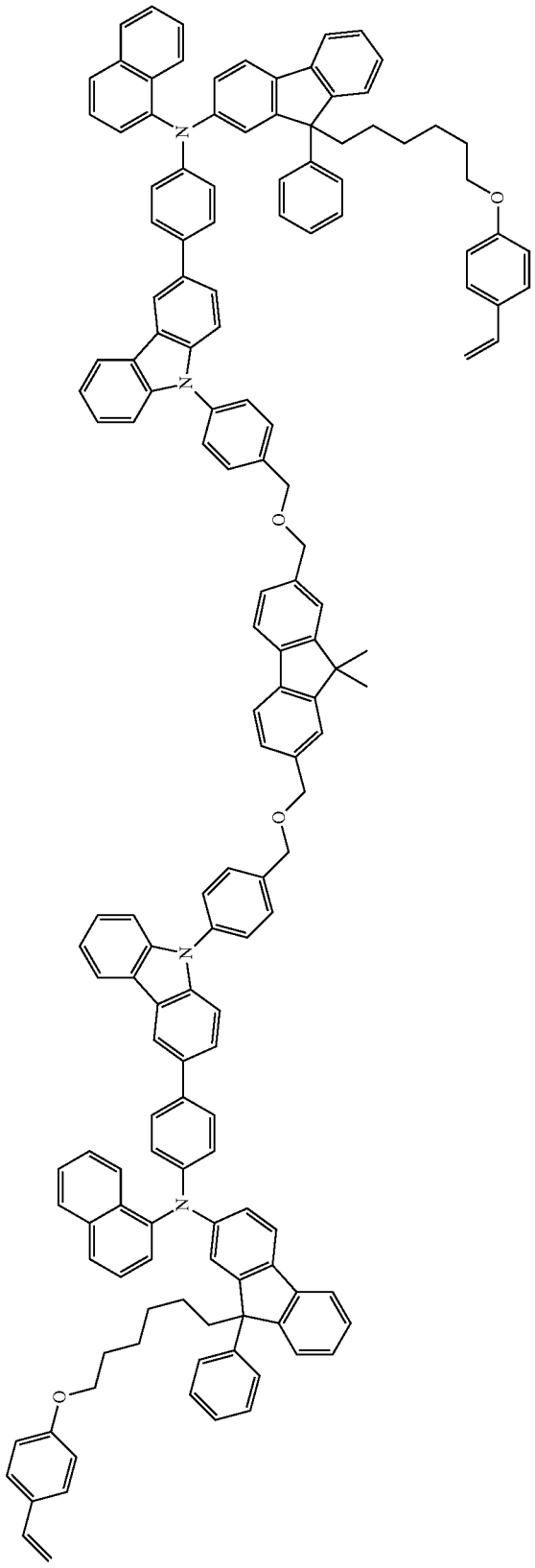
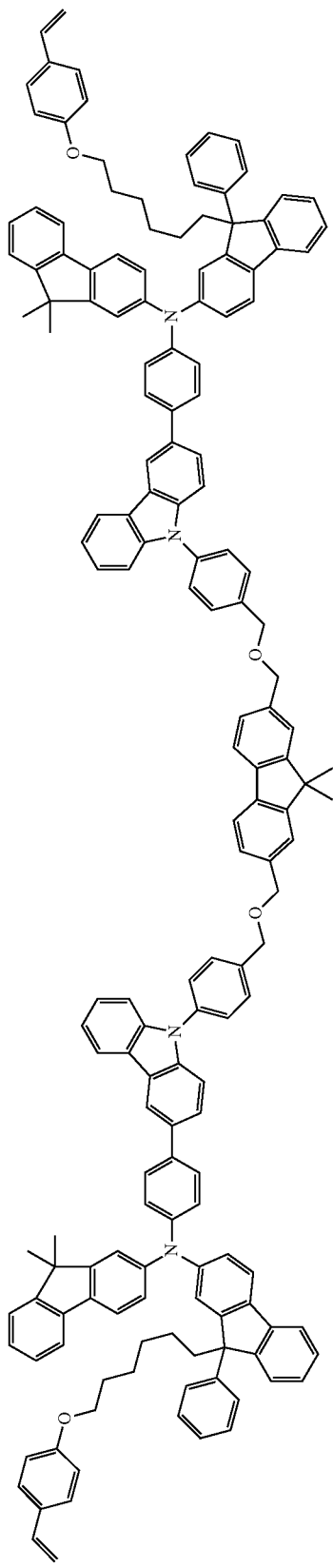

-continued
[Compound 68]
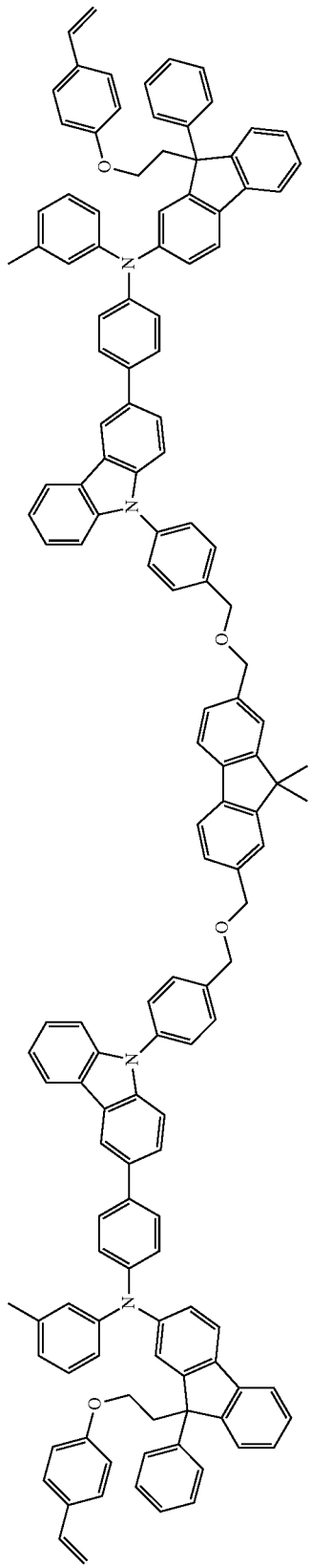
[Compound 69]
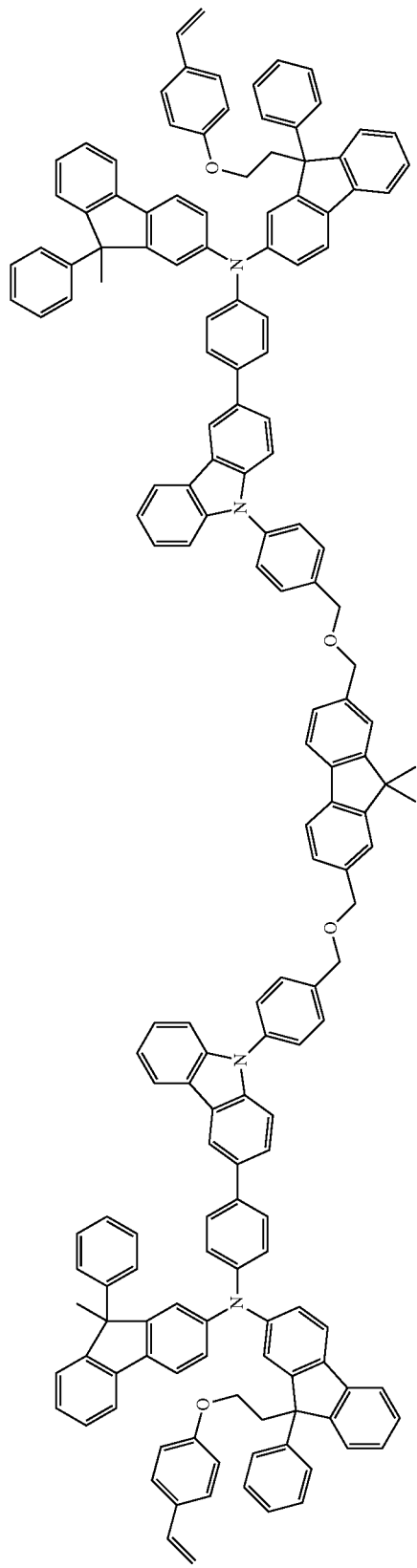

-continued
[Compound 70]
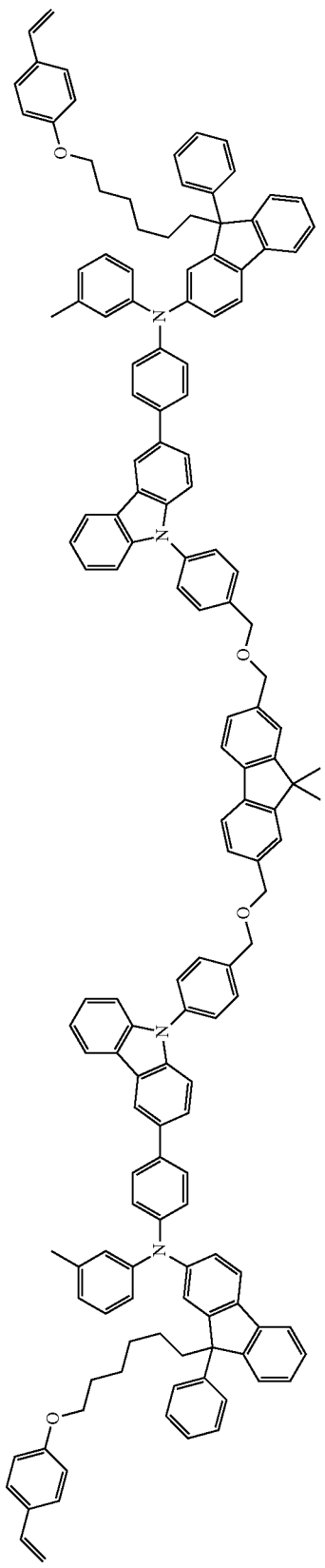
[Compound 71]
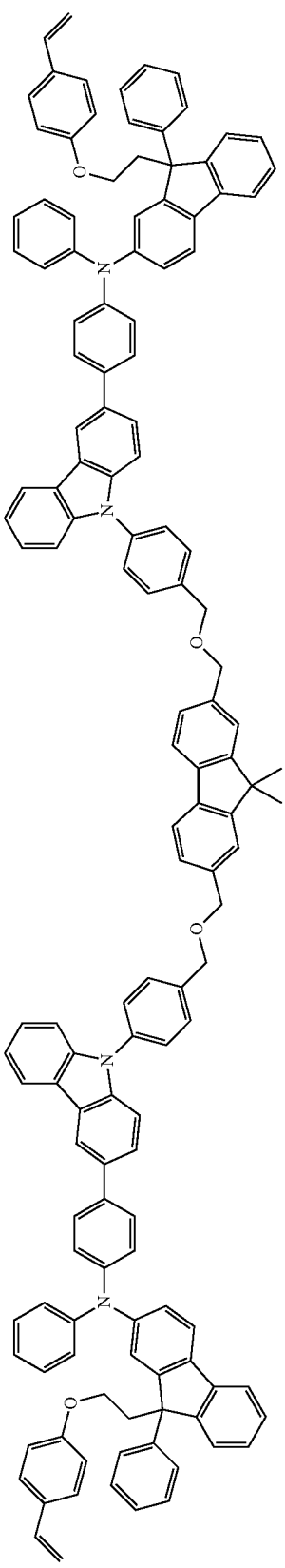

113
[Compound 72]
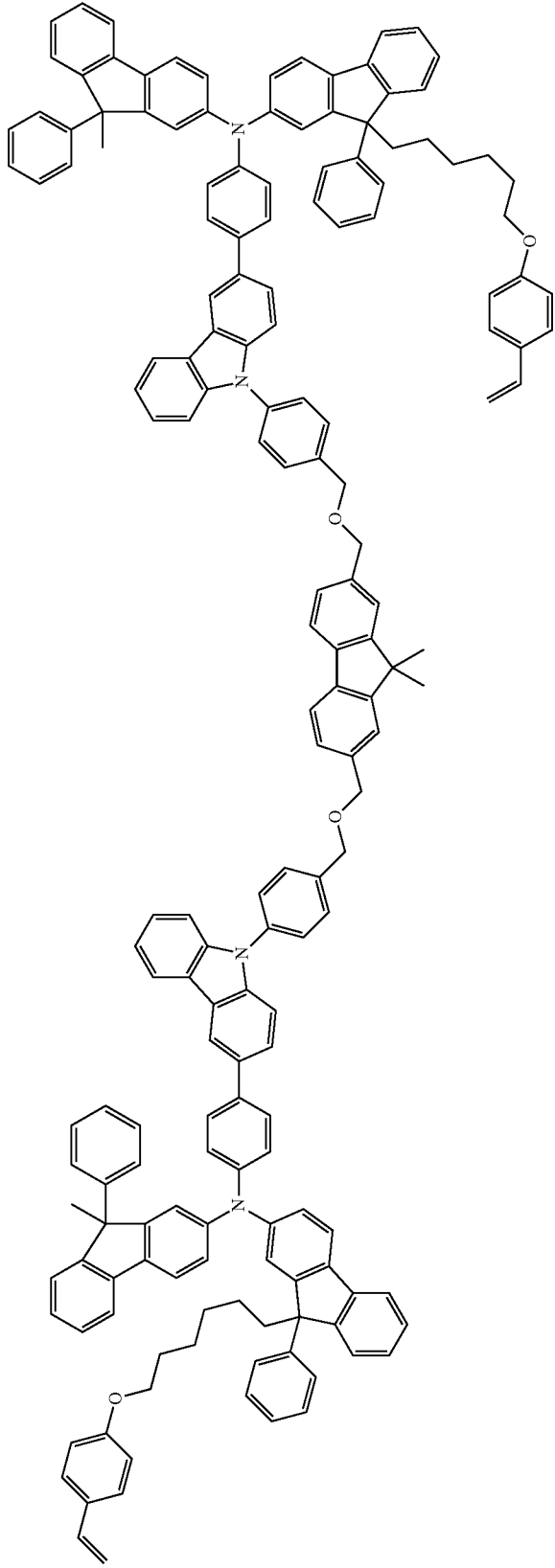
114
[Compound 73]
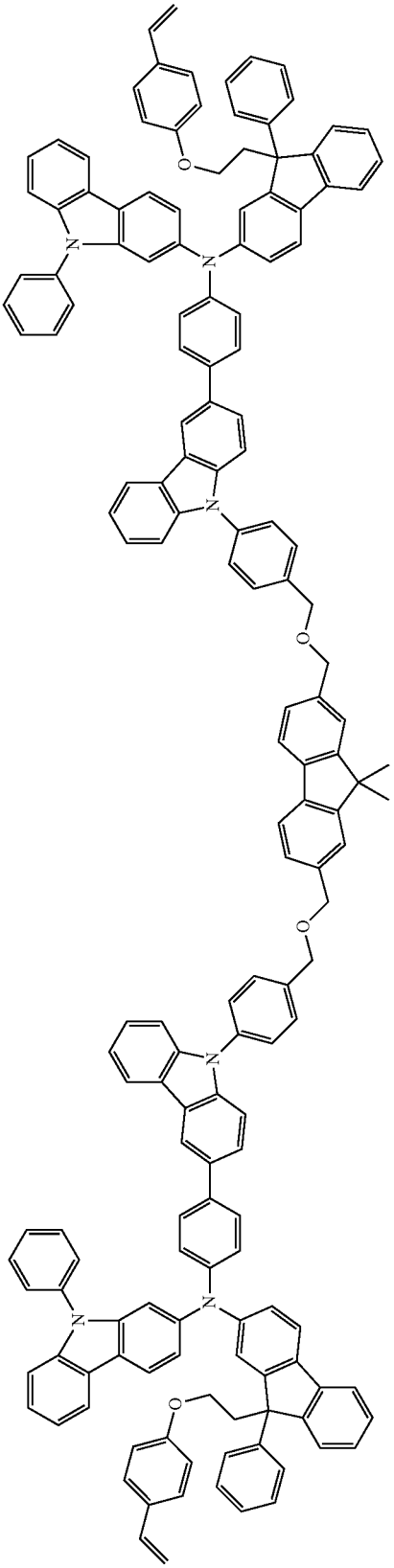

[Compound 74]
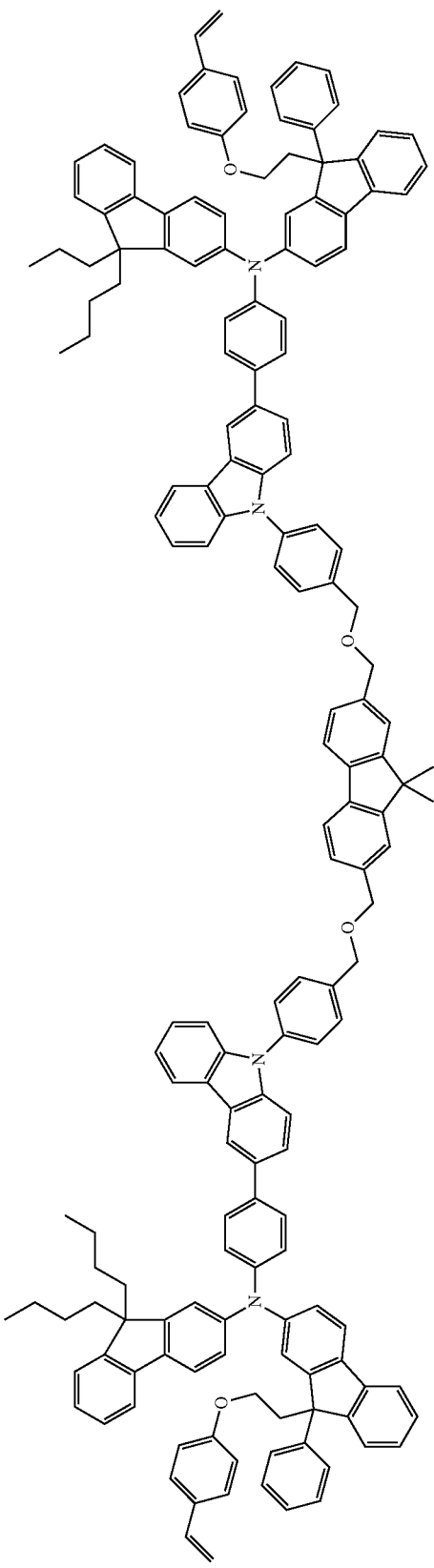
[Compound 75]
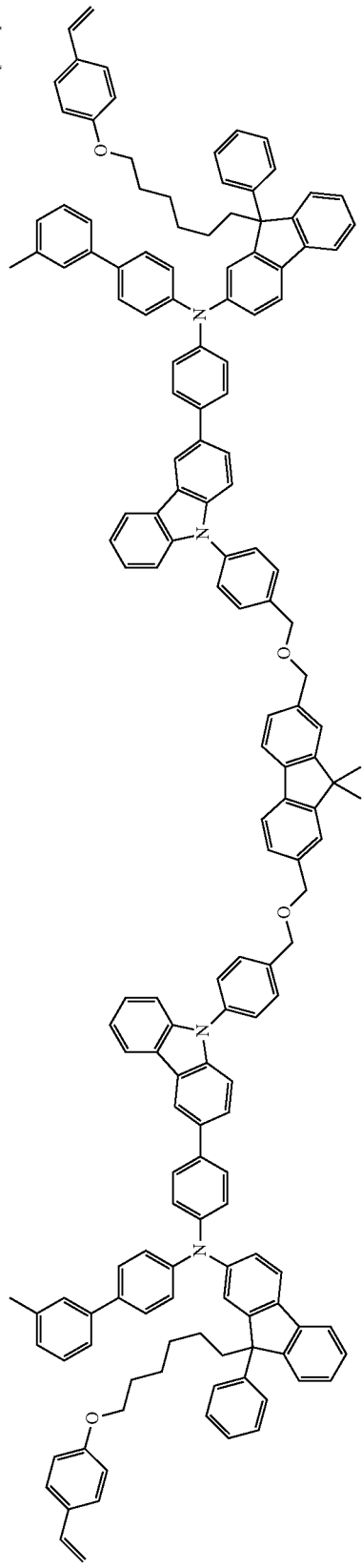

[Compound 76]
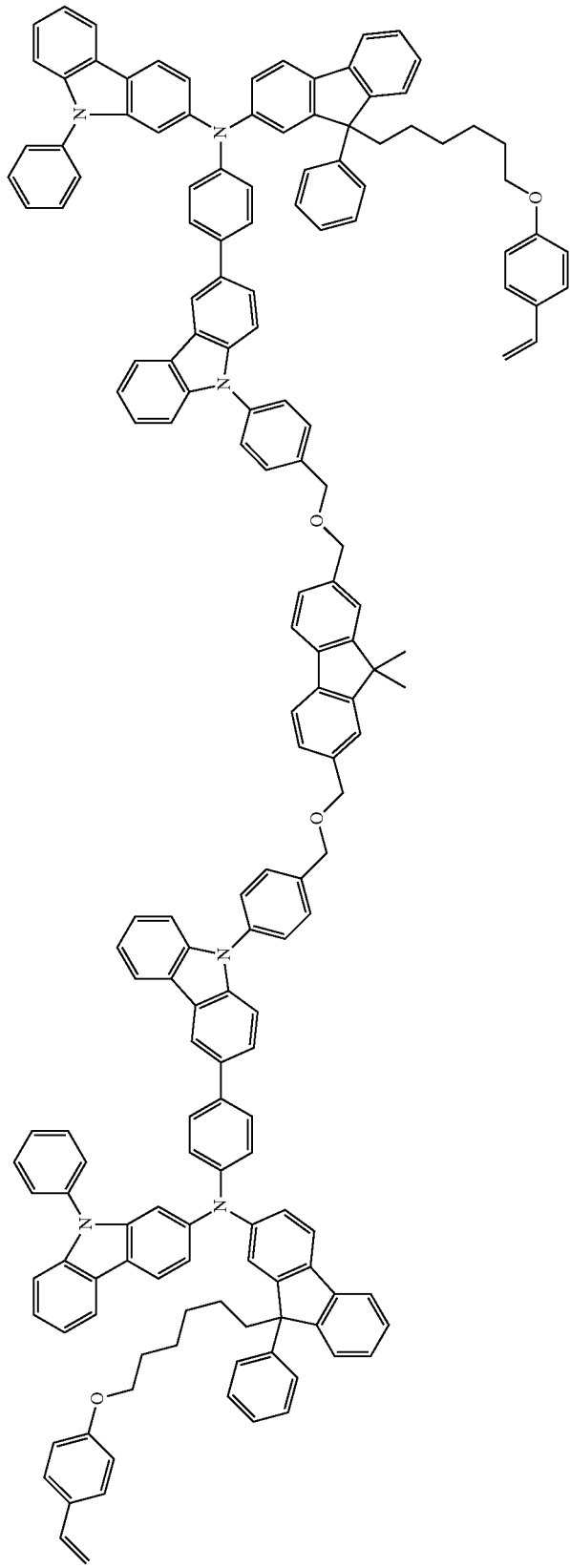
[Compound 77]
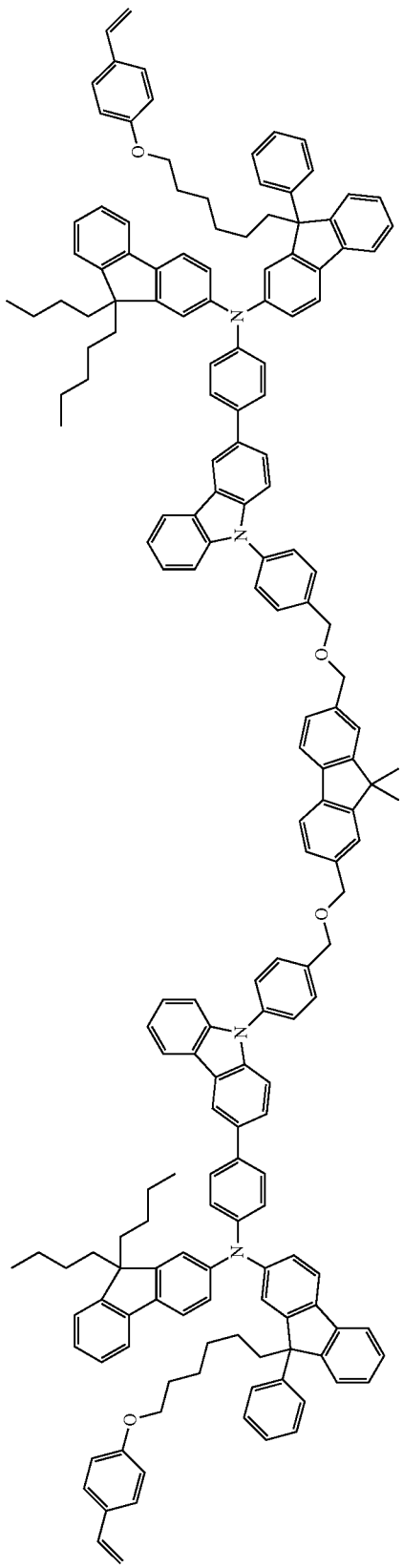

[Compound 78]
[Compound 79]
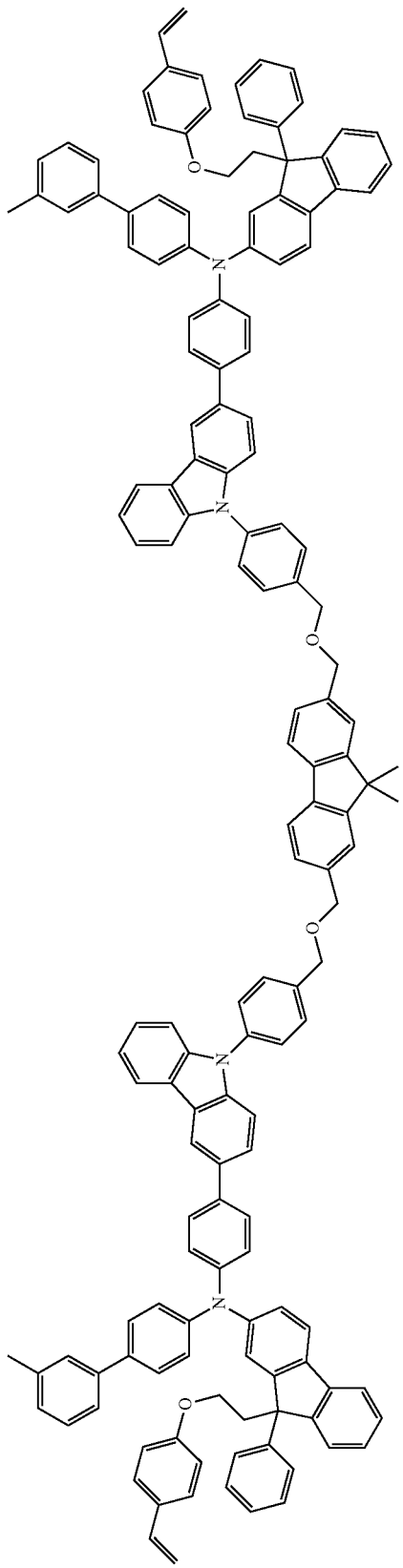
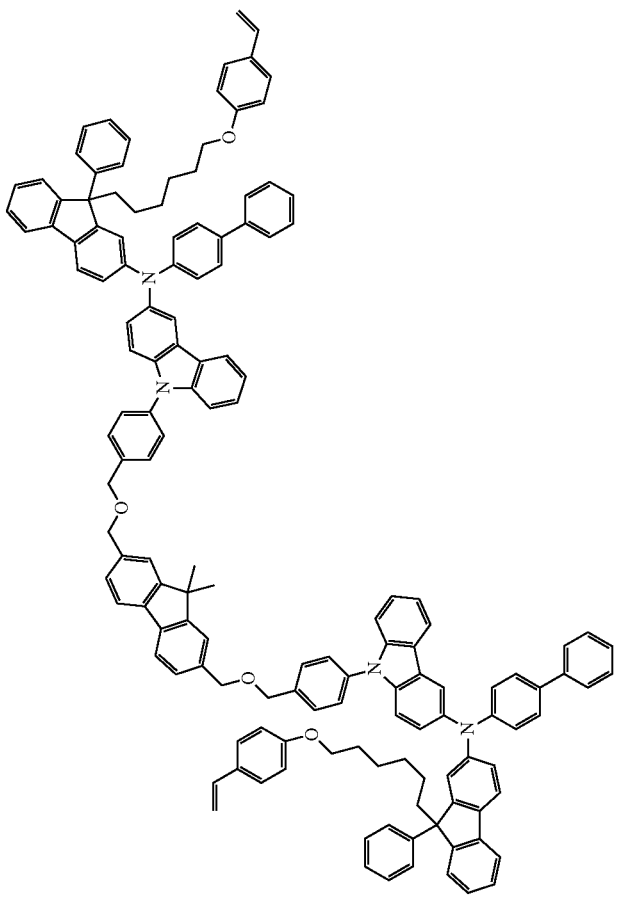

[Compound 80]
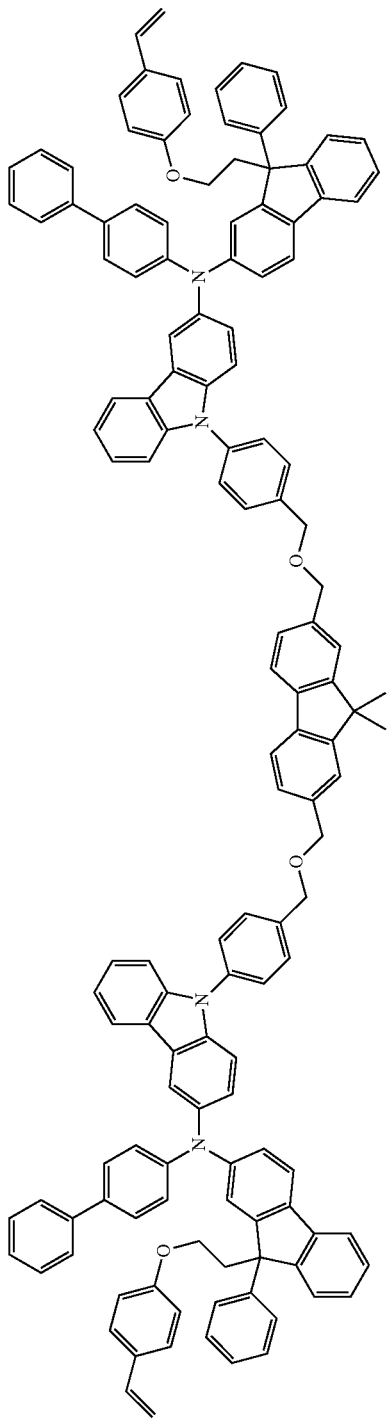
[Compound 81]
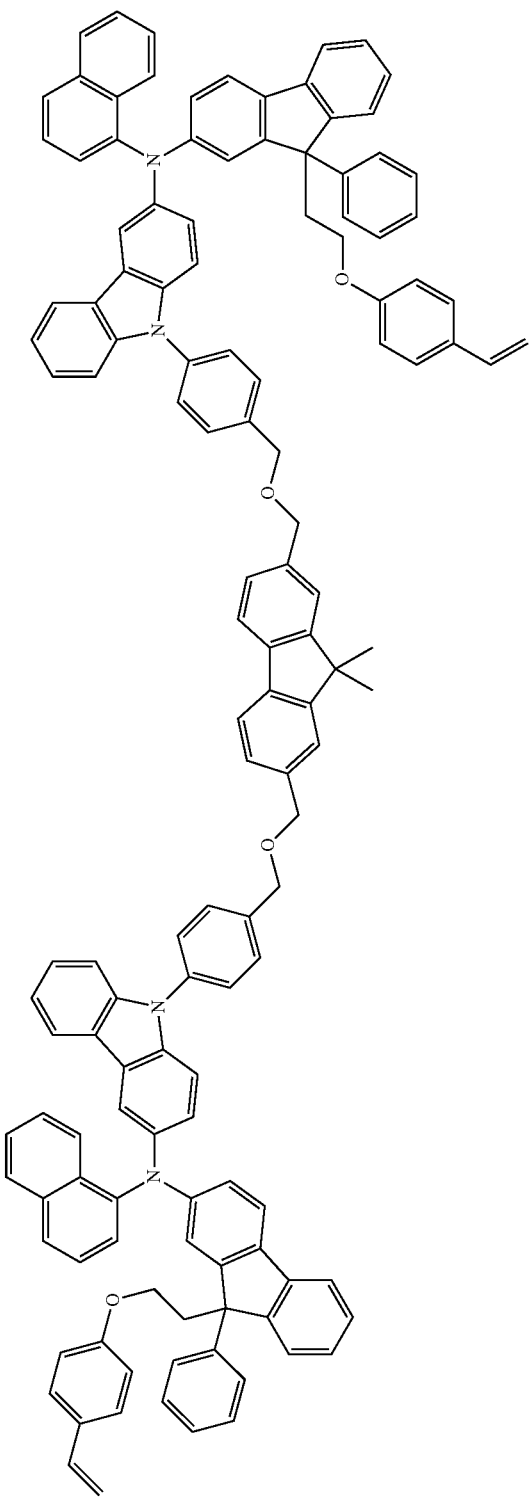

-continued
[Compound 82]
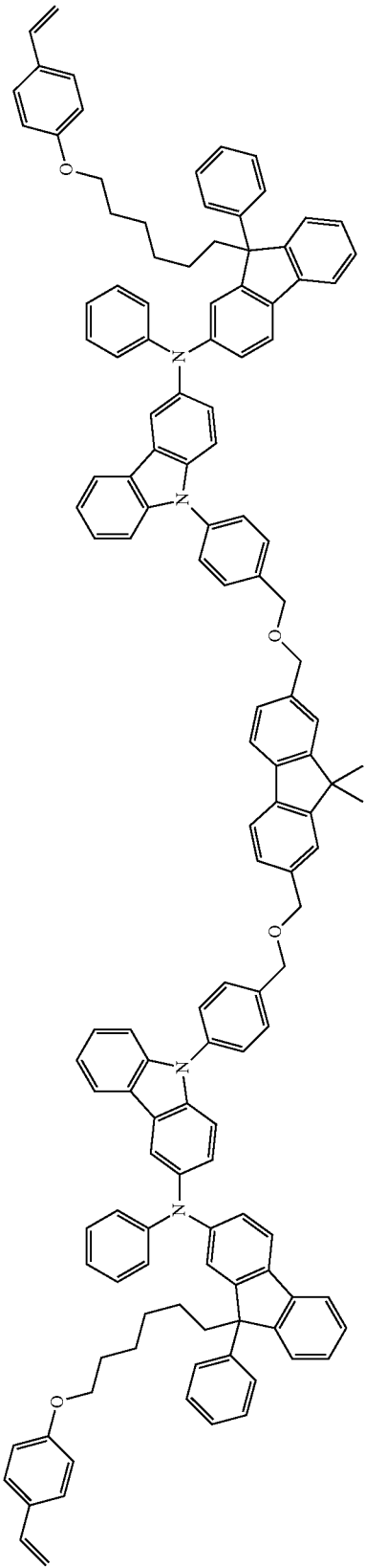
[Compound 83]
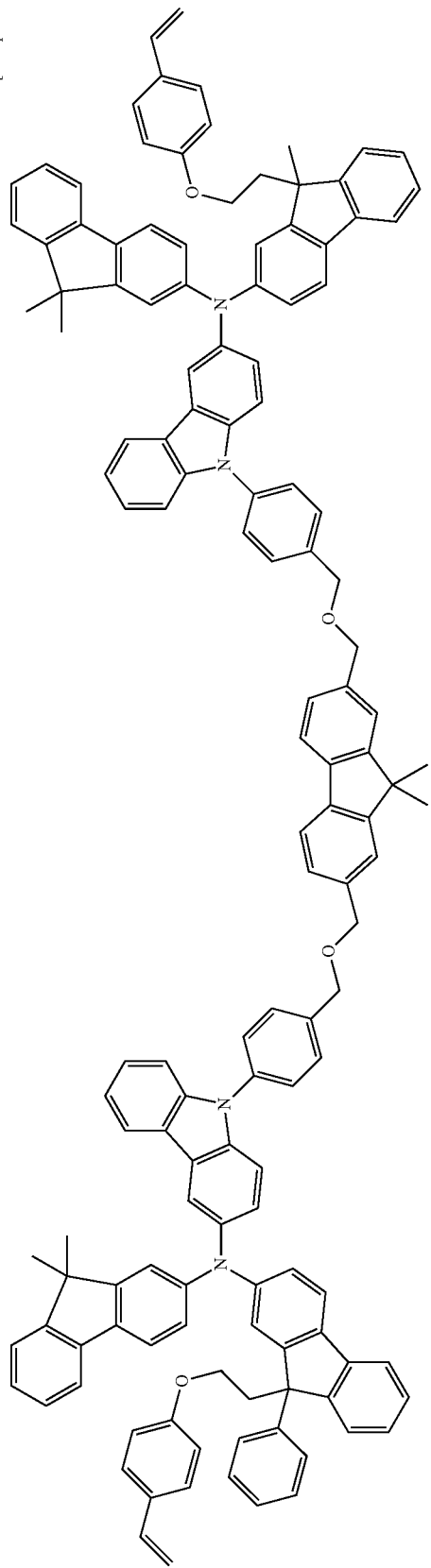

[Compound 84]
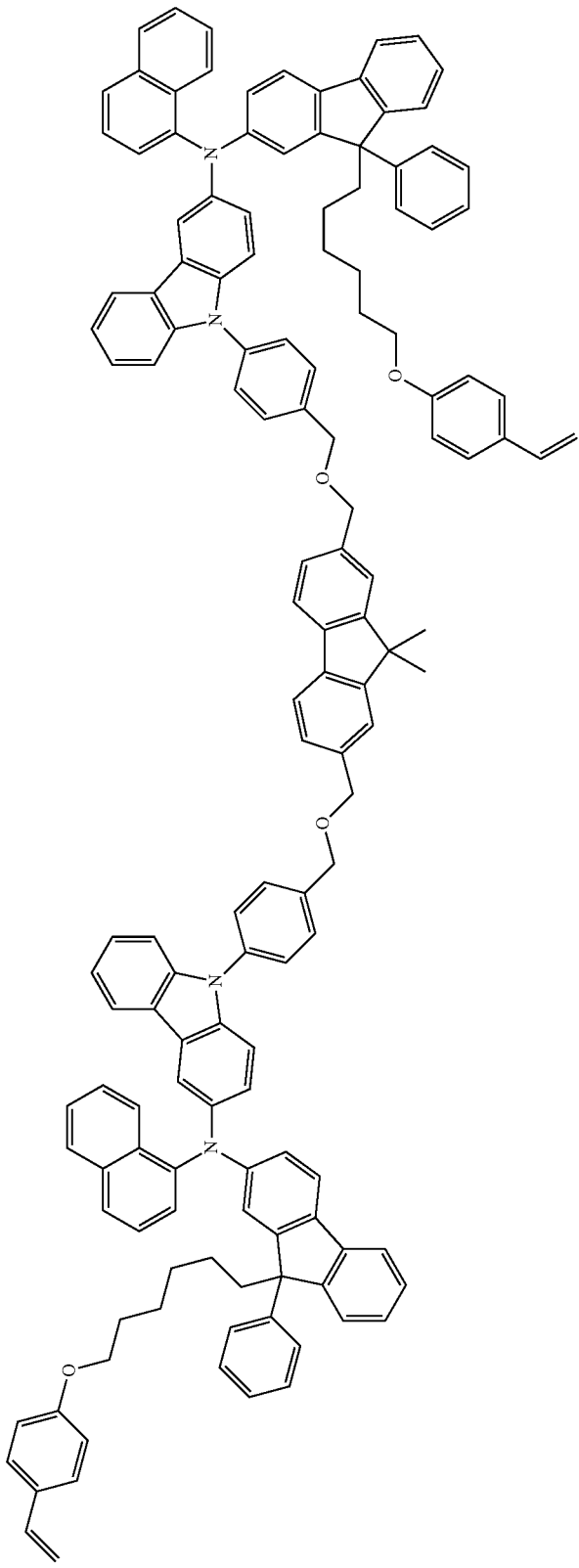
-continued

-continued
[Compound 85]
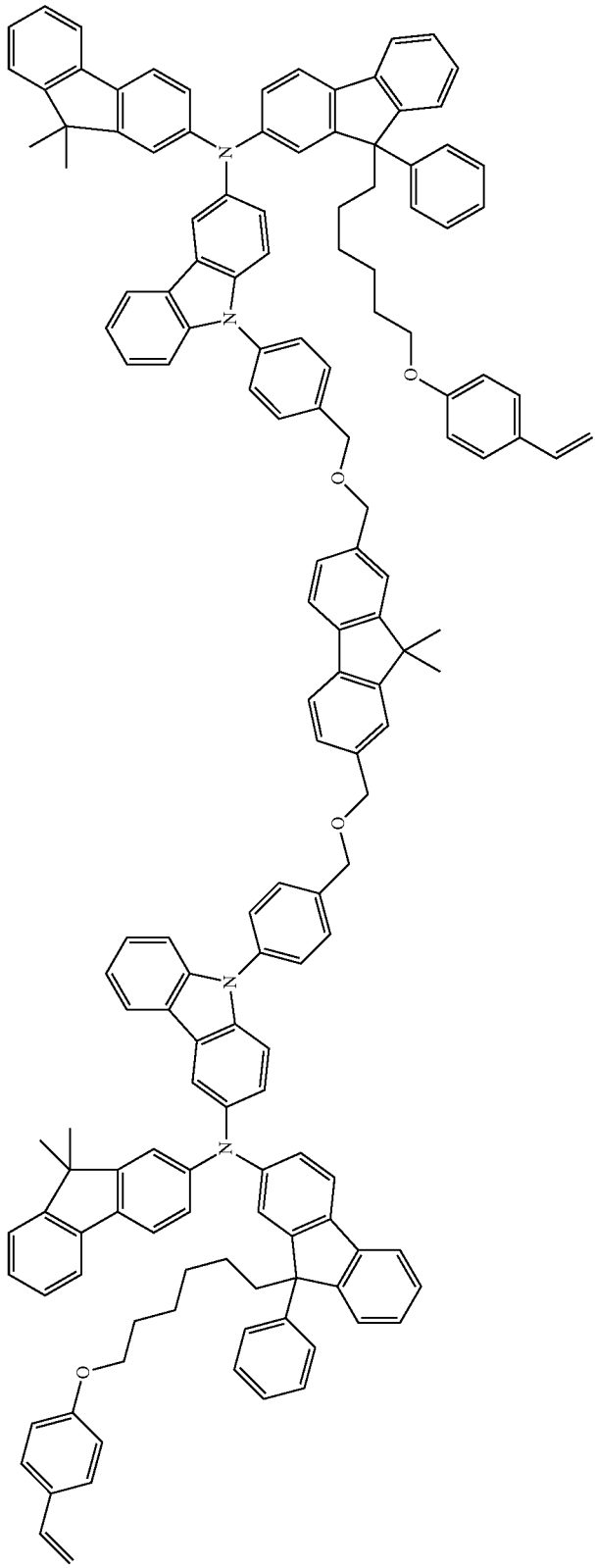
[Compound 86]
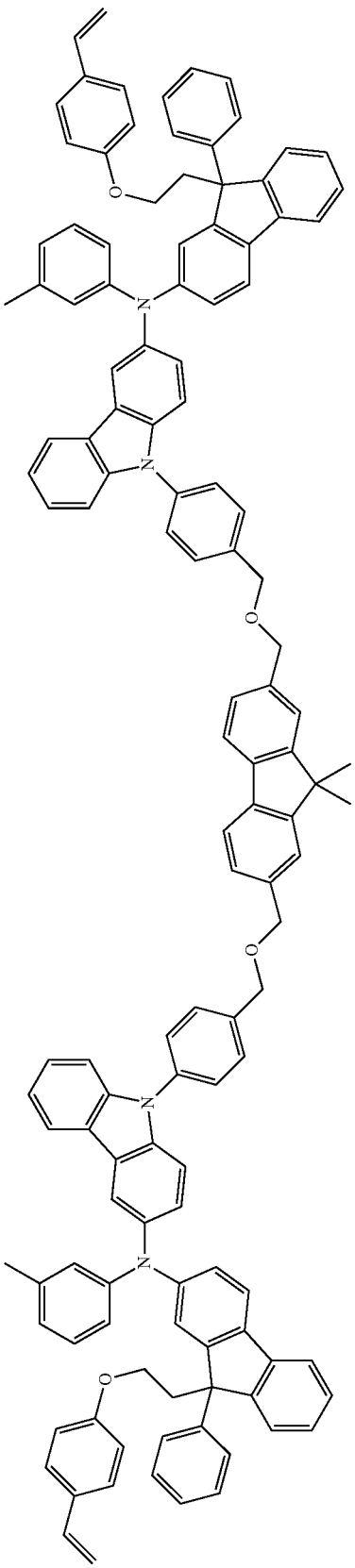

[Compound 87]
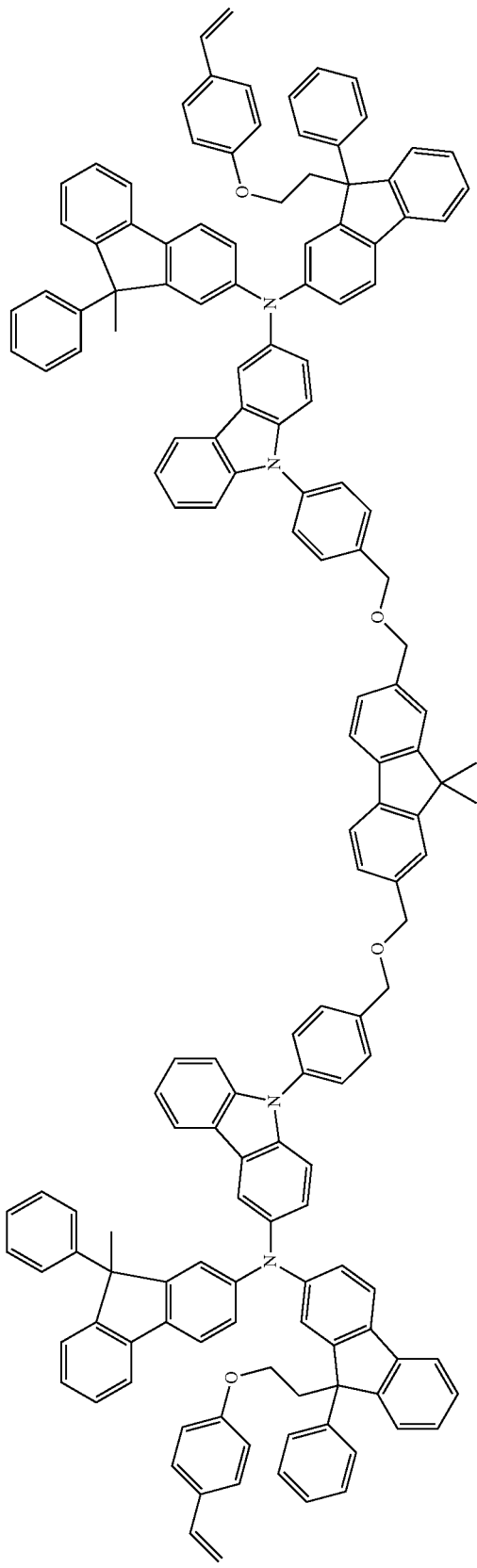
[Compound 88]
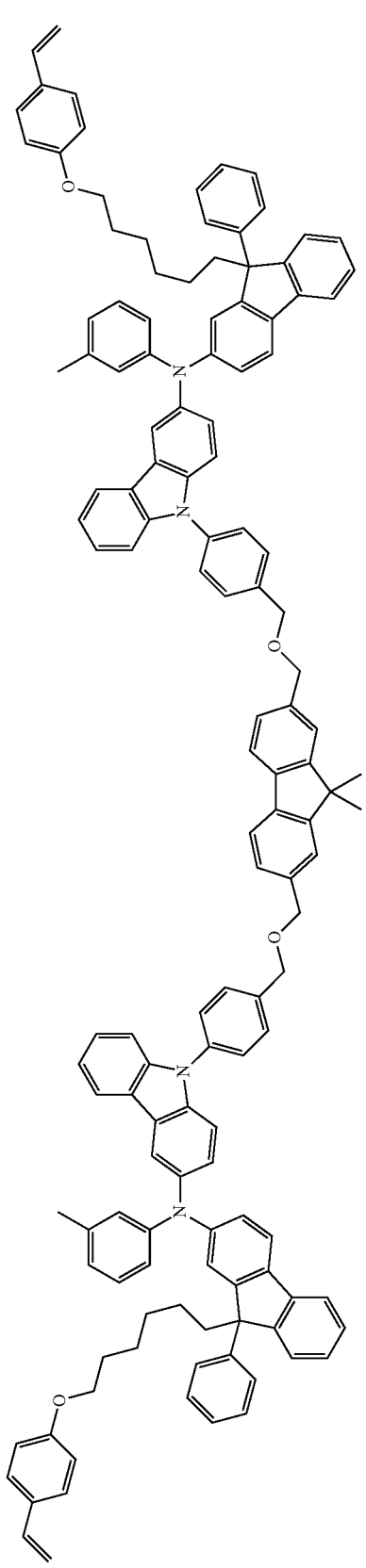

[Compound 89]
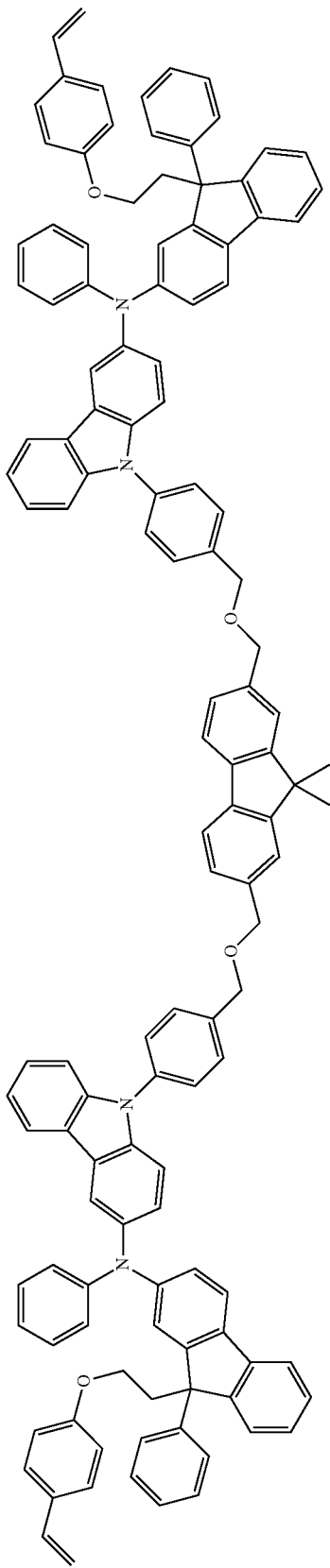
[Compound 90]
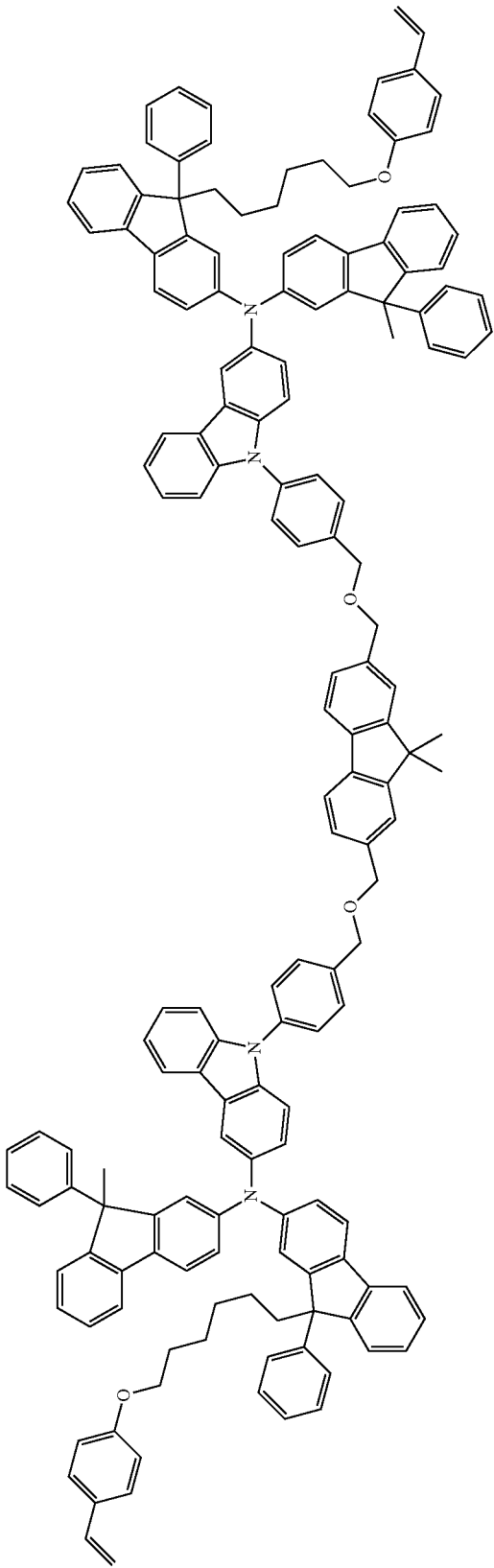

-continued
[Compound 91]
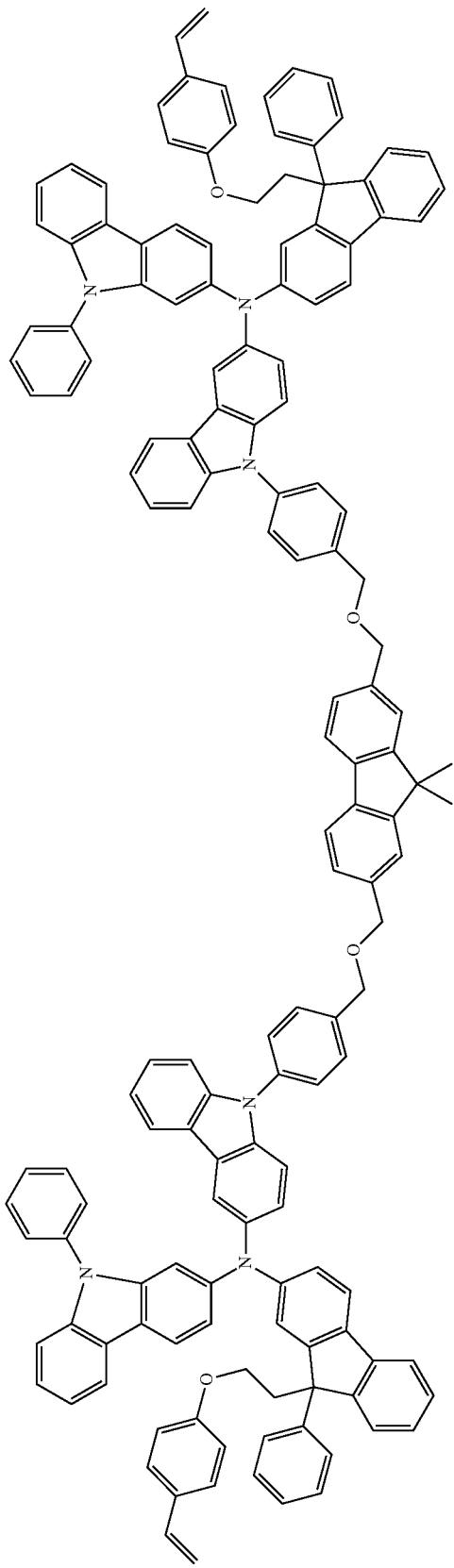
[Compound 92]
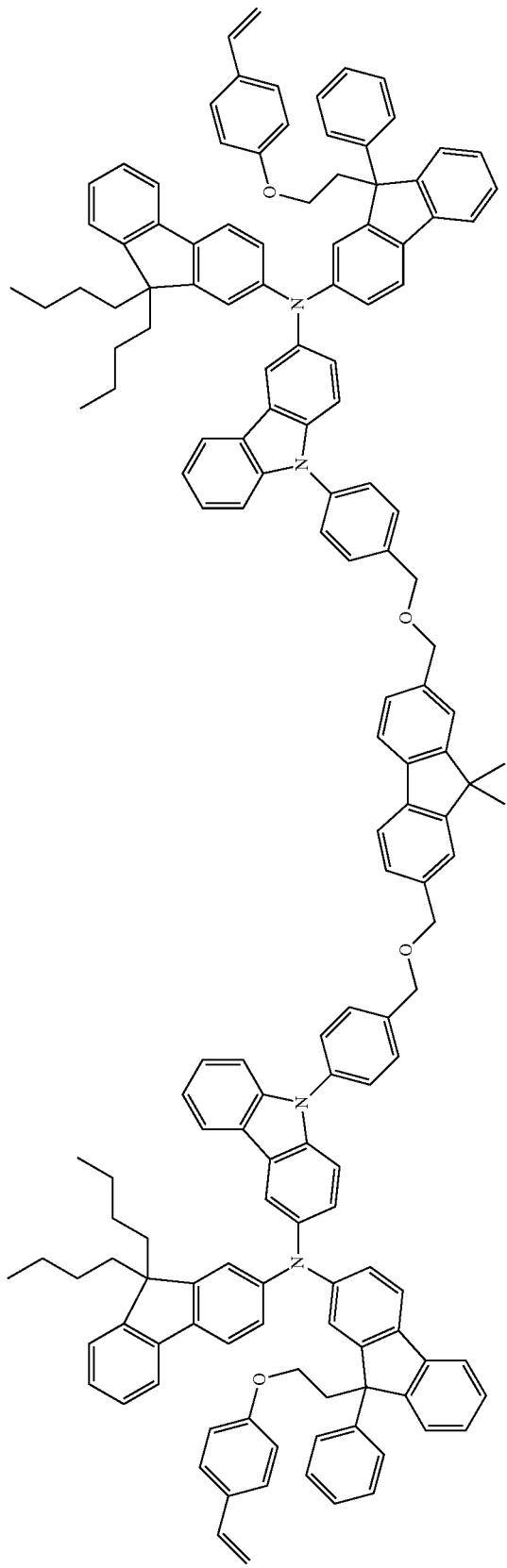

-continued
[Compound 93]
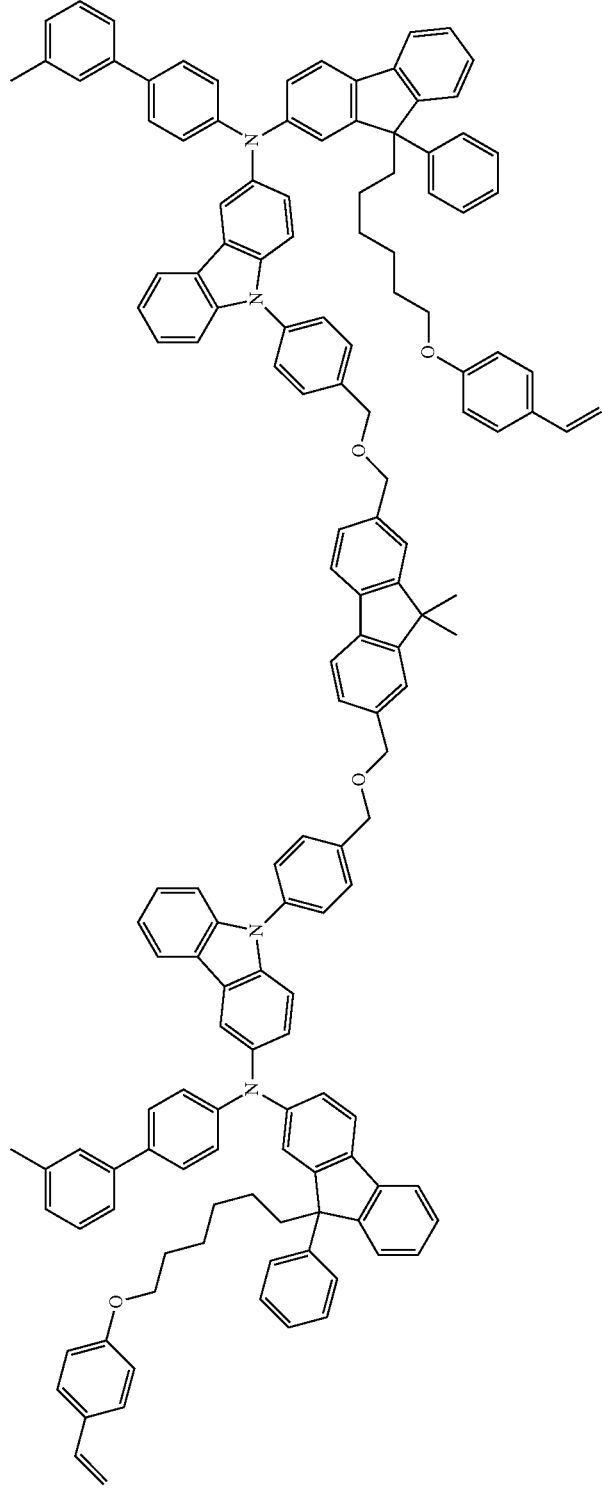
[Compound 94]
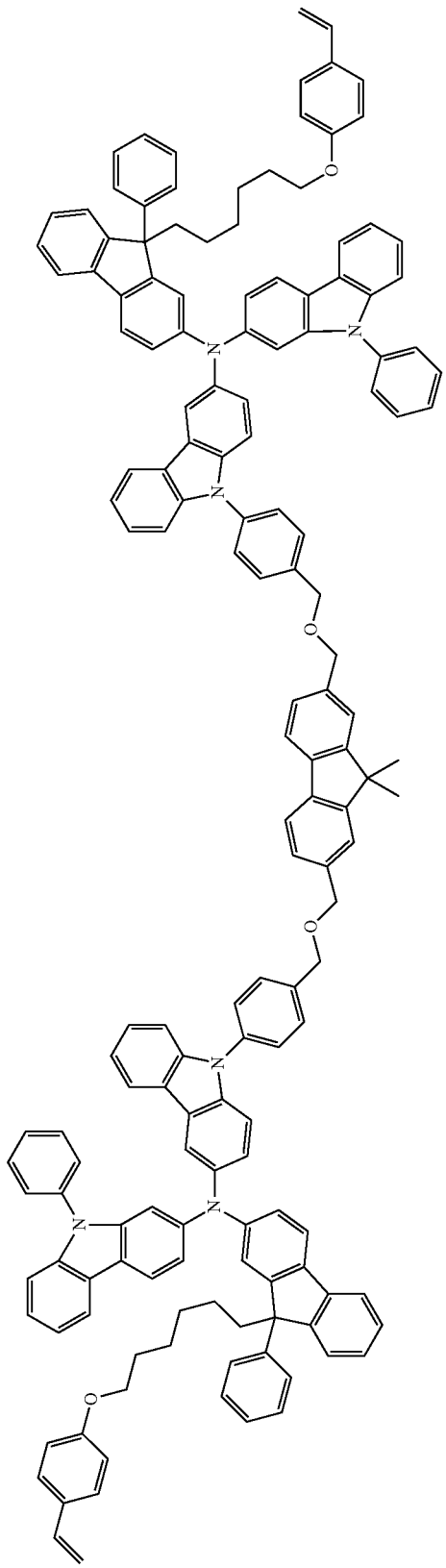

[Compound 95]
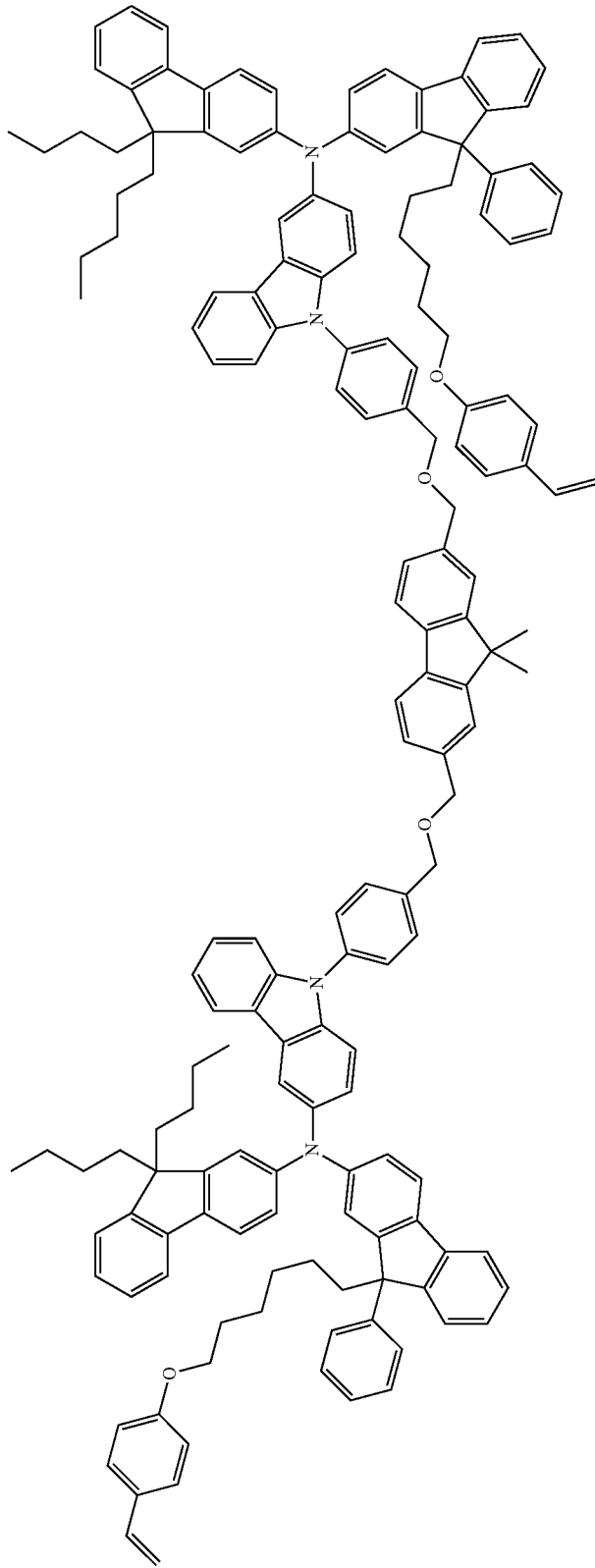
[Compound 96]
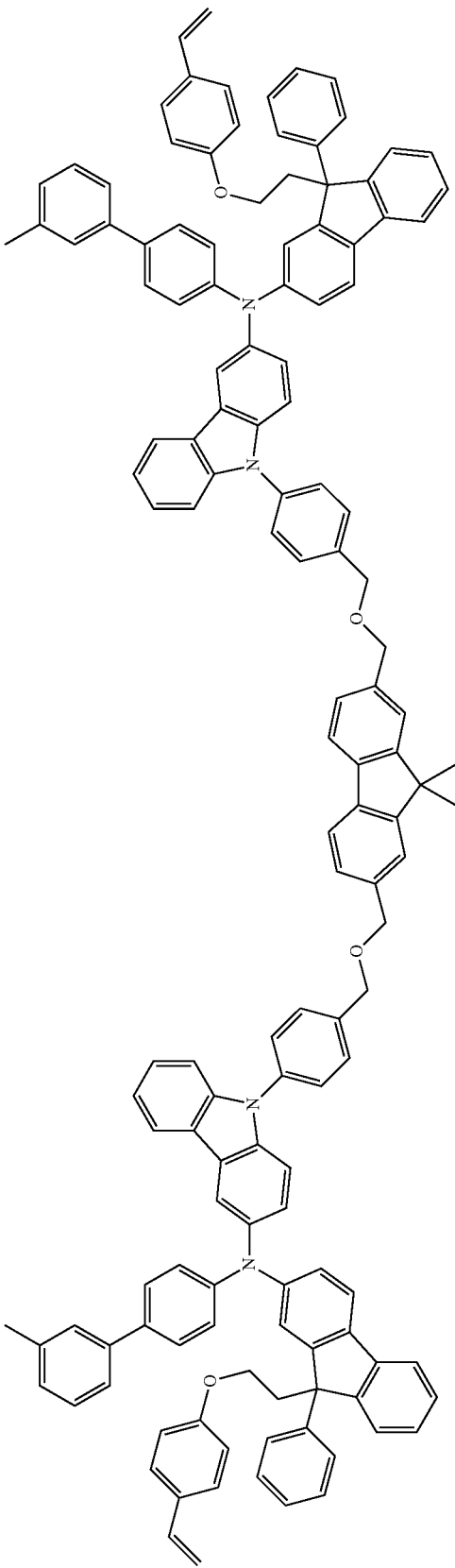

[Compound 97]
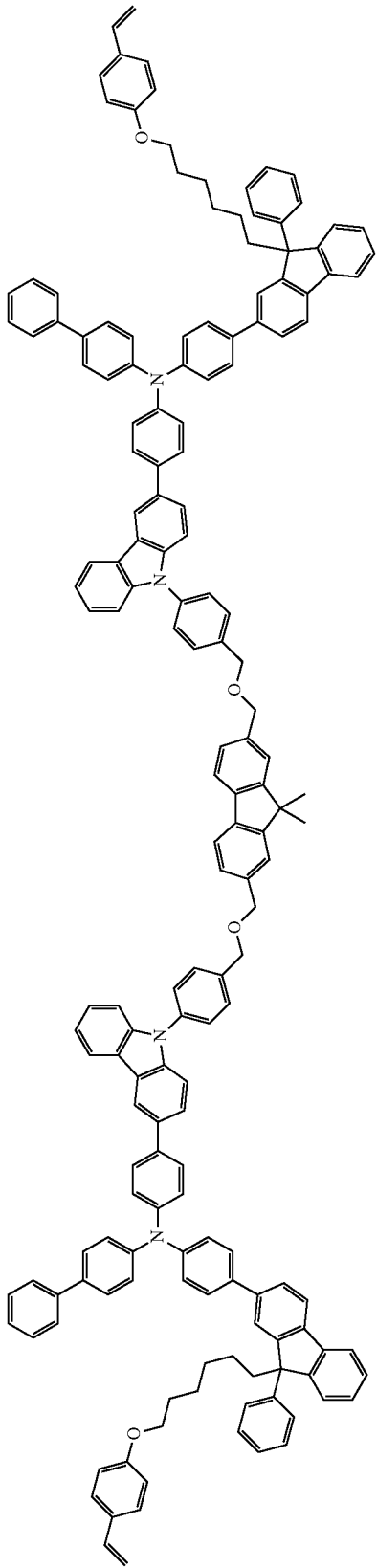
[Compound 98]
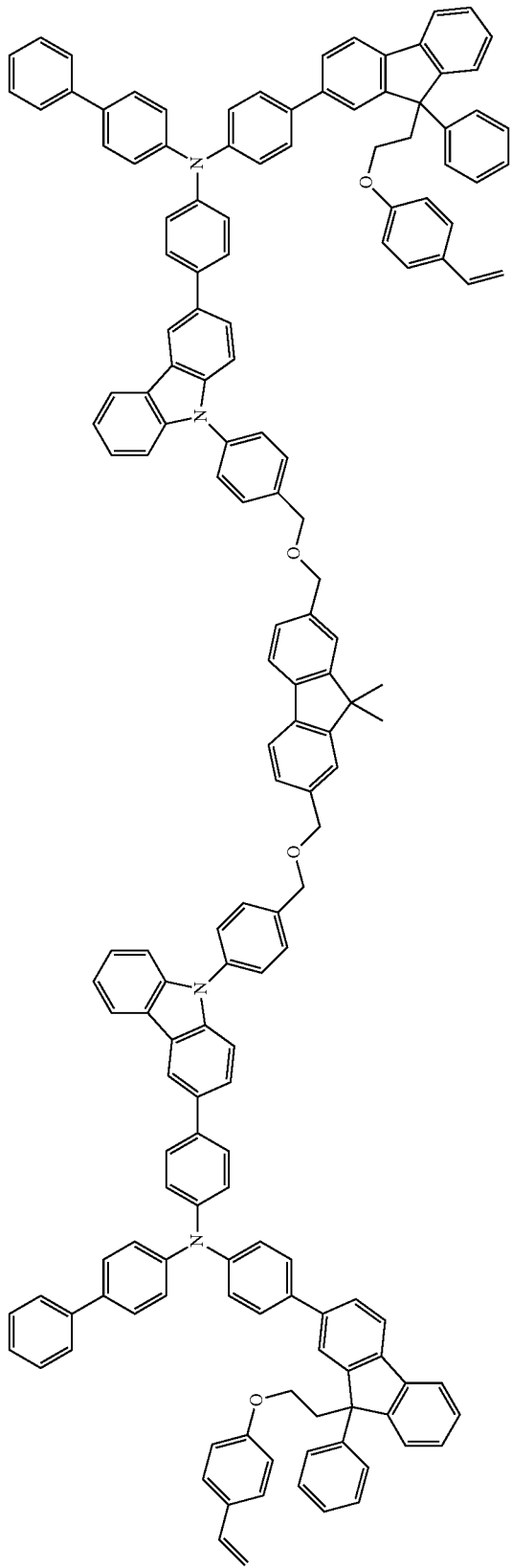

[Compound 99]
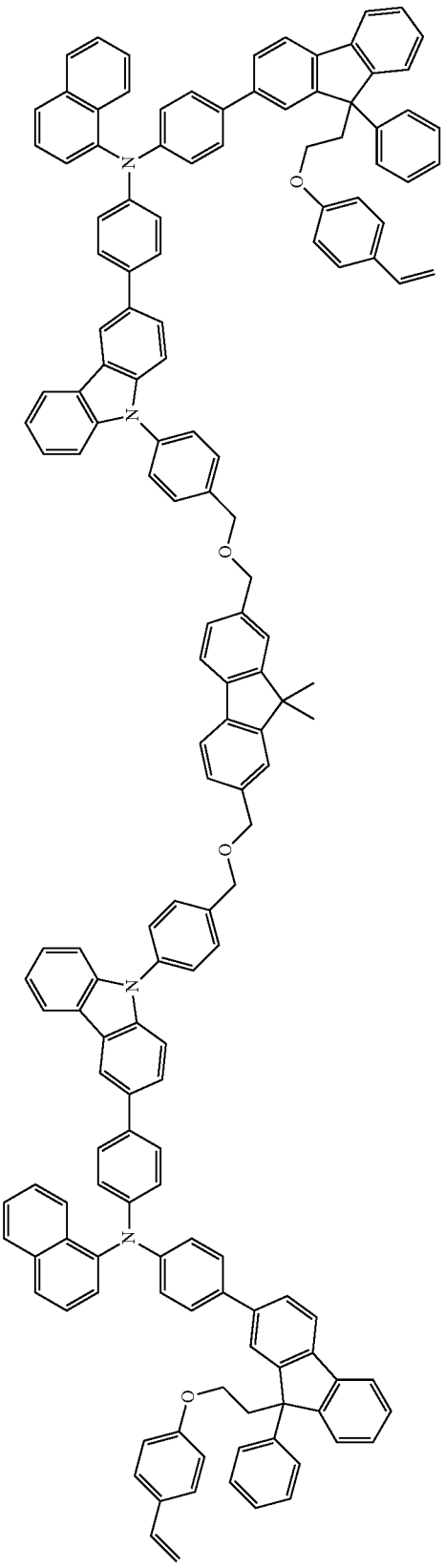
[Compound 100]
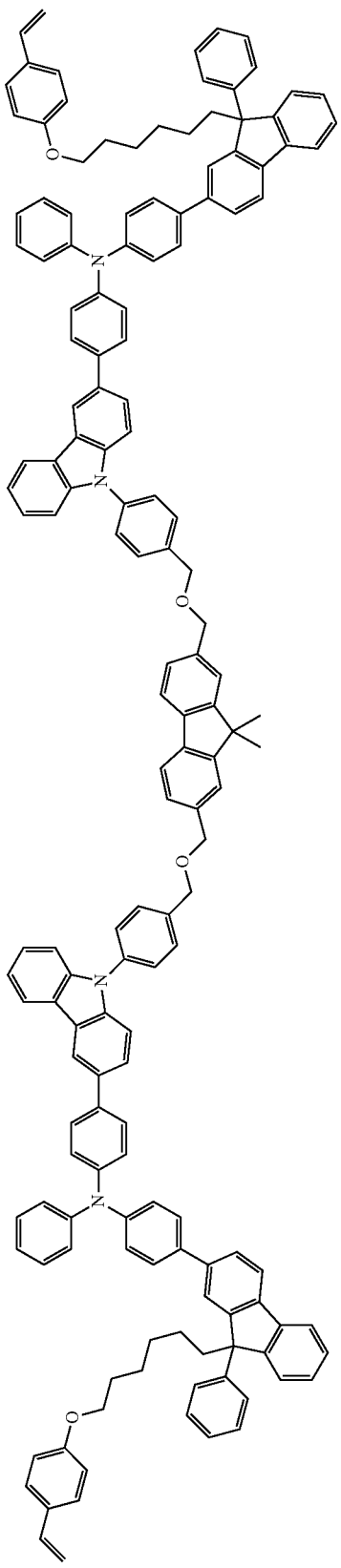

[Compound 101]
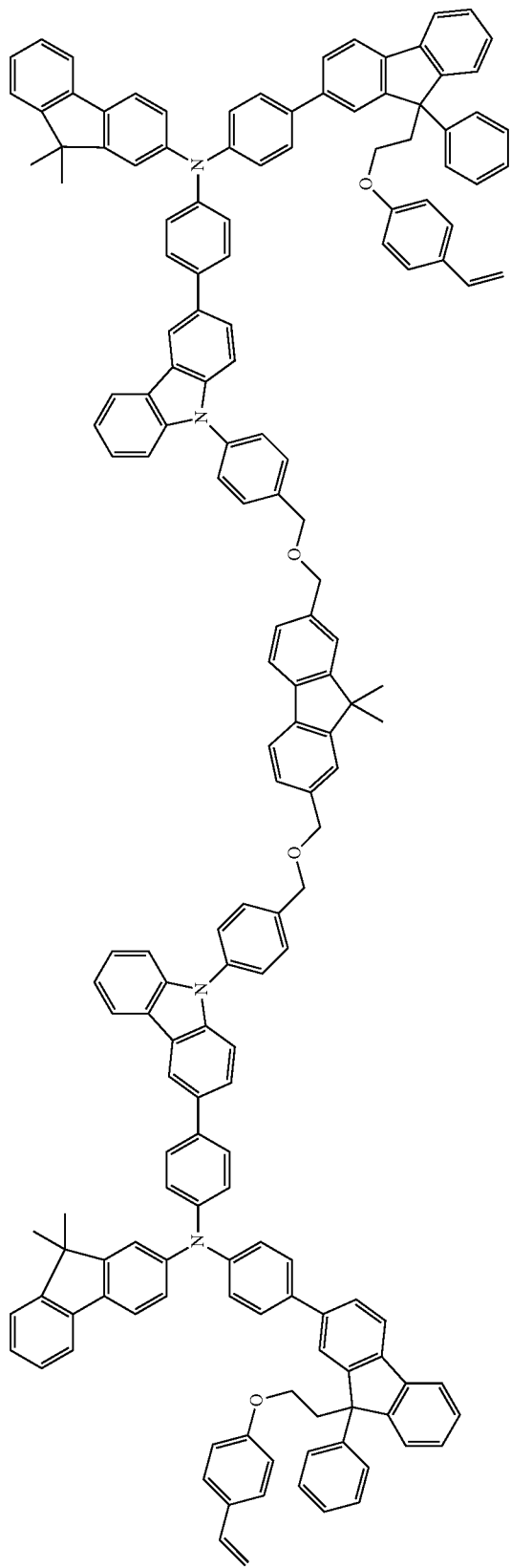

[Compound 102]
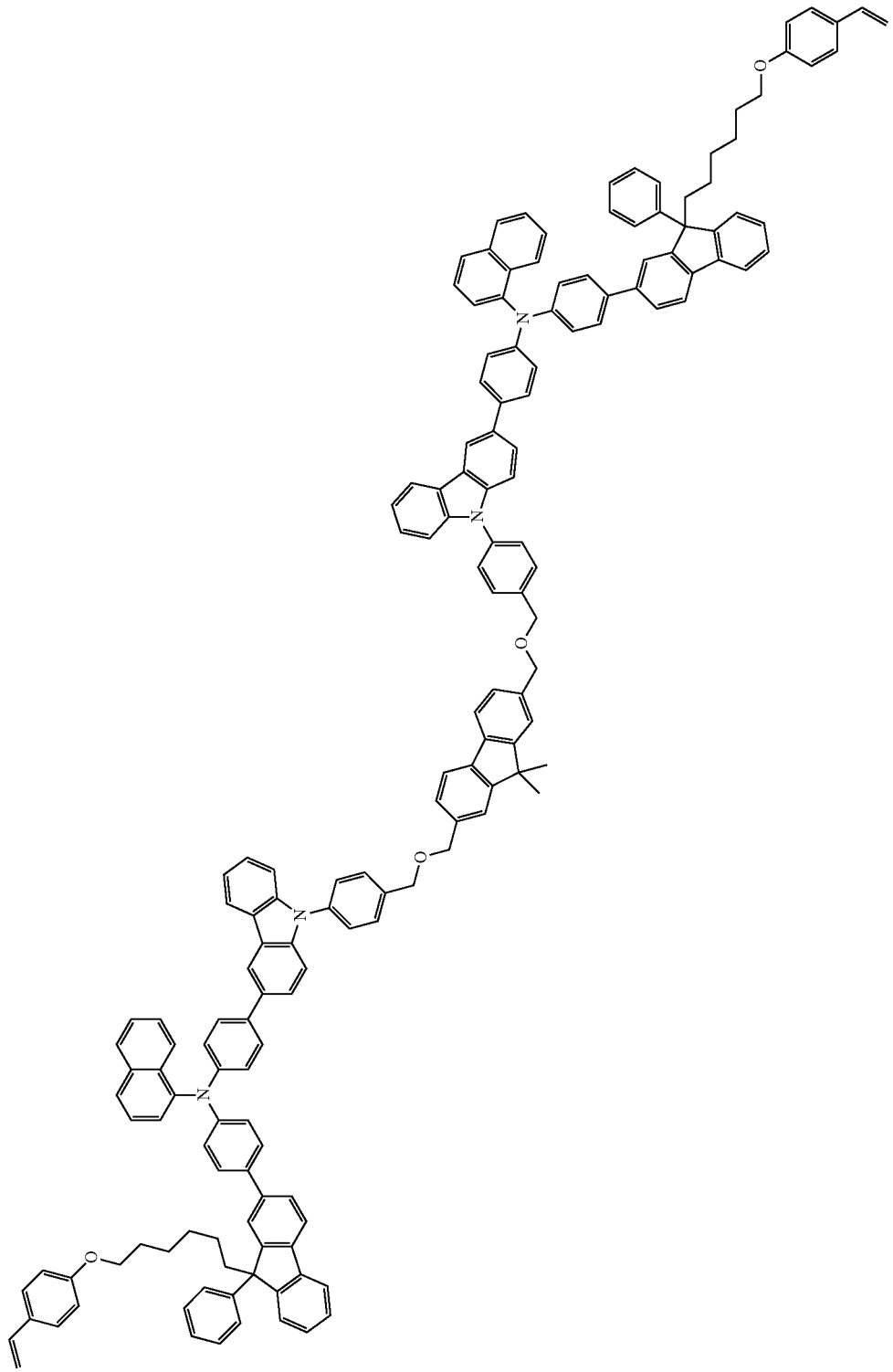

[Compound 103]
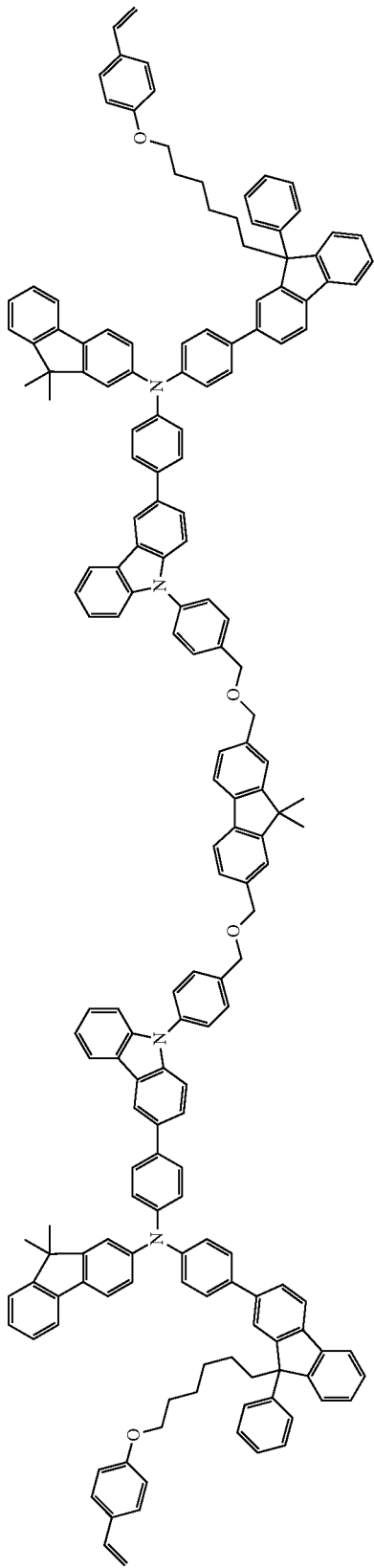
[Compound 104]
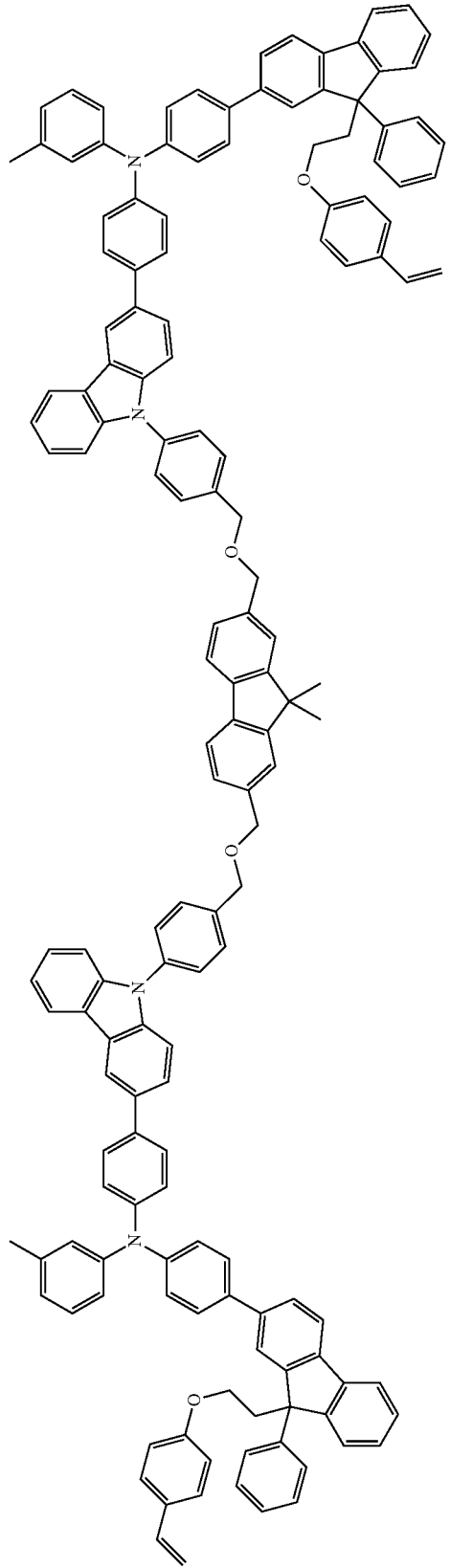

-continued
[Compound 105]
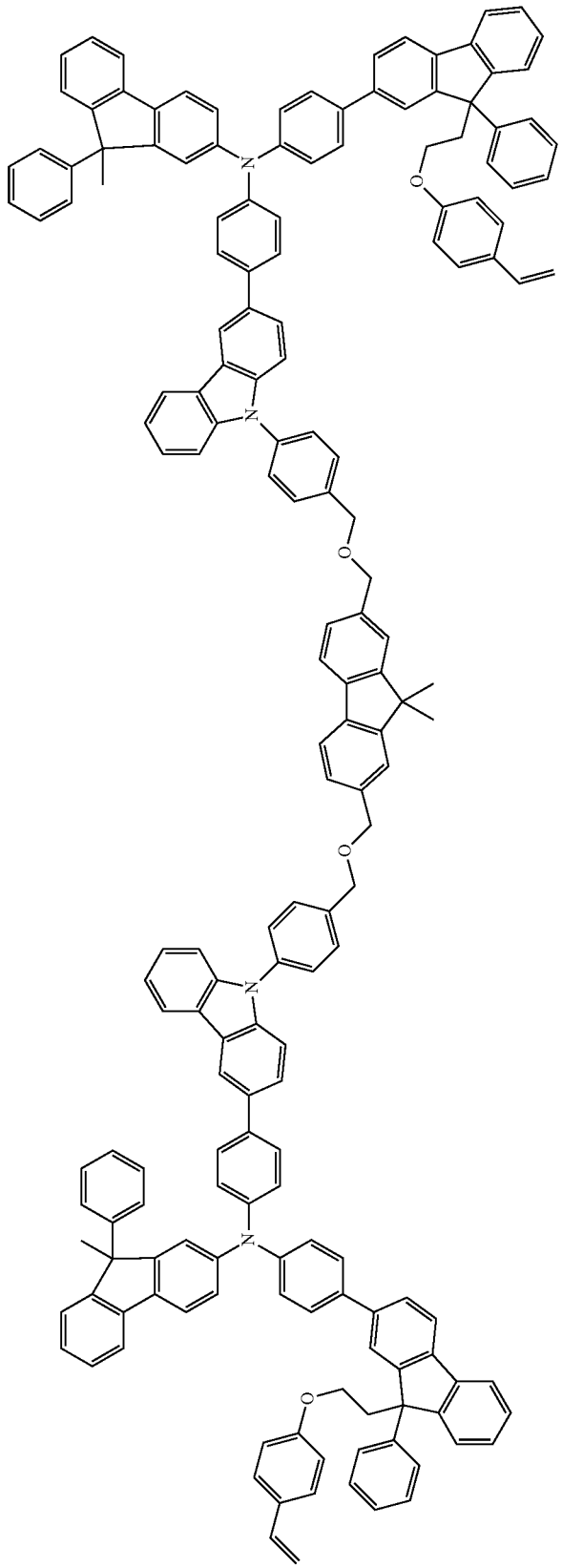
[Compound 106]
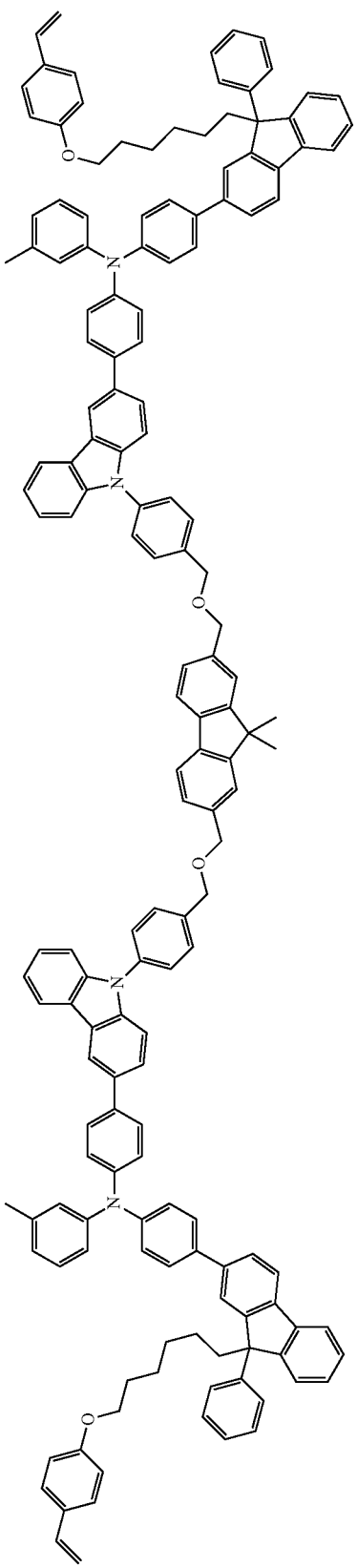

[Compound 107]
[Compound 108]
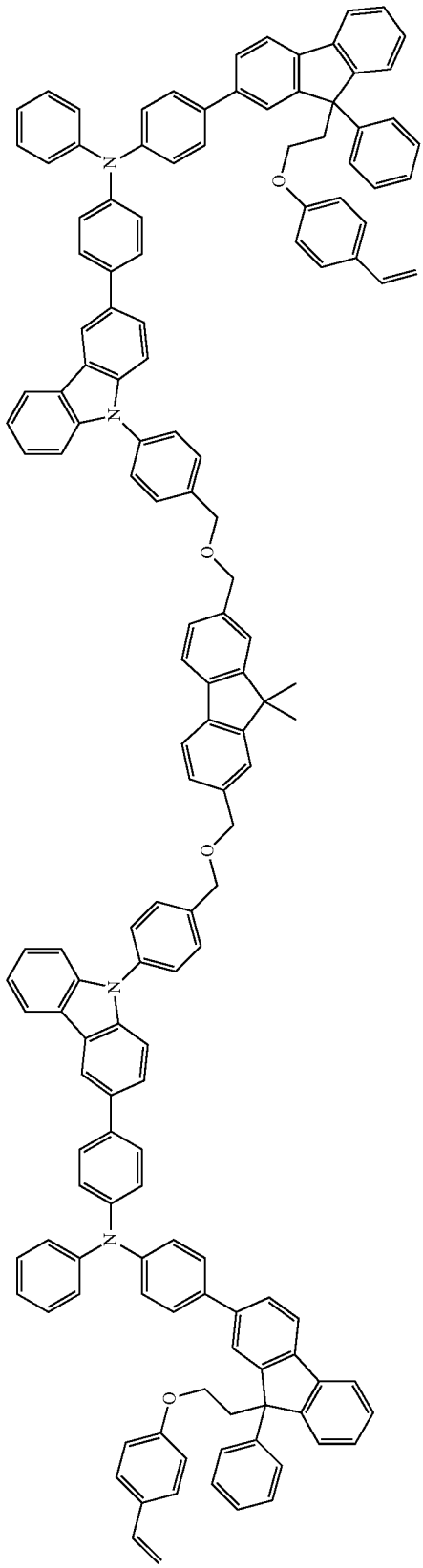
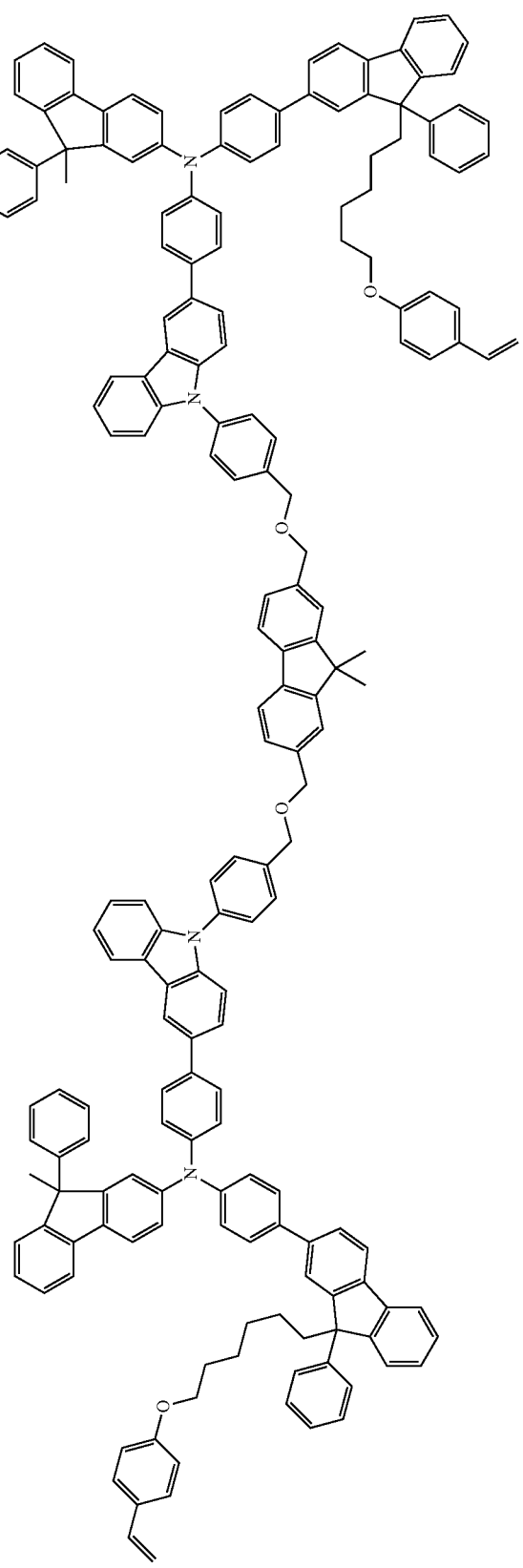

[Compound 109]
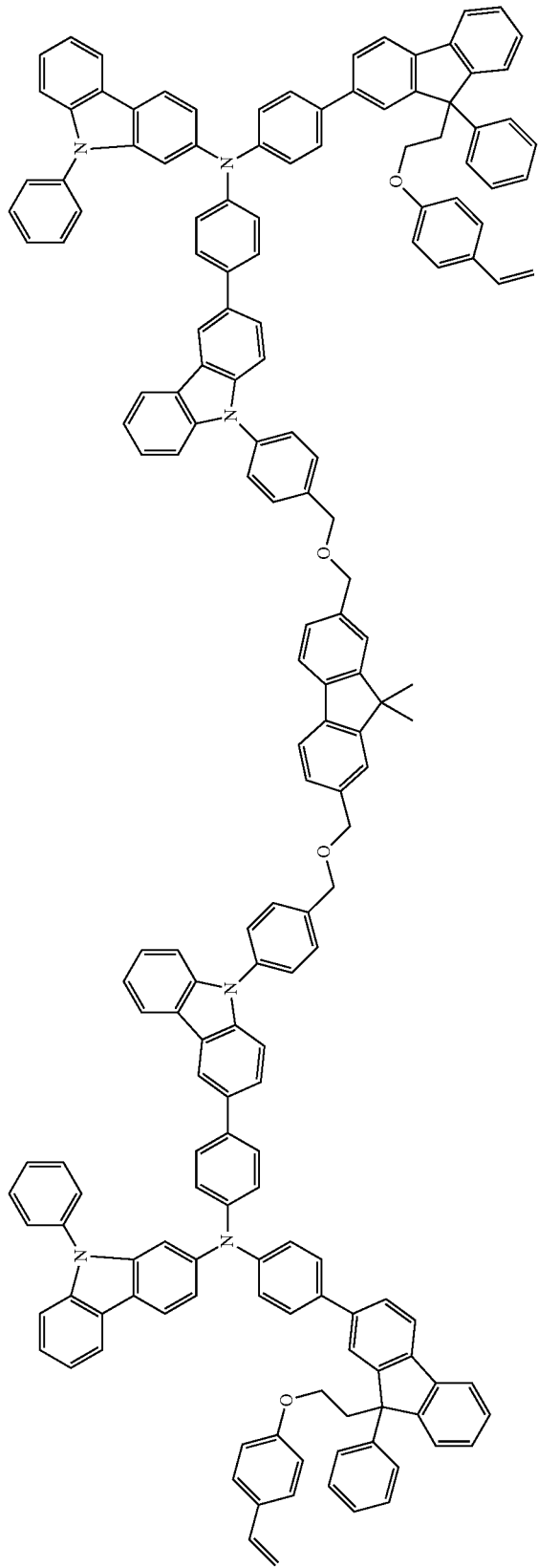

-continued
[Compound 110]
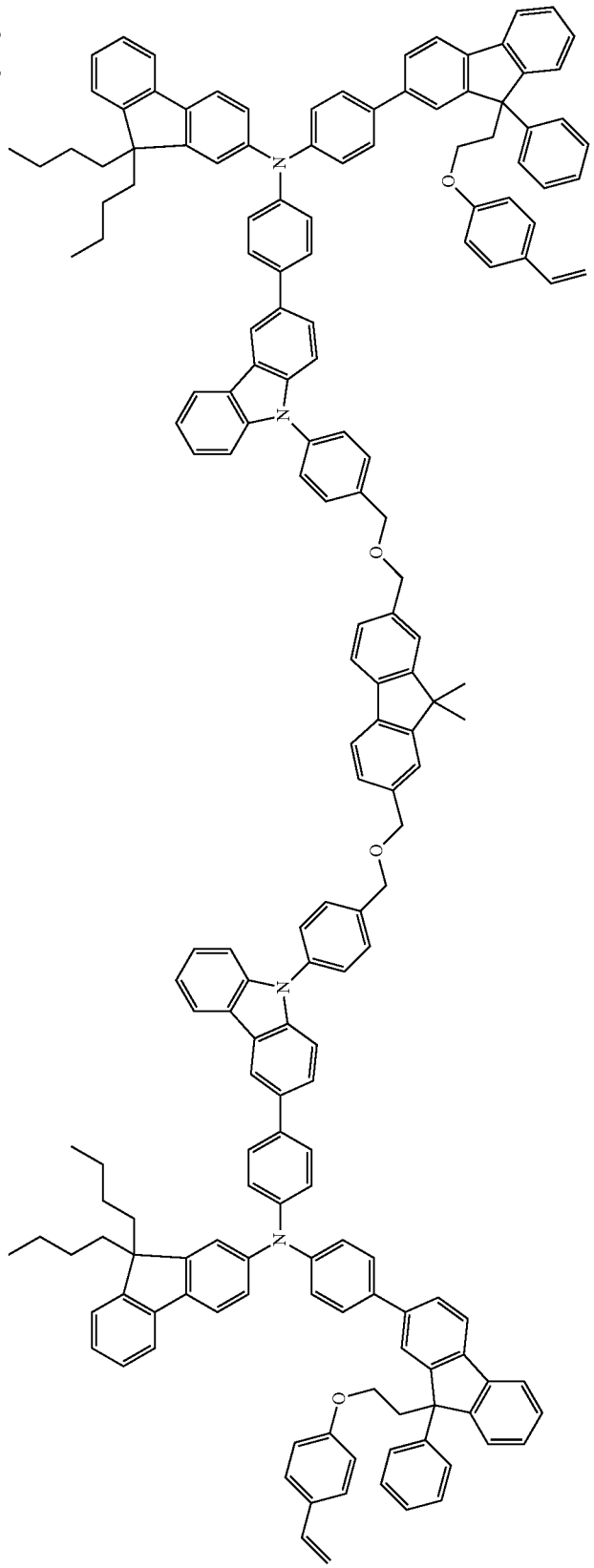
[Compound 111]
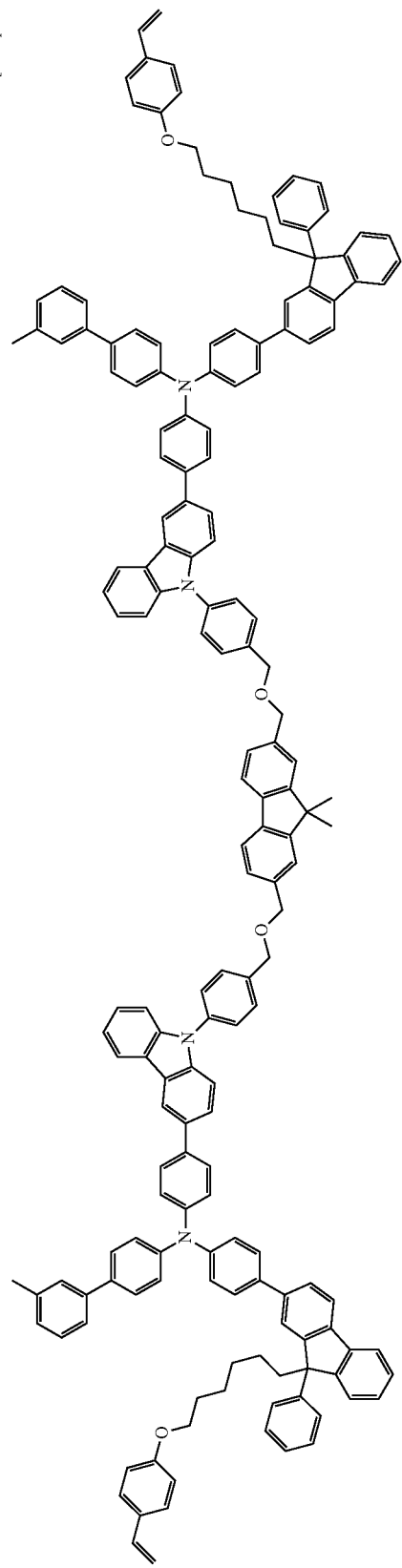

[Compound 112]
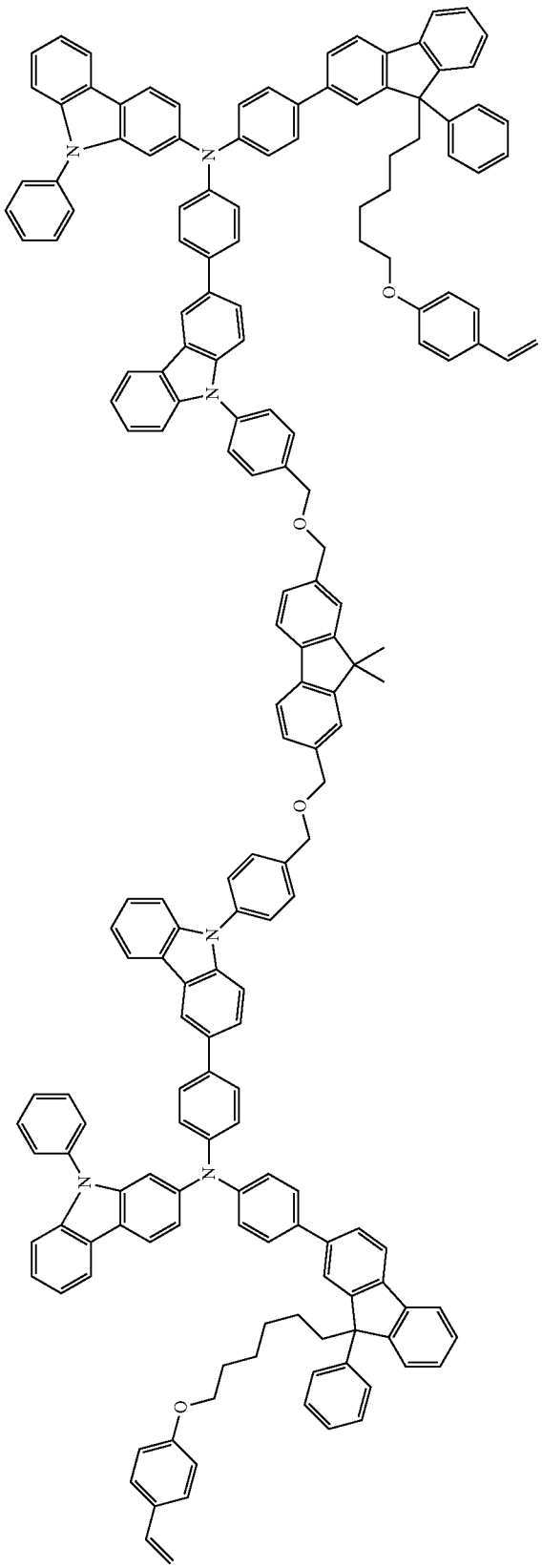
[Compound 113]
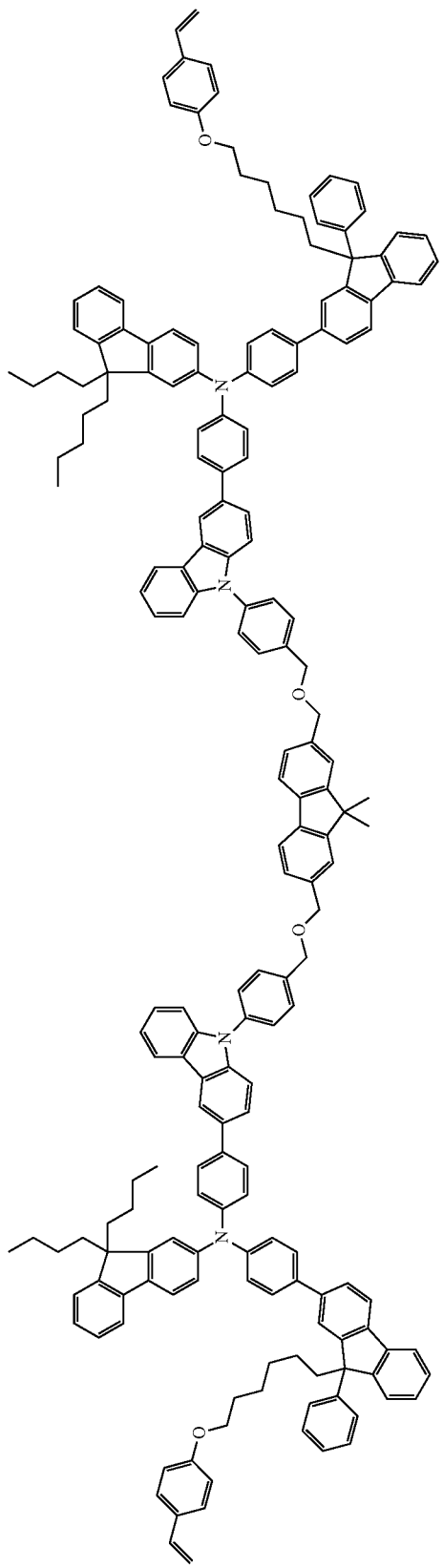

[Compound 114]
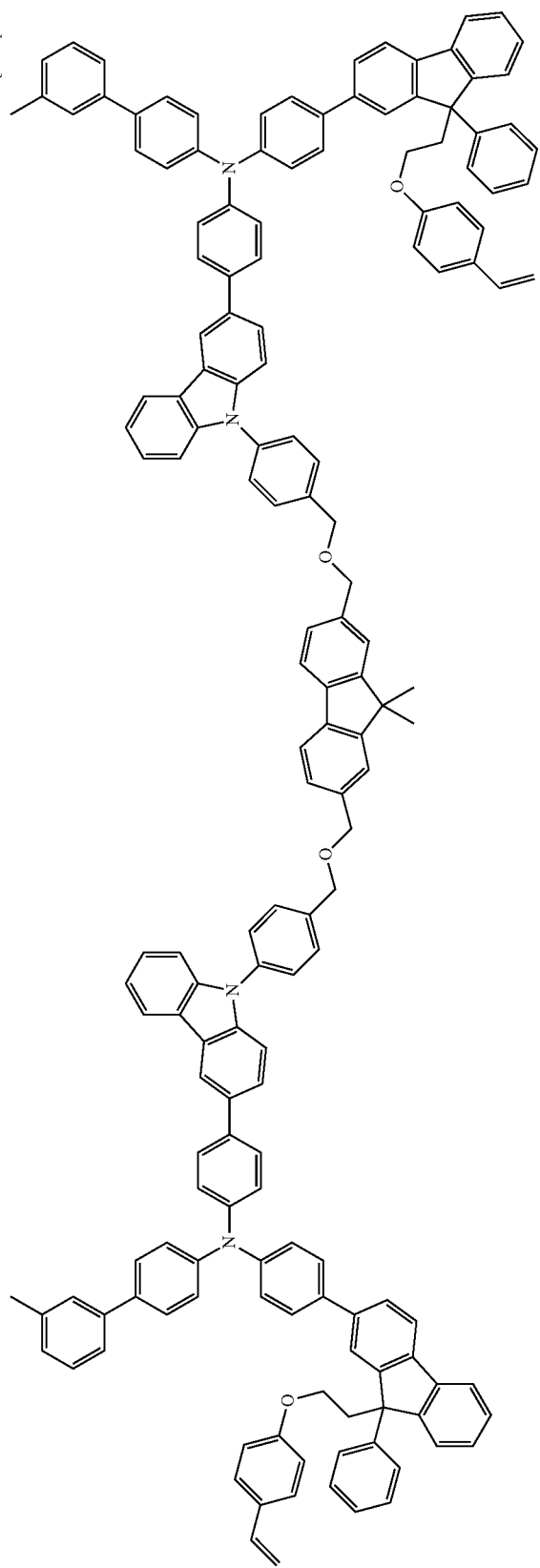

[Compound 115]
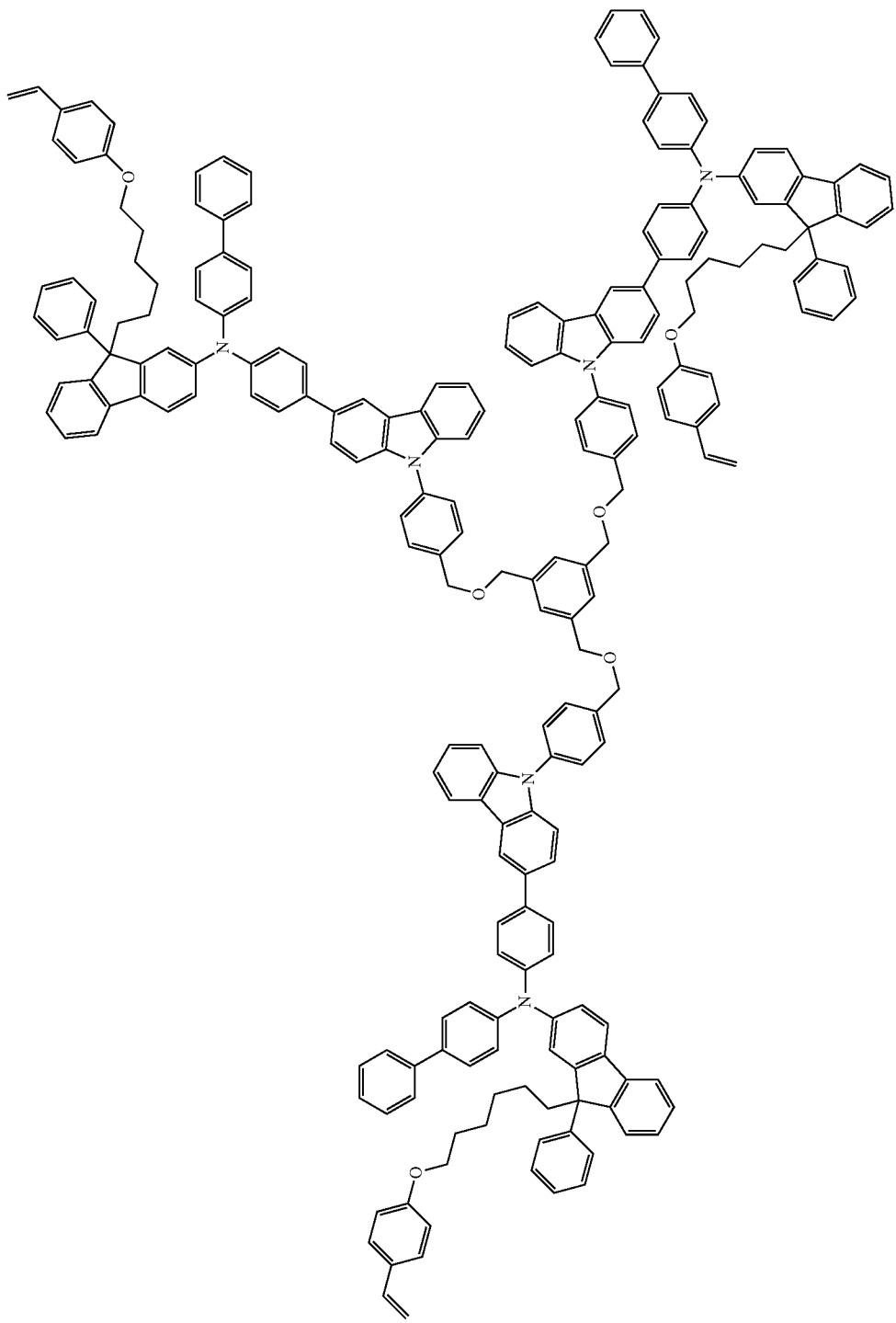

[Compound 116]
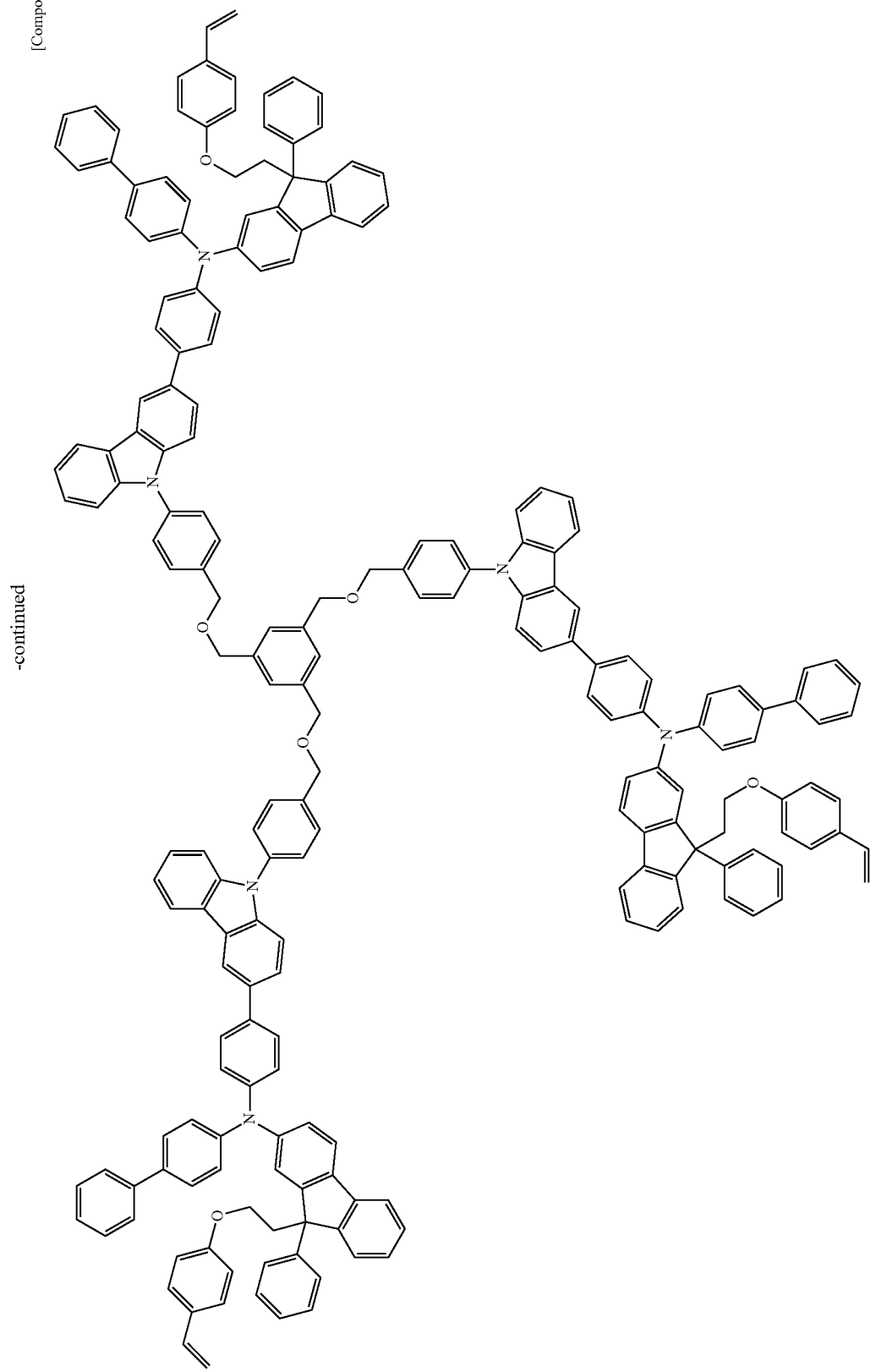

[Compound 117]
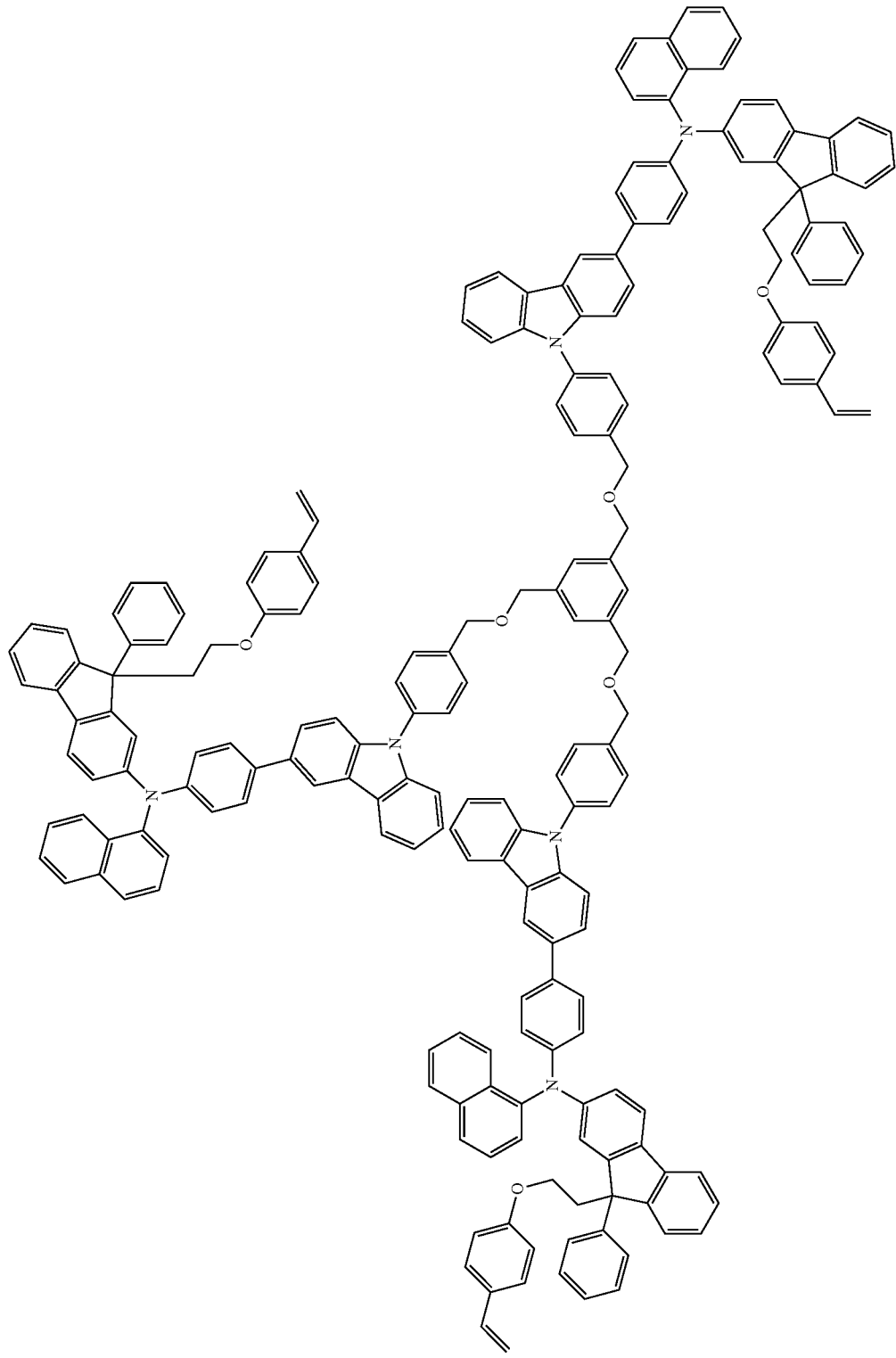

[Compound 118]
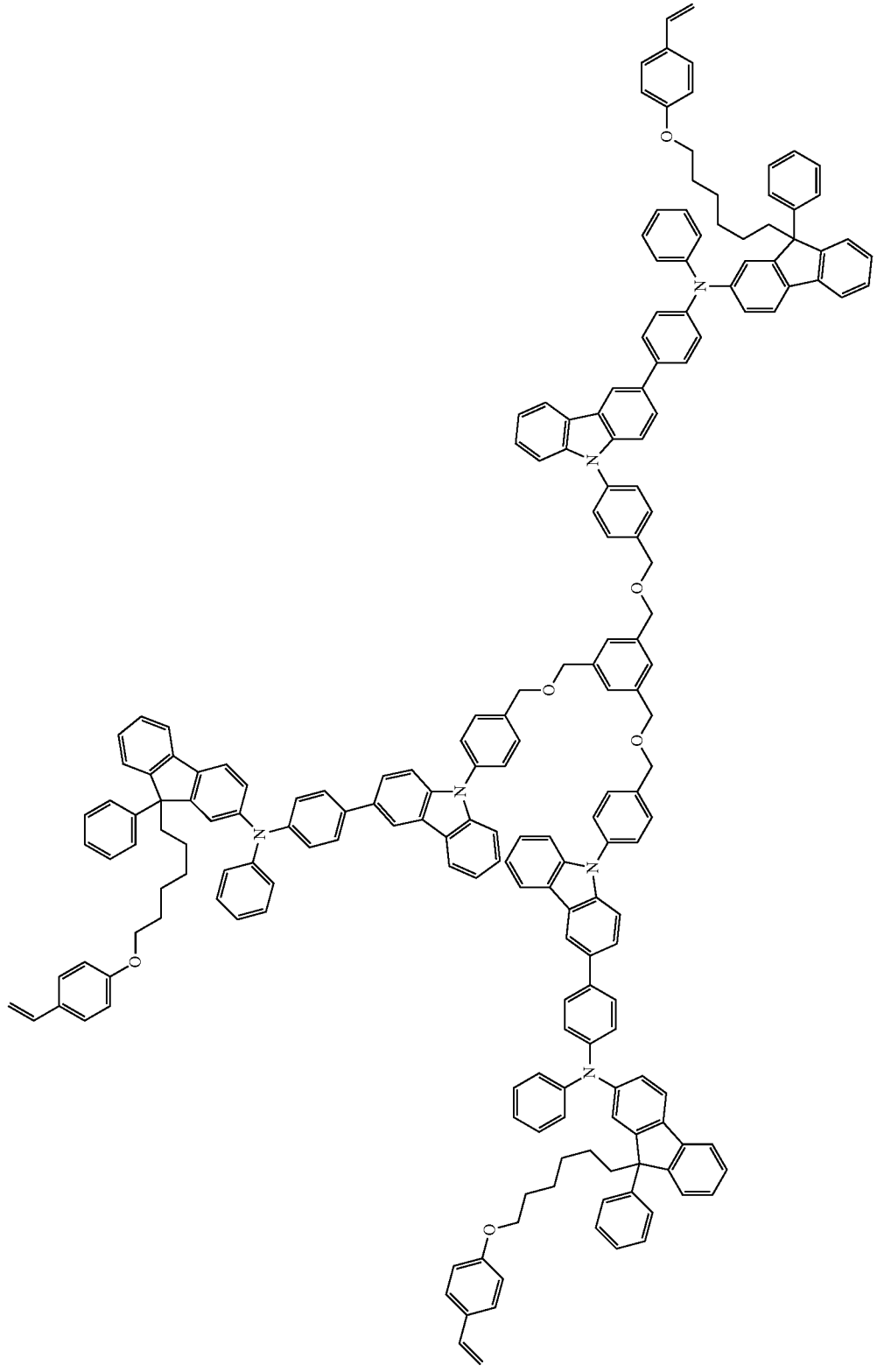

[Compound 119]
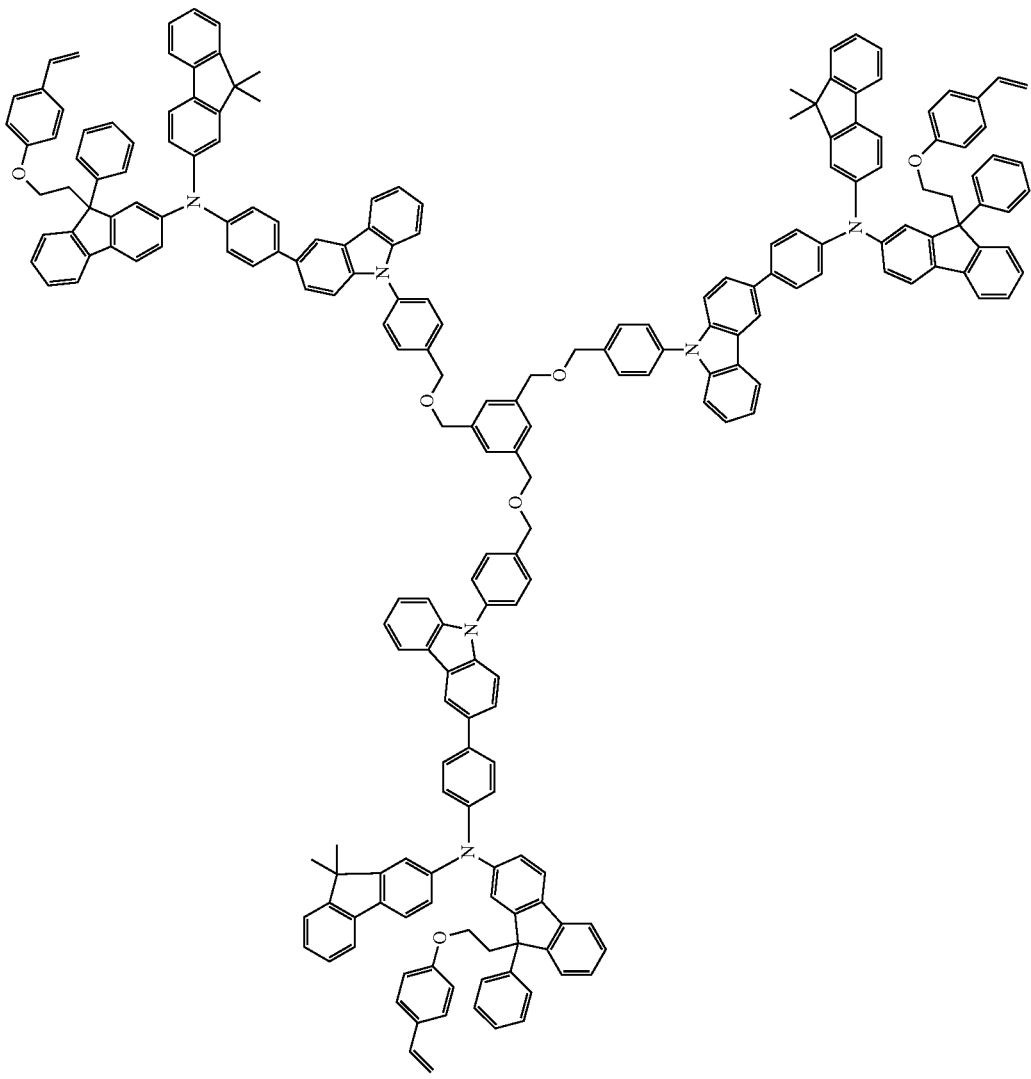

[Compound 120]
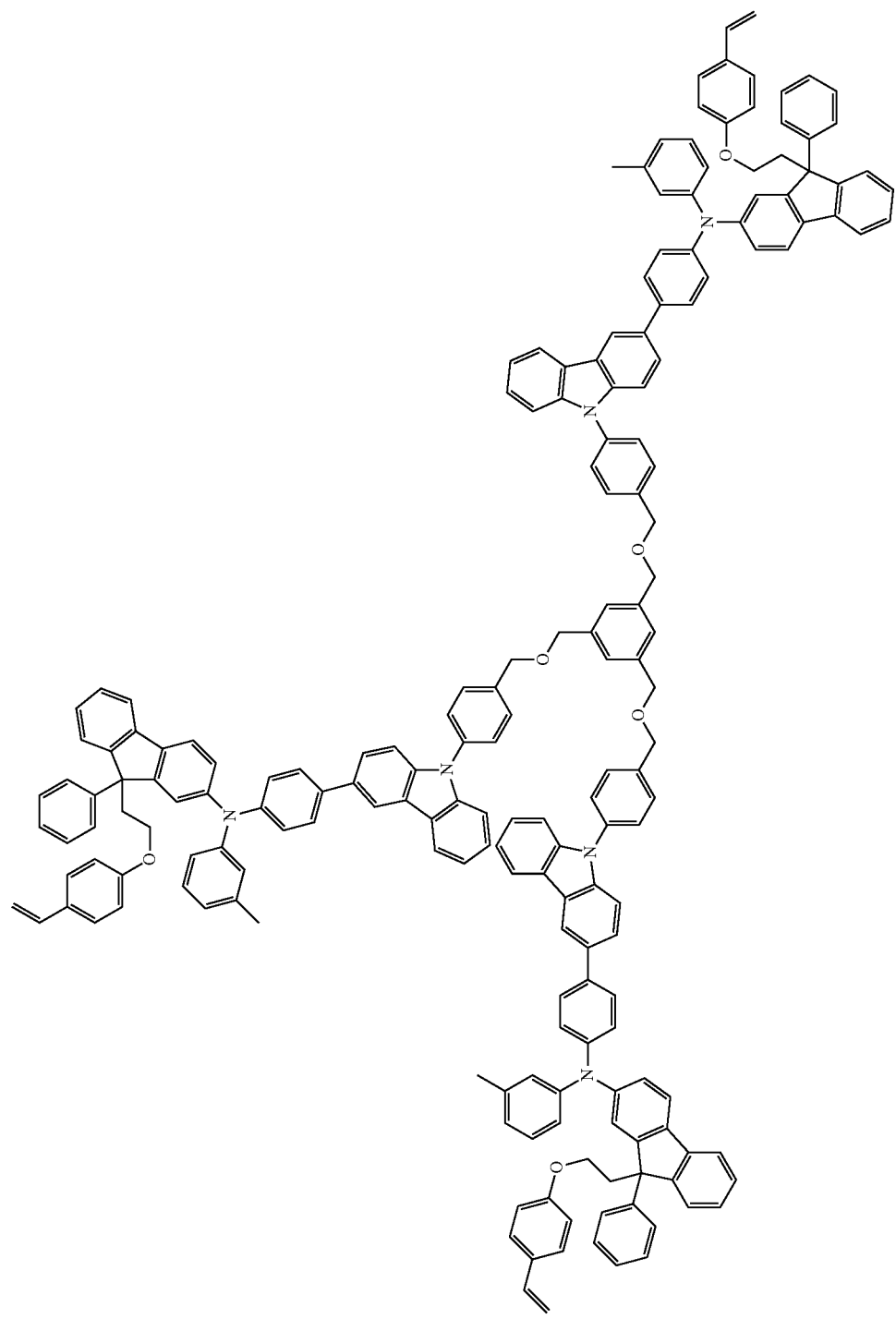

[Compound 121]
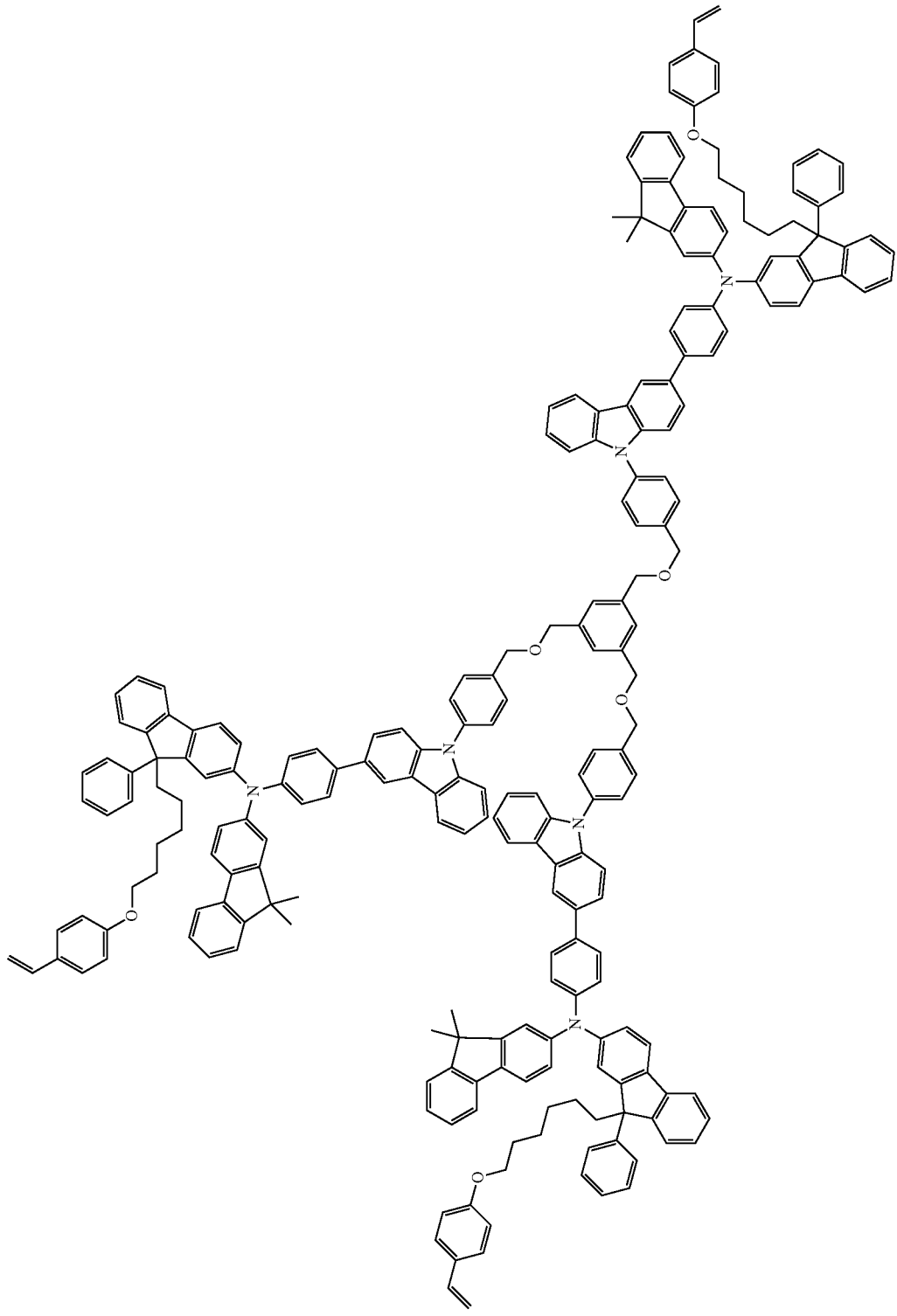

[Compound 122]
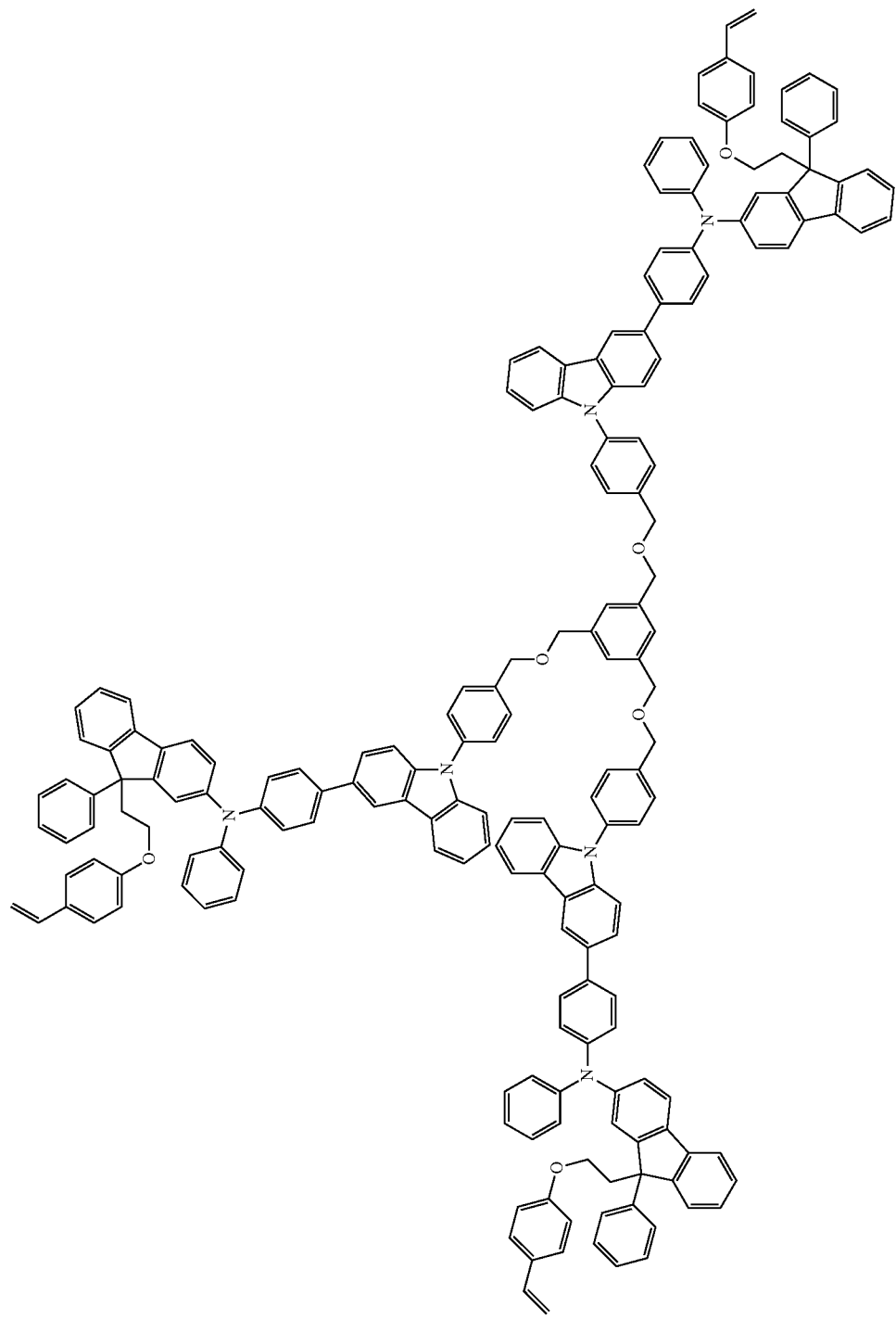

[Compound 123]
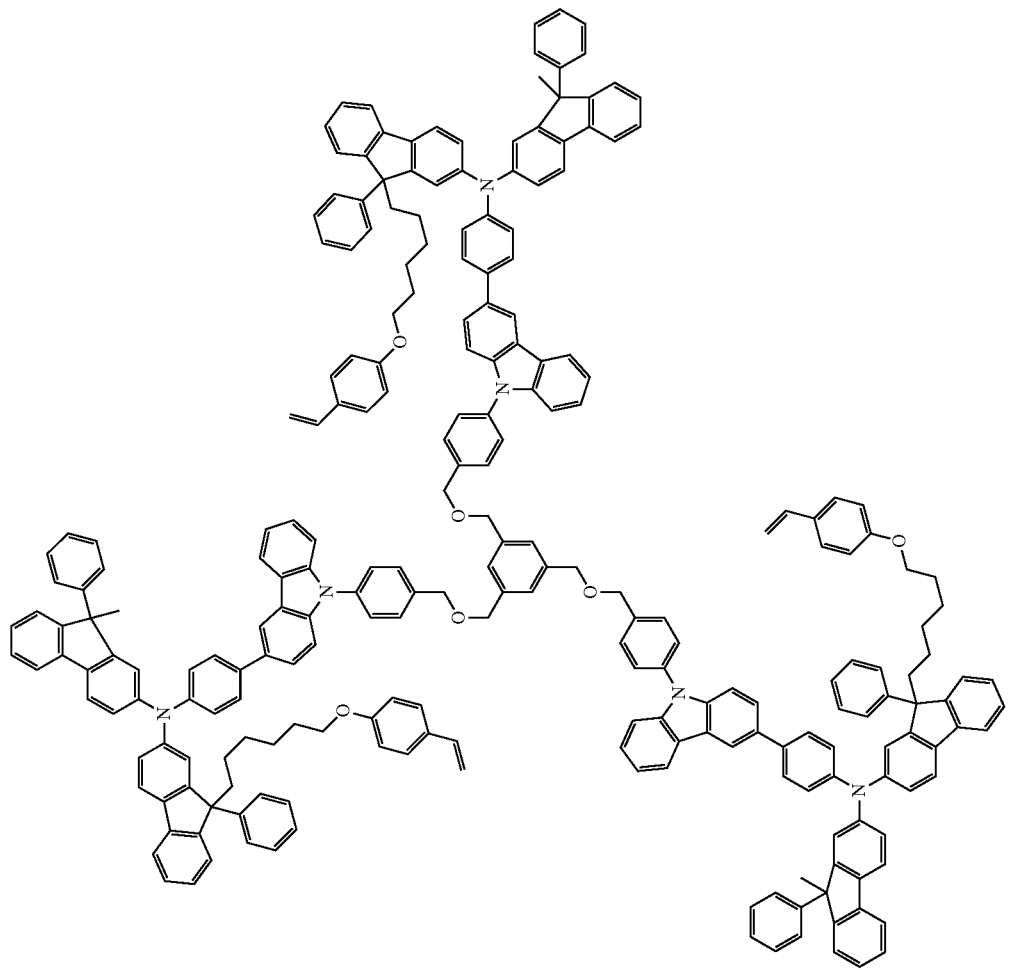

[Compound 124]
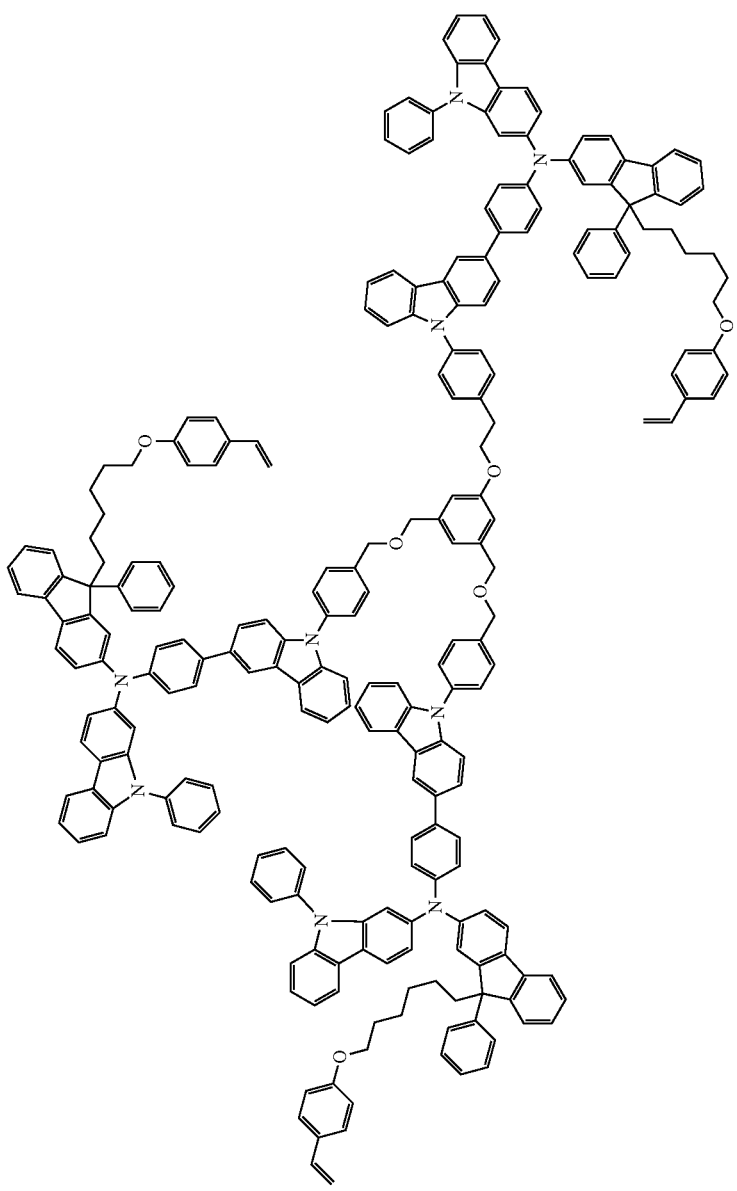

[Compound 125]
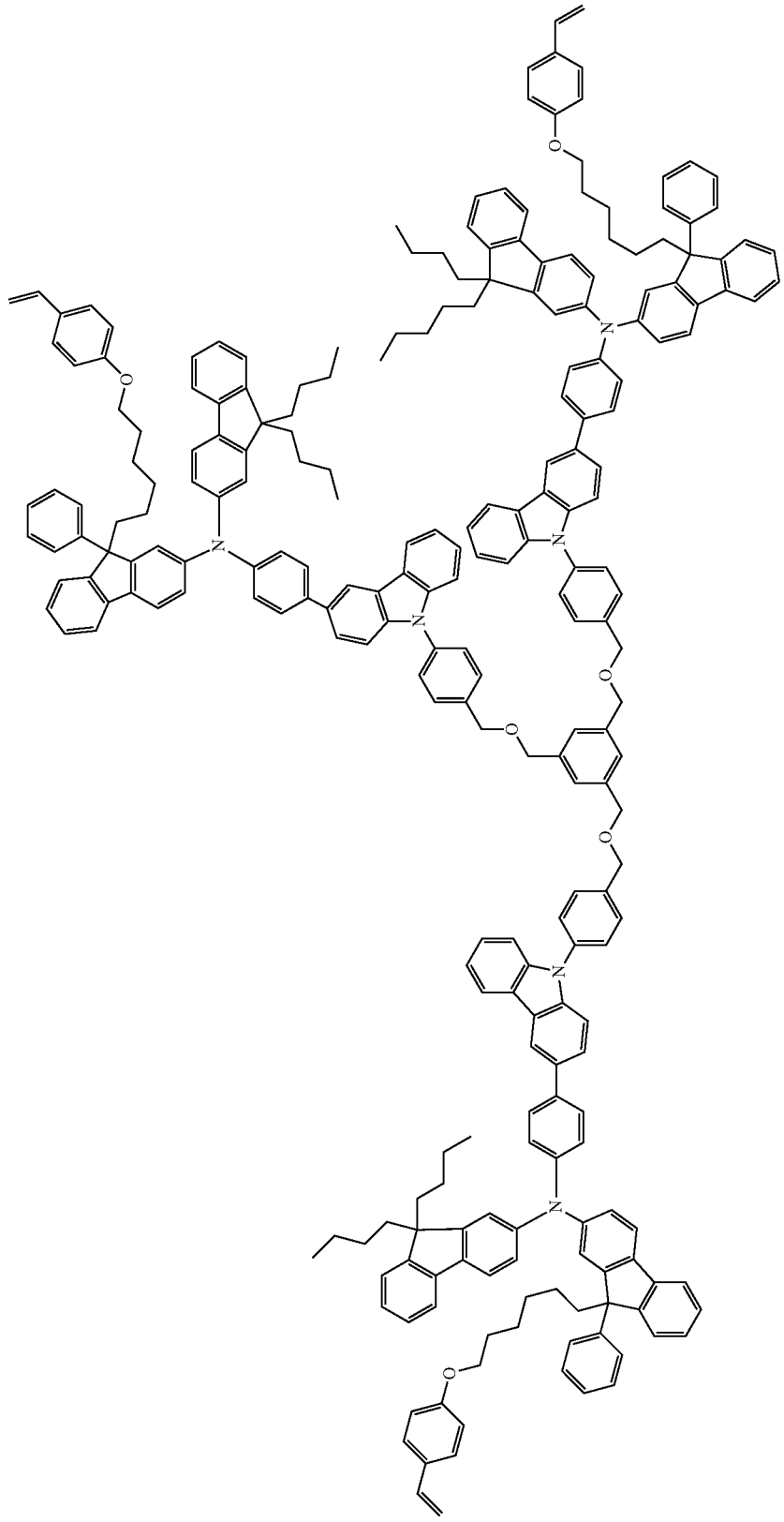

[Compound 126]

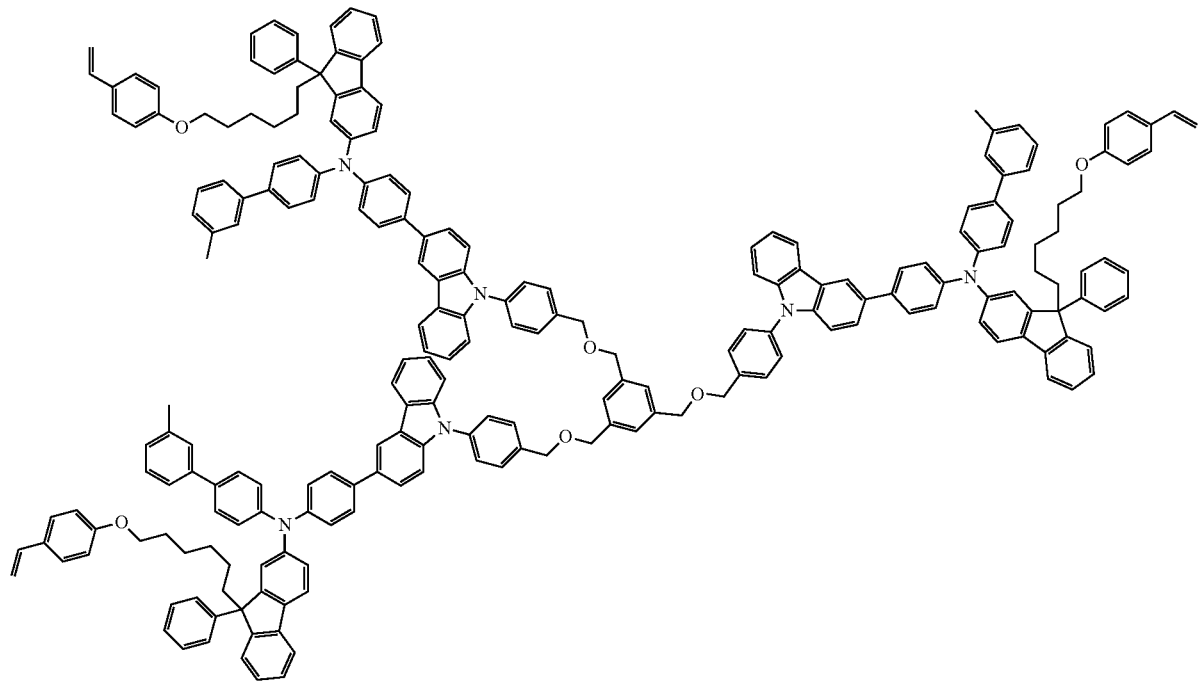

30

The compound according to one embodiment of the present specification may be prepared using a preparation method to describe below.

For example, the compound of Chemical Formula 1 may be prepared using a method described in the following general preparation method of Chemical Formula 1. Substituents may bond using methods known in the art, and types, positions or the number of the substituents may vary depending on technologies known in the art.

<General Preparation Method of Chemical Formula 1>

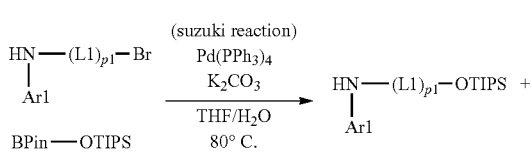 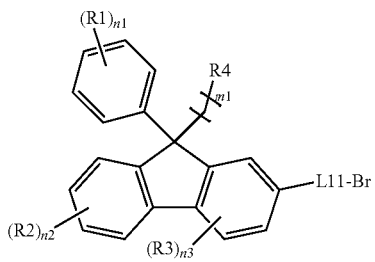

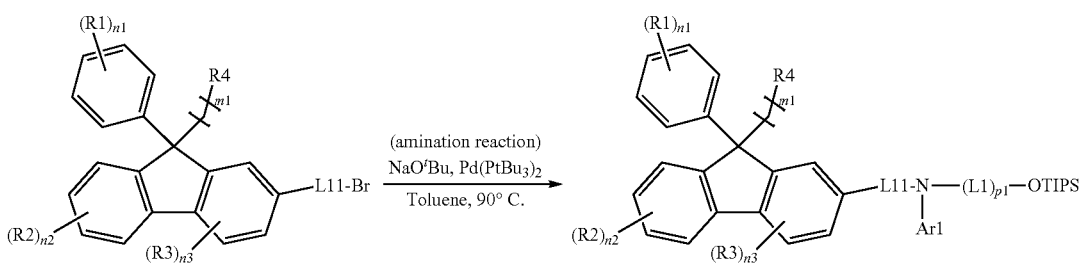

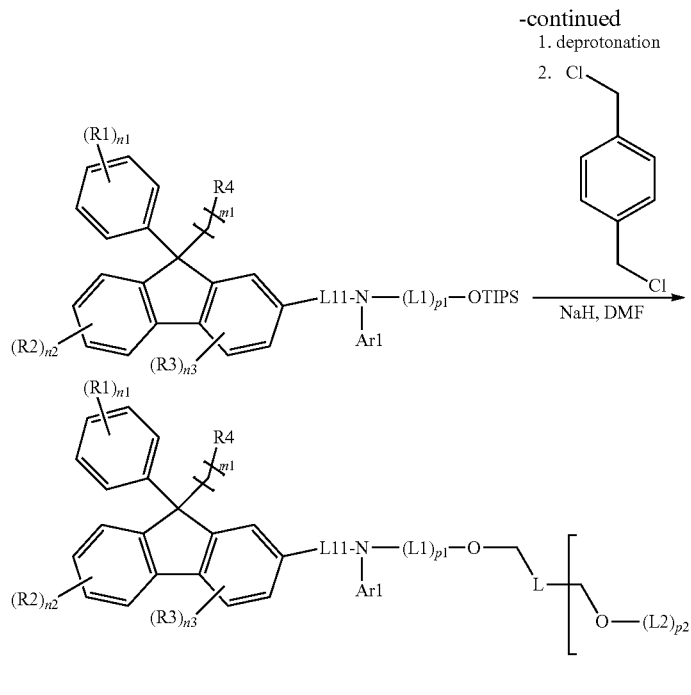

One embodiment of the present specification provides a coating composition comprising the compound of Chemical Formula 1 described above.

In one embodiment of the present specification, the coating composition comprises the compound of Chemical Formula 1 and a solvent.

In one embodiment of the present specification, the coating composition may further comprise one or two types of compounds selected from the group consisting of a compound having a functional group crosslinkable by heat or light introduced into the molecule, and a polymer compound.

In one embodiment of the present specification, the coating composition may further comprise a compound having a functional group crosslinkable by heat or light introduced into the molecule. When the coating composition further comprises a compound having a functional group crosslinkable by heat or light introduced into the molecule, the degree of curing of the coating composition may be further increased.

In one embodiment of the present specification, the compound having a functional group crosslinkable by heat or light introduced into the molecule has a molecular weight of 100 g/mol to 3,000 g/mol.

In one embodiment of the present specification, the coating composition may further comprise a polymer compound. When the coating composition further comprises a polymer compound, ink properties of the coating composition may be further increased. In other words, the coating composition further comprising a polymer compound may provide proper viscosity for coating or ink jetting.

In one embodiment of the present specification, the polymer compound has a molecular weight of 10,000 g/mol to 200,000 g/mol.

In one embodiment of the present specification, the coating composition may be a liquid phase. The "liquid phase" means in a liquid state at room temperature and atmospheric pressure.

In one embodiment of the present specification, examples of the solvent may comprise chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone, cyclohexanone, isophorone, tetralone, decalone or acetylacetone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; tetraline, and the like, however, the solvent is not limited thereto as long as it is a solvent capable of dissolving or dispersing the compound of Chemical Formula 1 according to one embodiment of the present disclosure.

In another embodiment, the solvent may be used either alone as one type, or as a mixture mixing two or more solvent types.

In one embodiment of the present specification, the coating composition does not further comprise a p-doping material.

In one embodiment of the present specification, the coating composition further comprises a p-doping material.

In the present specification, the p-doping material means a material enabling a host material to have a p semiconductor property. The p semiconductor property means a property receiving holes through injection or transferring holes at a highest occupied molecular orbital (HOMO) energy level, that is, a property of a material having high hole conductivity.

In one embodiment of the present specification, the p-doping material may be represented by any one of the following Chemical Formula A or B, but is not limited thereto.

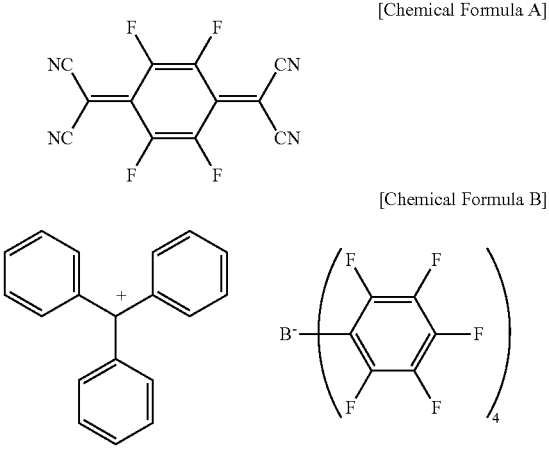

[Chemical Formula A]

[Chemical Formula B]

In the present specification, the p-doping material is not limited as long as it has a p semiconductor property, and one, two or more types thereof may be used, and types thereof are not limited.

In one embodiment of the present specification, a content of the p-doping material is from 0% by weight to 50% by weight based on the compound of Chemical Formula 1.

In one embodiment of the present specification, a content of the p-doping material is from 0% by weight to 30% by weight based on a total solid content of the coating composition. In one embodiment of the present specification, a content of the p-doping material is preferably from 1% by weight to 30% by weight based on a total solid content of the coating composition, and in another embodiment, a content of the p-doping material is more preferably from 10% by weight to 30% by weight based on a total solid content of the coating composition.

In another embodiment, the coating composition has viscosity of 2 cP to 15 cP.

Satisfying the above-mentioned viscosity is advantageous in manufacturing a device.

Another embodiment of the present specification provides an organic light emitting device formed using the coating composition.

In one embodiment of the present specification, the organic light emitting device comprises a first electrode; a second electrode; and one or more organic material layers provided between the first electrode and the second electrode, wherein one or more layers of the organic material layers comprise a cured material of the coating composition, and the cured material of the coating composition is in a cured state by heat treating or light treating the coating composition.

In one embodiment of the present specification, the organic material layer comprising the cured material of the coating composition is a hole transfer layer or a hole injection layer.

In one embodiment of the present specification, the organic material layer comprising the cured material of the coating composition is an electron transfer layer or an electron injection layer.

In another embodiment, the organic material layer comprising the cured material of the coating composition is a light emitting layer.

In another embodiment, the organic material layer comprising the cured material of the coating composition is a light emitting layer, and the light emitting layer comprises the compound of Chemical Formula 1 as a host of the light emitting layer.

In another embodiment, the organic material layer comprising the coating composition is a light emitting layer, and the light emitting layer comprises the compound of Chemical Formula 1 as a dopant of the light emitting layer.

In one embodiment of the present specification, the organic light emitting device further comprises one, two or more layers selected from the group consisting of a hole injection layer, a hole transfer layer. an electron transfer layer, an electron injection layer, an electron blocking layer and a hole blocking layer.

In one embodiment of the present specification, the first electrode is an anode, and the second electrode is a cathode.

According to another embodiment, the first electrode is a cathode, and the second electrode is an anode.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

FIG. 1 illustrates the organic light emitting device, however, the organic light emitting device is not limited thereto.

When the organic light emitting device comprises a plurality of organic material layers, the organic material layers may be formed with materials that are the same as or different from each other.

The organic light emitting device of the present specification may be manufactured using materials and methods known in the art, except that one or more layers of the organic material layers are formed using the coating composition comprising the compound of Chemical Formula 1.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer thereon through a deposition or solution process, and then depositing a material capable of being used as a cathode thereon. In addition to such a method, the organic light emitting device may also be manufactured by consecutively depositing a cathode material, an organic material layer and an anode material on a substrate.

In addition, one embodiment of the present specification provides a method for manufacturing an organic light emitting device formed using the coating composition.

Specifically, in one embodiment of the present specification, the method for manufacturing an organic light emitting device comprises preparing a substrate; forming a first electrode on the substrate; forming one or more organic material layers on the first electrode; and forming a second electrode on the organic material layer, wherein the forming of organic material layers comprises forming one or more organic material layers using the coating composition.

In one embodiment of the present specification, the forming of one or more organic material layers using the coating composition uses a spin coating method.

In another embodiment, the forming of one or more organic material layers using the coating composition uses a printing method.

In an embodiment of the present specification, examples of the printing method comprise inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the heat treating may be performed through heat treatment, and a heat treatment temperature in the heat treating is from 80° C. to 250° C. According to one embodiment, the heat treating may be performed in two steps, and after progressing heat treatment at 80° C. to 250° C. as a first step, heat treatment may be progressed at 100° C. to 250° C. as a second step. According to another embodiment, heat treatment may be progressed at 80° C. to 150° C. in the first step, and heat treatment may be progressed at 120° C. to 200° C. in the second step.

In another embodiment, a heat treatment time in the heat treating is from 1 minute to 2 hours. According to one embodiment, the time may be from 1 minute to 1 hours, and in another embodiment, the time may be from 30 minutes to 1 hour.

According to another embodiment, the heat treating may be progressed in the air or under the nitrogen atmosphere.

When the heat treatment or the light treatment is included in the forming of an organic material layer formed using the coating composition, an organic material layer comprising a thin-filmed structure by a plurality of the compounds included in the coating composition forming crosslinkage may be provided. In this case, being dissolved by a solvent or being morphologically affected or decomposed may be prevented when other layers are laminated on a surface of the organic material layer formed using the coating composition.

Accordingly, when the organic material layer formed using the coating composition is formed comprising the heat treatment or the light treatment, resistance for the solvent increases, and multiple layers may be formed by repeatedly performing solution deposition and crosslinking methods, and as a result, lifetime properties of a device may be enhanced by increasing stability.

As the anode material, materials having large work function are normally preferred so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material comprise metals such as barium, magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof comprise arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)- based polymers; spiro compounds; polyfluorene, rubrene, or the like, but are not limited thereto.

The light emitting layer may comprise a host material and a dopant material.

The host material comprises fused aromatic ring derivatives, heteroring-containing compounds or the like. Specifically, the fused aromatic ring derivative comprises anthracene derivatives, pyrene derivatives, naphthalene derivatives, pentacene derivatives, phenanthrene compounds, fluoranthene compounds and the like, and the heteroring-containing compound comprises carbazole derivatives, dibenzofuran derivatives, ladder-type furan compounds, pyrimidine derivatives and the like, however, the material is not limited thereto.

The dopant material comprises aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and comprises arylamino group-comprising pyrene, anthracene, chrysene, periflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex comprises iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof comprise Al complexes of 8-hydroxyquinoline; complexes comprising Alq$_3$; organic radical compounds; hydroxyflavon-metal complexes, or the like, but are not limited thereto. The electron transfer layer may be used together with any desired cathode material as used in the art. Particularly, examples of the suitable cathode material comprise common materials that have small work function, and in which an aluminum layer or a silver layer follows. Specifically, the cathode material comprises cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound comprises 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

PREPARATION EXAMPLE

Preparation Example 1. Preparation of Compound 1

1) Preparation of Intermediate 1

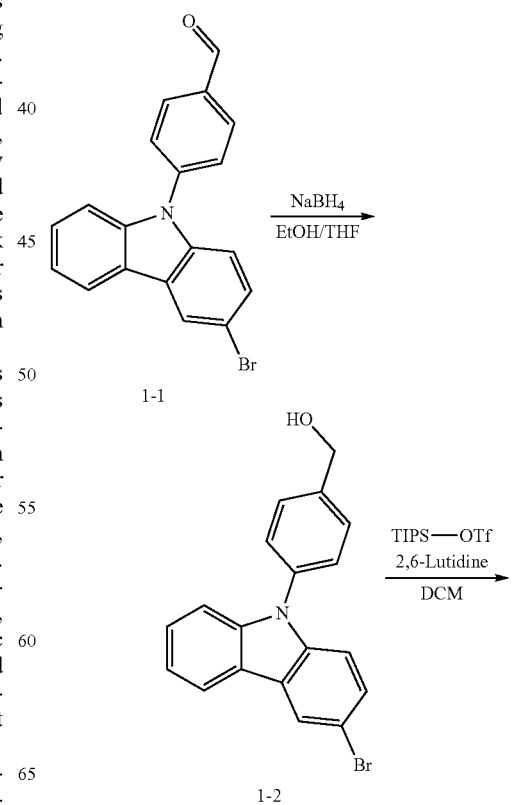

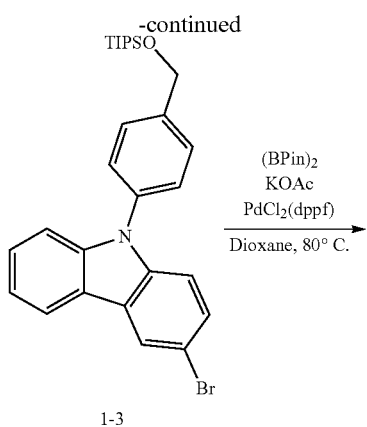

1-3

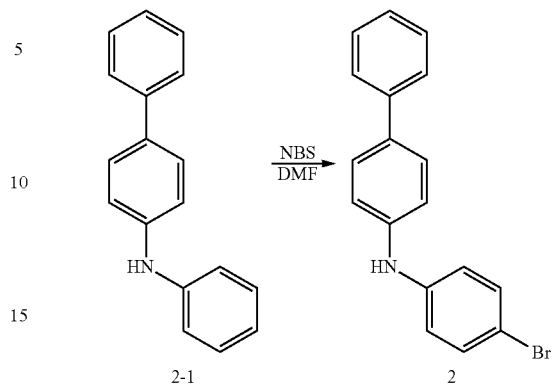

2) Preparation of Intermediate 2

After dissolving 2-1 (1 eq.) in dimethylformamide (DMF) at room temperature, N-bromosuccinimide (NBS, 1 eq.) was introduced thereto, and the result was stirred together. When the reaction was completed after 2 hours, ethanol was poured thereto for precipitation, and Intermediate 2 was obtained. (Yield: 90%)

3) Preparation of Intermediate 3

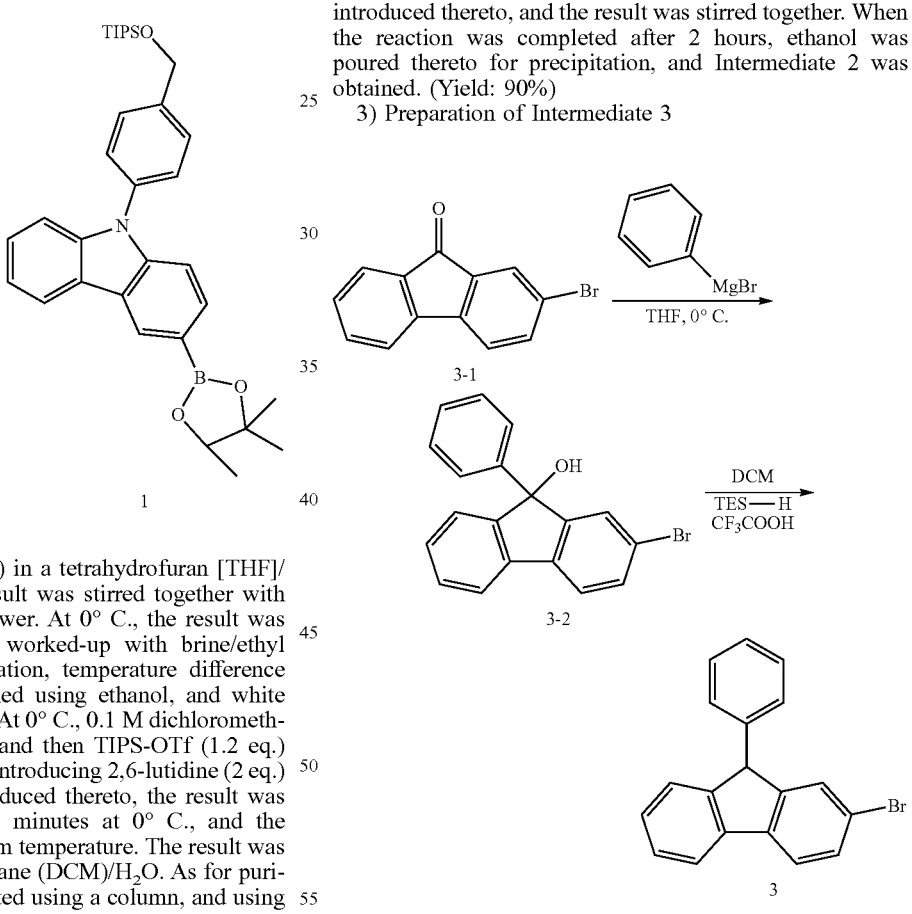

After dissolving 1-1 (1 eq.) in a tetrahydrofuran [THF]/ethanol mixture (2:1), the result was stirred together with NaBH$_4$ (1 eq.) at 0° C. or lower. At 0° C., the result was quenched with NH$_4$Cl, and worked-up with brine/ethyl acetate (EA). As for purification, temperature difference recrystallization was performed using ethanol, and white powders (1-2) were obtained. At 0° C., 0.1 M dichloromethane (DCM) was introduced, and then TIPS-OTf (1.2 eq.) was introduced thereto. After introducing 2,6-lutidine (2 eq.) thereto, 1-2 (1 eq.) was introduced thereto, the result was stirred for approximately 15 minutes at 0° C., and the temperature was raised to room temperature. The result was worked-up with dichloromethane (DCM)/H$_2$O. As for purification, the result was separated using a column, and using a hexane/DCM (20:1) mixture solution, 1-3 was obtained. 1-3 (1 eq.), KOAc (6 eq.) and (BPin)$_2$ (2 eq.) were introduced, and then dioxane was introduced thereto. After maintaining the temperature at 80° C., PdCl$_2$(dppf) (0.06 eq.) was introduced thereto, and the result was refluxed overnight under the N$_2$ atmosphere. The result was worked-up with ethyl acetate (EA)/H$_2$O, stirred for approximately 30 minutes after introducing acid clay was MgSO$_4$ thereto, and then passed through a celite/silica pad. As for purification, the result was separated using a column, and herein, an EA/hexane (1:50) mixture solution was used as an eluent to obtain Intermediate 1 (4.2 g).

Synthesis of 2-bromo-9-phenyl-9H-fluoren-9-ol (3-2): A flask holding a solution dissolving 2-bromo-9H-fluoren-9-one (1) (5 g, 19.3 mmol) in anhydrous tetrahydrofuran (THF) was placed in an ice water bath. Phenylmagnesium bromide (3 M in THF, 9.65 ml, 29.0 mmol) was introduced thereto, and the result was stirred for 20 minutes at 0° C. The reaction was stopped using NH$_4$Cl (aq.), and the result was extracted with diethyl ether (Et$_2$O). The organic layer was dried using MgSO$_4$, and the organic solvent was removed using a vacuum rotary evaporator. The residue was column purified to obtain Intermediate 3-2 (6.5 g, quantitive yield).

Synthesis of 2-bromo-9-phenyl-9H-fluorene (3): After dissolving 3-2 (3.6 g, 10.6 mmol) in dichloromethane [DCM], triethyl silane (2.6 ml, 16.1 mmol) and trifluoroacetic acid (1.3 ml) were introduced thereto, and the result was stirred overnight at room temperature. After identifying disappearance of 3-2 through thin layer identification, silica gel was introduced thereto, and the organic solvent was removed using a vacuum rotary evaporator. The product-adsorbed silica gel was column purified to obtain Intermediate 3 (3.26 g, yield 95%).

4) Synthesis of Intermediate 4

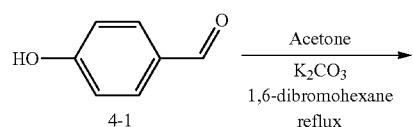

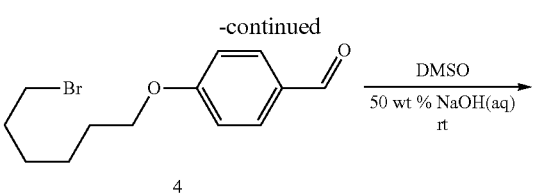

Synthesis of 4-((6-bromohexyl)oxy)benzaldehyde (4): After dissolving 4-hydroxybenzaldehyde (6.1 g, 50 mmol), potassium carbonate (10 g, 75 mmol) and 1,6-dibromohexane (15 ml, 100 mmol) in acetone, the result was refluxed for 3 hours. After filtering the reactant, the organic solvent was removed using a vacuum rotary evaporator. The result was column purified to obtain Intermediate 4 (9.9 g, yield 69%).

5) Synthesis of Intermediates 5 and 6

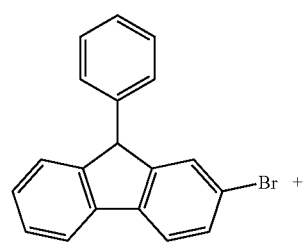

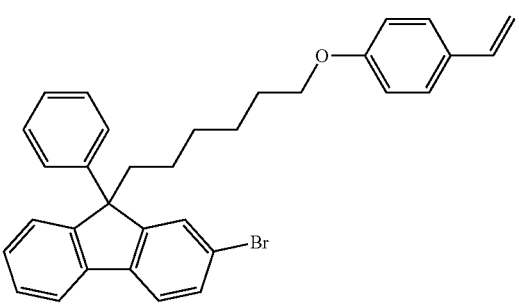

Synthesis of 4-((6-(2-bromo-9-phenyl-9H-fluoren-9-yl)hexyl)oxy)benzaldehyde (5): Intermediate 3 (3.7 g, 11.5 mmol) and Intermediate 4 (3 g, 10.5 mmol) were dissolved in dimethyl sulfoxide (DMSO) (20 ml) in a 50° C. oil bath. 50 wt % NaOH (aq.) (0.5 ml) was introduced thereto, the result was stirred overnight, 50 wt % NaOH (aq.) (0.5 ml) was introduced once again, and the result was further stirred for 2 hours. The reactant was introduced to water (400 ml) for precipitation, and the result was filtered. Solids obtained from the filtration was introduced to ethanol (100 ml), the result was stirred for approximately 10 minutes, and then filtered again. The filter cake was dried in a vacuum oven to obtain Intermediate 5 (4.48 g, yield 81%).

Synthesis of 2-bromo-9-phenyl-9-(6-(4-vinylphenoxy)hexyl)-9H-fluorene (6): A flask holding methylphosphonium bromide (5.1 g, 14.3 mmol) was placed in ice water, and anhydrous tetrahydrofuran [THF] (100 ml) was introduced thereto. KOtBu (1.6 g, 14.3 mmol) was introduced thereto, and the result was stirred for 30 minutes. 4-((6-(2-Bromo-9-phenyl-9H-fluoren-9-yl)hexyl)oxy)benzaldehyde (3 g, 5.7 mmol) dissolved in anhydrous THF was introduced to the reaction flask, and the result was stirred again for 1 hour. Water was introduced thereto to stop the reaction, and the result was extracted with dichloromethane [DCM]. The organic solvent was dried with MgSO$_4$, the result was filtered, and the organic solvent was removed using a vacuum rotary evaporator. The residue was column purified to obtain Intermediate 6 (2.63 g, yield 88%).

6) Preparation of Compound 1
(1) Preparation of Compound 1-1

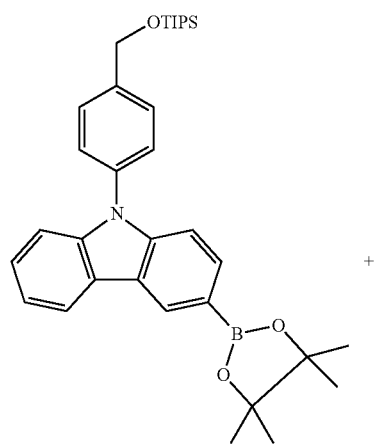

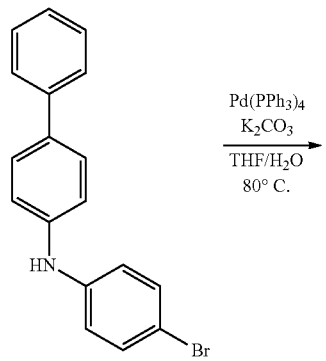

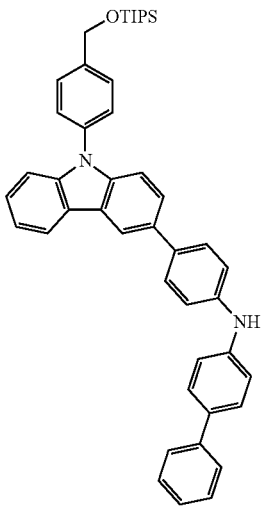

[Compound 1-1]

Intermediate 1 (1.1 eq.), Intermediate 2 (1 eq.) and K$_2$CO$_3$ (3 eq.) were introduced to a round flask, and degassed THF/H$_2$O was introduced thereto. After maintaining the temperature at 80° C., Pd(PPh$_3$)$_4$ (0.1 eq.) was introduced thereto, and the result was refluxed overnight under the N$_2$ atmosphere. The result was worked-up with EA/H$_2$O, stirred for approximately 30 minutes after introducing acid clay was MgSO$_4$ thereto, and then passed through a celite/silica pad. As for purification, the result was separated using a column, and herein, an ethyl acetate [EA]/Hexane (1:20) mixture solution was used as an eluent. Compound 1-1 was obtained in 1.05 g.

(2) Preparation of Compound 1
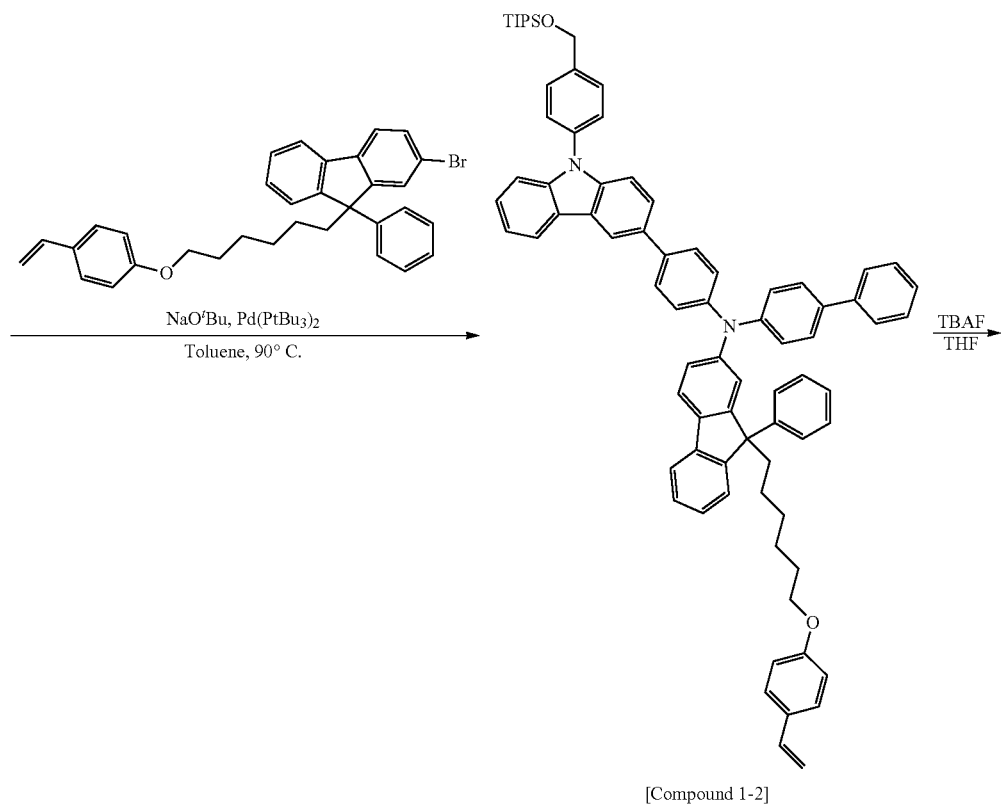
[Compound 1-2]
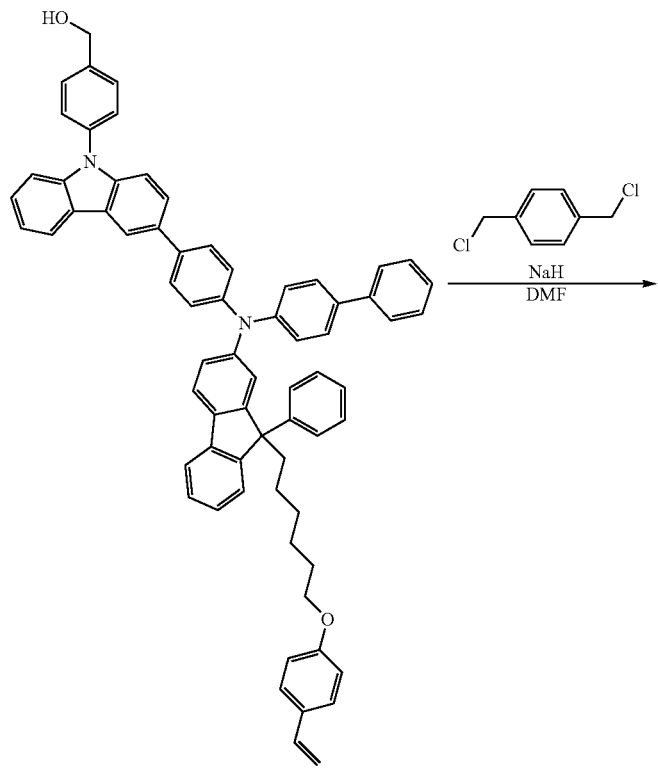
[Compound 1-3]

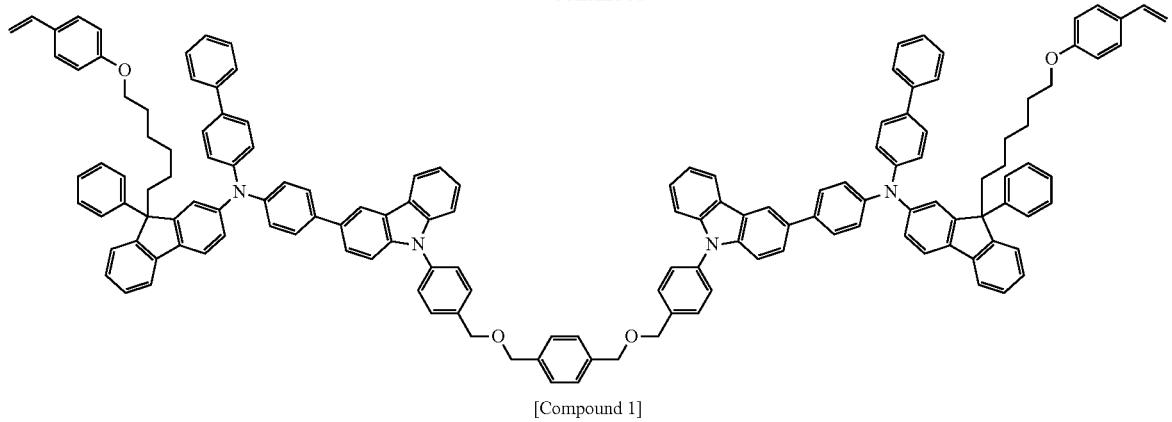 [SMILES: C=Cc1ccc(OCCCCCCC2(c3ccccc3)c3ccccc3-c3ccc(N(c4ccc(-c5ccccc5)cc4)c4ccc(-c5ccc6c(c5)c5ccccc5n6-c5ccc(COCc6ccc(COCc7ccc(-n8c9ccccc9c9cc(-c%10ccc(N(c%11ccc(-c%12ccccc%12)cc%11)c%11ccc%12c(c%11)C(CCCCCCOc%11ccc(C=C)cc%11)(c%11ccccc%11)c%11ccccc%11-%12)cc%10)ccc98)cc7)cc6)cc5)cc4)cc32)cc1]

[Compound 1]

Compound 1-1 (1 eq.), Intermediate 6 (1.1 eq.) and NaO$^t$Bu (3 eq.) were introduced to a round flask, and dissolved in toluene. After maintaining the temperature at 90° C., Pd(PtBu$_3$)$_2$ (0.2 eq.) was introduced thereto, and the result was refluxed under the N$_2$ atmosphere. After 5 hours, the reaction was finished, and the result was worked-up with DCM/H$_2$O, stirred for approximately 30 minutes after introducing acid clay was MgSO$_4$ thereto, and then passed through a celite/silica pad to obtain Compound 1-2. After dissolving Compound 1-2 in THF (5 mL), tetrabutylammonium fluoride [TBAF] (1 mL) was slowly dropped thereto. The result was purified through a flash column using an EA/Hexane (1:3) mixture solution to obtain Compound 1-3 (2.3 g).

Compound 1-3 was dissolved in anhydrous dimethylformamide [DMF]. NaH was first introduced thereto, the result was stirred, and then 1,4-bis(chloromethyl)benzene (1 eq.) was introduced thereto. While stirring the result at room temperature, progression of the reaction to a monomer and a dimer was identified through thin layer chromatography monitoring (TLC monitoring). After the reaction was finished, H$_2$O was poured thereto, and precipitates were filtered. The precipitates were sufficiently washed with water [H$_2$O] and ethanol, and further purified using a column. A DCM/Hex (1:1) mixture solution was used as an eluent, and after removing upper spots based on the major, Compound 1 was separated by flowing with DCM. The final material had a molecular weight of 2,020.63 and purity of 98%, and was obtained in 0.6 g. An MS graph of Compound 1 is shown in FIG. 2, and a graph measuring with a differential scanning calorimeter (DSC) is shown in FIG. 3.

Preparation Example 2. Comparative Compound 2

(1) Preparation of Compound 2-2

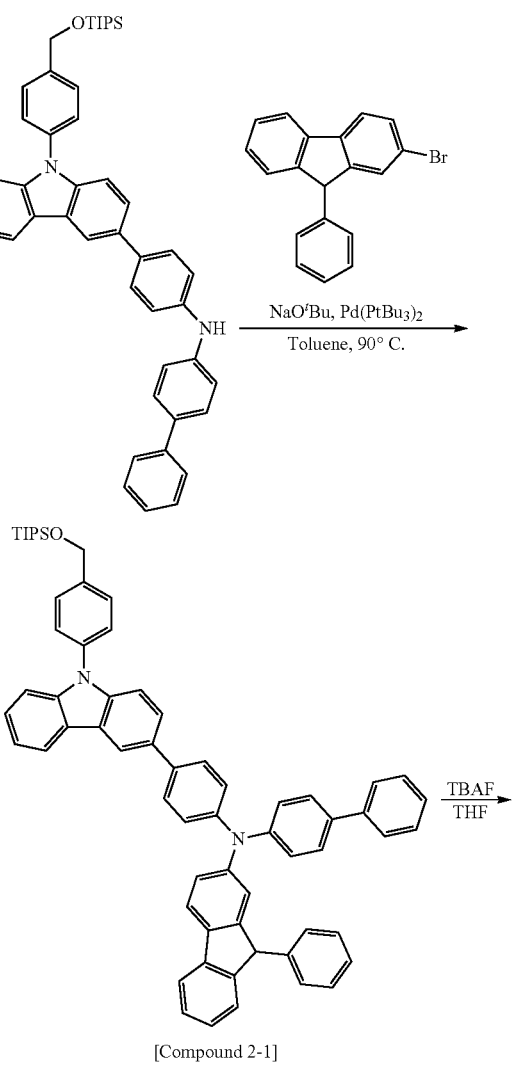

[Compound 2-1]

-continued

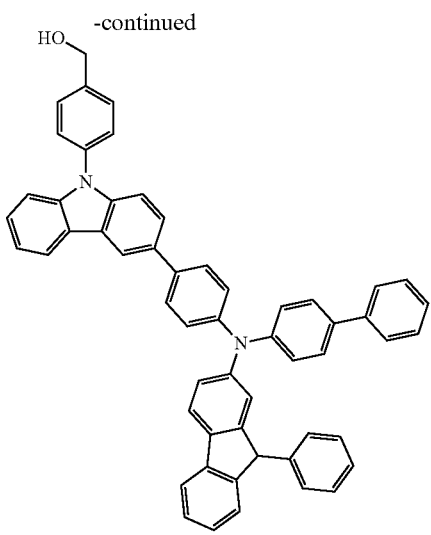

[Compound 2-2]

Compound 1-1 (1 eq.), Intermediate 3 (1.1 eq.) and NaO$^t$Bu (3 eq.) were introduced to a round flask, and dissolved in toluene. After maintaining the temperature at 90° C., Pd(PtBu$_3$)$_2$ (0.2 eq.) was introduced thereto, and the result was refluxed under the N$_2$ atmosphere. After 5 hours, the reaction was finished, and the result was worked-up with DCM/H$_2$O, stirred for approximately 30 minutes after introducing acid clay was MgSO$_4$ thereto, and then passed through a celite/silica pad to obtain Compound 2-1. After dissolving Compound 2-1 in THF (5 mL), tetrabutylammonium fluoride [TBAF] (1 mL) was slowly dropped thereto. The result was purified through a flash column using an EA/Hexane (1:3) mixture solution to obtain Compound 2-2 (2.6 g).

(2) Preparation of Comparative Compound 2

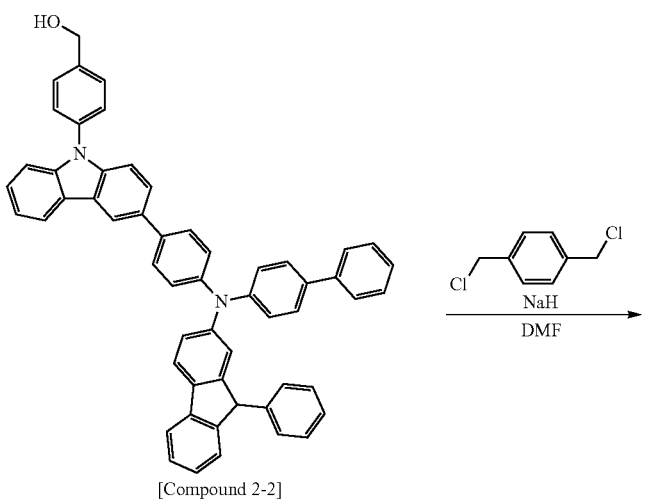

[Compound 2-2]

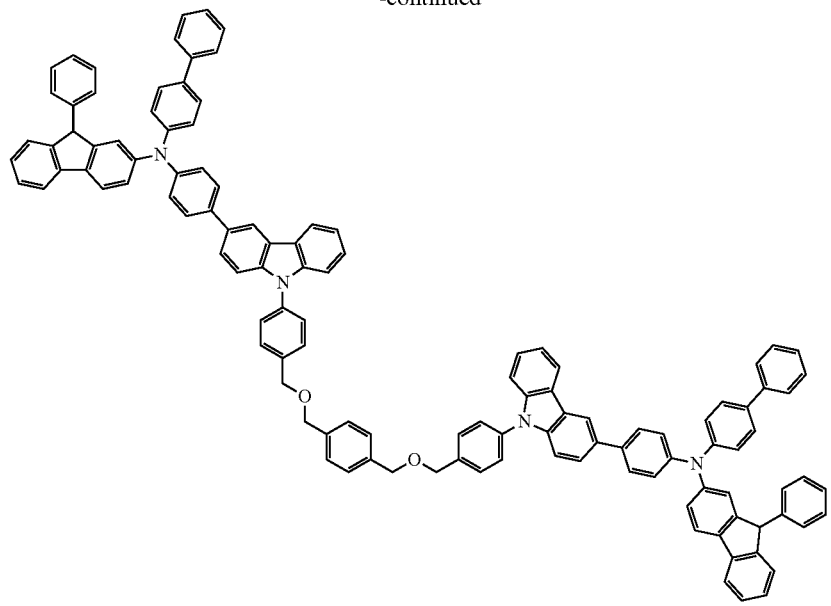

[Comparative Compound 2]

Compound 2-2 was dissolved in anhydrous DMF. NaH was first introduced thereto, the result was stirred, and then 1,4-bis(chloromethyl)benzene (1 eq.) was introduced thereto. While stirring the result at room temperature, progression of the reaction to a monomer and a dimer was identified through TLC monitoring. After the reaction was finished, H$_2$O was poured thereto, and precipitates were filtered. The precipitates were sufficiently washed with H$_2$O and ethanol, and further purified using a column. A DCM/Hex (1:1) mixture solution was used as an eluent, and after removing upper spots based on the major, Comparative Compound 2 was separated by flowing with DCM (0.5 g, quantitive yield).

Preparation Example 3. Comparative Compound 3

(1) Synthesis of Intermediate 14

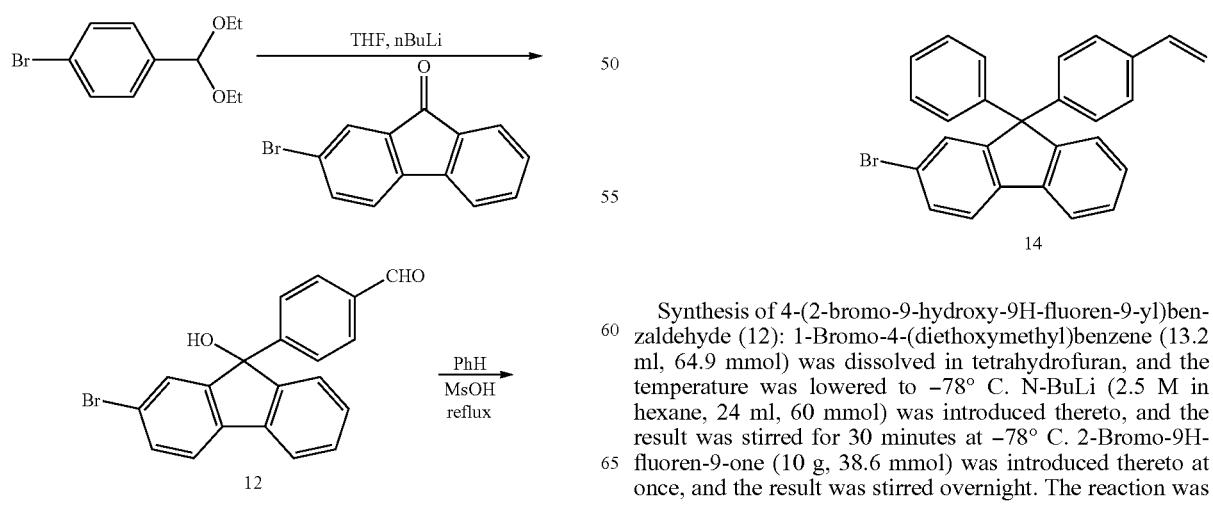

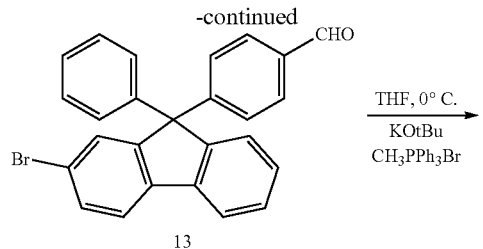

Synthesis of 4-(2-bromo-9-hydroxy-9H-fluoren-9-yl)benzaldehyde (12): 1-Bromo-4-(diethoxymethyl)benzene (13.2 ml, 64.9 mmol) was dissolved in tetrahydrofuran, and the temperature was lowered to −78° C. N-BuLi (2.5 M in hexane, 24 ml, 60 mmol) was introduced thereto, and the result was stirred for 30 minutes at −78° C. 2-Bromo-9H-fluoren-9-one (10 g, 38.6 mmol) was introduced thereto at once, and the result was stirred overnight. The reaction was terminated with 1 N HCl (aq.), and the result was extracted with ethyl acetate. The collected organic solution was dried using magnesium sulfate (MgSO$_4$), filtered, and the organic solvent was removed using a vacuum rotary evaporator. The residue was column purified and then recrystallized (toluene/hexane) to obtain Intermediate 12 (13 g, yield 55%).

Synthesis of 4-(2-bromo-9-phenyl-9H-fluoren-9-yl)benzaldehyde (13): Benzene (140 ml) was introduced to 12 (4.5 g, 12.3 mmol), and after introducing methanesulfonic acid (400 μl, 6.16 mmol) thereto, the result was refluxed using a dean-stark apparatus. The acid was neutralized with saturated NaHCO$_3$ (aq.), and the result was column purified to obtain Intermediate 13 (2.73 g, yield 52%).

Synthesis of 2-bromo-9-phenyl-9-(4-vinylphenyl)-9H-fluorene (14): After introducing 13 (2.9 g, 6.82 mmol) and CH$_3$BrPPh$_3$ (4.89 g, 13.7 mmol) to THF, potassium tert-butoxide (1.553 g, 13.7 mmol) was introduced thereto at 0° C., and the result was stirred for 1 hour. The reaction was stopped using water, and the result was extracted with ethyl acetate [EA]. The collected organic solution was dried using magnesium sulfate (MgSO$_4$), filtered, and the organic solvent was removed using a vacuum rotary evaporator. The residue was column purified to obtain Intermediate 14 (2.8 g, yield 97%).

(2) Synthesis of Comparative Compound 3 with dichloromethane (DCM), the organic layer was dried with MgSO$_4$. After removing the organic solvent using a vacuum rotary evaporator, the residue was column purified to obtain Comparative Compound 3 (950 mg, yield 55%).

NMR measurement values of Comparative Compound 3: $^1$H NMR (500 MHz, CD$_2$Cl$_2$) δ 7.71 (d, 2H), 7.65 (d, 2H), 7.42 (d, 4H), 7.35 (d, 4H), 7.27-7.20 (m, 18H), 7.17-7.13 (m, 4H), 7.11-7.06 (m, 14H), 7.03 (t, 2H), 6.70-6.64 (dd, 2H), 5.69 (d, 2H), 5.19 (d, 2H)

EXPERIMENTAL EXAMPLE

Experimental Example 1. Film Retention Rate Experiment (1) Preparation of Film

Example 1-1

Compound 1 (20 mg) was dissolved in cyclohexanone (1 ml). The obtained solution was spin coated on a glass substrate for minute at 1200 rpm. The result was heat treated

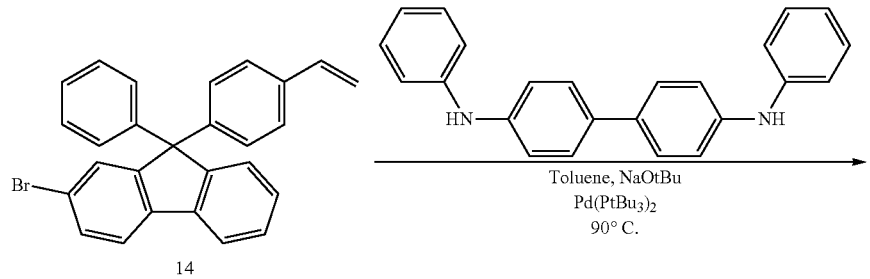

14

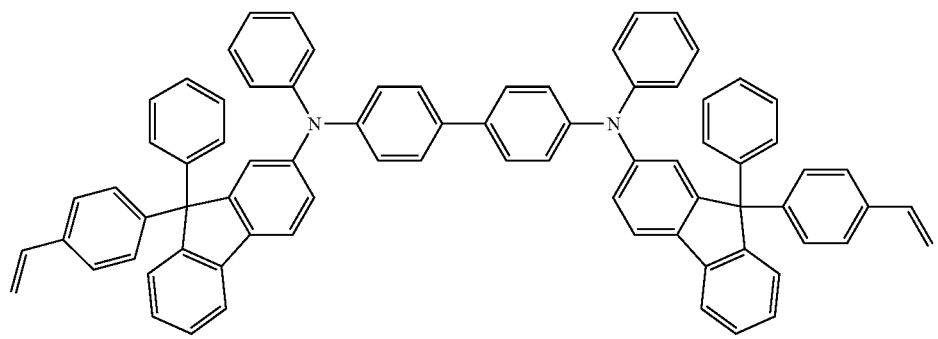

[Comparative Compound 3]

Synthesis of Comparative Compound 3: To a flask holding Intermediate 14 (1.58 g, 3.74 mmol), N4,N4'-diphenyl-[1,1'-biphenyl]-4,4'-diamine (572 mg. 1.7 mmol) and sodium tert-butoxide (980 mg, 10.2 mmol), toluene was introduced, and the result was bubbled with nitrogen. The flask holding the reactant was immersed in a 90° C. oil bath, Pd(PtBu$_3$)$_2$ (43 mg, 0.085 mmol) was introduced thereto, and the result was stirred for 24 hours. Water was introduced thereto to stop the reaction, and after extracting the result for 2 minutes at 80° C. and 30 minutes at 200° C. under the nitrogen atmosphere, and then cooled at room temperature to prepare a thin film.

Comparative Example 1-1

A thin film was prepared in the same manner as in Example 1-1 except that the following Comparative Compound 2 was used instead of Compound 1.

[Comparative Compound 2]

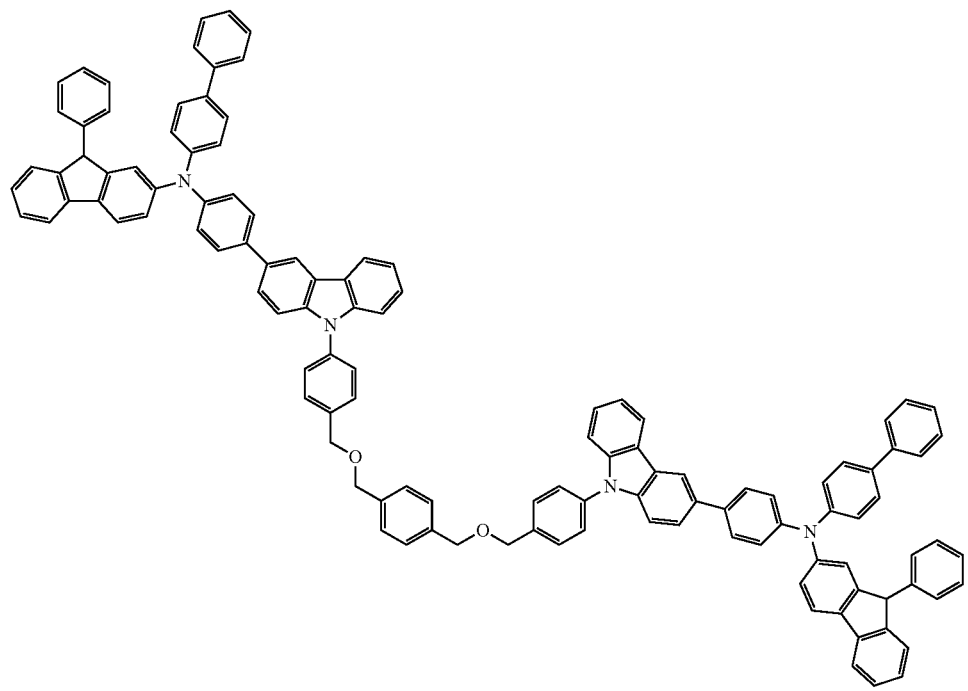

COMPARATIVE EXAMPLE 1-2

A thin film was prepared in the same manner as in Example 1-1 except that the following Comparative Compound 3 was used instead of Compound 1.

[Comparative Compound 3]

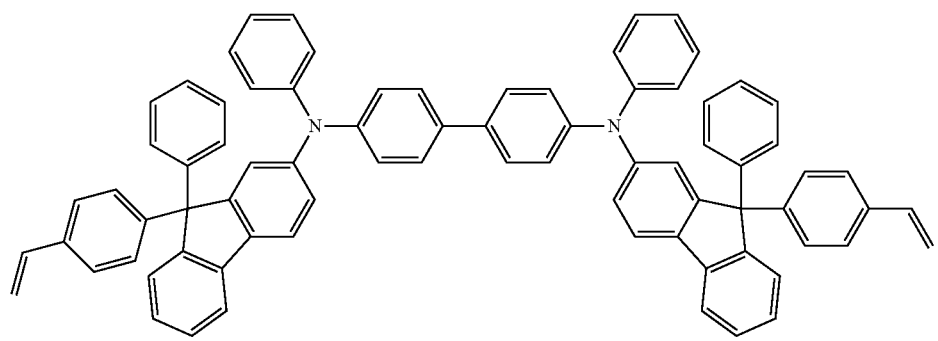

(2) Film Retention Rate Measurement

A film retention rate of each of the thin films prepared in Example 1-1 and Comparative Examples 1-1 and 1-2 was measured. The film retention rate was obtained by measuring a UV spectrum of the thin film without any treatment, measuring a UV spectrum after dipping the thin film in toluene for 10 minutes, and comparing the λmax values. In the following Table 1, measured values of the film retention rates of Example 1-1 and Comparative Examples 1-1 and 1-2 are described, and in FIG. 4, FIG. 5 and FIG. 6, graphs measuring UV spectra before/after dipping the thin films of Example 1-1, Comparative Example 1-1 and Comparative Example 1-2, respectively, in toluene are shown. In FIGS. 4 to 6, the vertical axis means optical density (OD). The film retention rate was calculated by the following equation.

Film retention rate (o)=λmax value after dipping in toluene/λmax value before dipping in toluene×100

TABLE 1

| | Film Retention Rate (%) |
|---|---|
| Example 1-1 | 99 |
| Comparative Example 1-1 | 0 |
| Comparative Example 1-2 | 12 |

In a solution process, when a hole transfer layer material is dissolved in a solvent used for forming each adjacent layer in light emitting device manufacture, a design to avoid the material from being dissolved in the solvent is required. For this, the hole transfer layer material preferably has a crosslinking group, and preferably becomes insoluble by being crosslinked at a heat treatment temperature range of the hole transfer layer (process temperature of 80° C. to 220° C.)

In Table 1, it was seen that, in Example 1-1, the film was retained through being sufficiently crosslinked at 200° C. compared to Comparative Example 1-1 that did not have a crosslinking group. Comparative Compound 3 having a curing group directly bonding to the fluorene was not able to maintain a thin film (FIG. 6, thin film retention rate 12% (toluene), 3% (cyclohexanone)), however, Compound 1 having proper space between the fluorene monomer (fluorene moiety) and a curing group had excellent tolerance for solvents (FIG. 4, thin film retention rate 99% (toluene, cyclohexanone)). It can be seen that reducing steric hinderance around the curing group and increasing mobility of the curing group itself help with the curing reaction.

Experimental Example 2. Manufacture of Organic Light Emitting Device

Example 2-1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer having a thickness of 400 Å was formed by spin coating a composition mixing VNPB and a p-dopant (the following Chemical Formula 6) in a weight ratio of 0.8:0.2, and curing the result under a condition of 220° C. and 30 minutes on a hot plate under nitrogen atmosphere.

On the hole injection layer formed as above, a hole transfer layer having a thickness of 200 Å was formed by spin coating a solution dissolving Compound 1 in toluene, and curing the result under a condition of 200° C. and 30 minutes on a hot plate.

On the hole transfer layer formed as above, a light emitting layer having a thickness of 550 Å was formed by spin coating a solution dissolving the following Compound C in toluene, and heat treating the result for 30 minutes at 180° C.

This was introduced into a vacuum depositor, and when the base pressure became $2 \times 10^{-5}$ Pa or lower, LiF (10 Å) and Al (1,000 Å) were consecutively deposited to manufacture an organic light emitting device. In the above-mentioned process, the deposition rate of the LiF was maintained at 0.01 nm/s to 0.05 nm/s, and the deposition rates of the materials other than the LiF were maintained at 0.1 nm/s to 0.5 nm/s.

[VNPB]

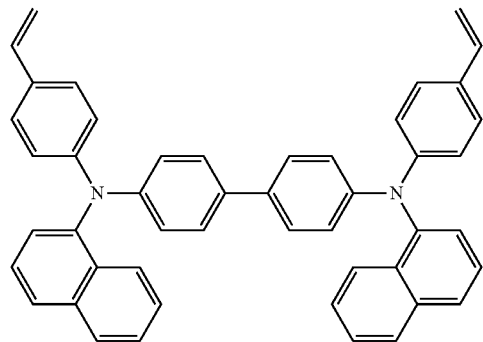

[Chemical Formula 6]

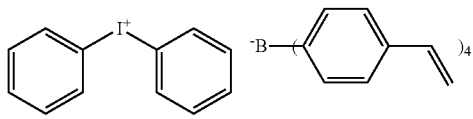

[Compound C]

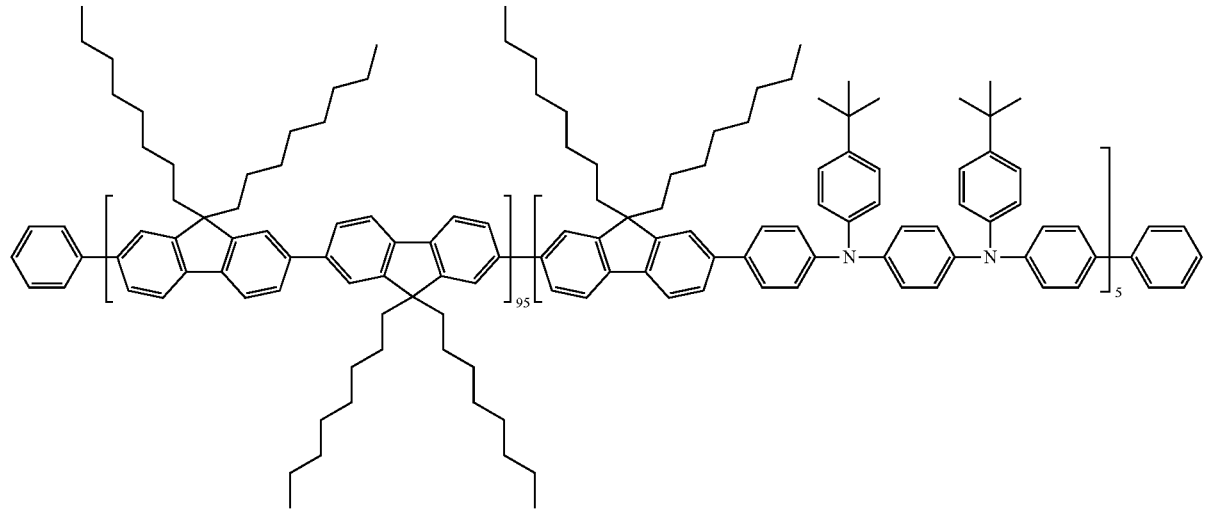

Comparative Example 2-1

An organic light emitting device was manufactured in the same manner as in Example 2-1 except that the following Comparative Compound 2 was used instead of Compound 1.

[Comparative Compound 2]

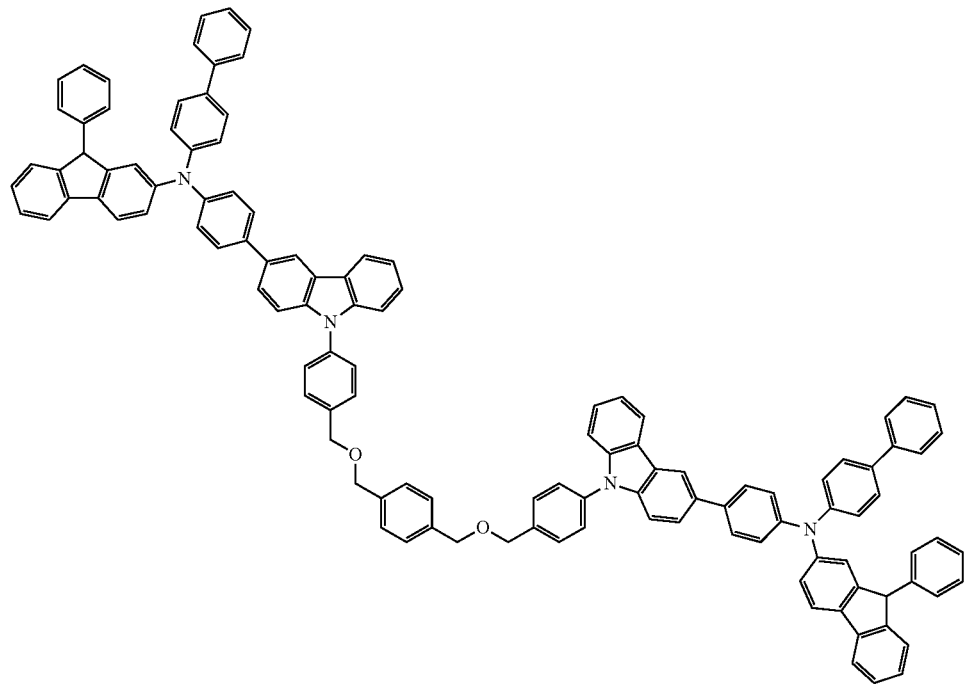

Comparative Example 2-2

An organic light emitting device was manufactured in the same manner as in Example 2-1 except that the following Comparative Compound 3 was used instead of Compound 2.

[Comparative Compound 3]

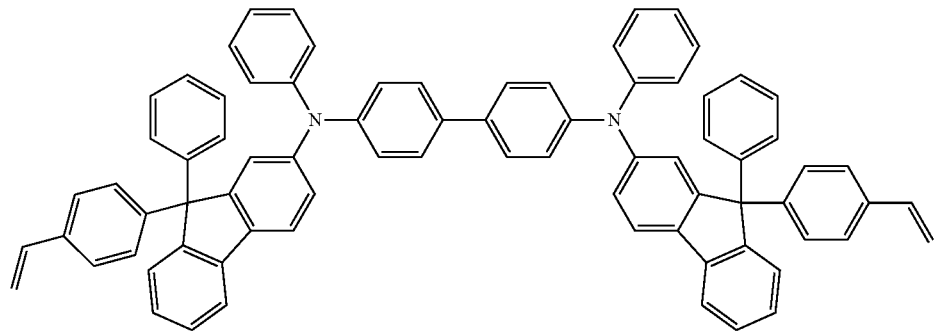

For the organic light emitting devices manufactured in Example 2-1 and Comparative Examples 2-1 and 2-2, driving voltage and light emission efficiency were measured at current density of 10 mA/cm², and time taken for the luminance decreasing to 95% compared to its initial luminance ($T_{95}$) was measured at current density of 10 mA/cm². The results are shown in the following Table 2.

TABLE 2

| | Voltage (V) | Current Density (mA/cm$^2$) | Voltage Efficiency (Cd/A) | Power Efficiency (lm/W) | Quantum Efficiency (%) | Luminance (Cd/m$^2$) | CIE x | CIE y | T95 |
|---|---|---|---|---|---|---|---|---|---|
| Example 2-1 | 4.71 | 10 | 3.86 | 2.60 | 4.07 | 378.0 | 0.137 | 0.105 | 47.3 |
| Comparative Example 2-1 | 11.48 | 10 | 2.05 | 0.56 | 1.74 | 0.156 | 0.143 | 0.132 | — |
| Comparative Example 2-2 | 10.4 | 10 | 2.15 | 0.65 | 2.34 | 215 | 0.141 | 0.129 | — |

As described in Table 2, it was identified that the organic light emitting device manufactured in Example 2-1 of the present application had a lower driving voltage, and had excellent efficiency and luminance compared to the organic light emitting devices manufactured in Comparative Examples 2-1 and 2-2, and, as identified in Table 1, it was identified that Comparative Examples 2-1 and 2-2 had a very low film retention rate, and, after measuring initial luminance, the film was not retained until the T95 measurement.

The invention claimed is:

1. A compound represented by the following Chemical Formula 1:

[Chemical Formula 1]

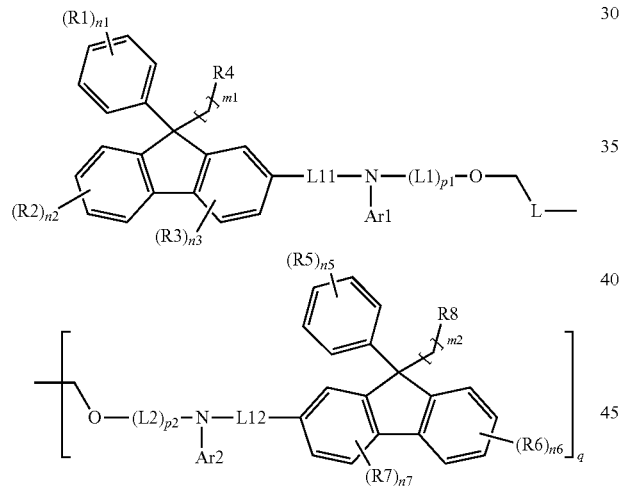

wherein, in Chemical Formula 1,

R1 to R3 and R5 to R7 are the same as or different from each other, and each independently hydrogen; deuterium; a halogen group; a nitrile group; —SiR$_a$R$_b$R$_c$; —BR$_d$R$_e$; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group; wherein R$_a$, R$_b$, R$_c$, R$_d$ and R$_e$ are each independently hydrogen; a substituted or unsubstituted alkyl group; or a substituted or unsubstituted aryl group;

R4 and R8 are the same as or different from each other, and each independently a functional group crosslinkable by heat or light;

Ar1 and Ar2 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group;

L1 and L2 are the same as or different from each other, and each independently a direct bond; a substituted or unsubstituted divalent alkyl group; a substituted or unsubstituted divalent aryl group; or a substituted or unsubstituted divalent heteroaryl group;

L11 and L12 are the same as or different from each other, and each independently a direct bond; or a substituted or unsubstituted divalent aryl group;

L is a substituted or unsubstituted divalent or trivalent aryl group; a substituted or unsubstituted divalent or trivalent heteroaryl group; or a substituted or unsubstituted divalent or trivalent arylamine group;

m1 and m2 are each an integer of 0 to 12;
n1 and n5 are each an integer of 0 to 5;
n2 and n6 are each an integer of 0 to 4;
n3 and n7 are each an integer of 0 to 3;
p1 and p2 are each an integer of 1 to 4;
q is 1 or 2;

when n1 to n3, n5 to n7, p1 and p2 are each 2 or greater, R1s to R3s, R5s to R7s, L1s and L2s are each independently the same as or different from each other; and when q is 2, each of the structure below

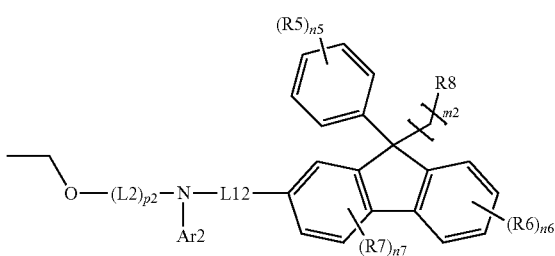

are independently the same as or different from each other wherein the functional group crosslinkable by heat or light is any one of the following structures:

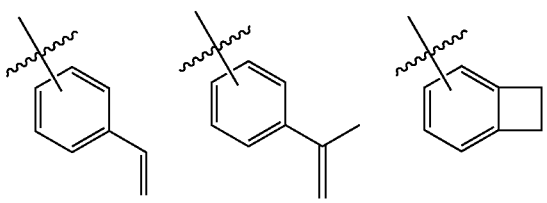

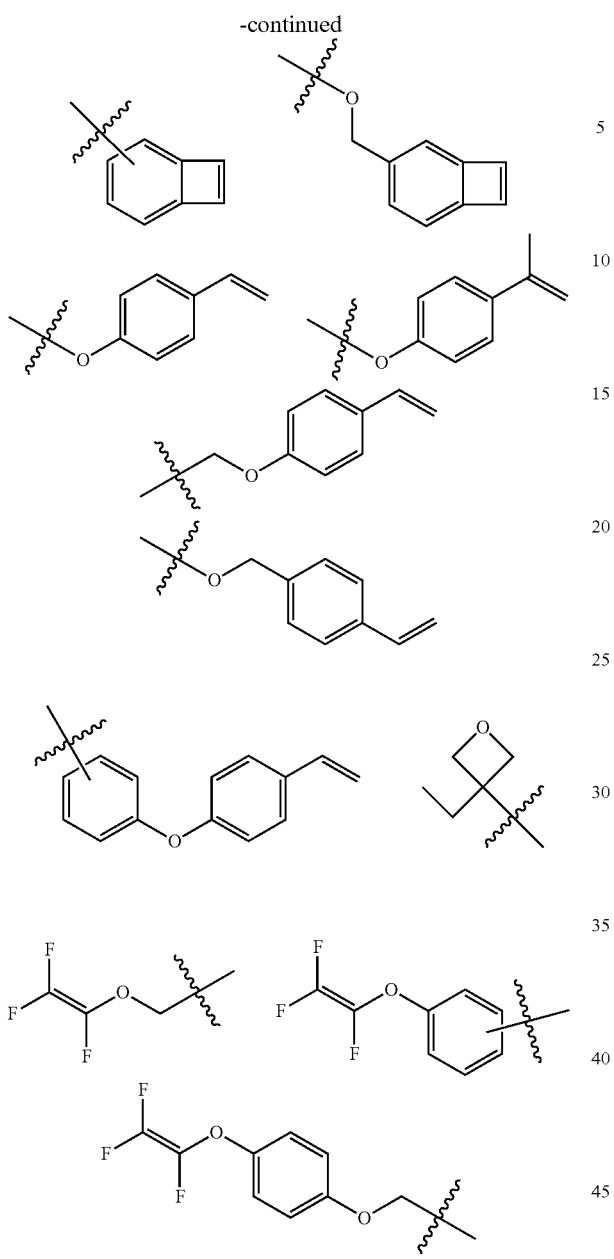
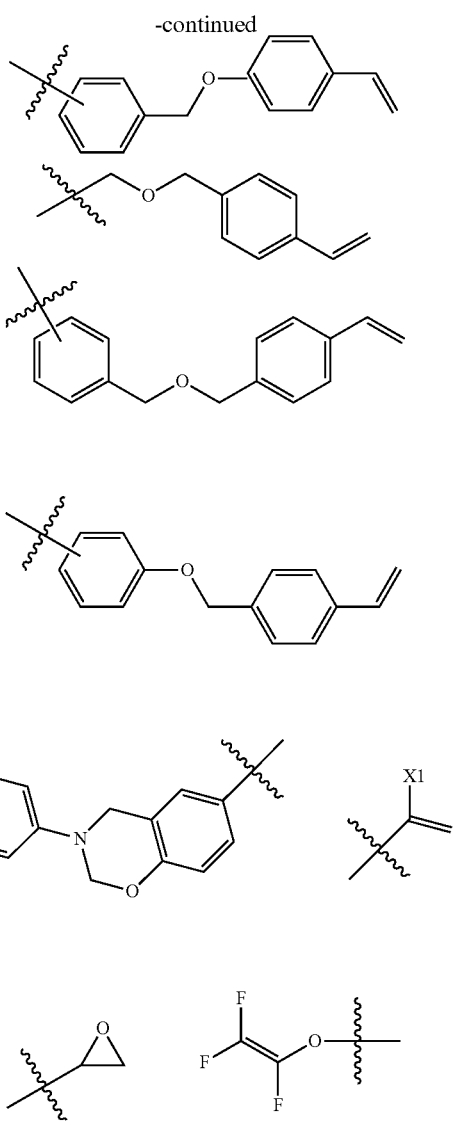
in the structures, X1 is hydrogen; or a substituted or unsubstituted alkyl group having 1 to 6 carbon atoms.
2. The compound of claim 1, wherein Chemical Formula 1 is represented by the following Chemical Formula 2:
[Chemical Formula 2]
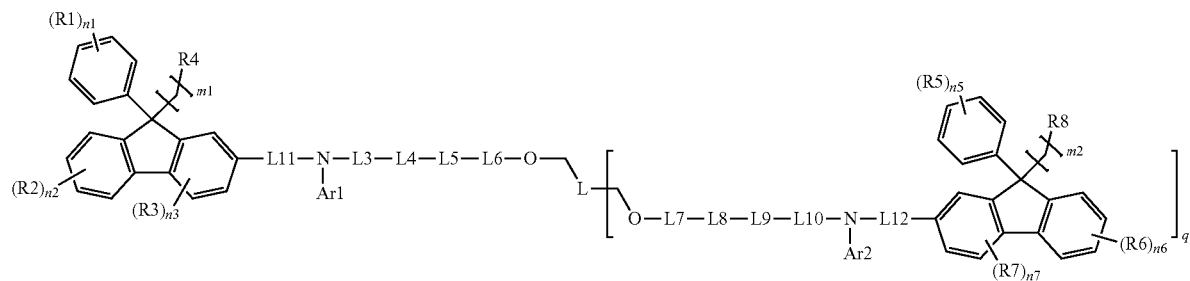

in Chemical Formula 2,

R1 to R8, n1 to n3, n5 to n7, Ar1, Ar2, L, L11, L12, q, m1 and m2 have the same definitions as in Chemical Formula 1; and L3 to L10 are the same as or different from each other, and each independently a direct bond; a substituted or unsubstituted divalent alkyl group; a substituted or unsubstituted divalent aryl group; or a substituted or unsubstituted divalent heteroaryl group.

3. The compound of claim 1, wherein Chemical Formula 1 is any one selected from among the following Compounds 1 to 126:

221
[Compound 1]
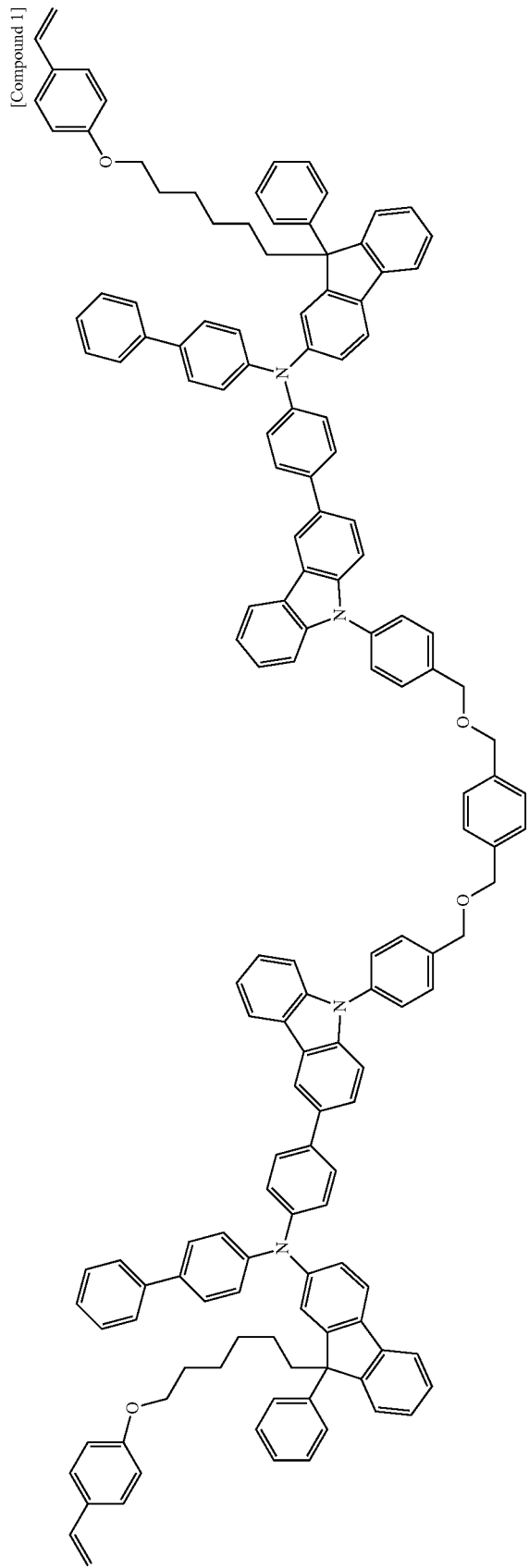
222
[Compound 2]
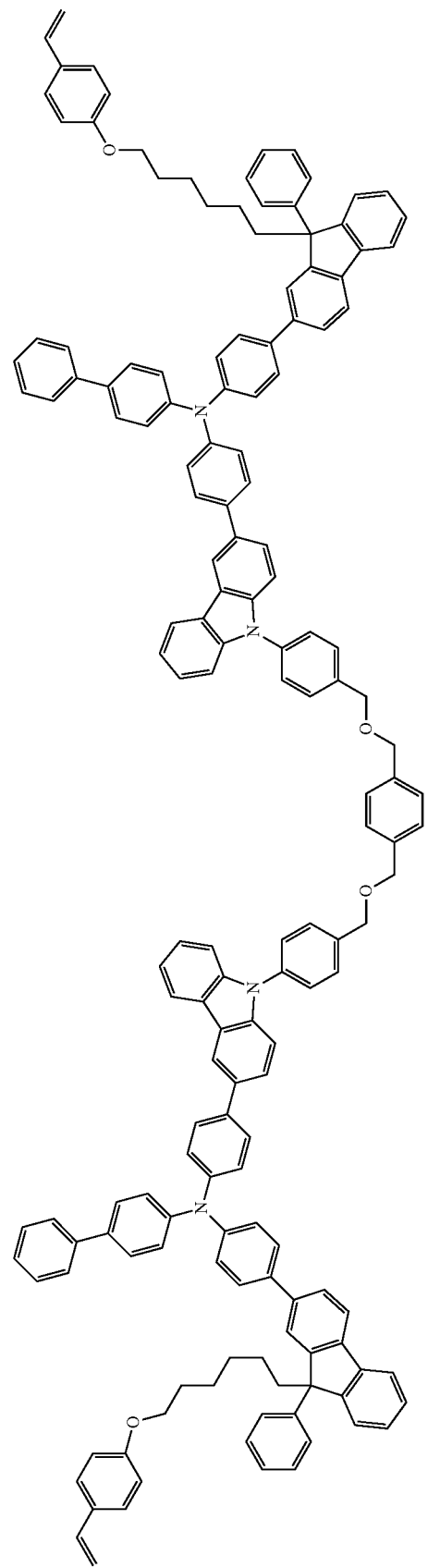

[Compound 3]
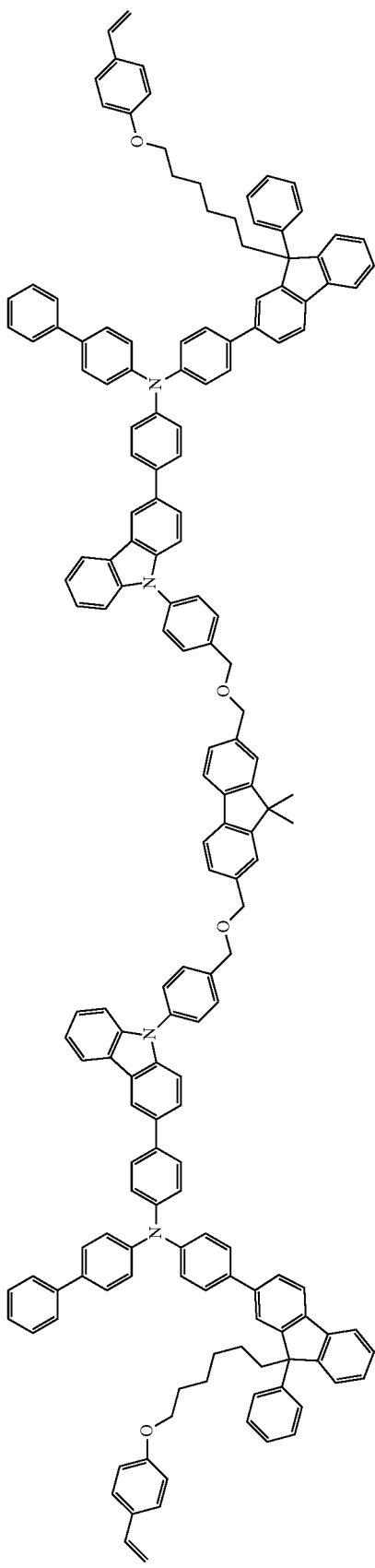
[Compound 4]
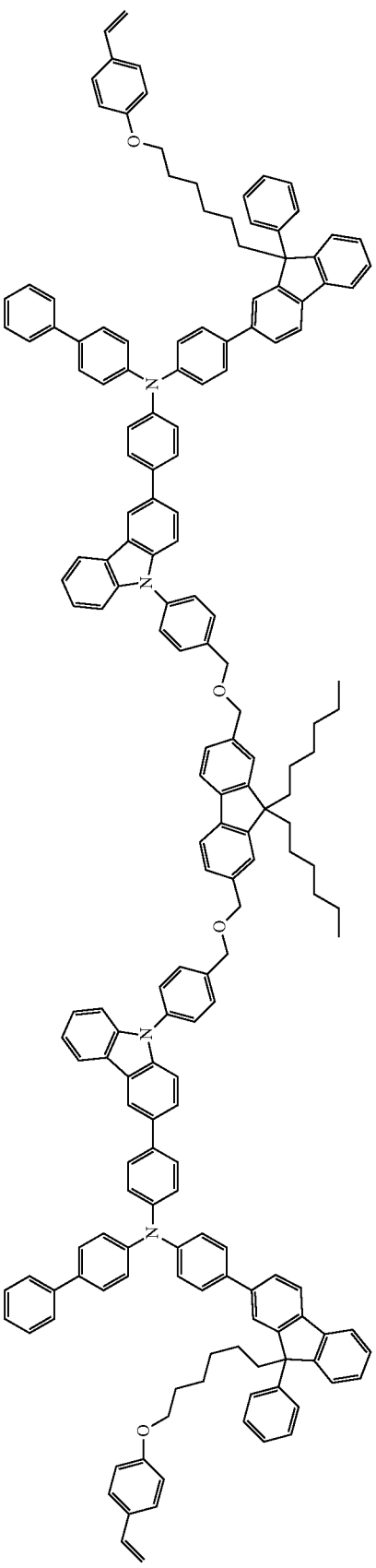

[Compound 5]
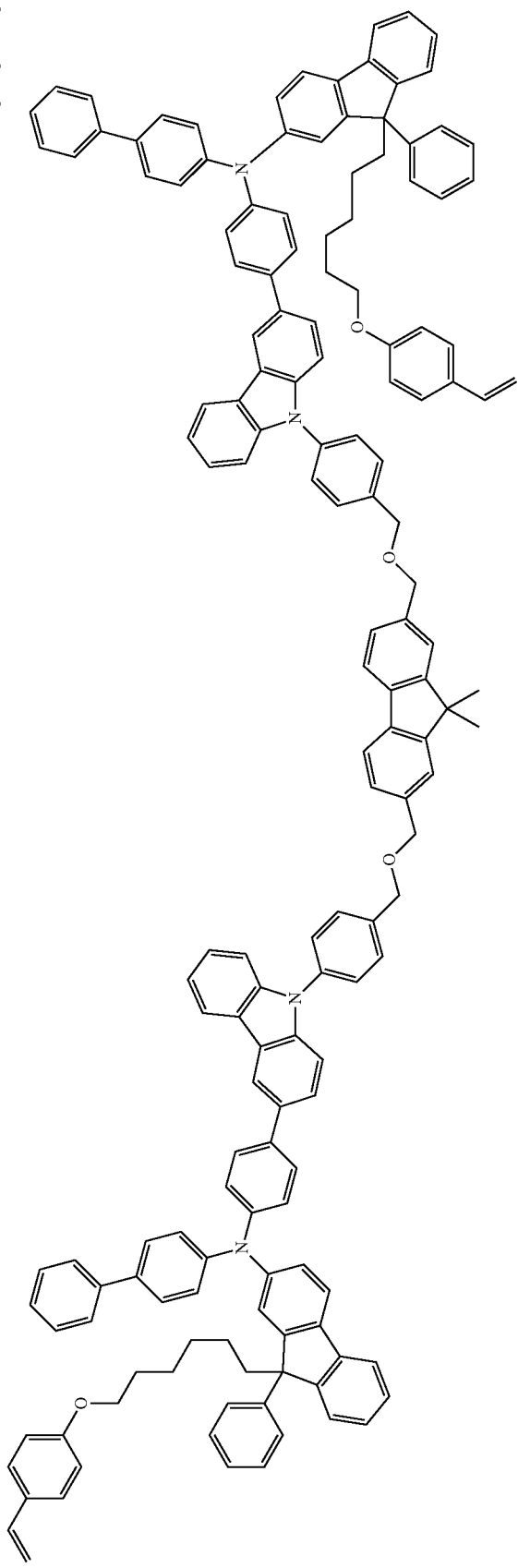

[Compound 6]
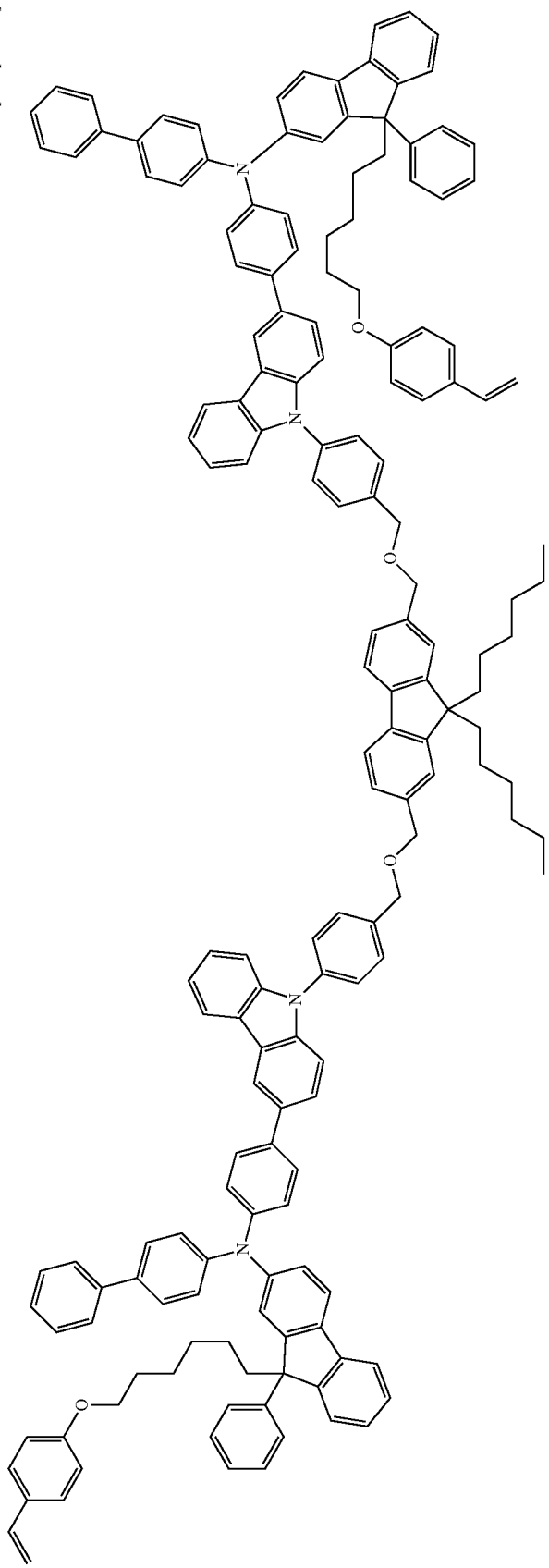

Compound 7
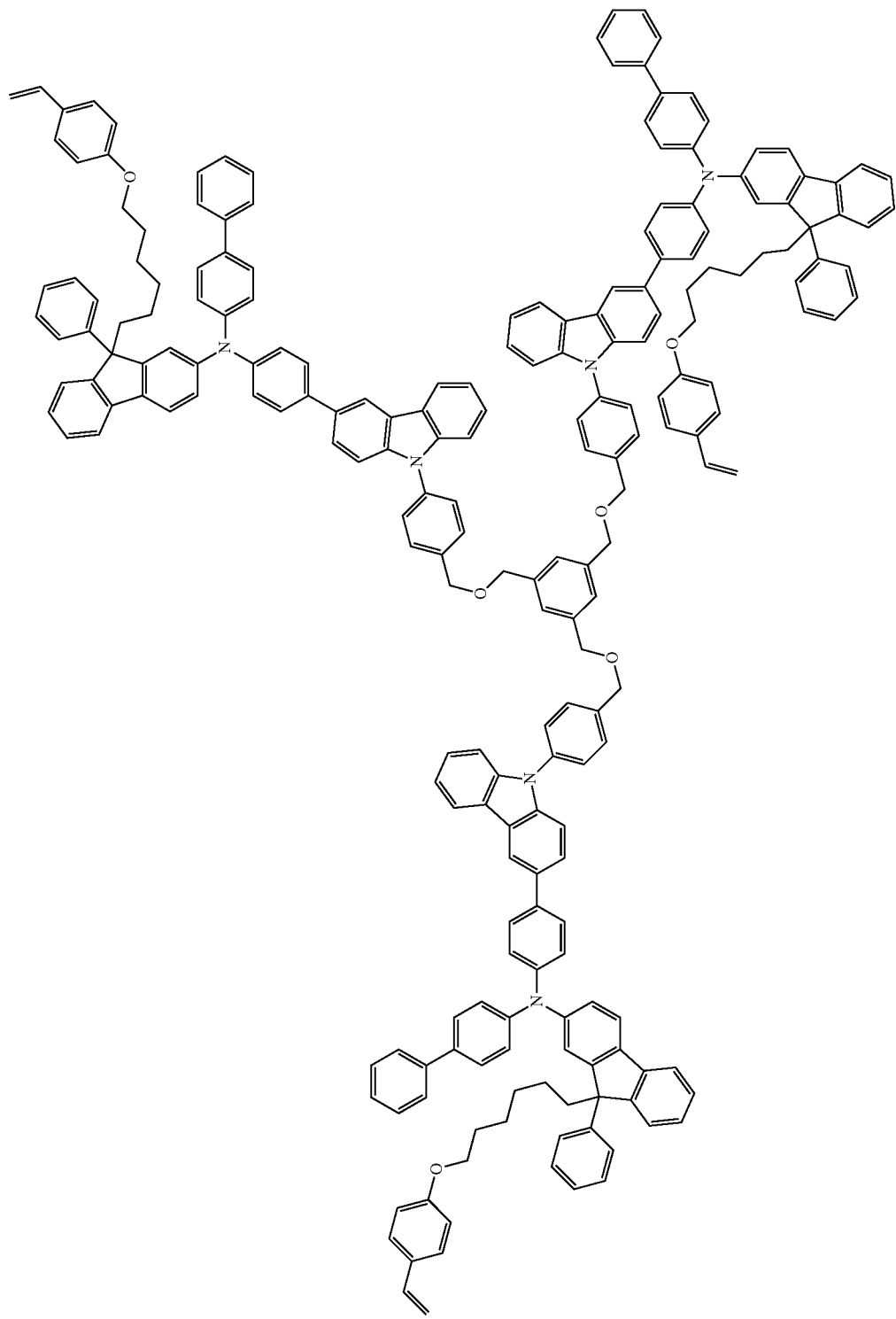

Compound 8
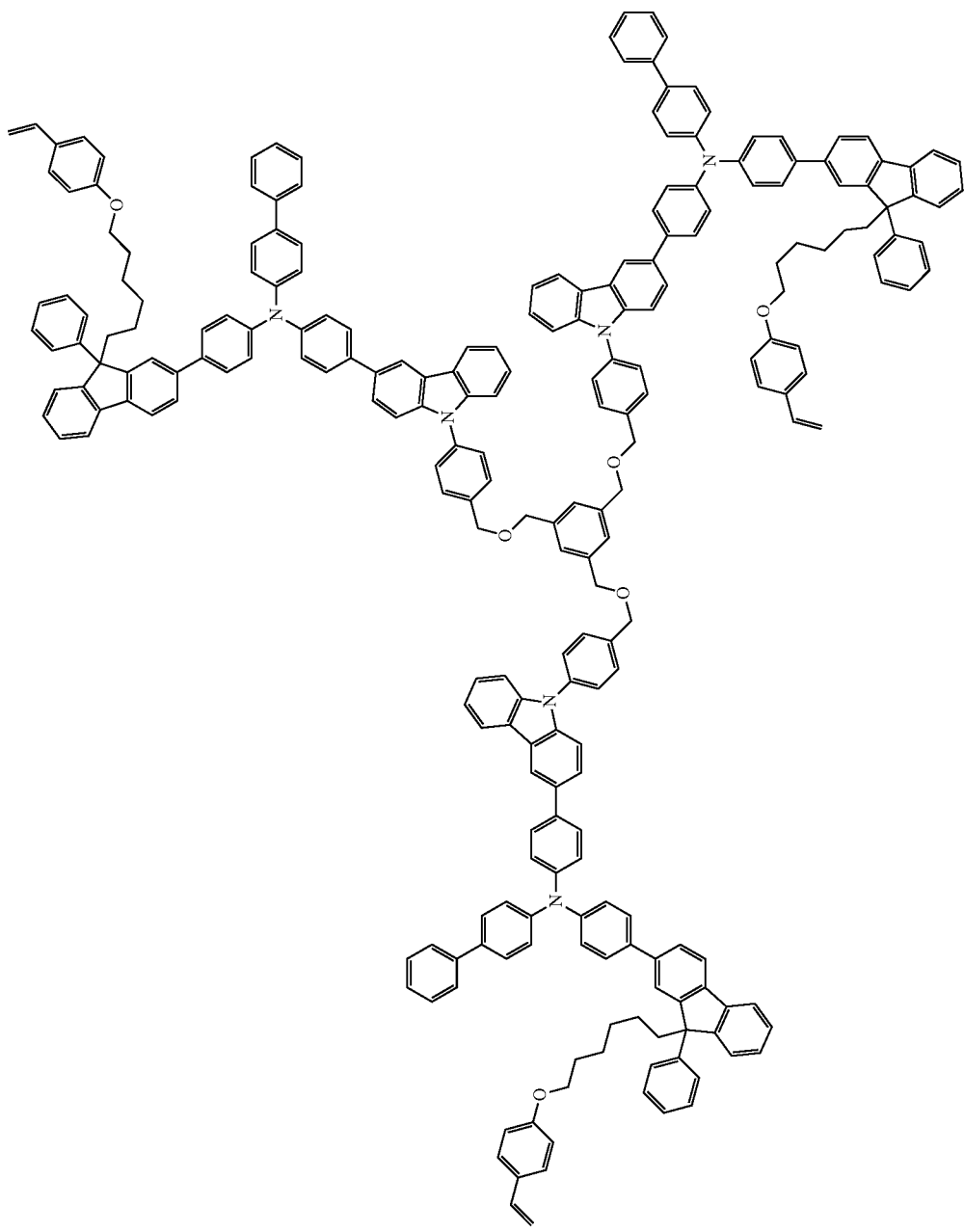

[Compound 9]
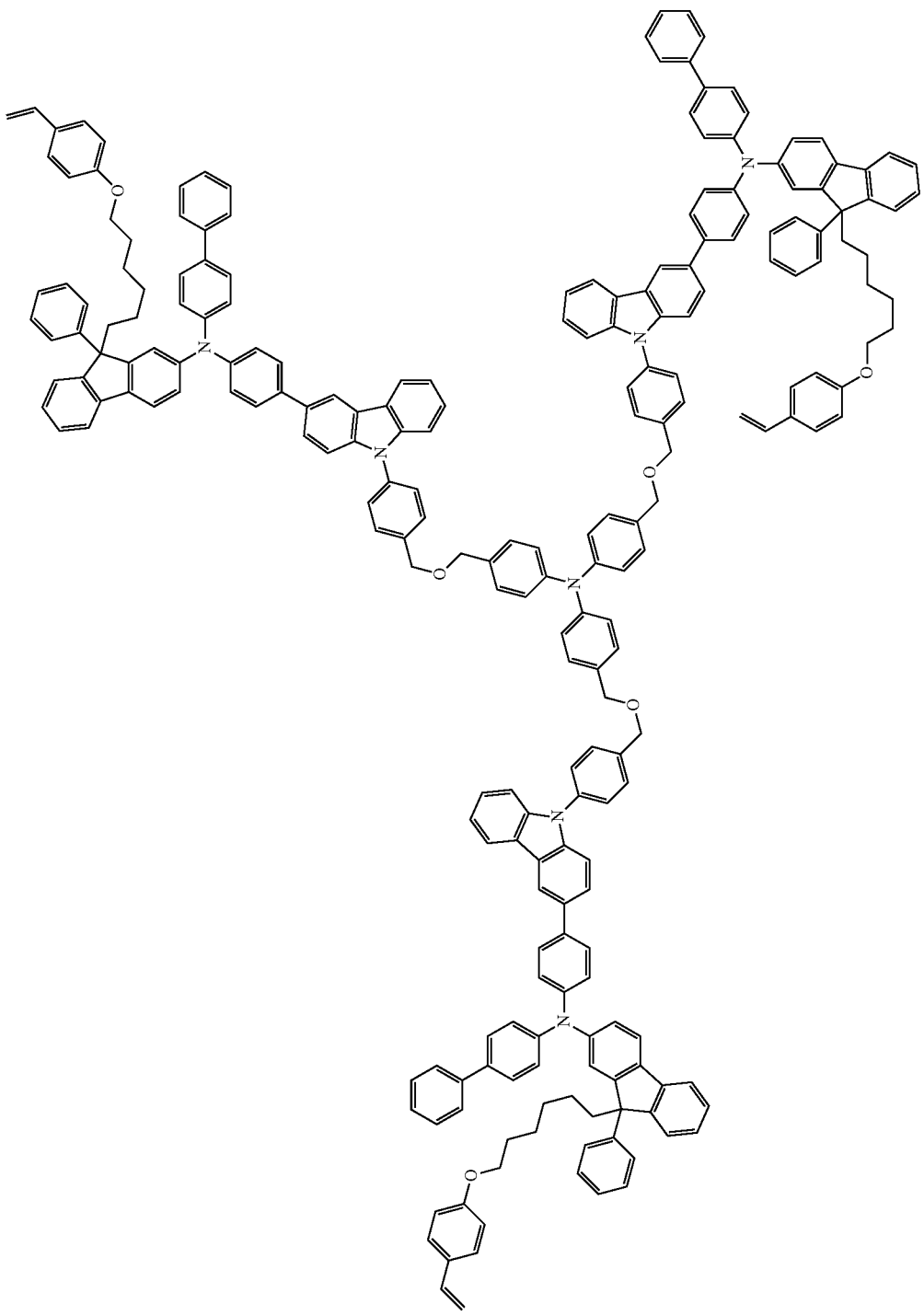

[Compound 10]
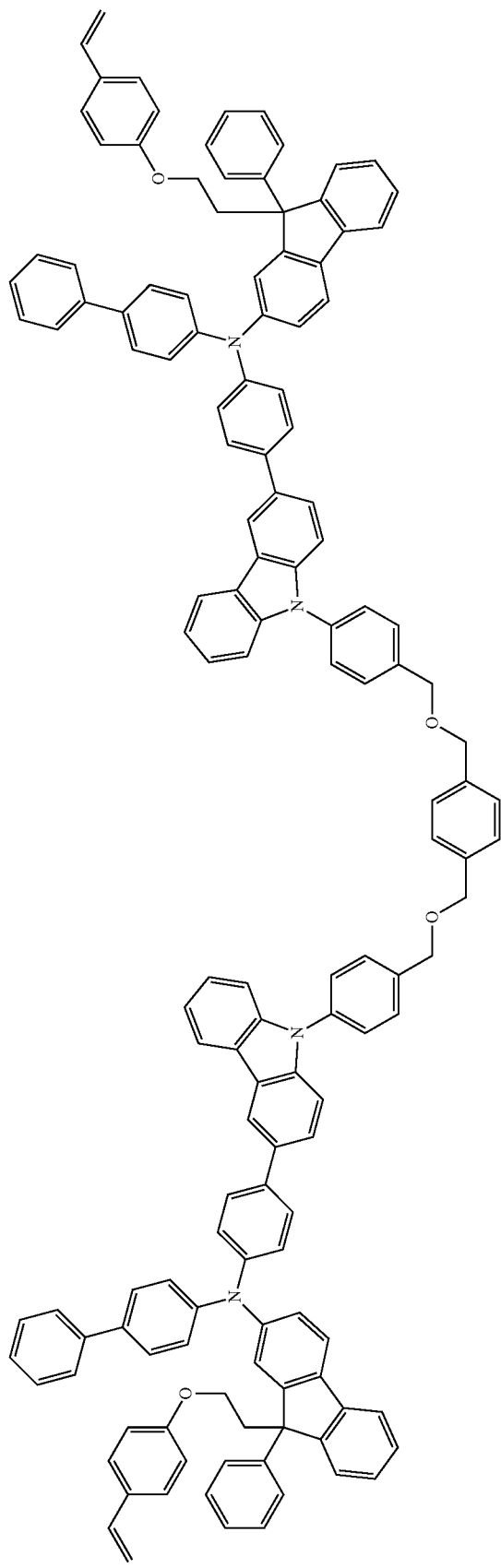
[Compound 11]
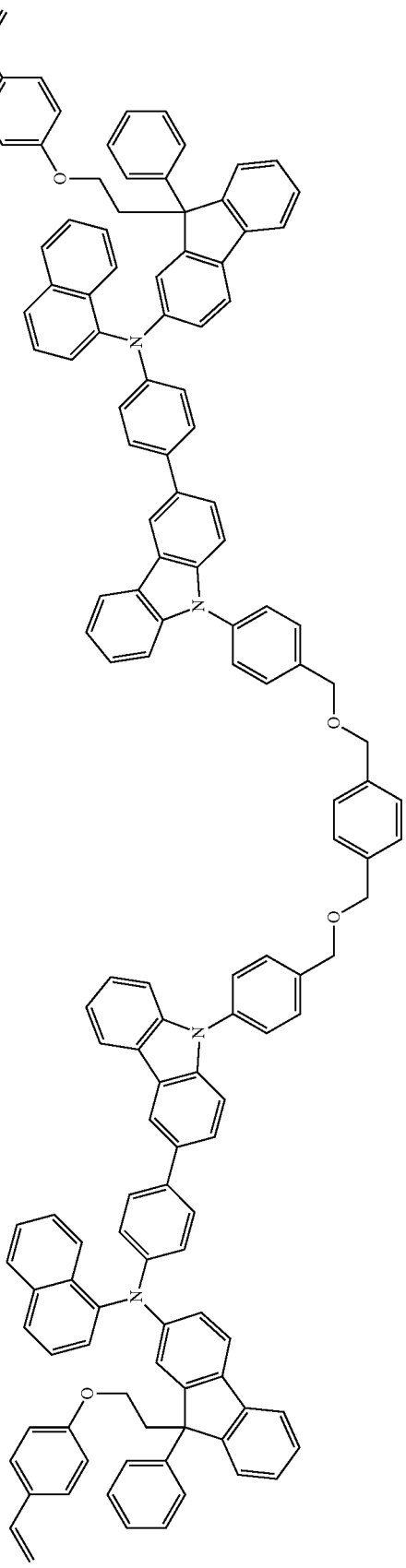

-continued
[Compound 12]
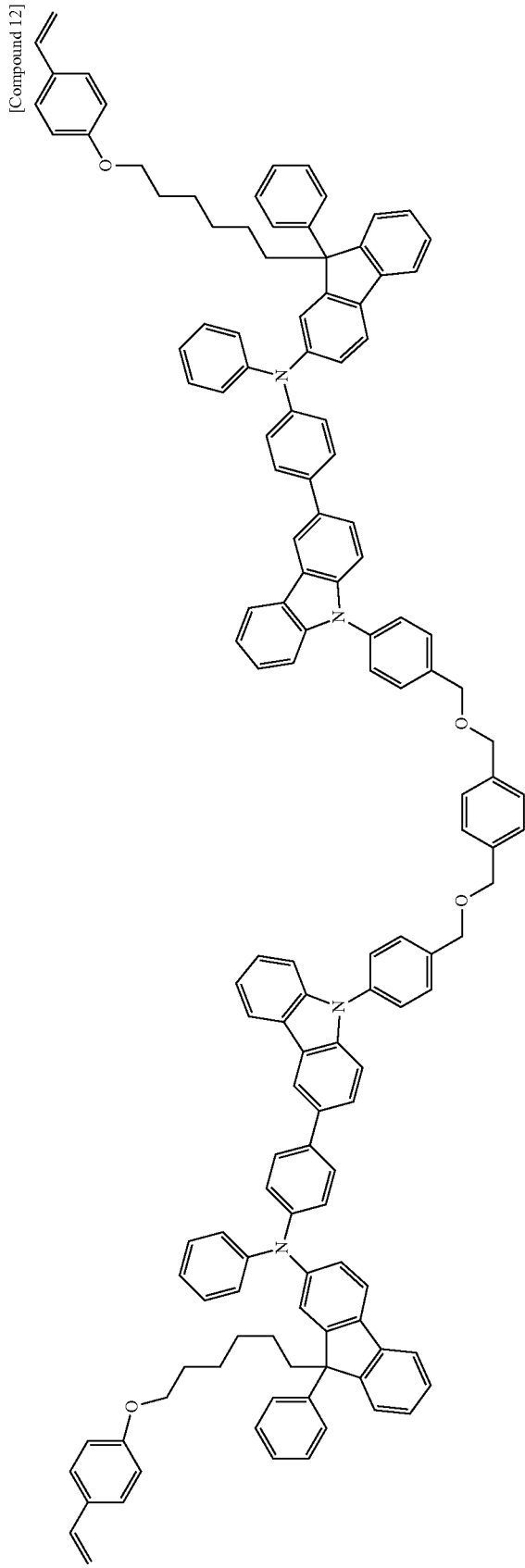
[Compound 13]
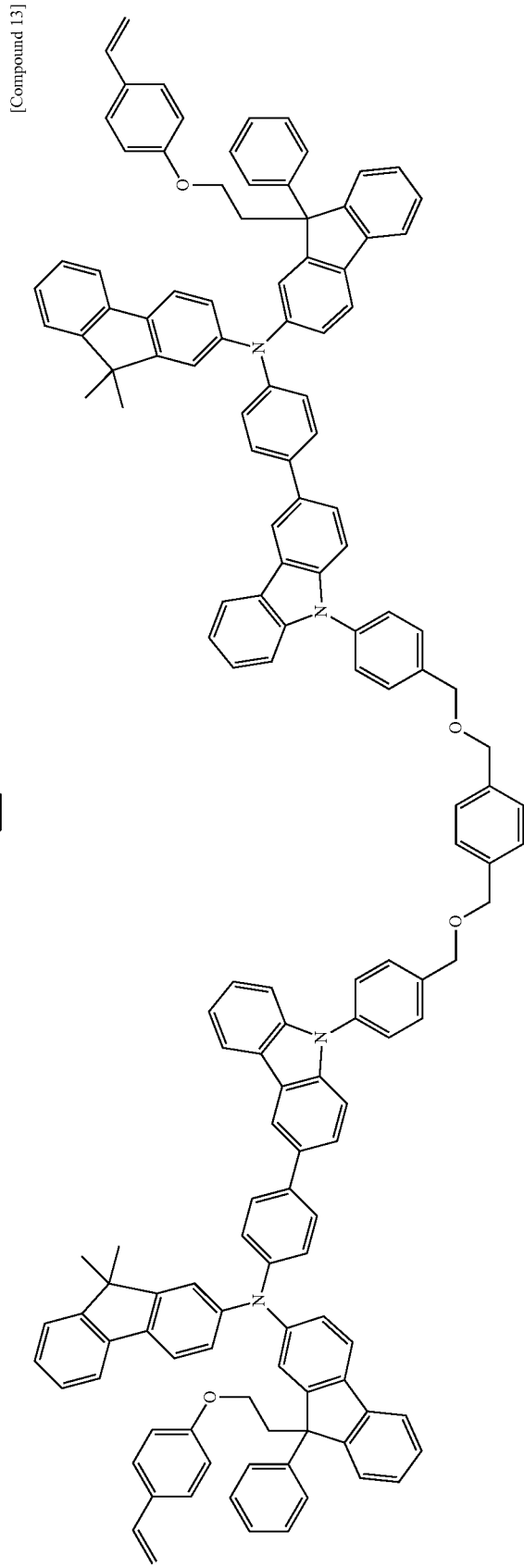

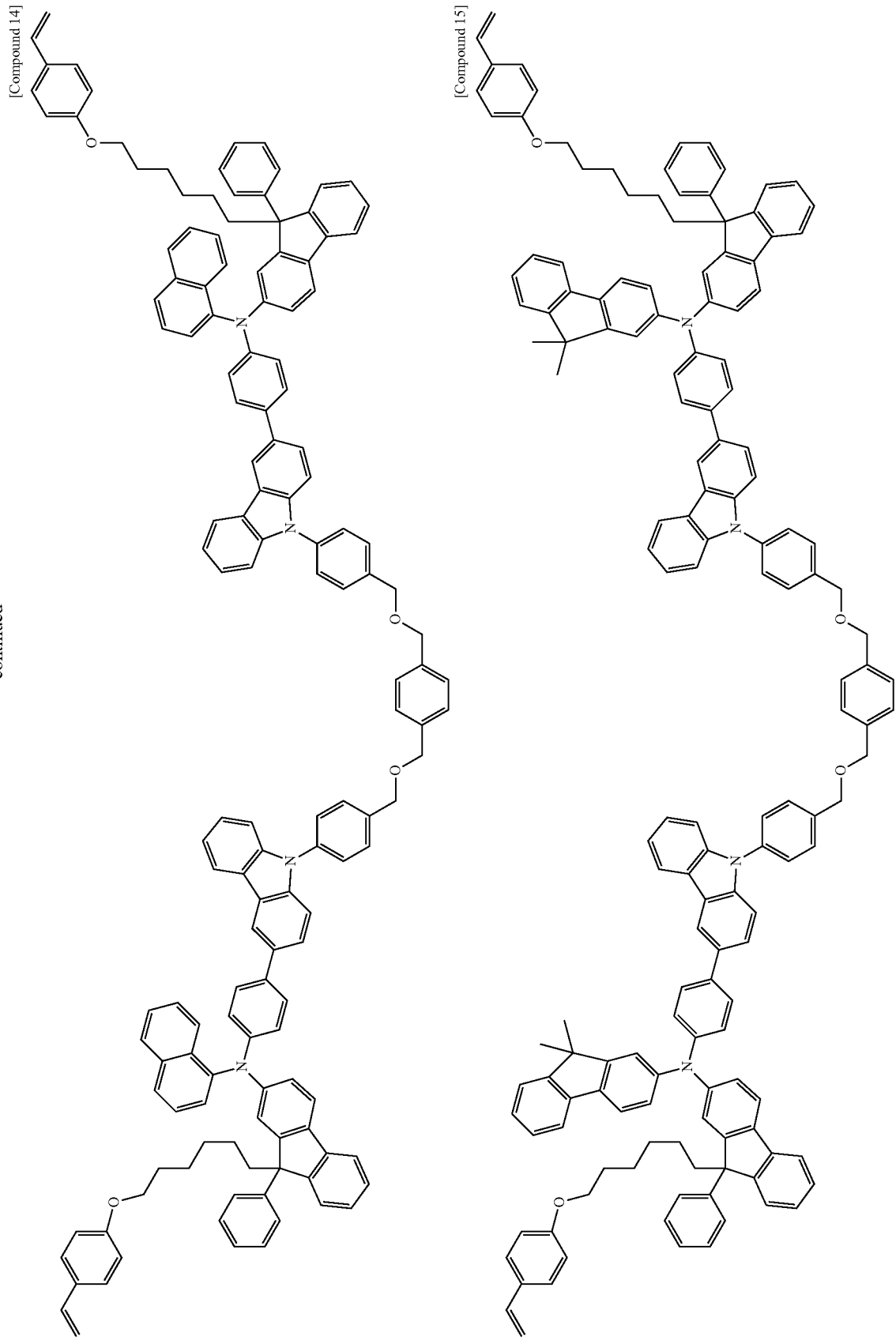

[Compound 16]
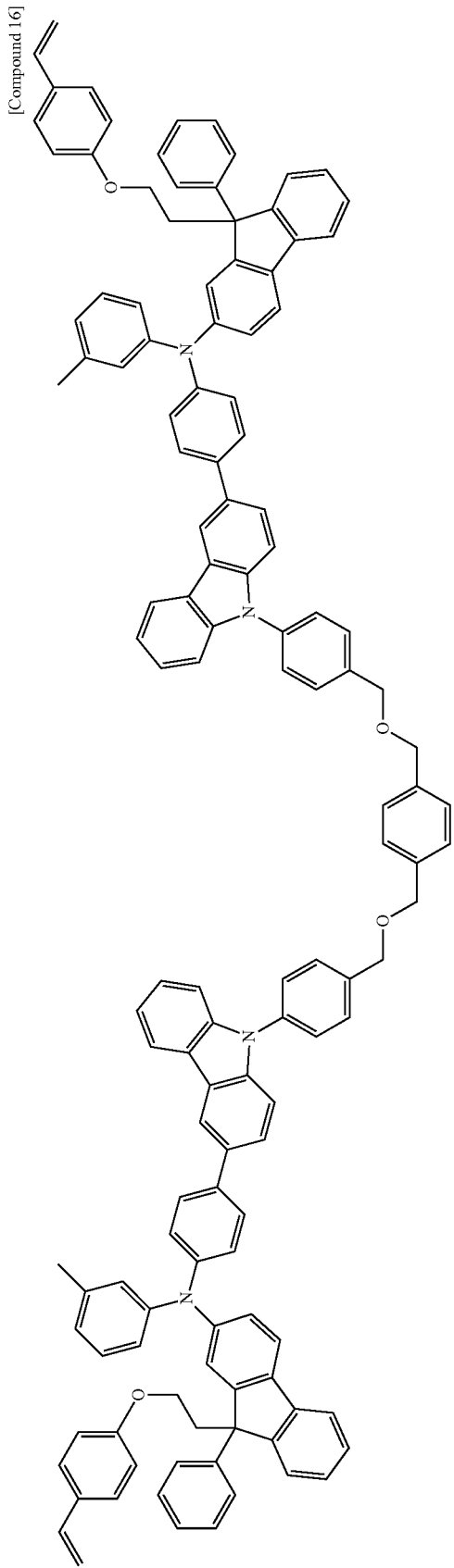
[Compound 17]
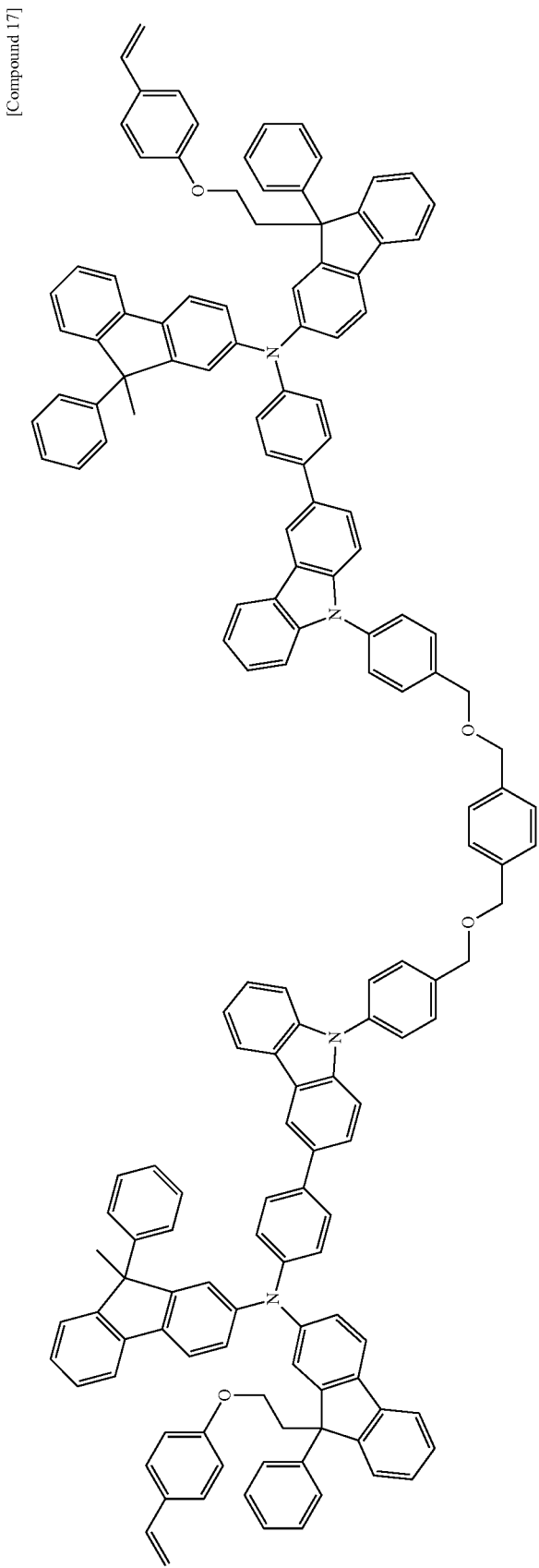

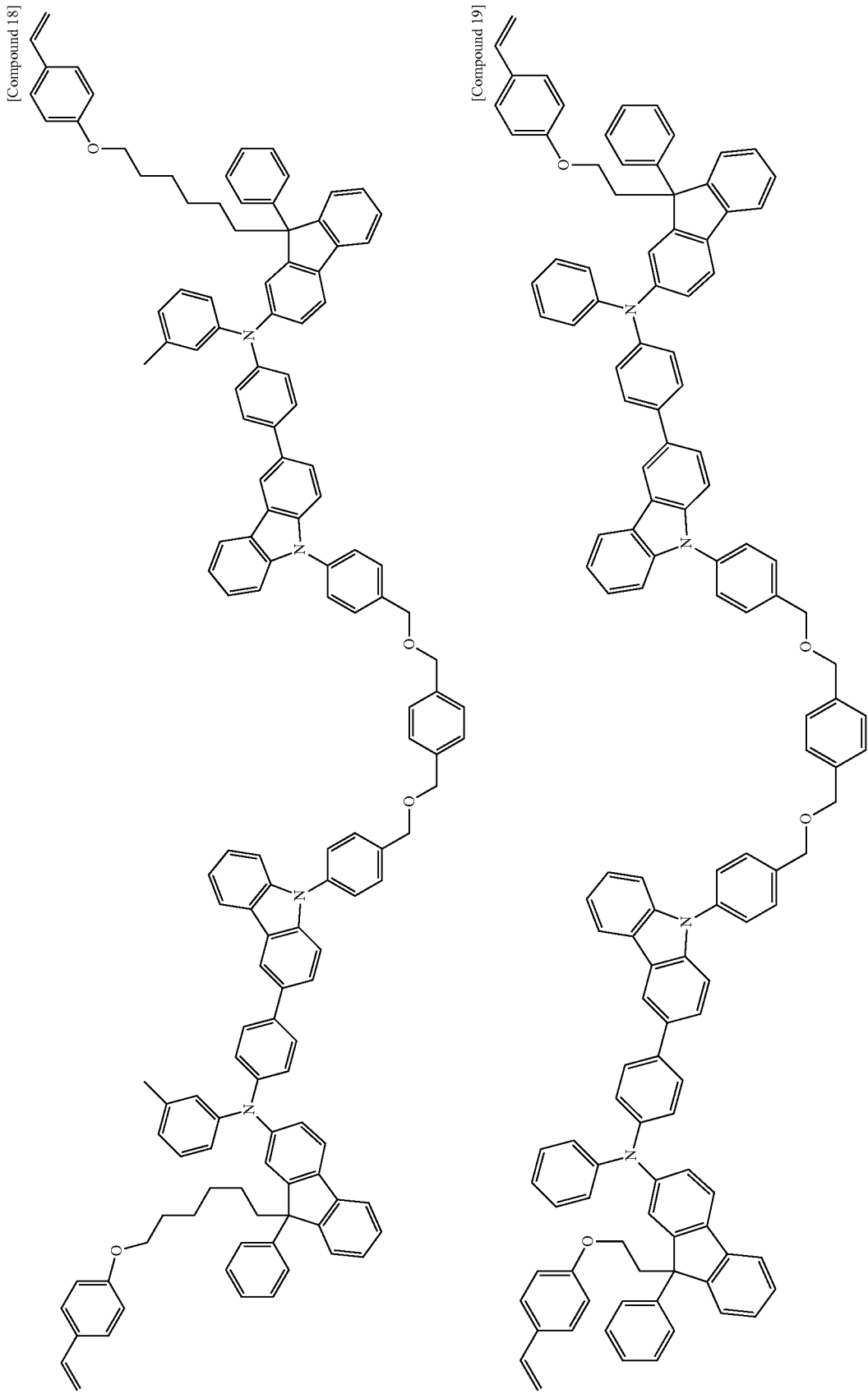

[Compound 20]
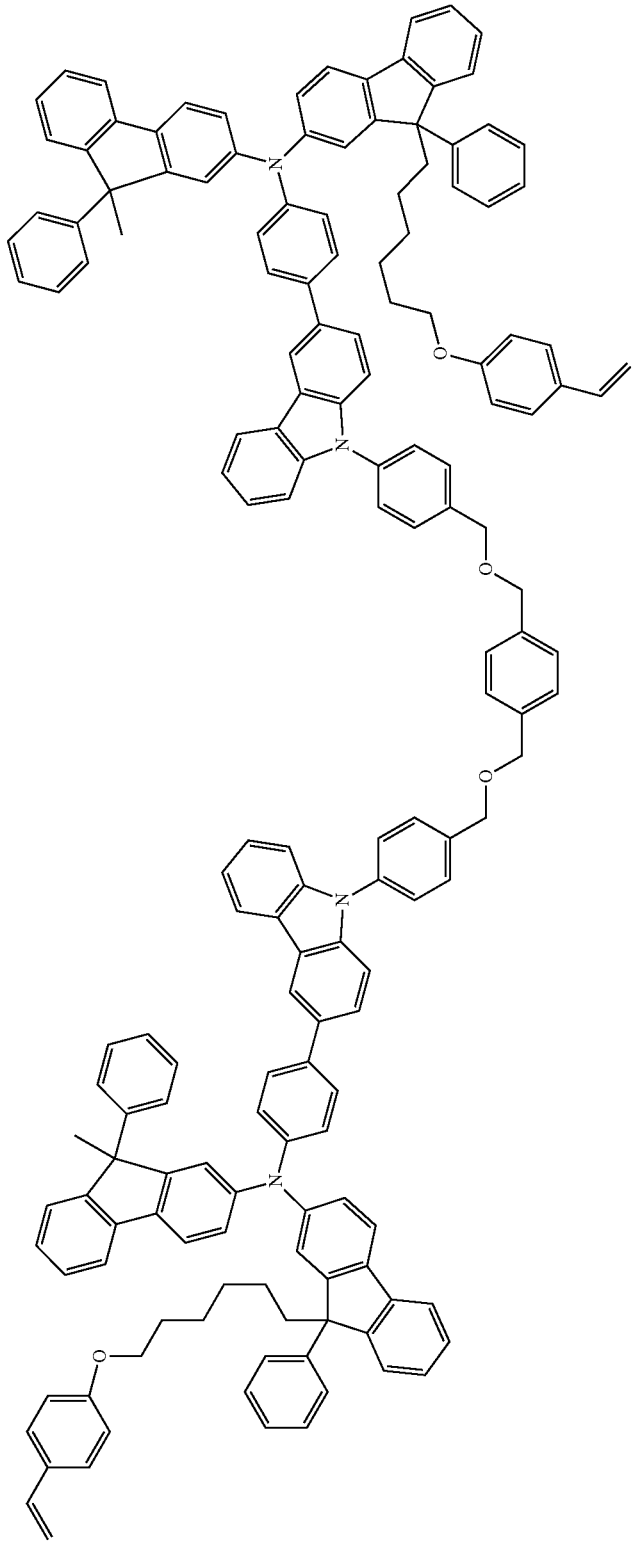

[Compound 21]
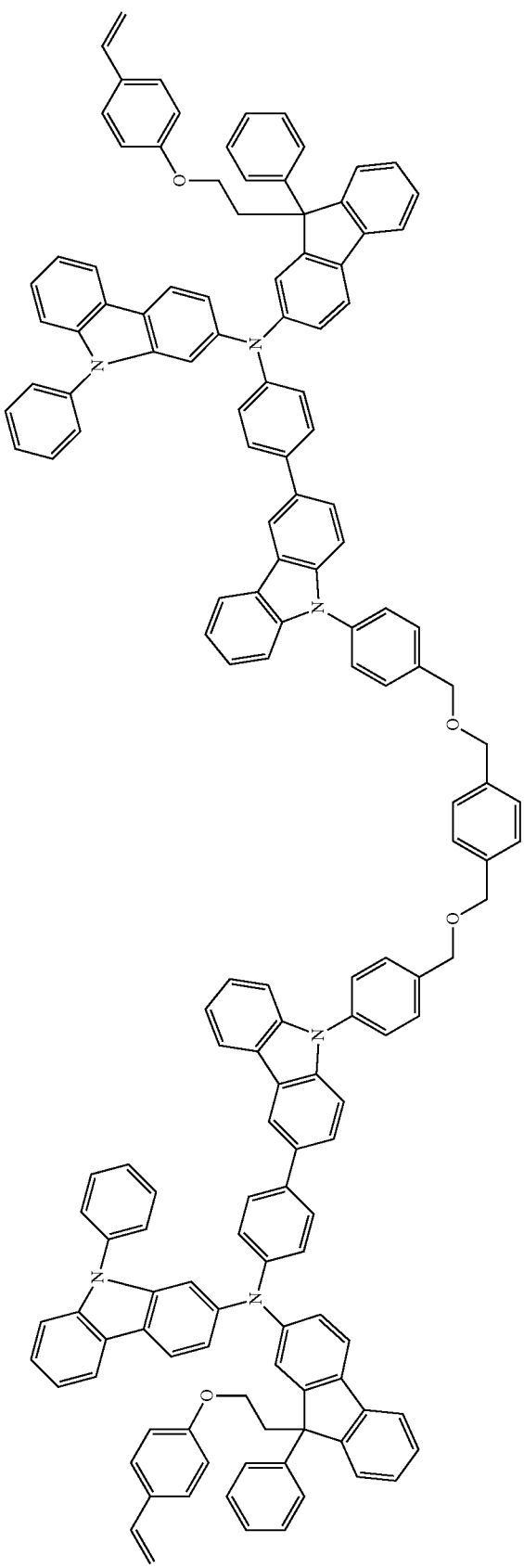

[Compound 22]
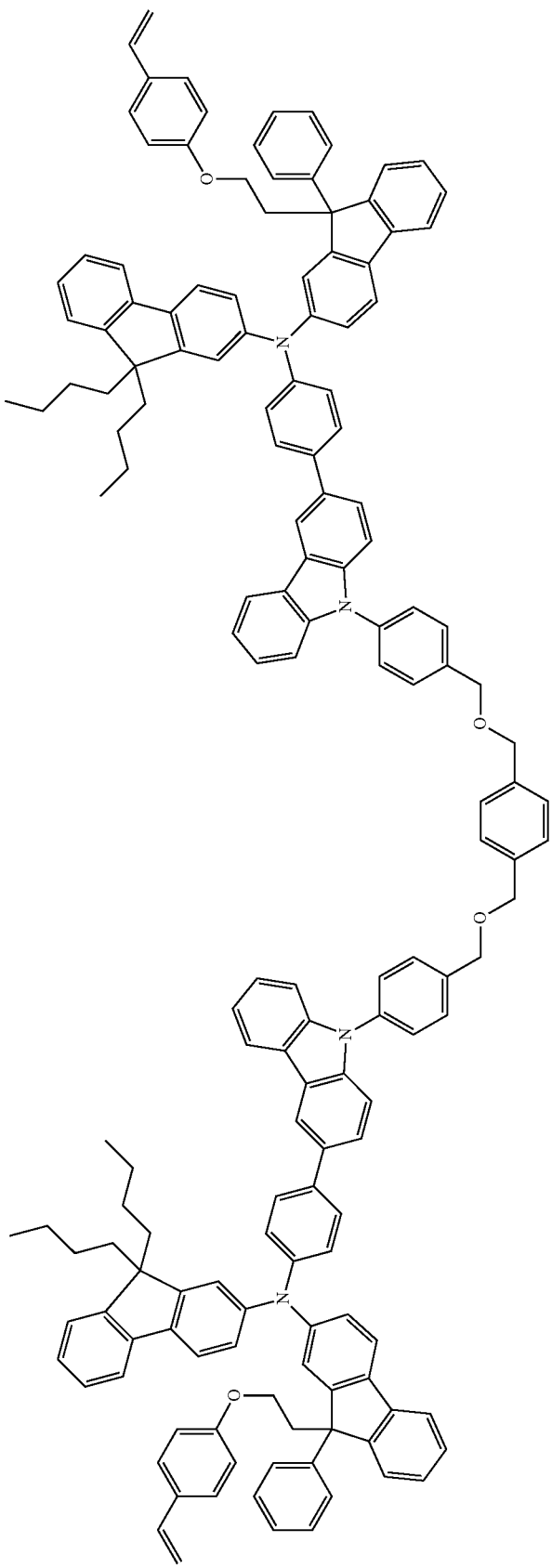

[Compound 23]
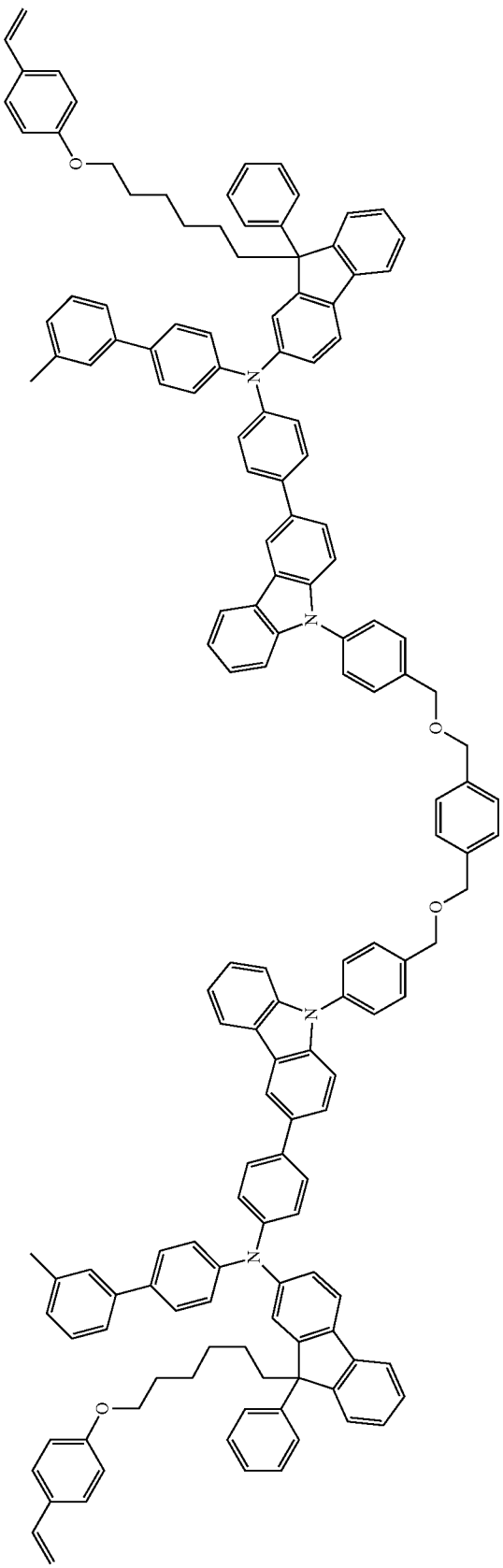

[Compound 24]
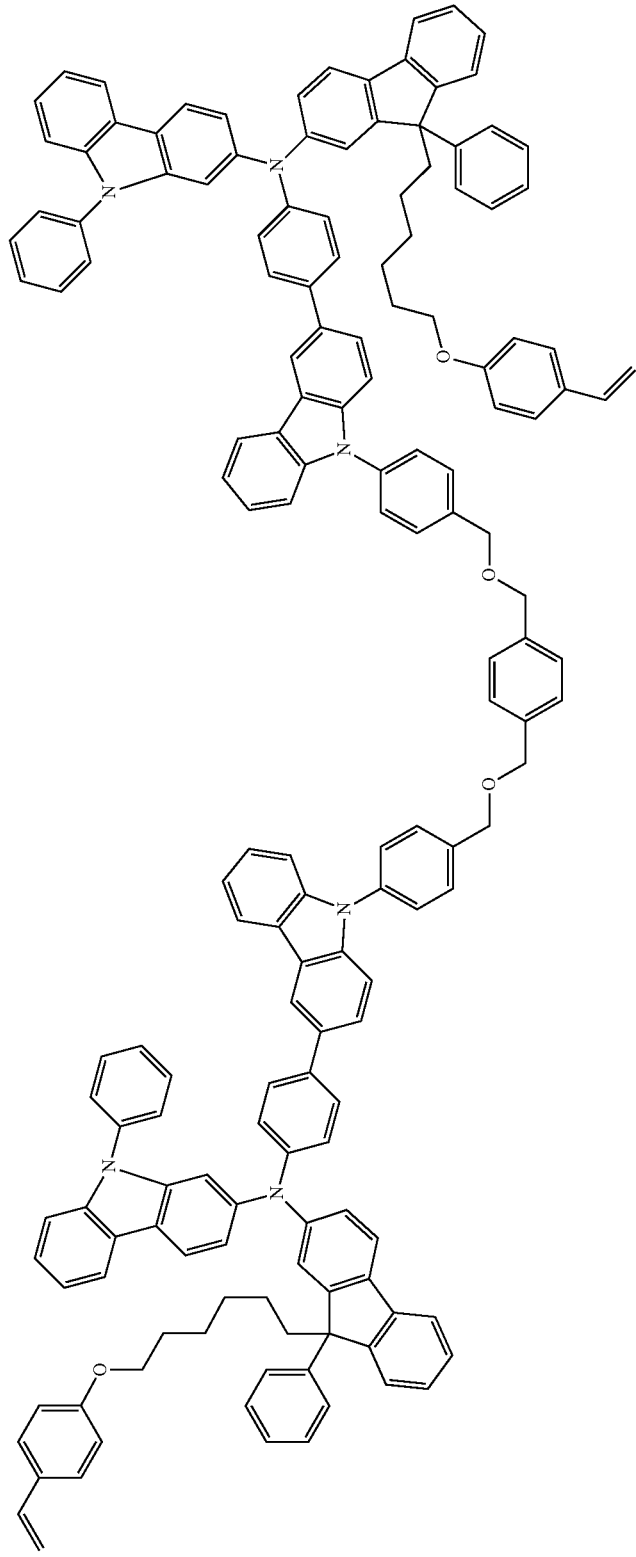

[Compound 25]
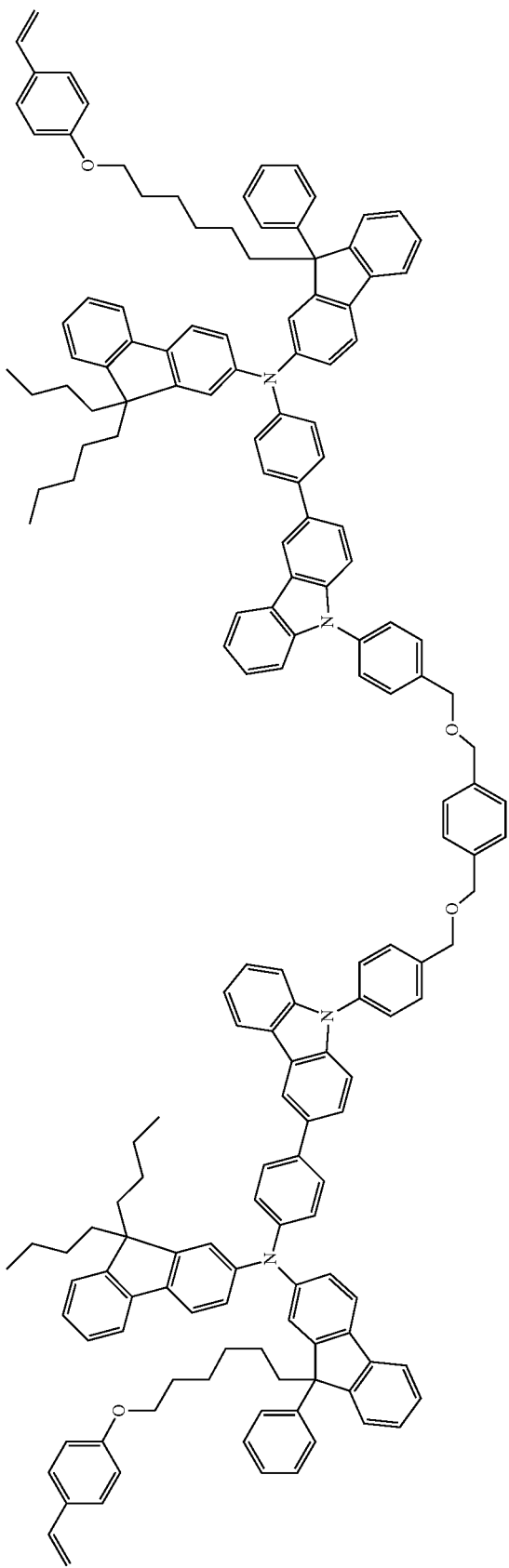
[Compound 26]
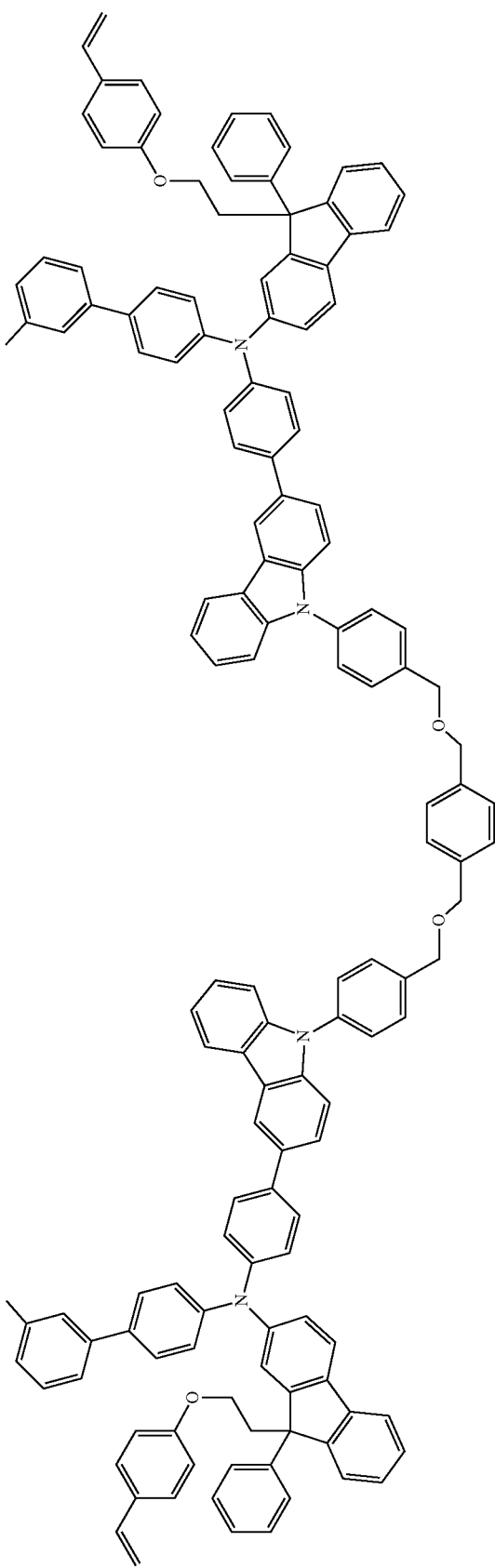

[Compound 27]
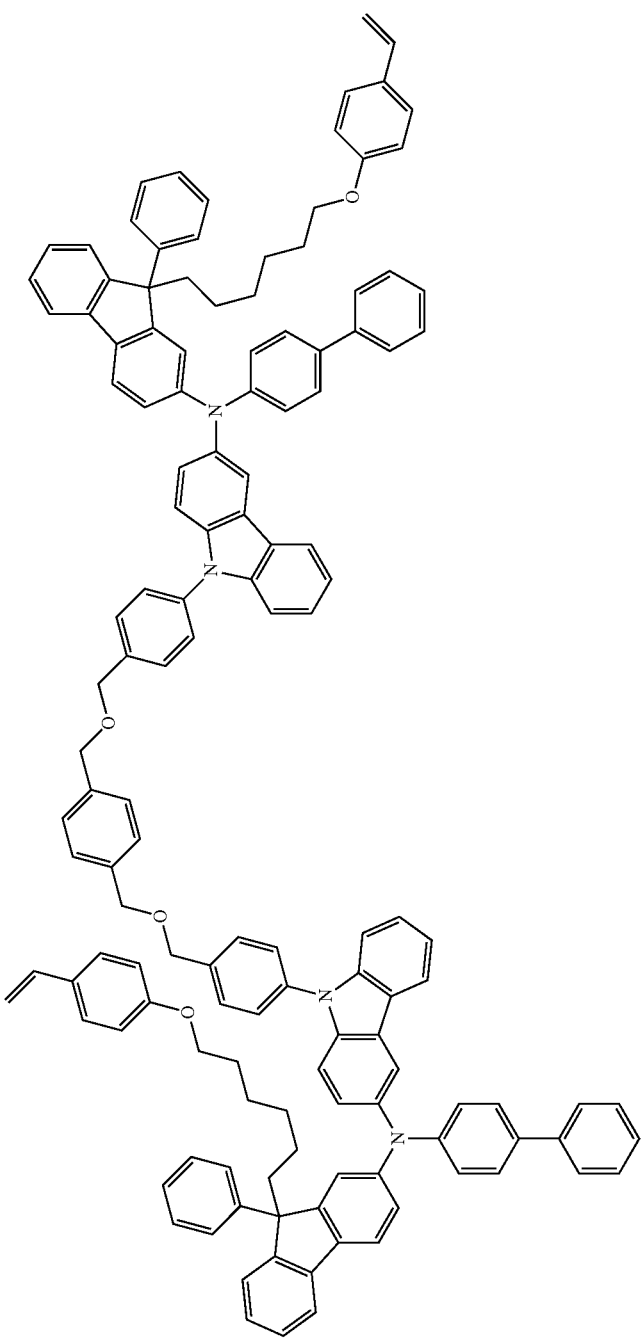

[Compound 28]
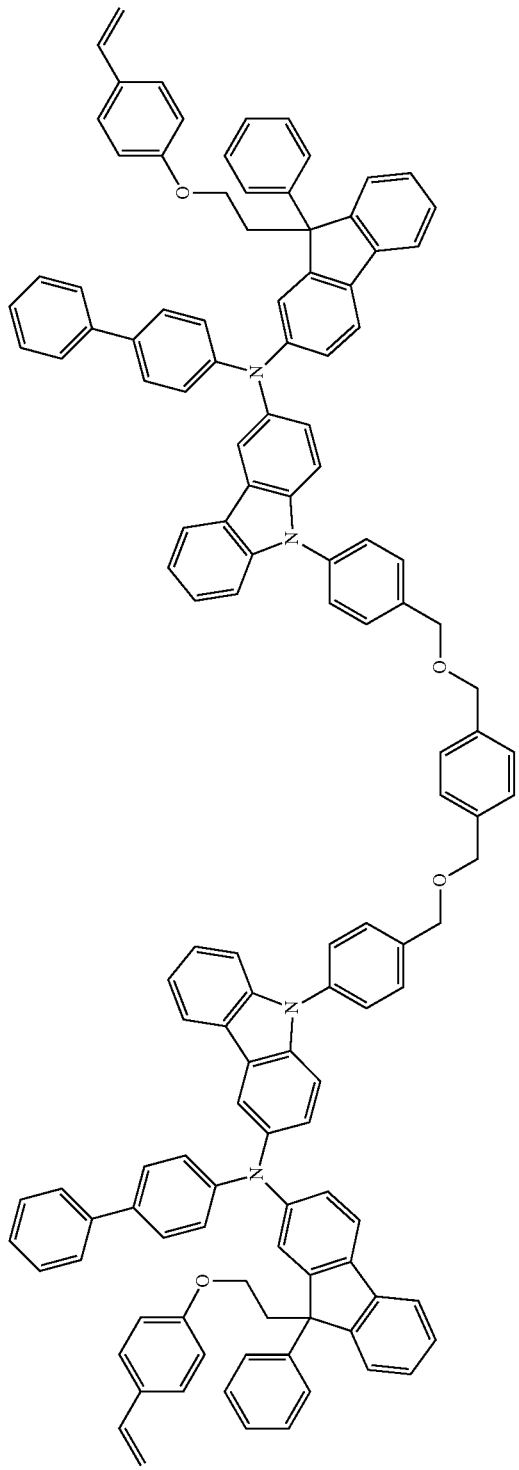
[Compound 29]
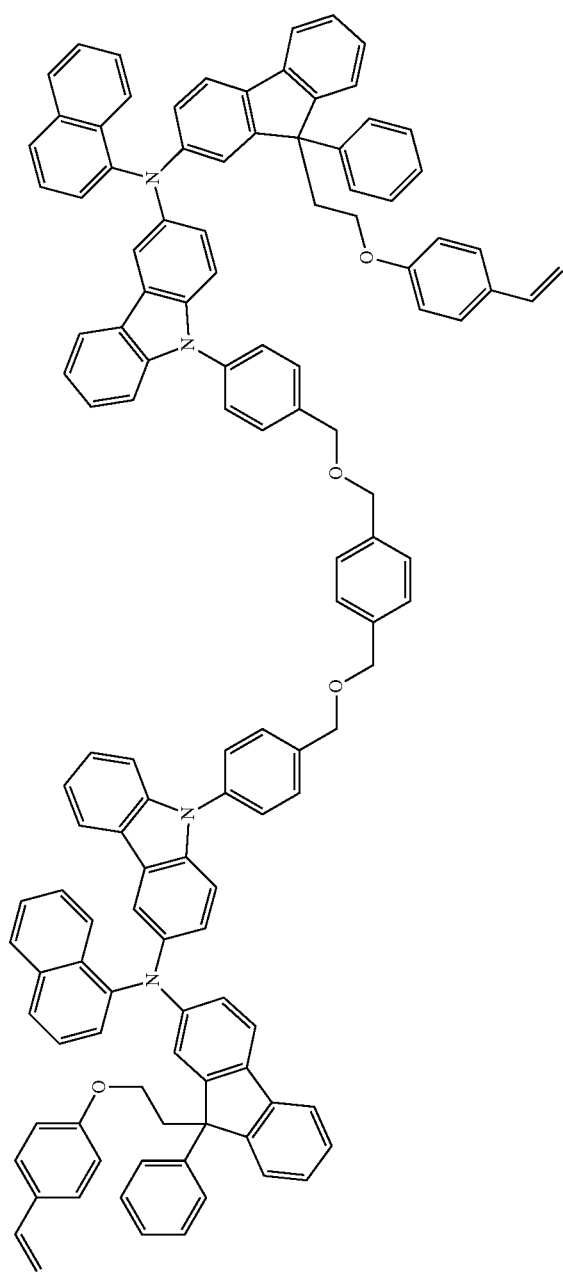

[Compound 30]
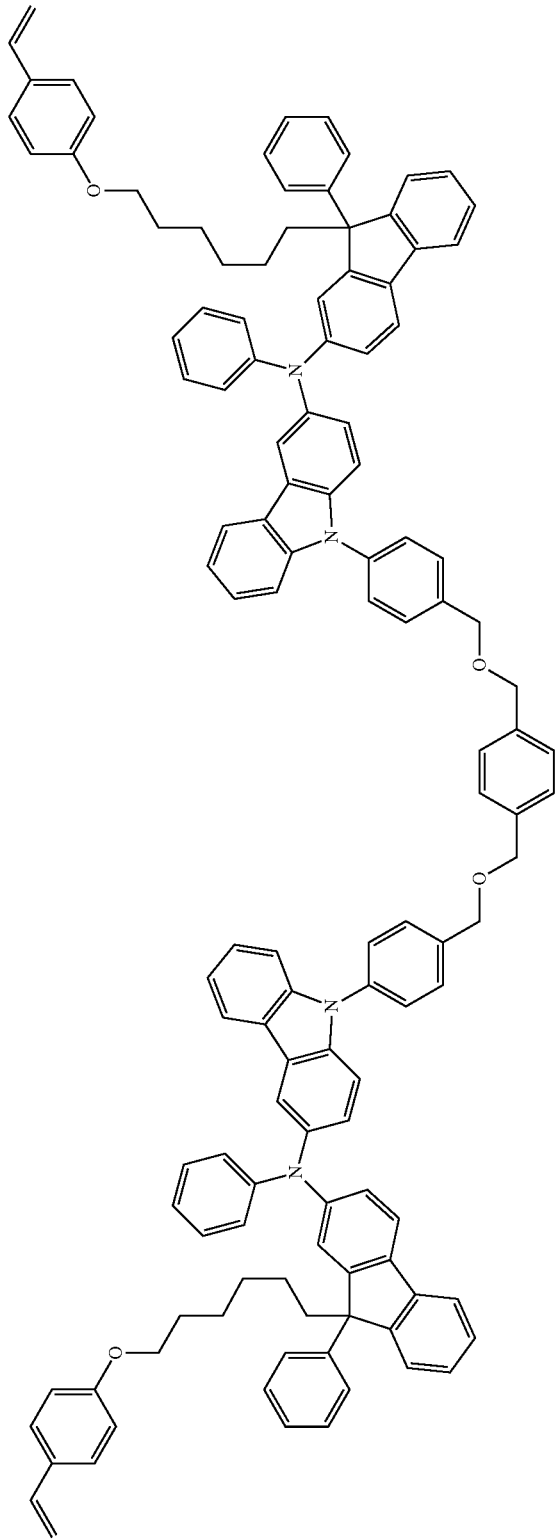
[Compound 31]
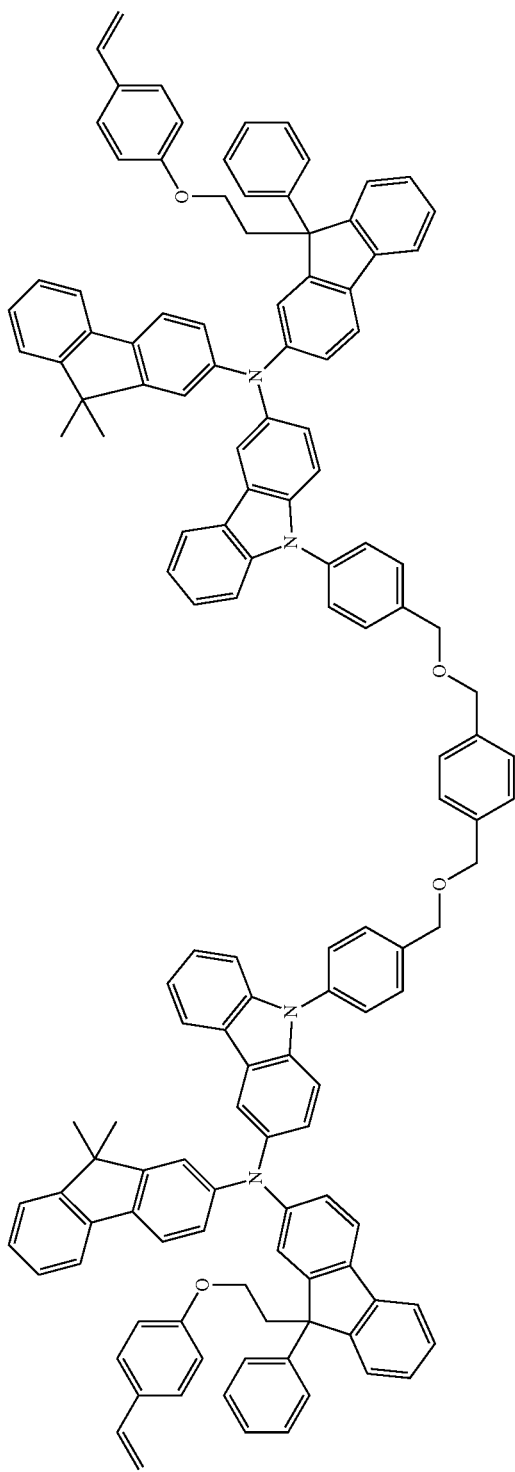

-continued
[Compound 32]
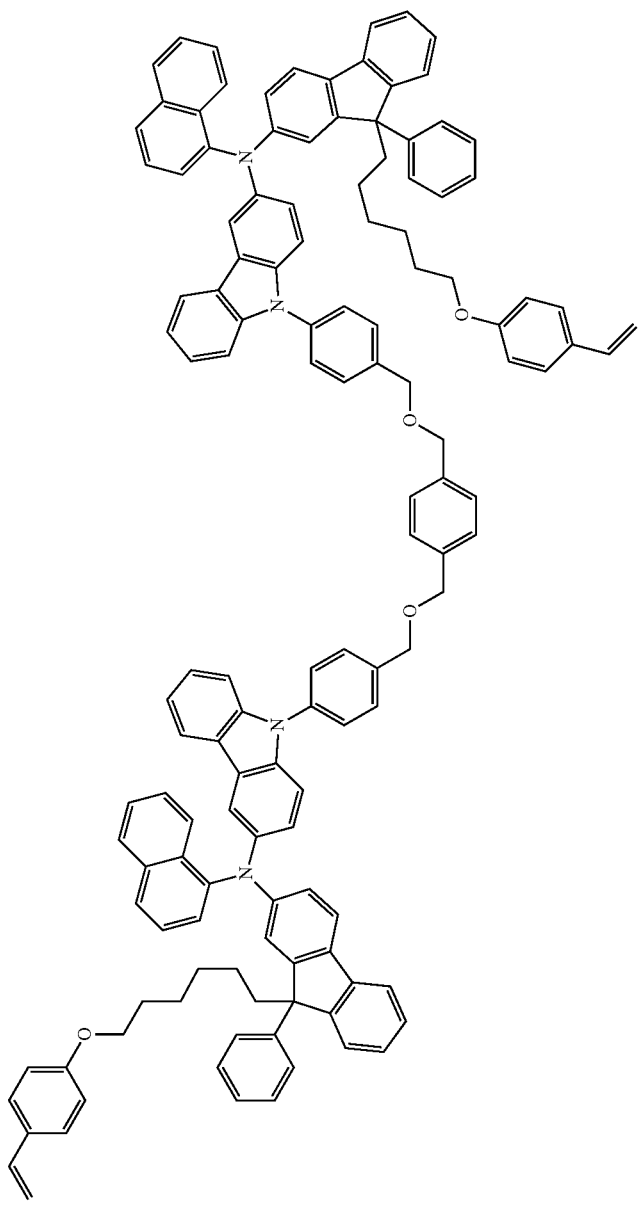

[Compound 33]
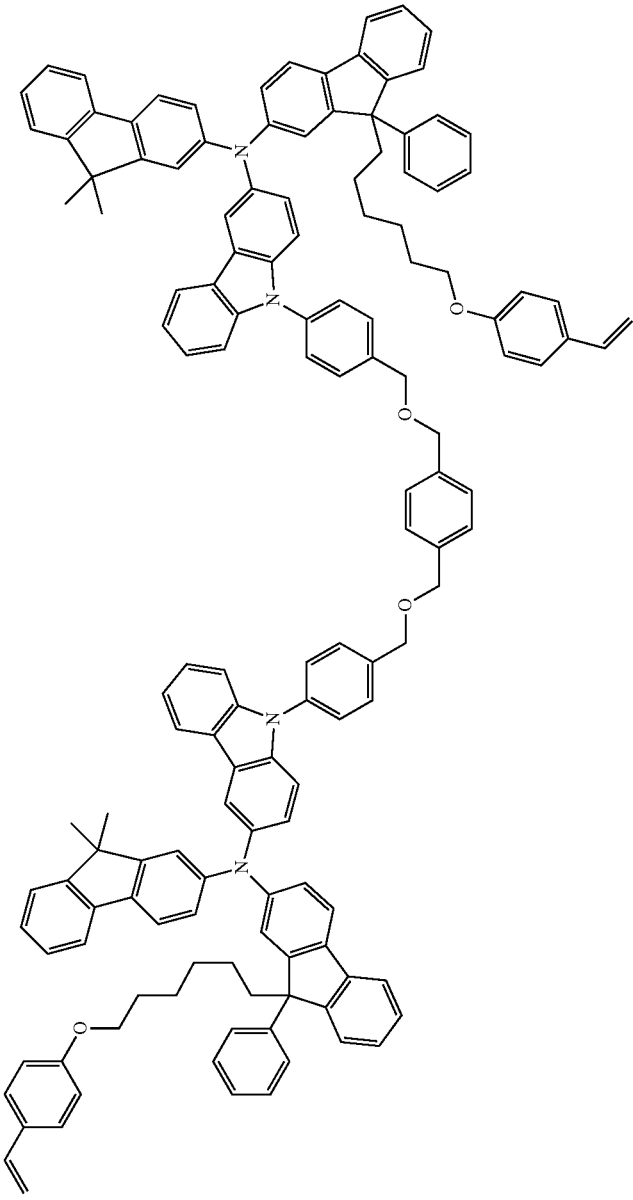
[Compound 34]
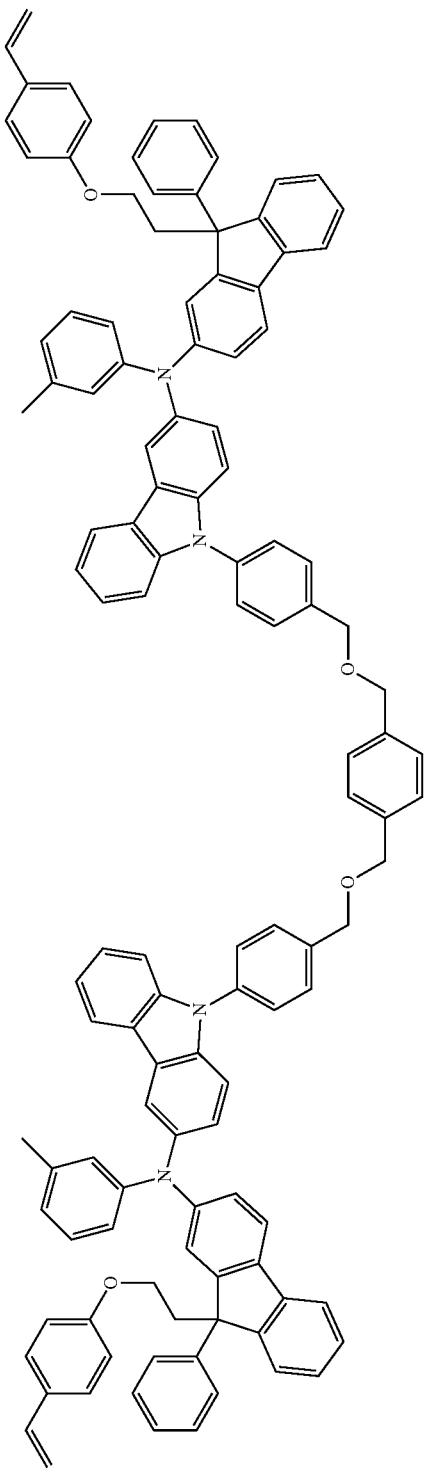

[Compound 35]
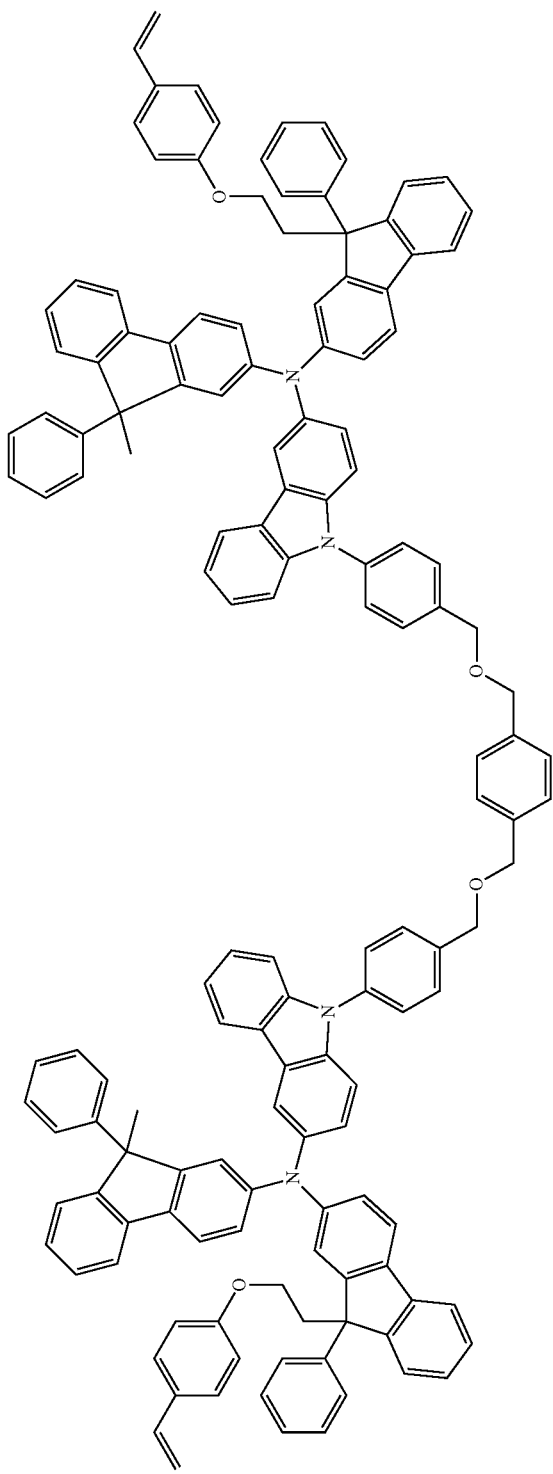
[Compound 36]
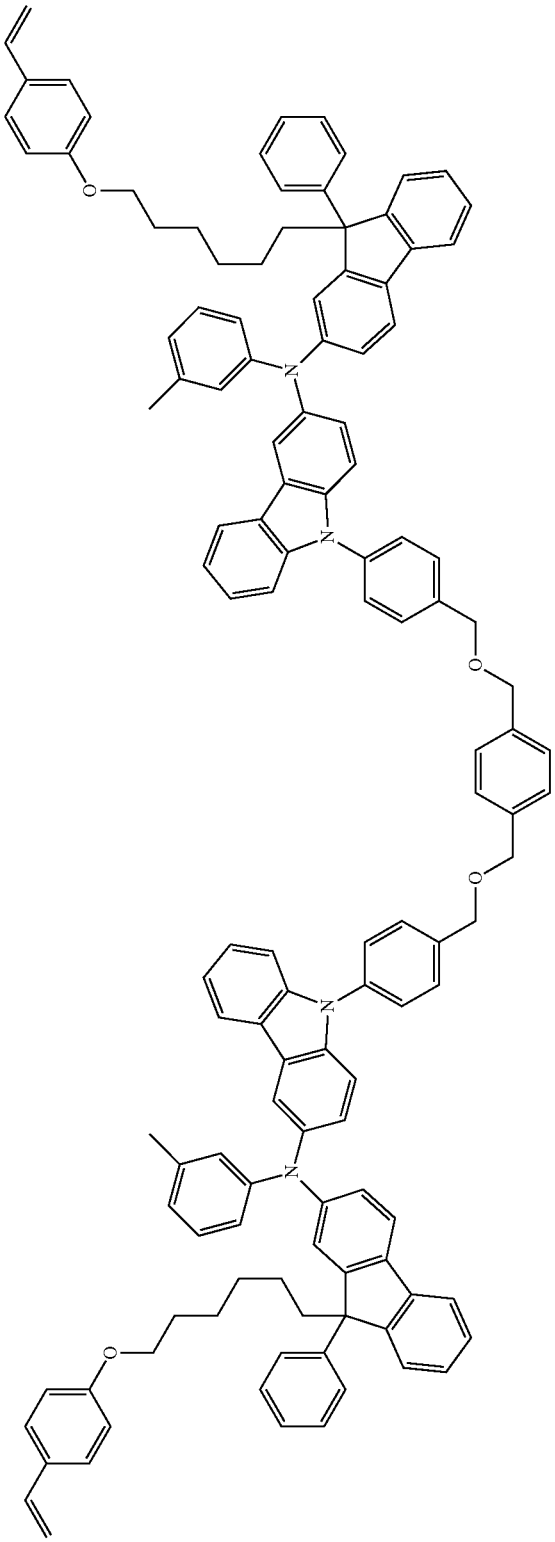

[Compound 37]
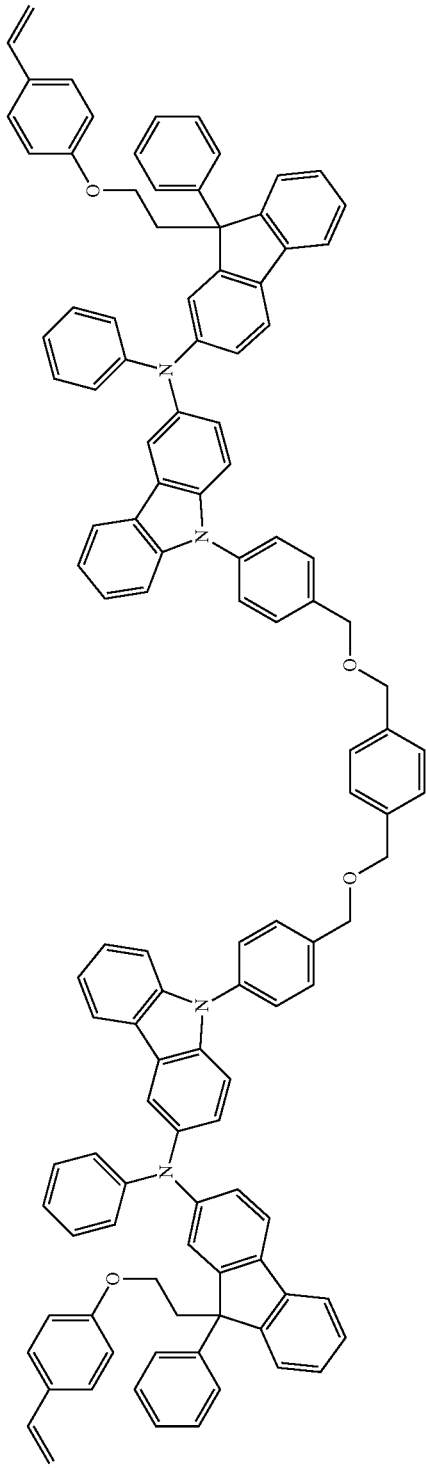
[Compound 38]
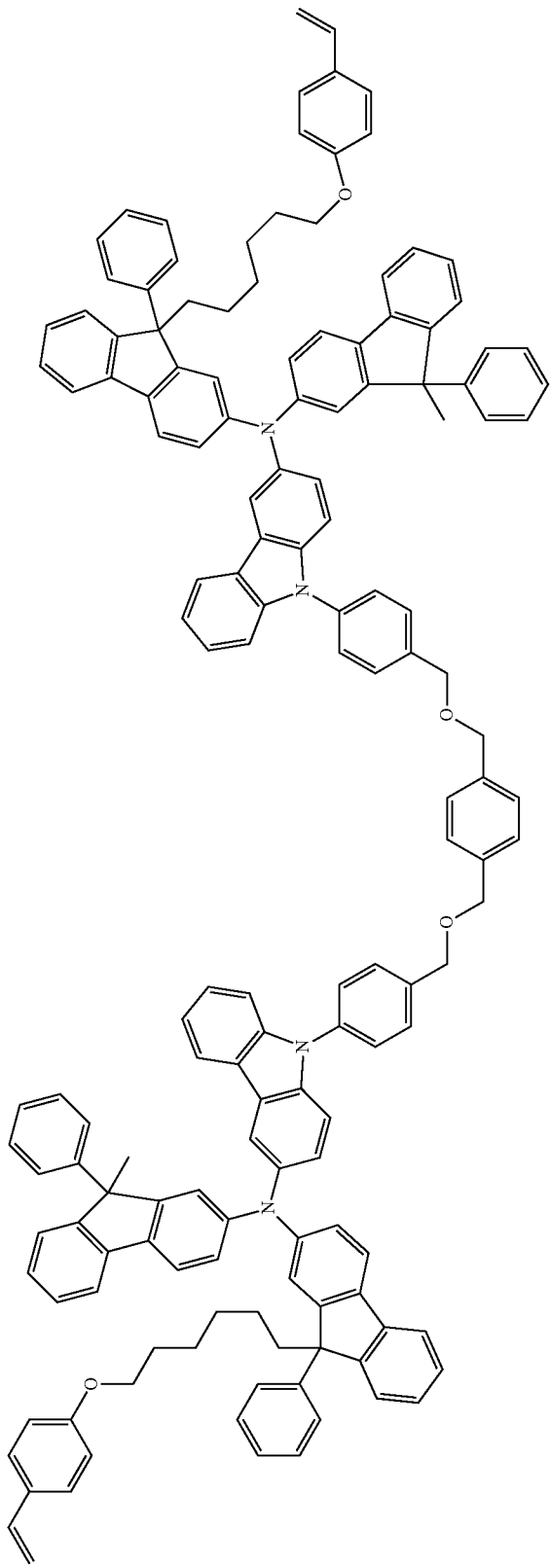

[Compound 39]
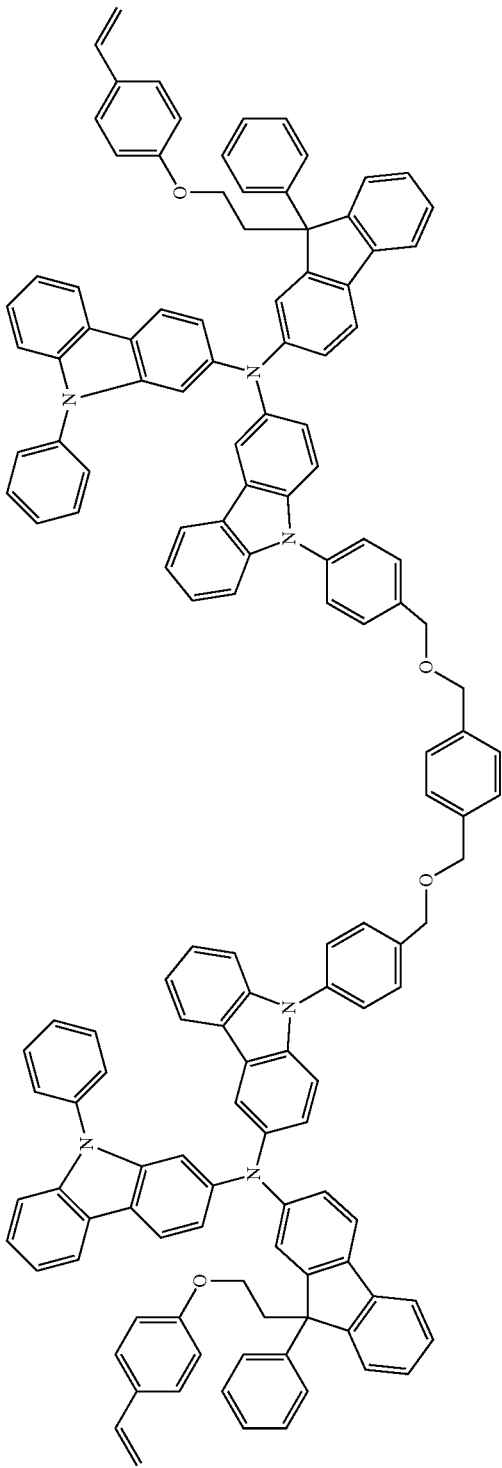
[Compound 40]
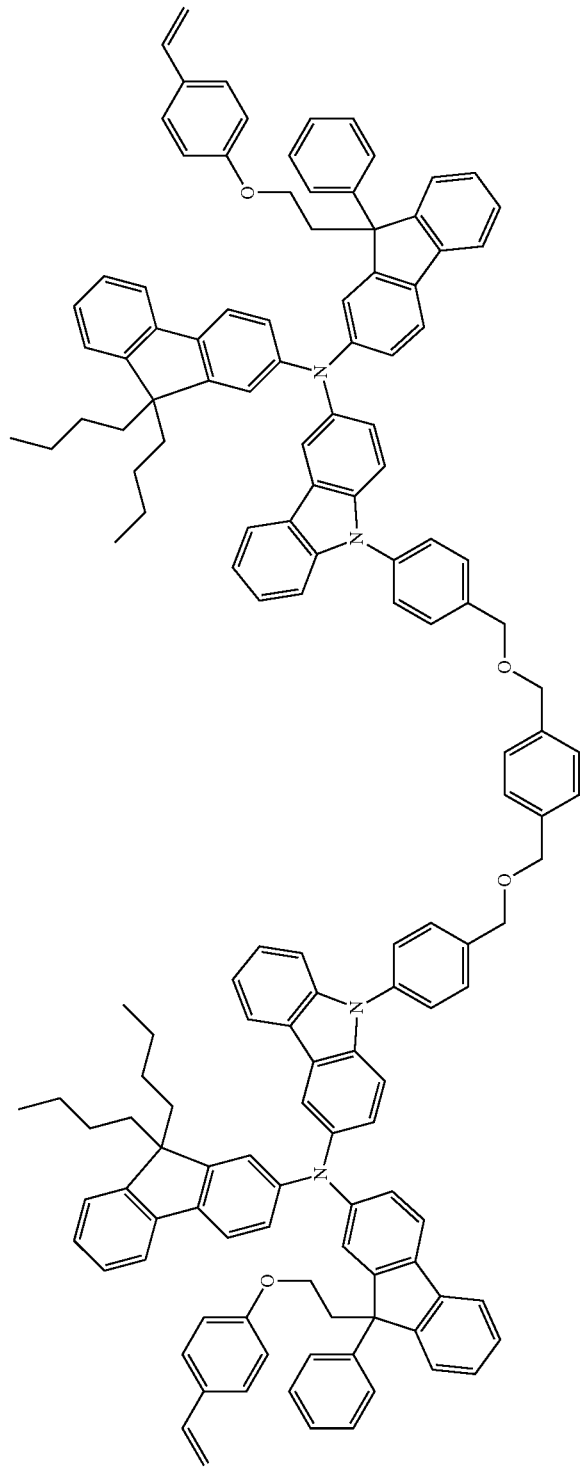

[Compound 41]
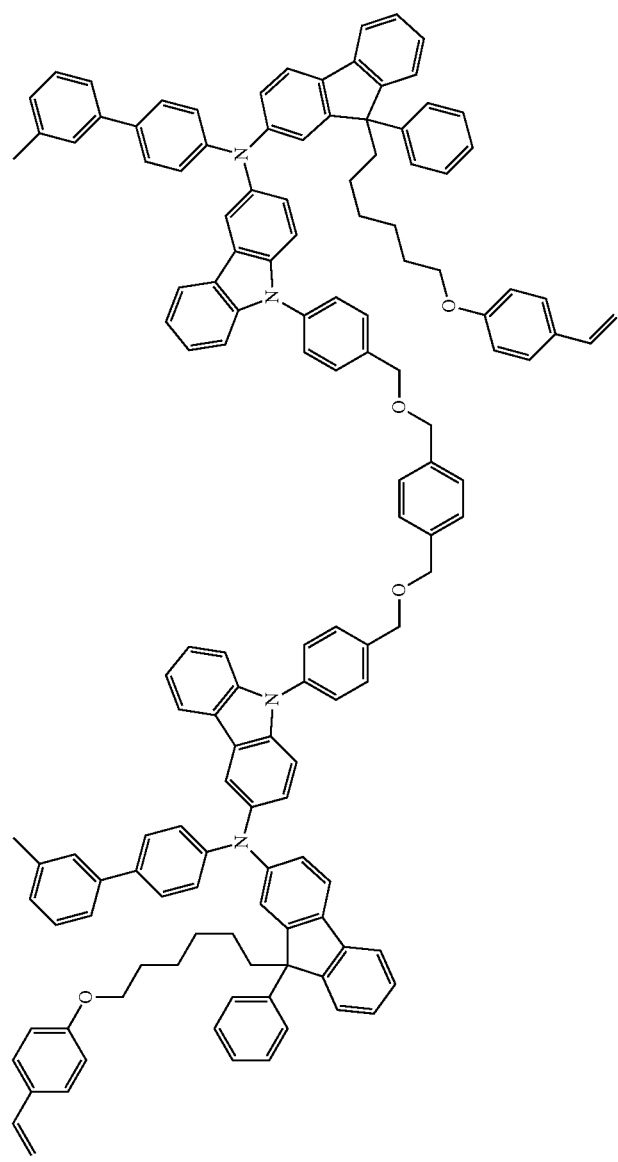

[Compound 42]
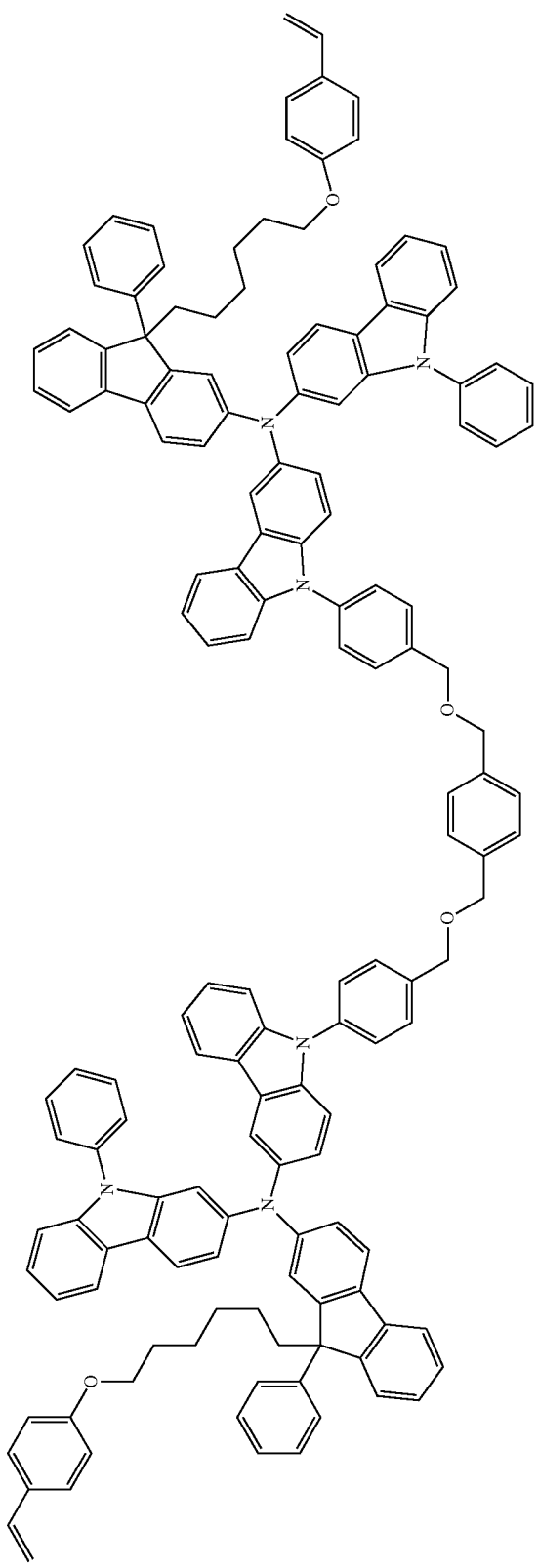

[Compound 43]
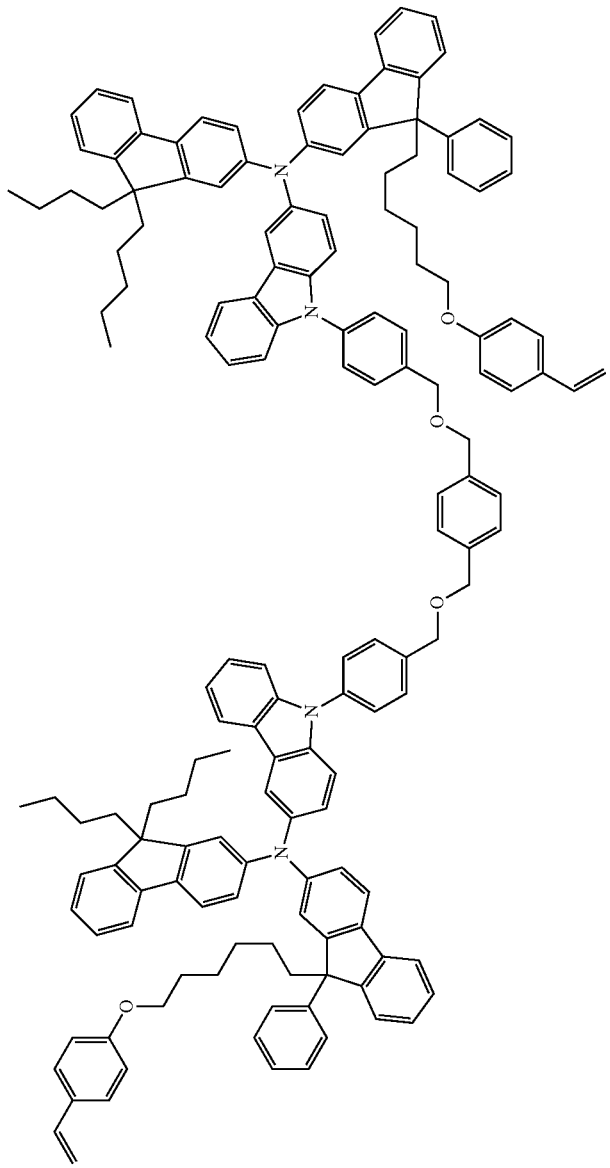

[Compound 44]
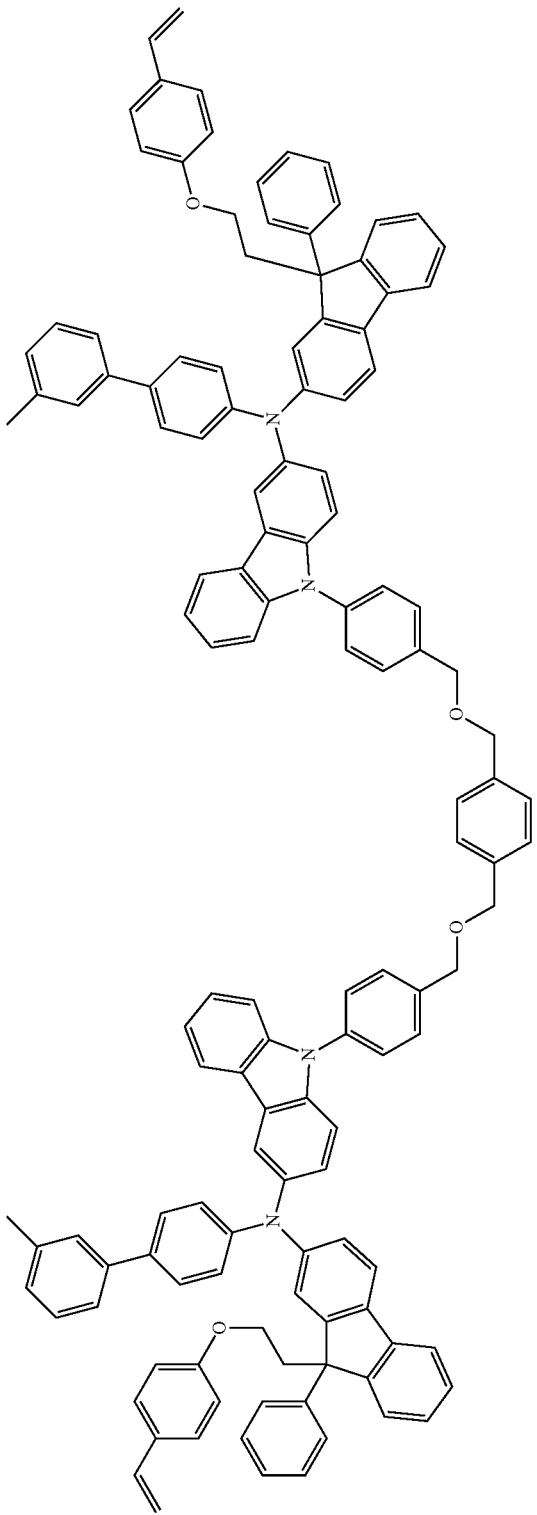
[Compound 45]
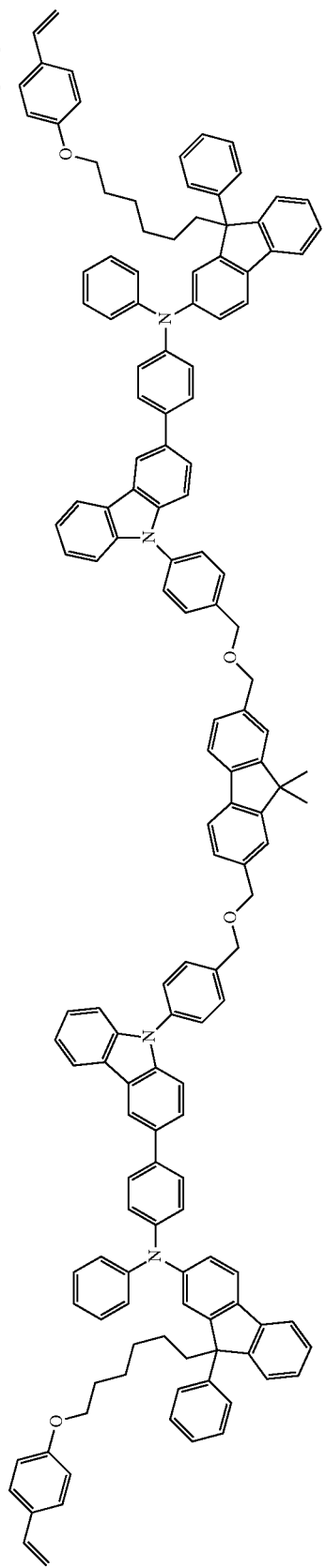

[Compound 46]
-continued
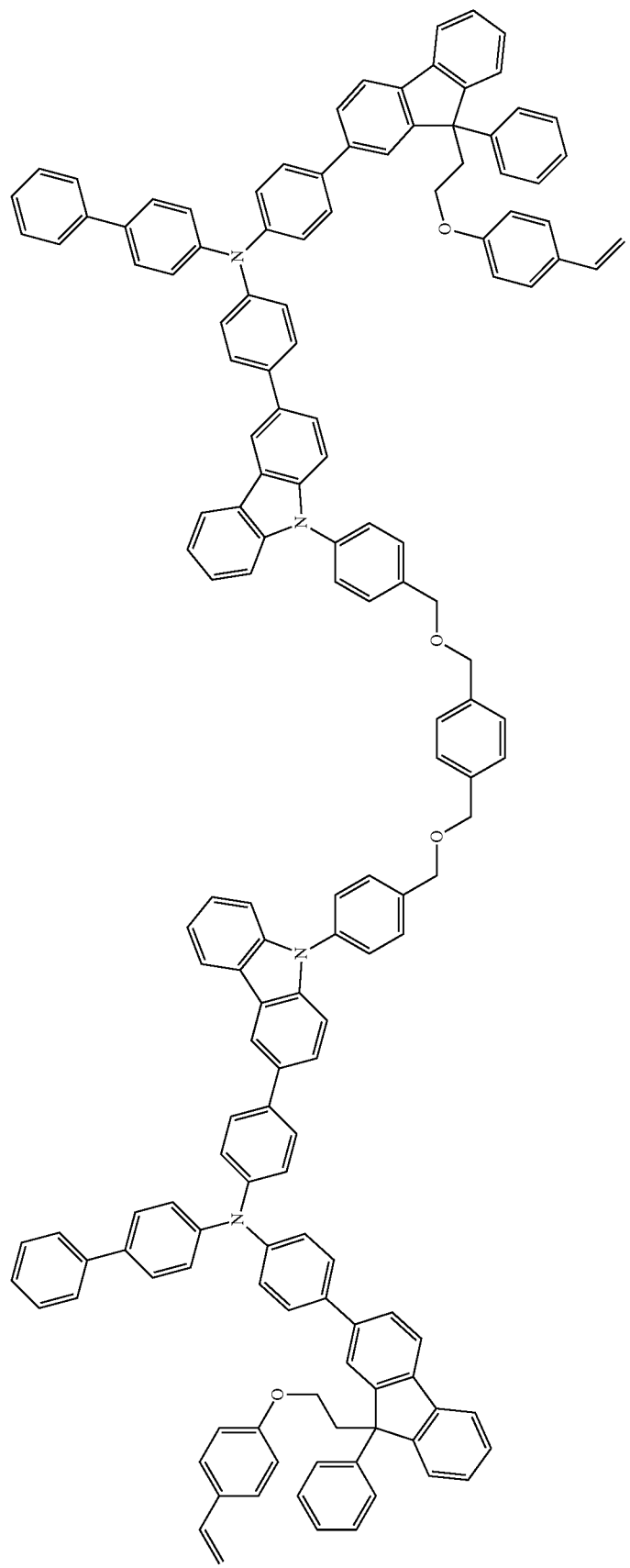

283
[Compound 47]
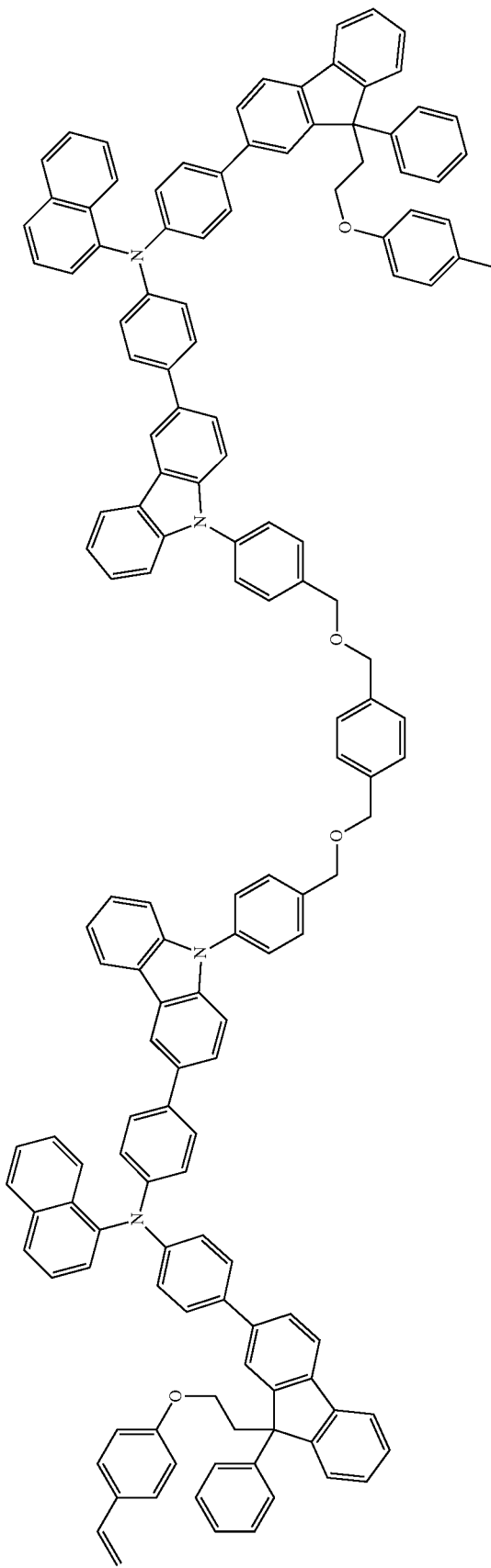
-continued
284
[Compound 48]
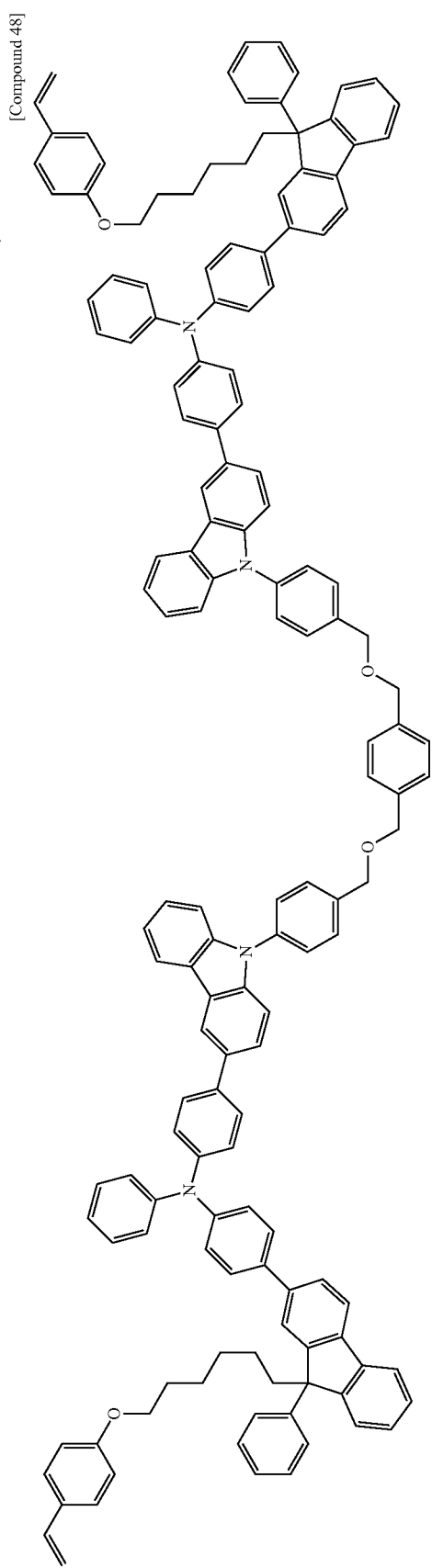

285
[Compound 49]
-continued
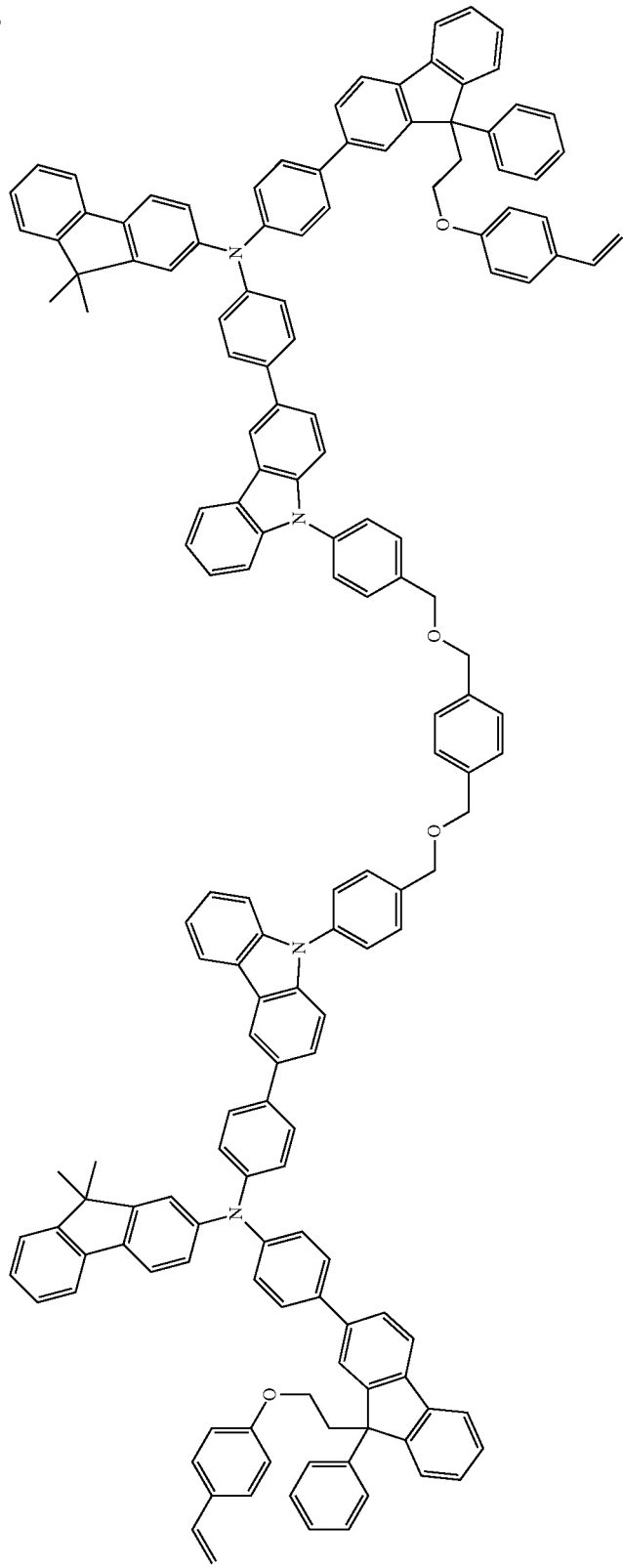
286
[Compound 50]
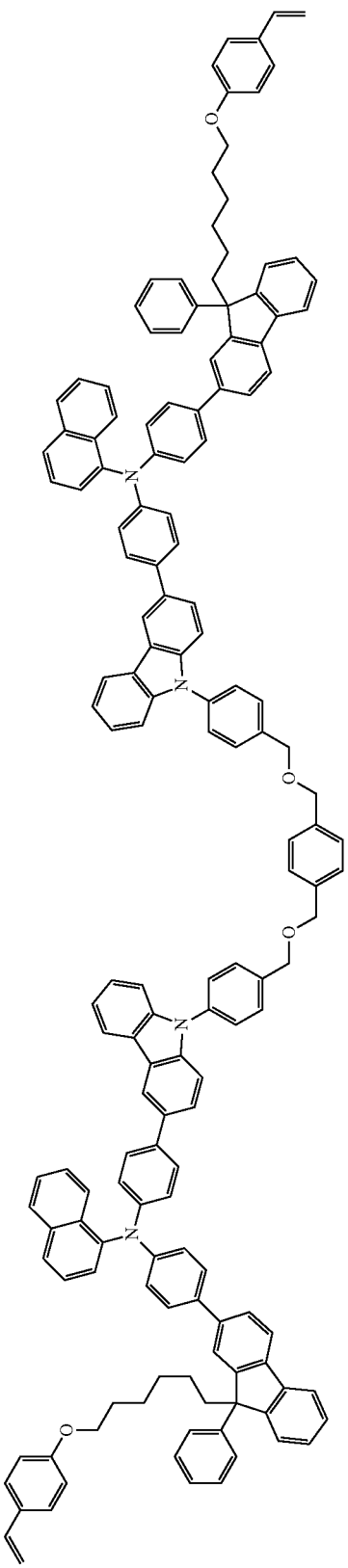

[Compound 51]
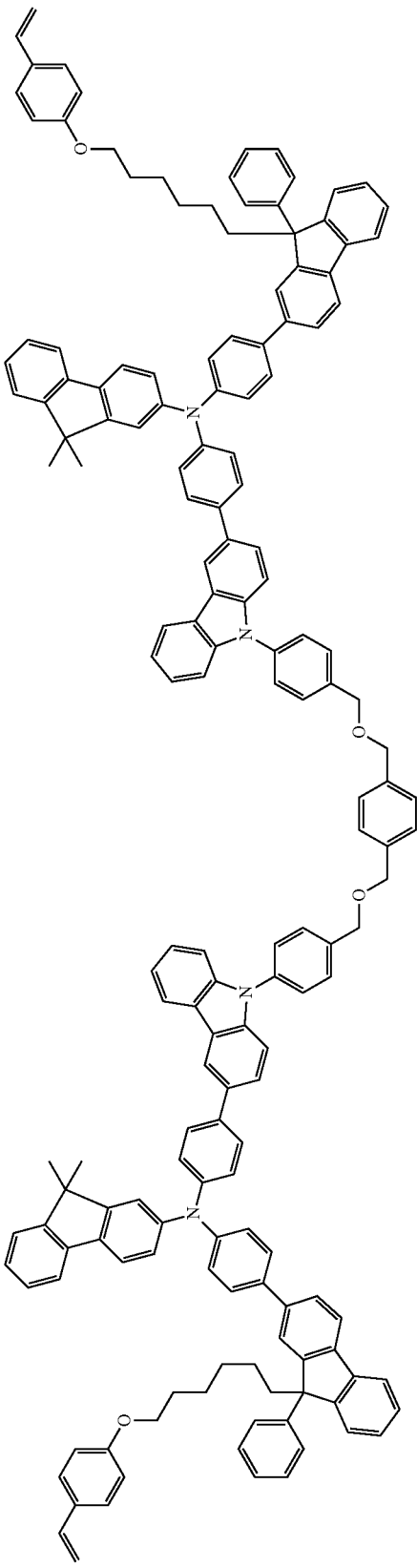
[Compound 52]
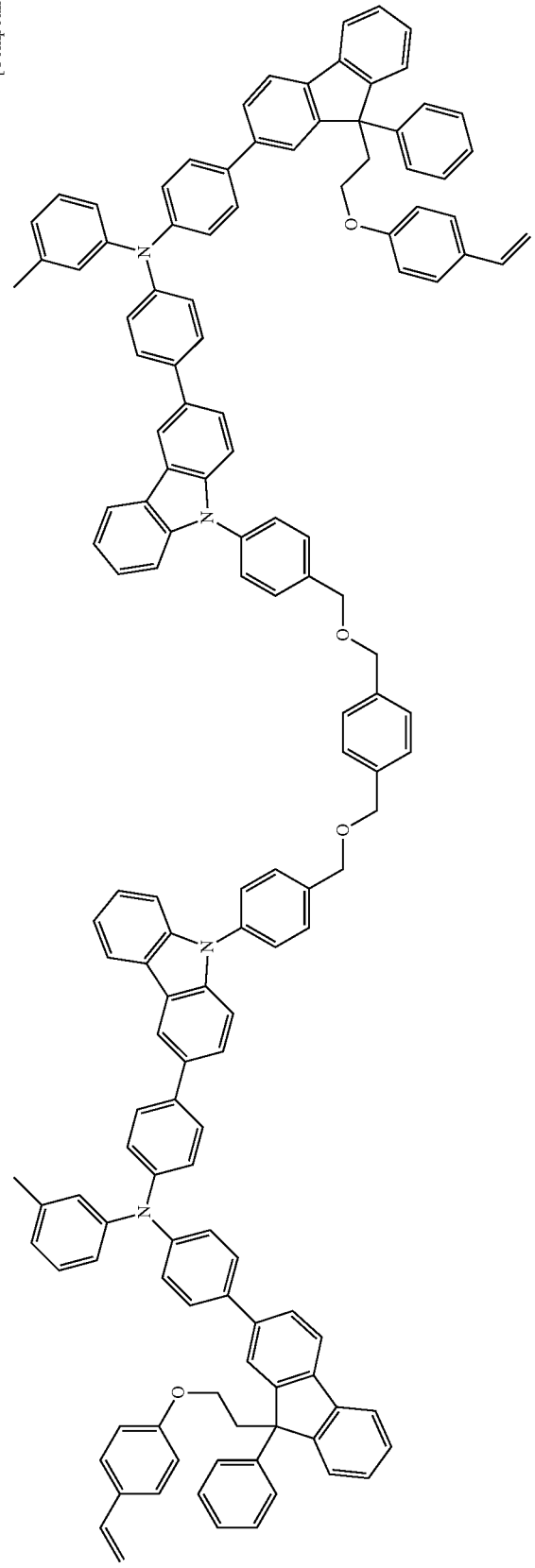

289    290
[Compound 53]
[Compound 54]
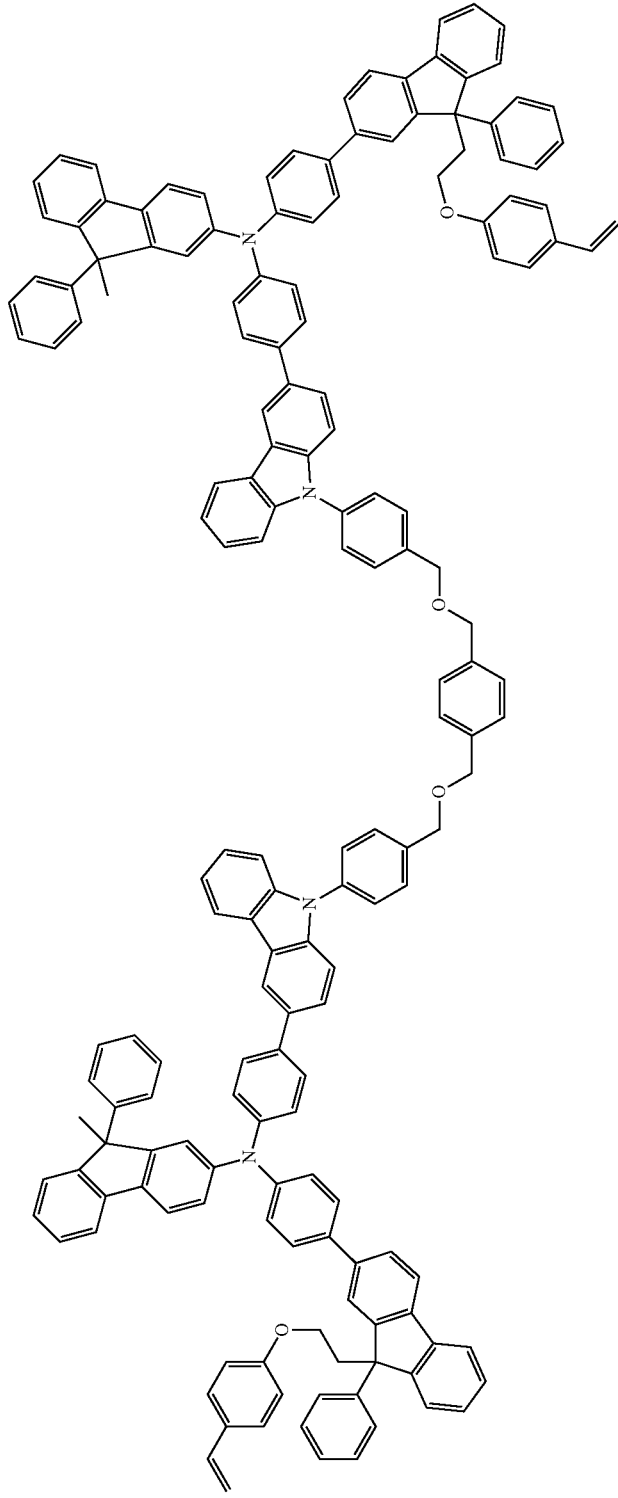
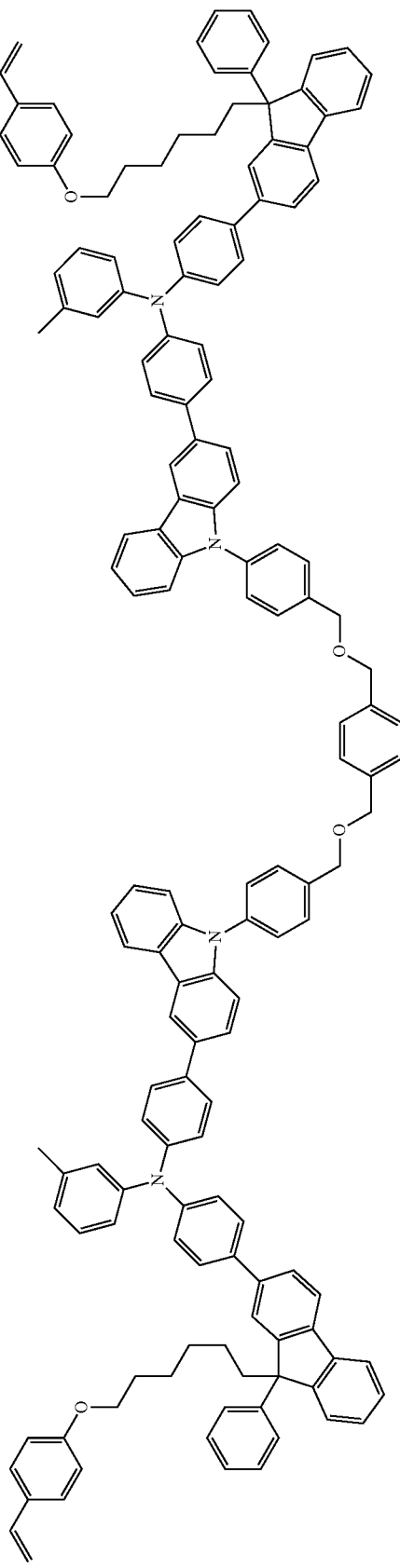

291
[Compound 55]
292
[Compound 56]
-continued
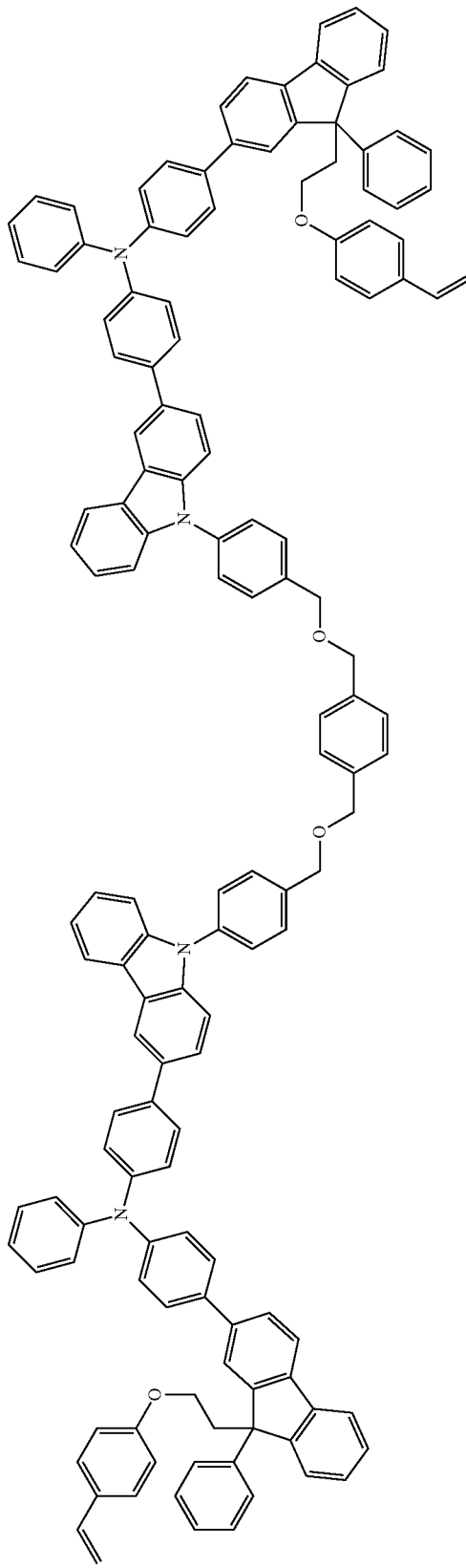
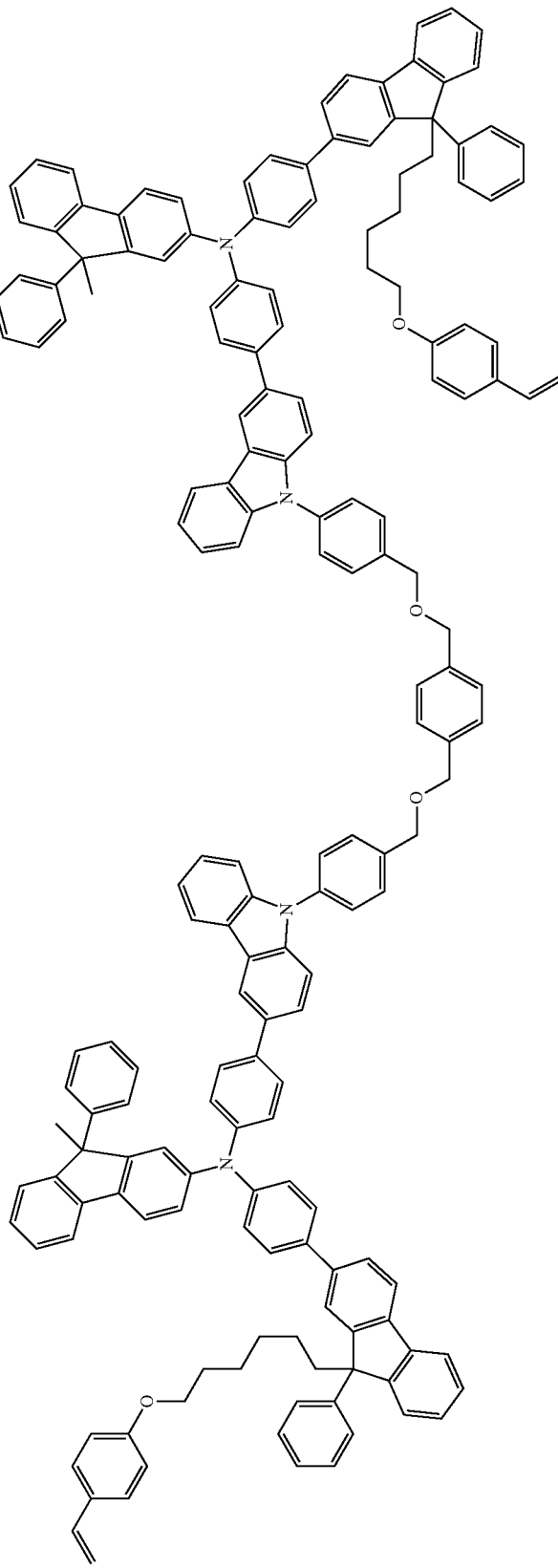

[Compound 57]
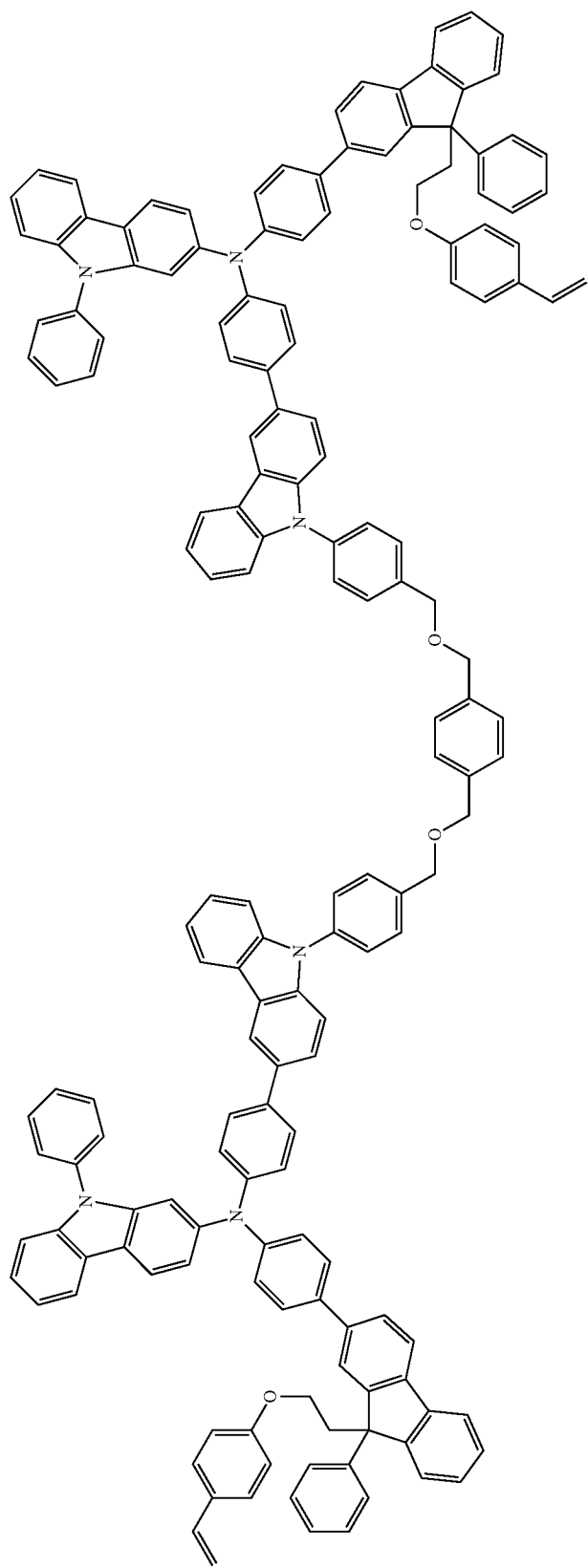

295
[Compound 58]
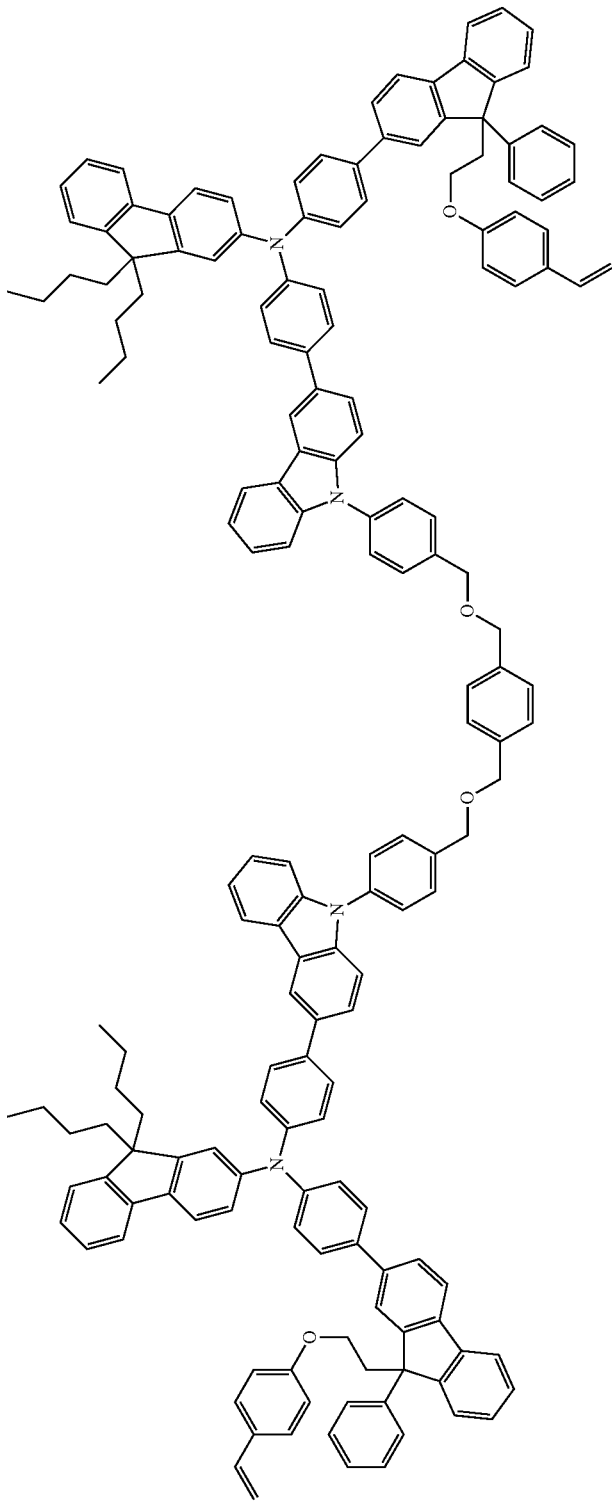
-continued
296
[Compound 59]
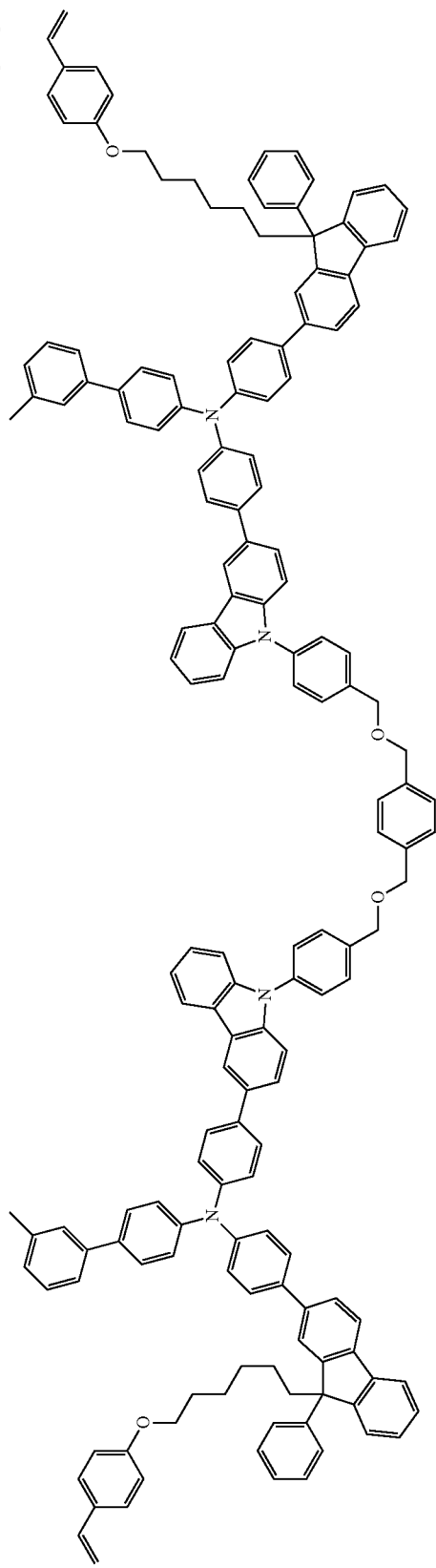

-continued
[Compound 60]
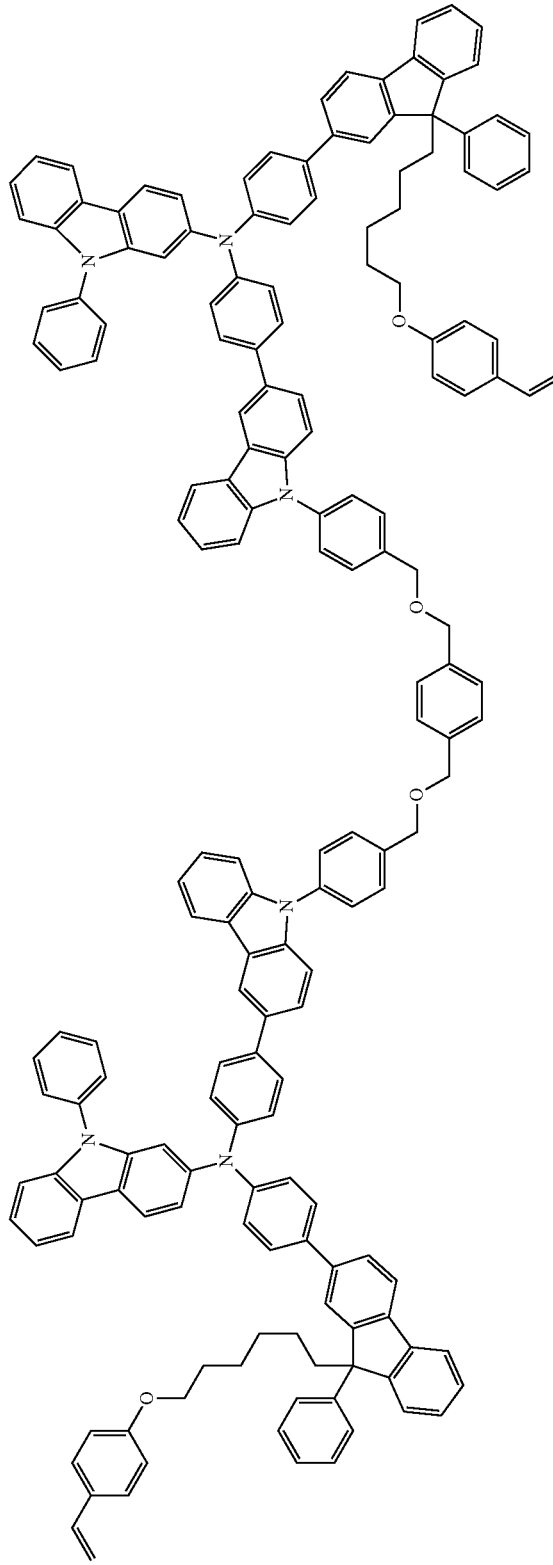
[Compound 61]
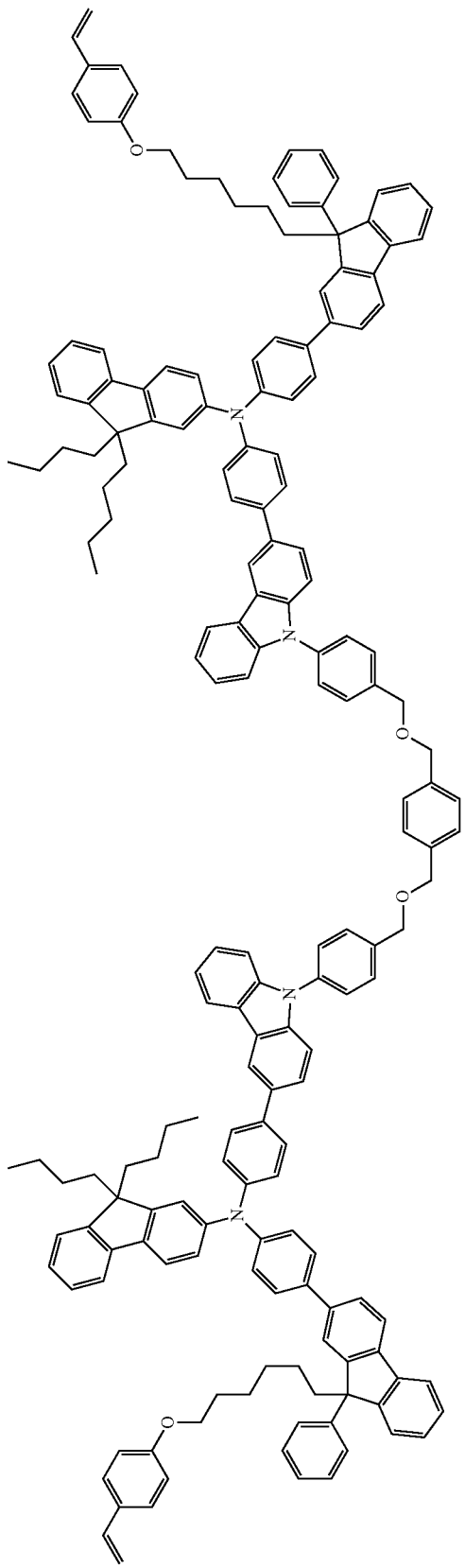

-continued
[Compound 62]
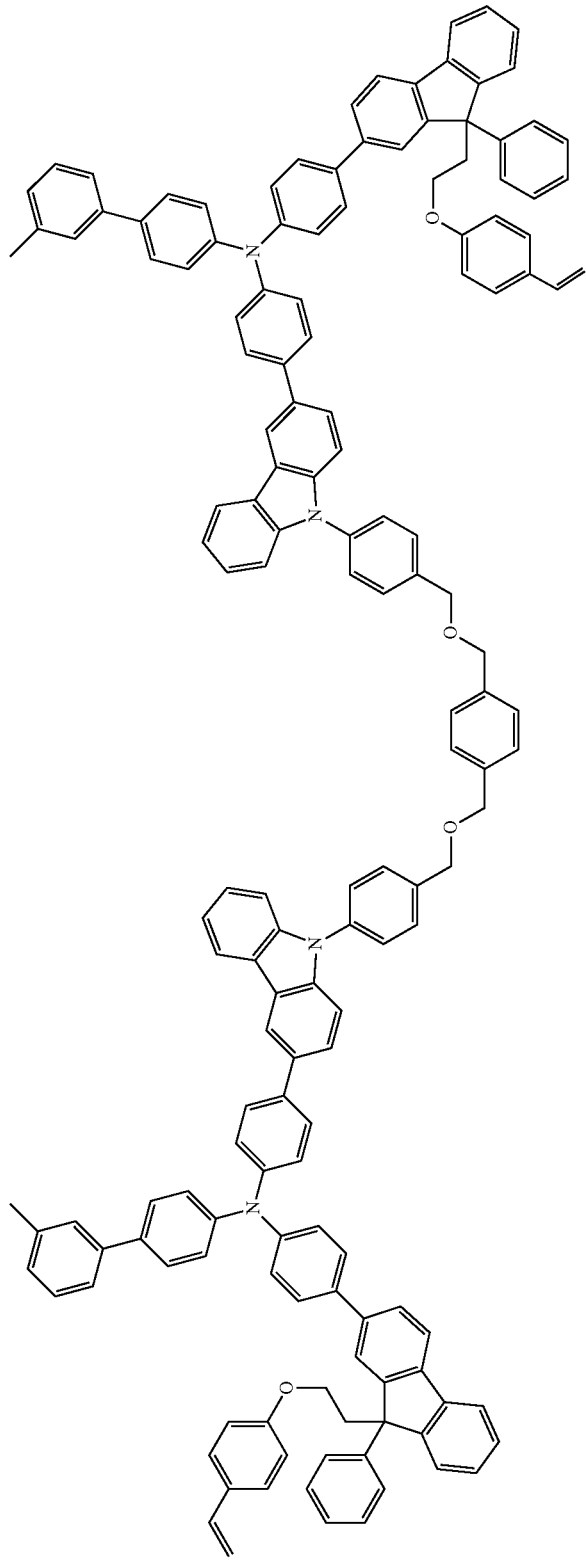
[Compound 63]
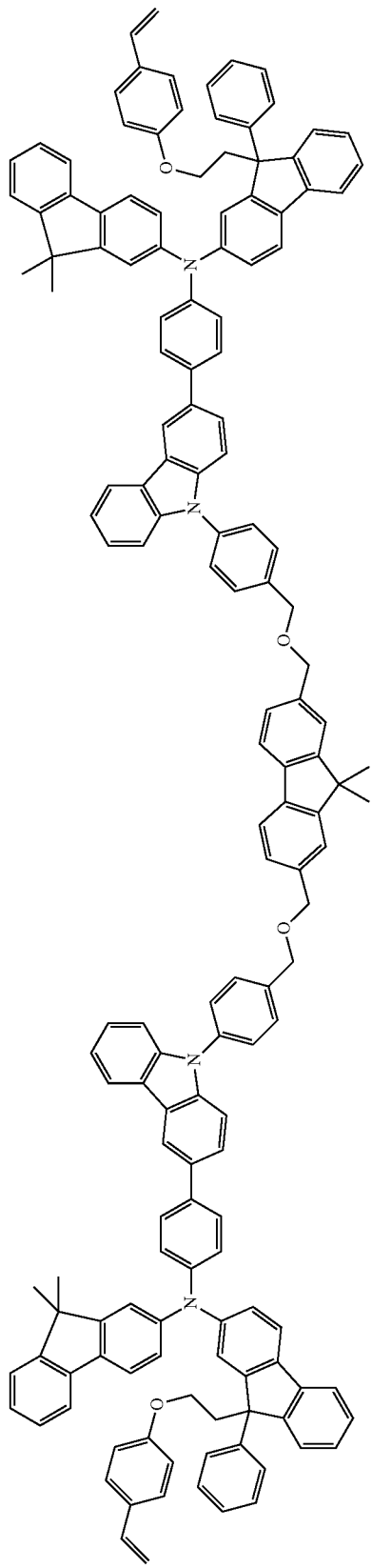

[Compound 64]
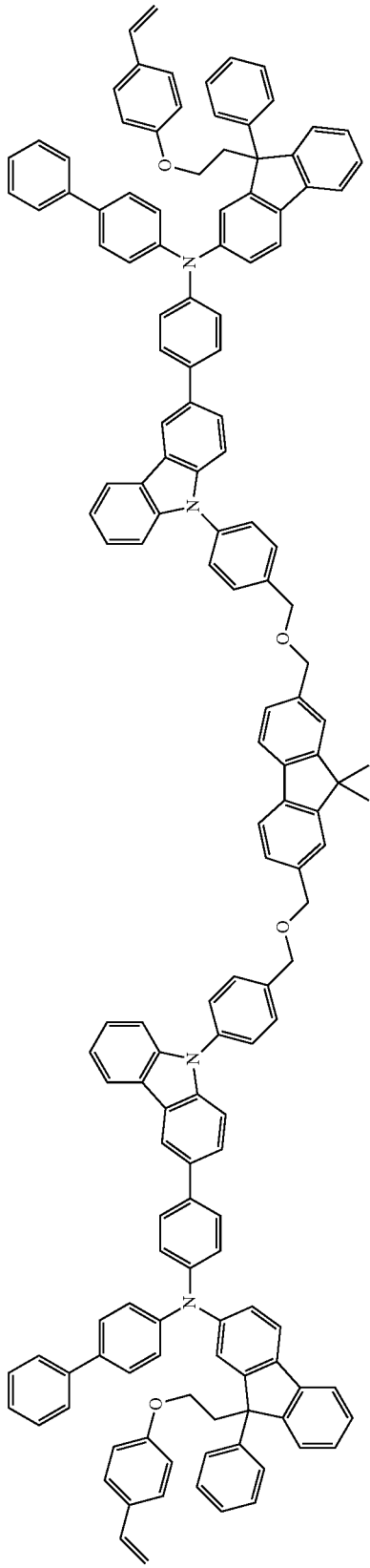
[Compound 65]
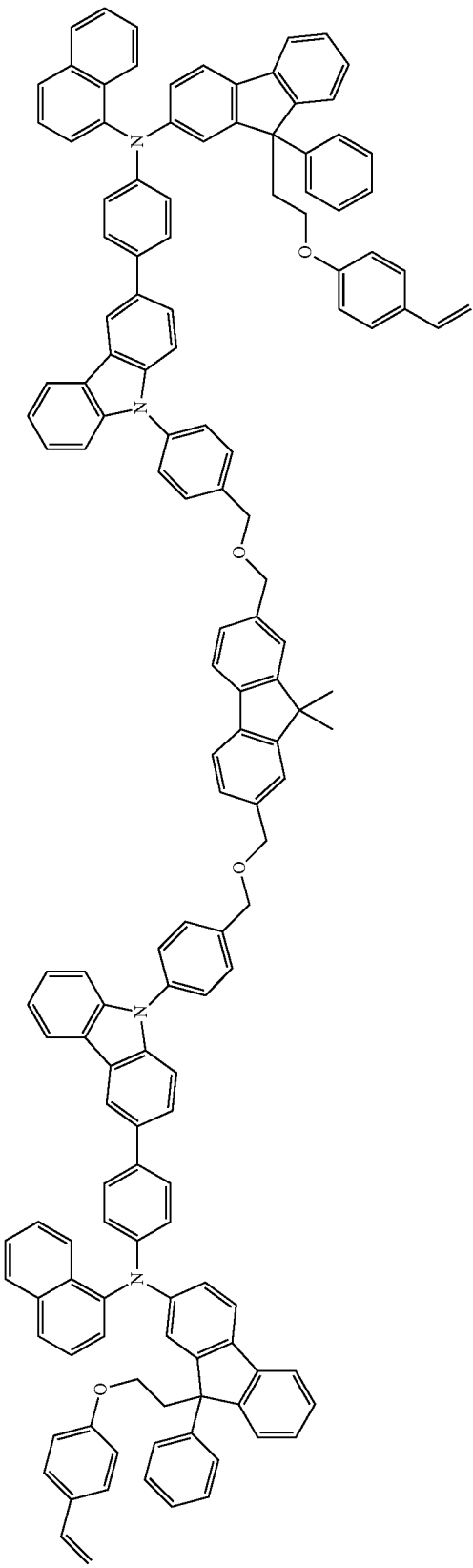

[Compound 66]
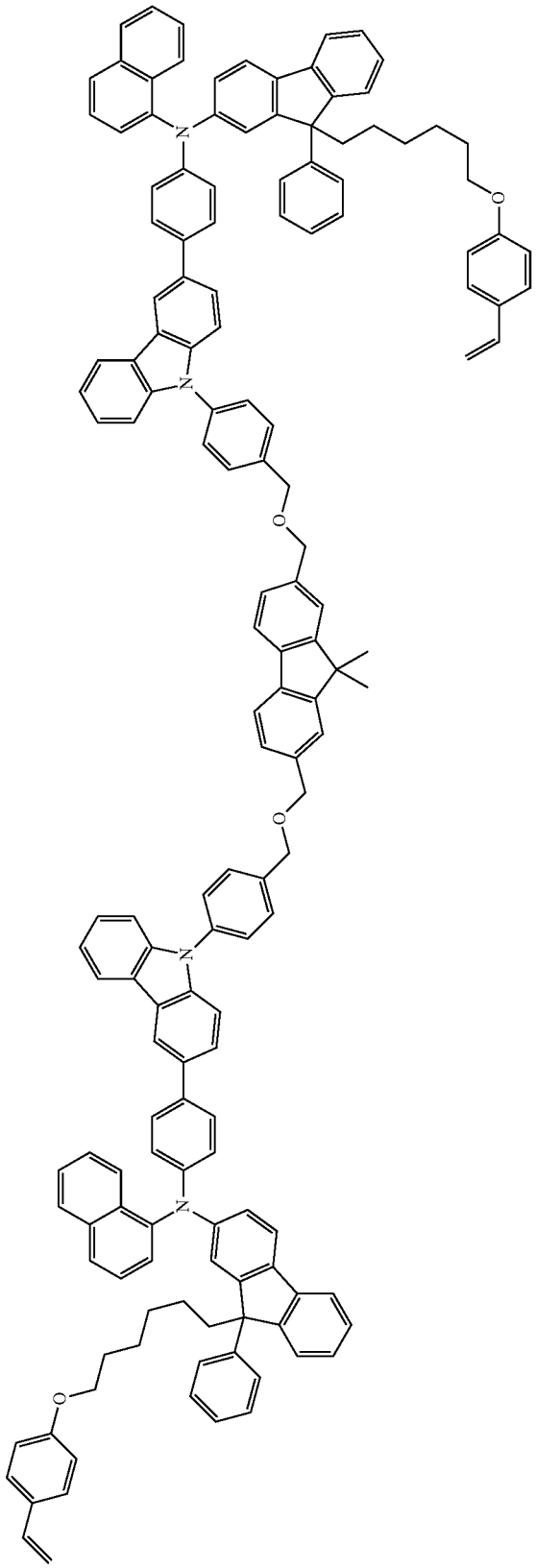
[Compound 67]
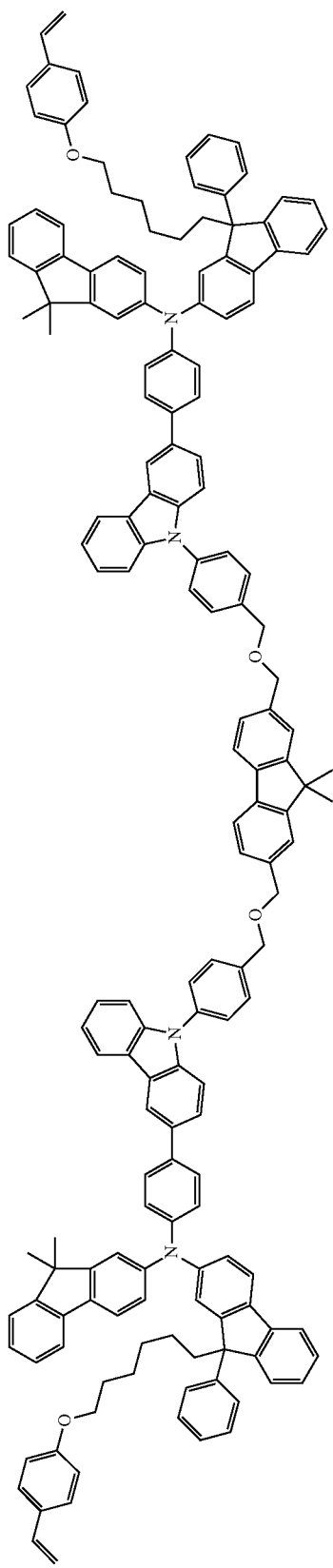

[Compound 68]
[Compound 69]
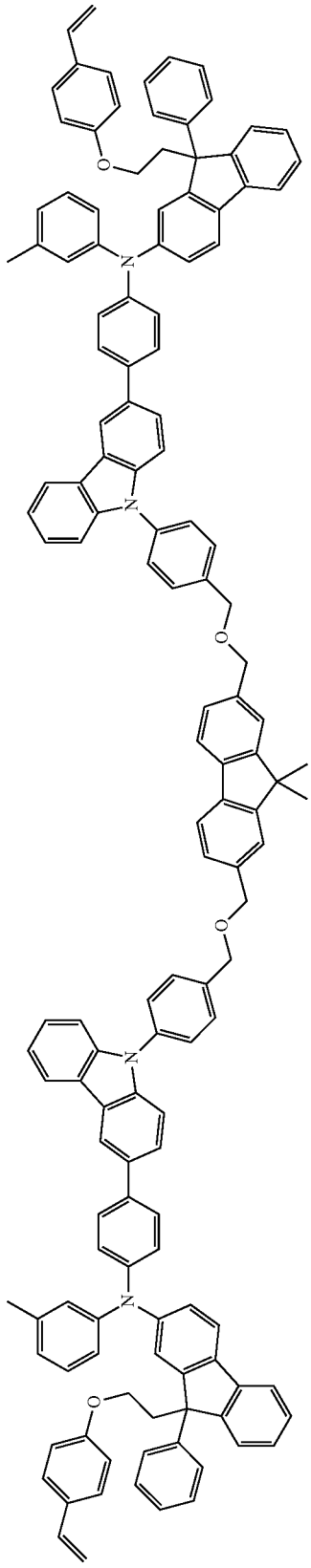
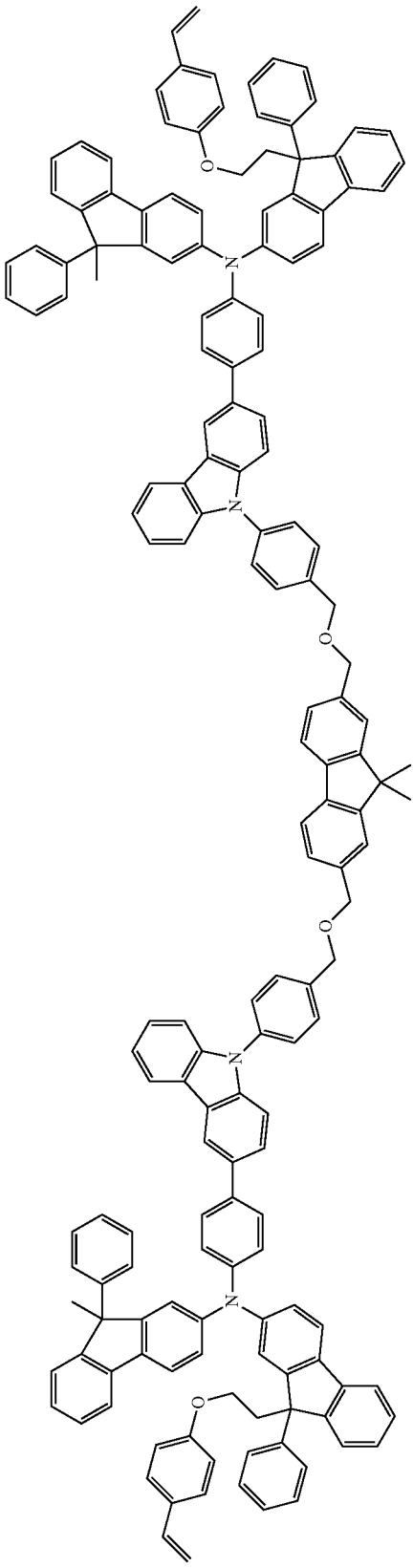

-continued
[Compound 70]
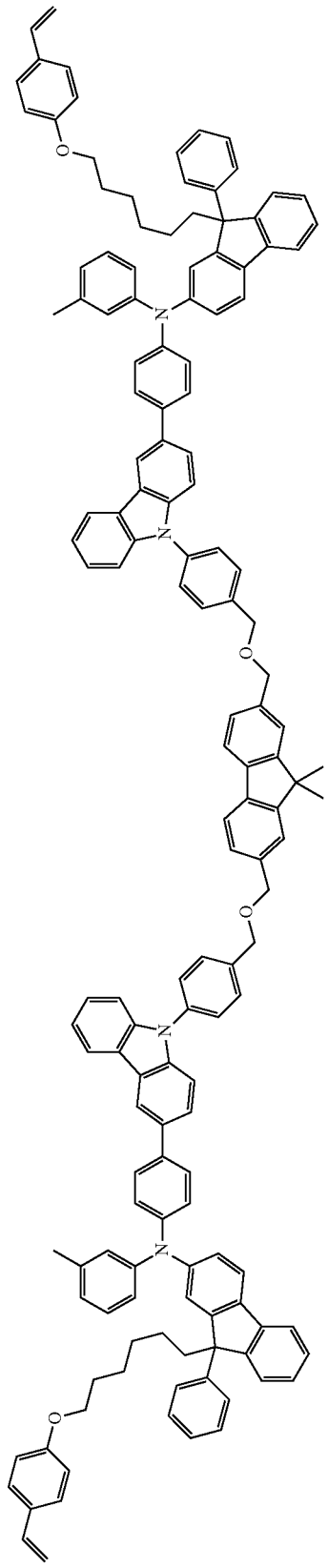
[Compound 71]
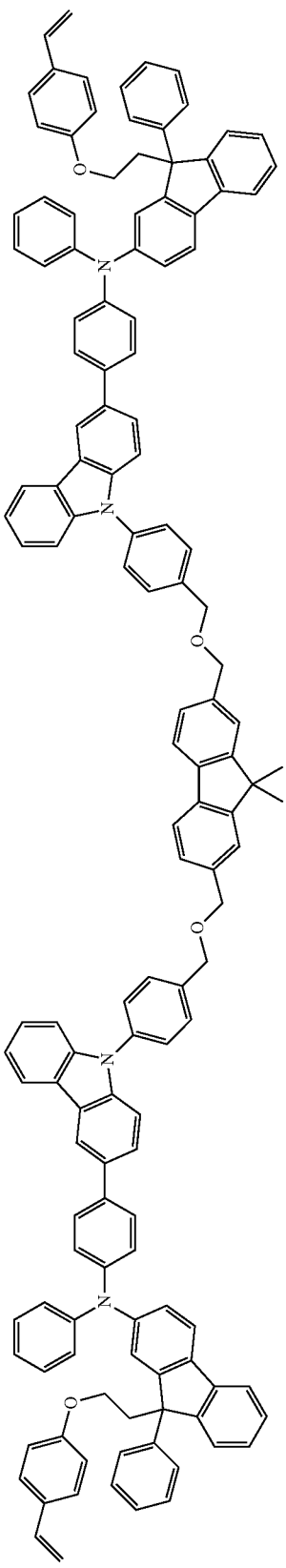

[Compound 72]
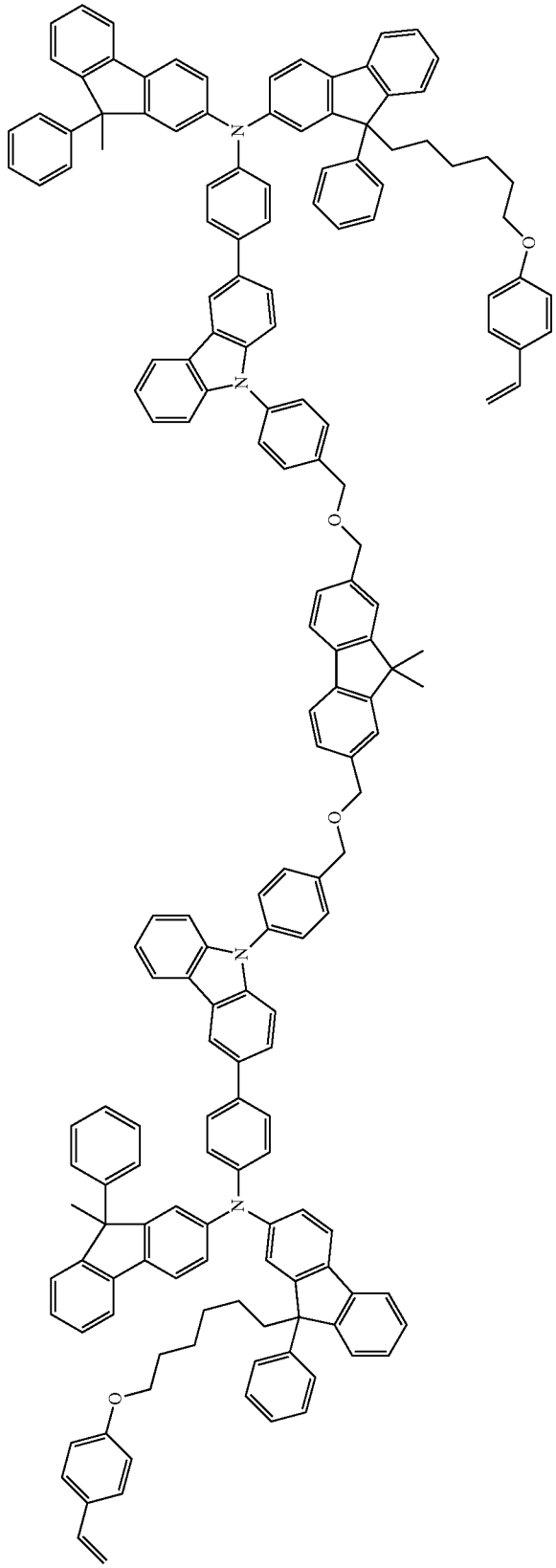
[Compound 73]
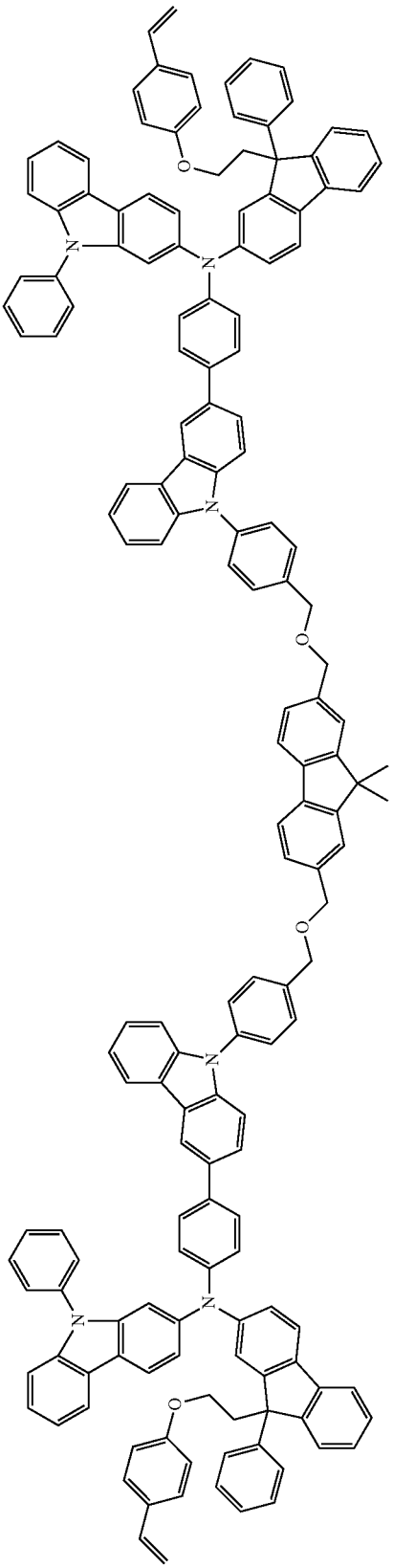

[Compound 74]
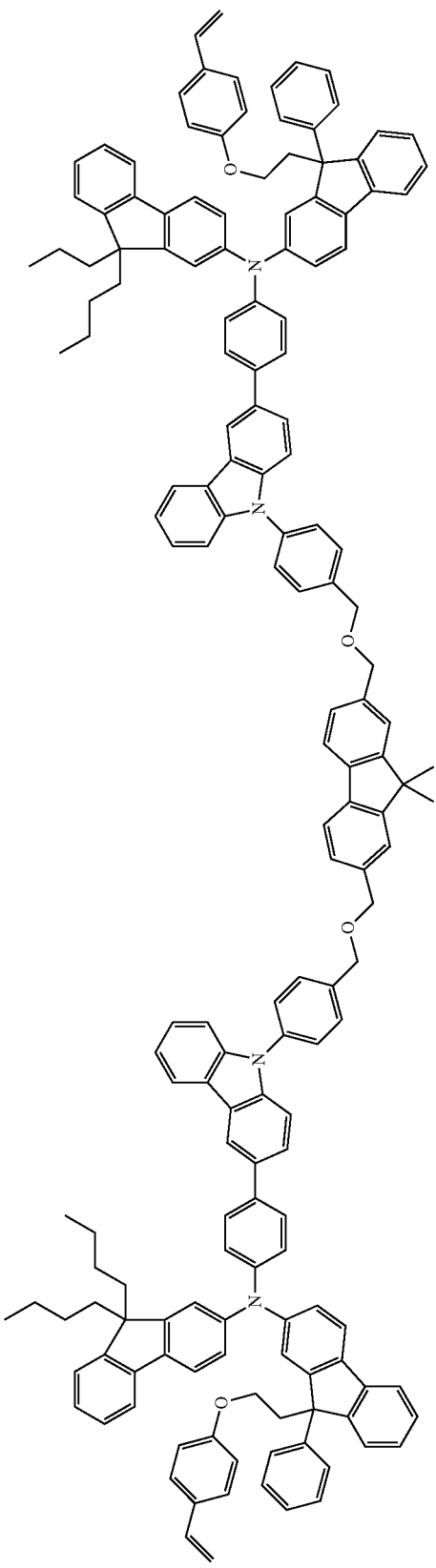
[Compound 75]
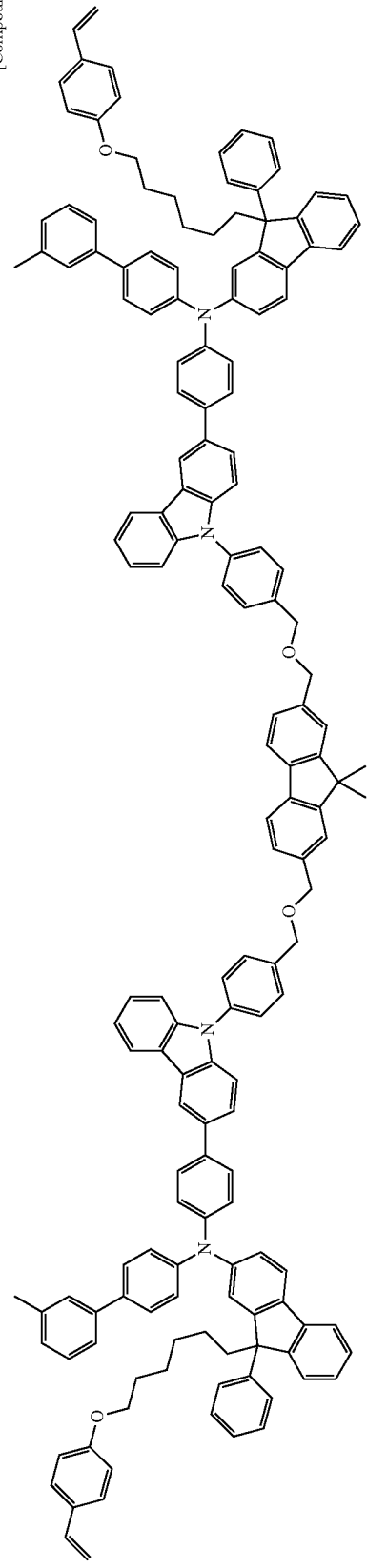

[Compound 76]
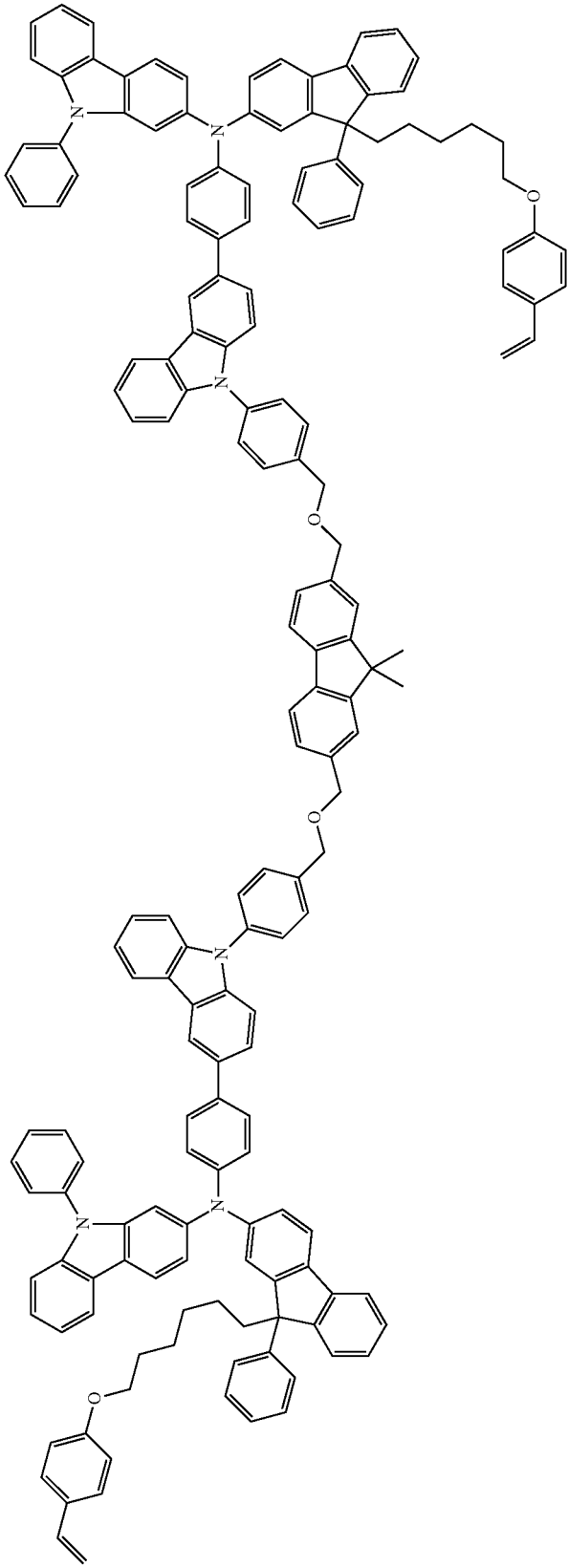
[Compound 77]
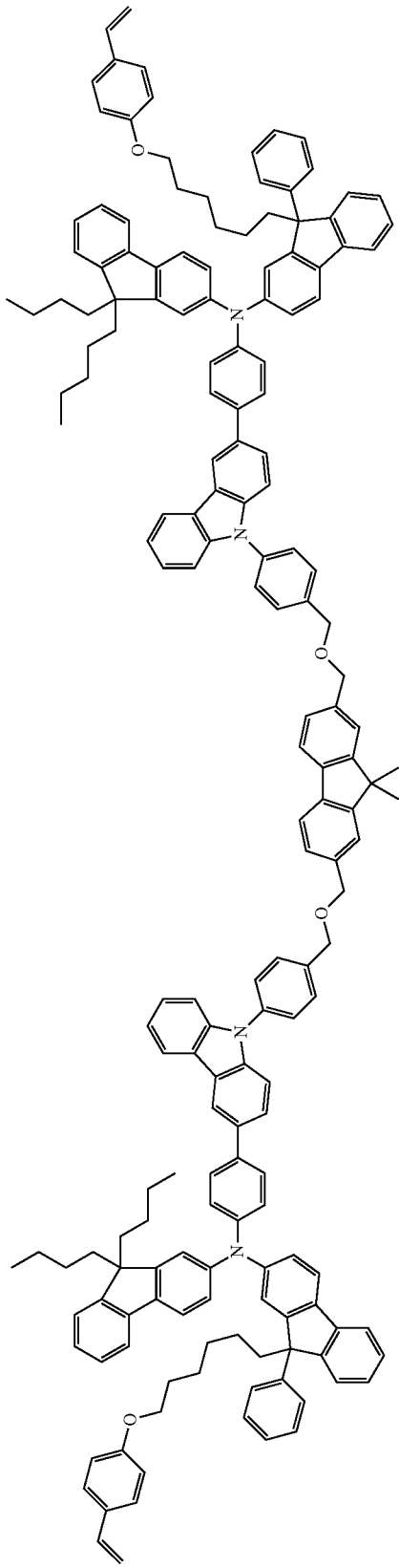

[Compound 78]
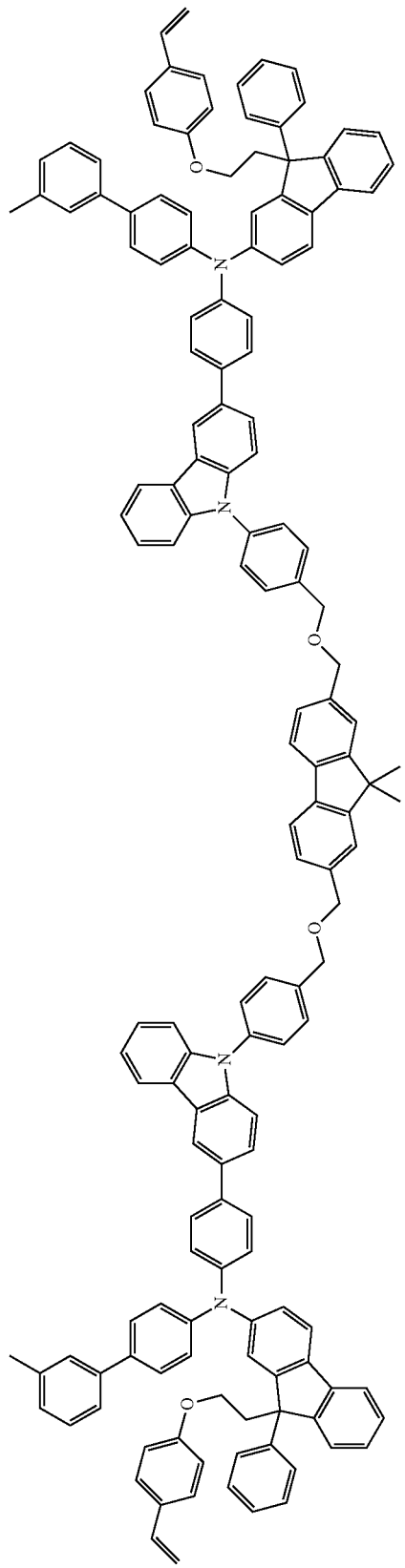
[Compound 79]
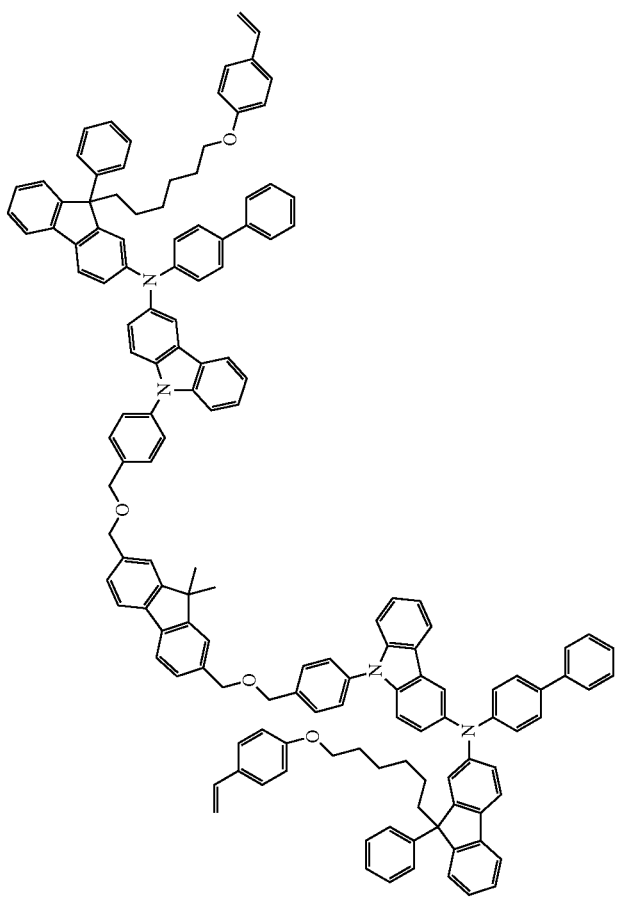

[Compound 80]
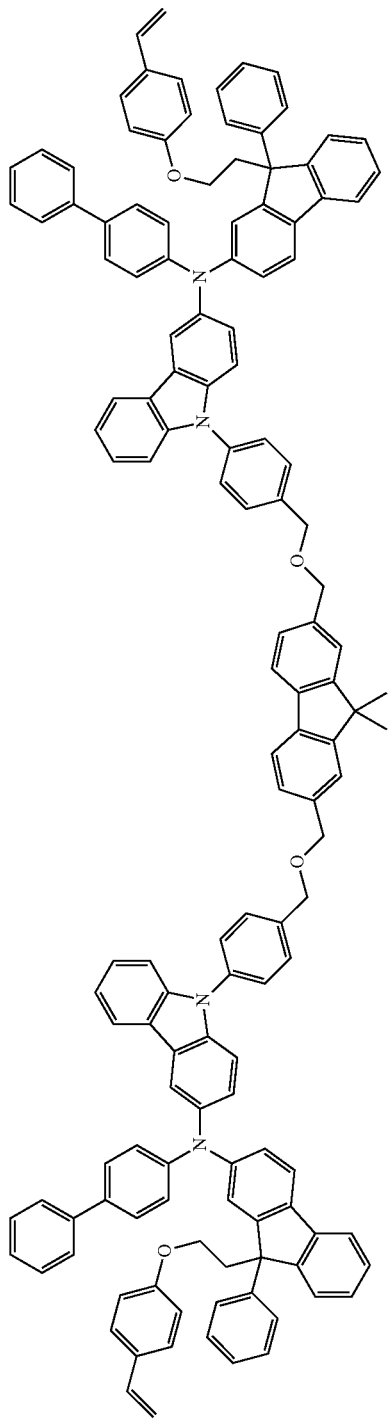
[Compound 81]
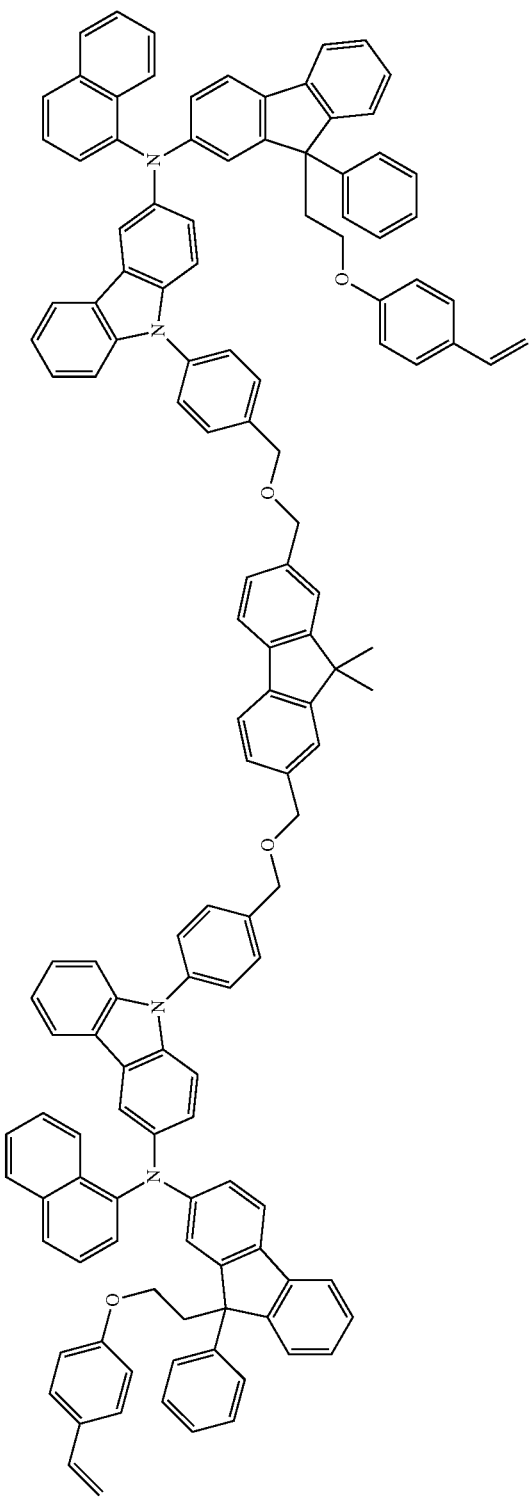

-continued
[Compound 82]
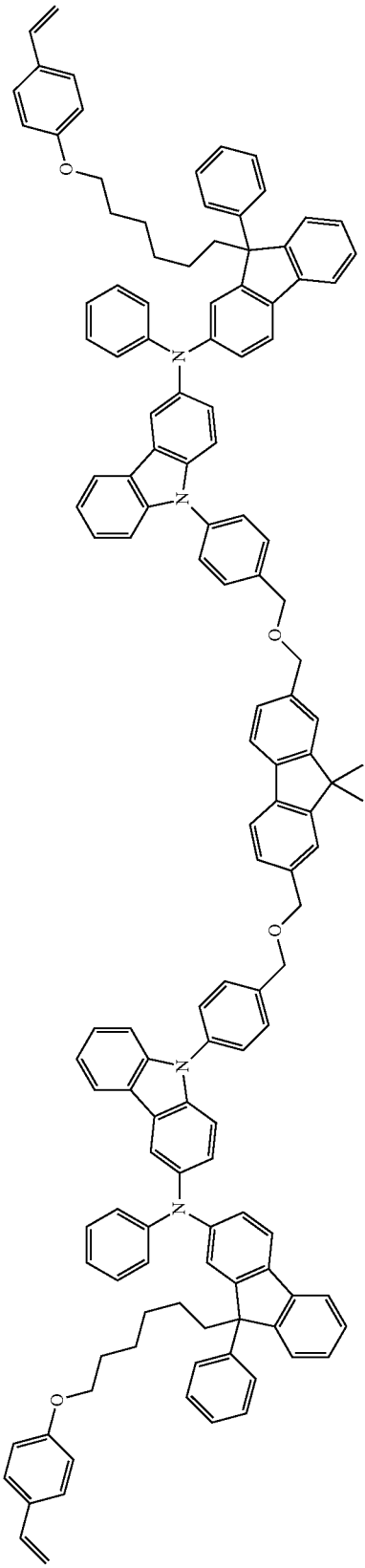
[Compound 83]
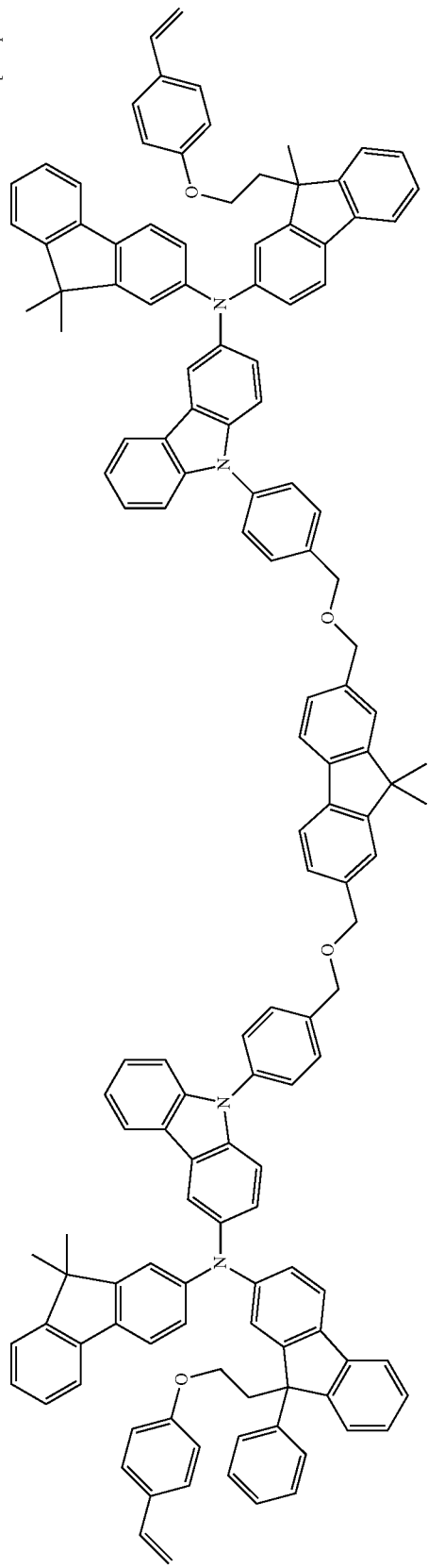

[Compound 84]
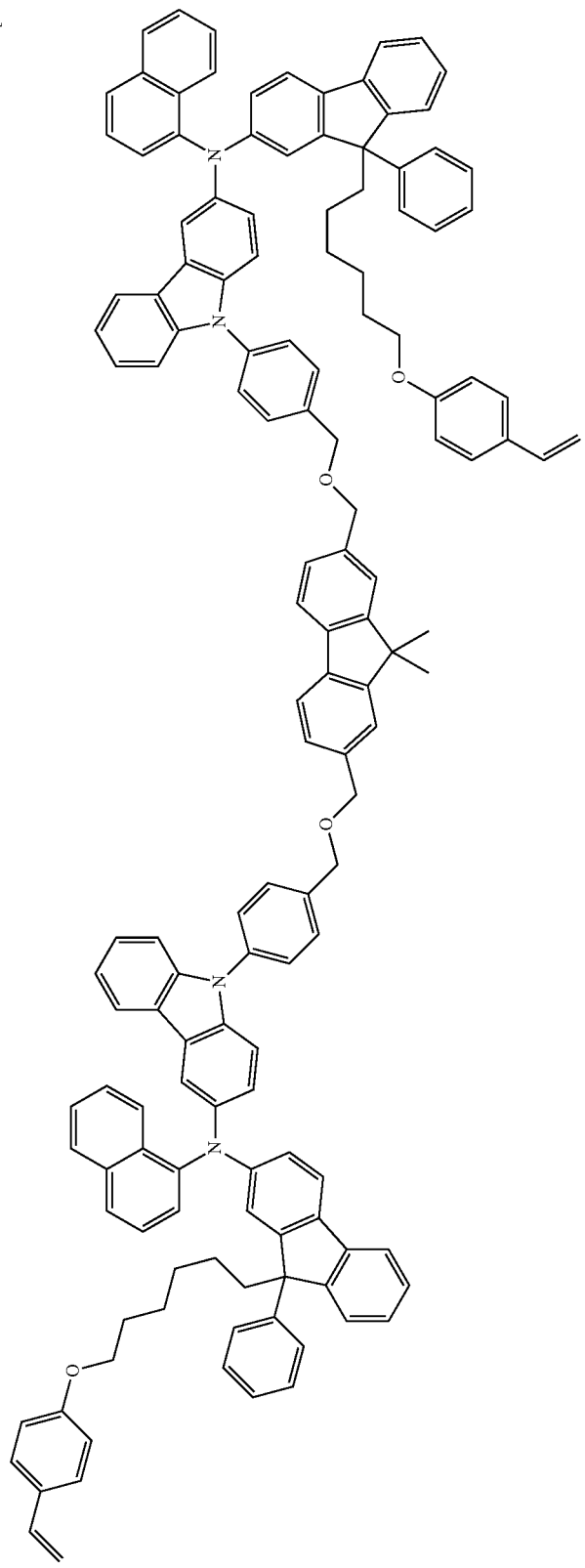

-continued
[Compound 85]
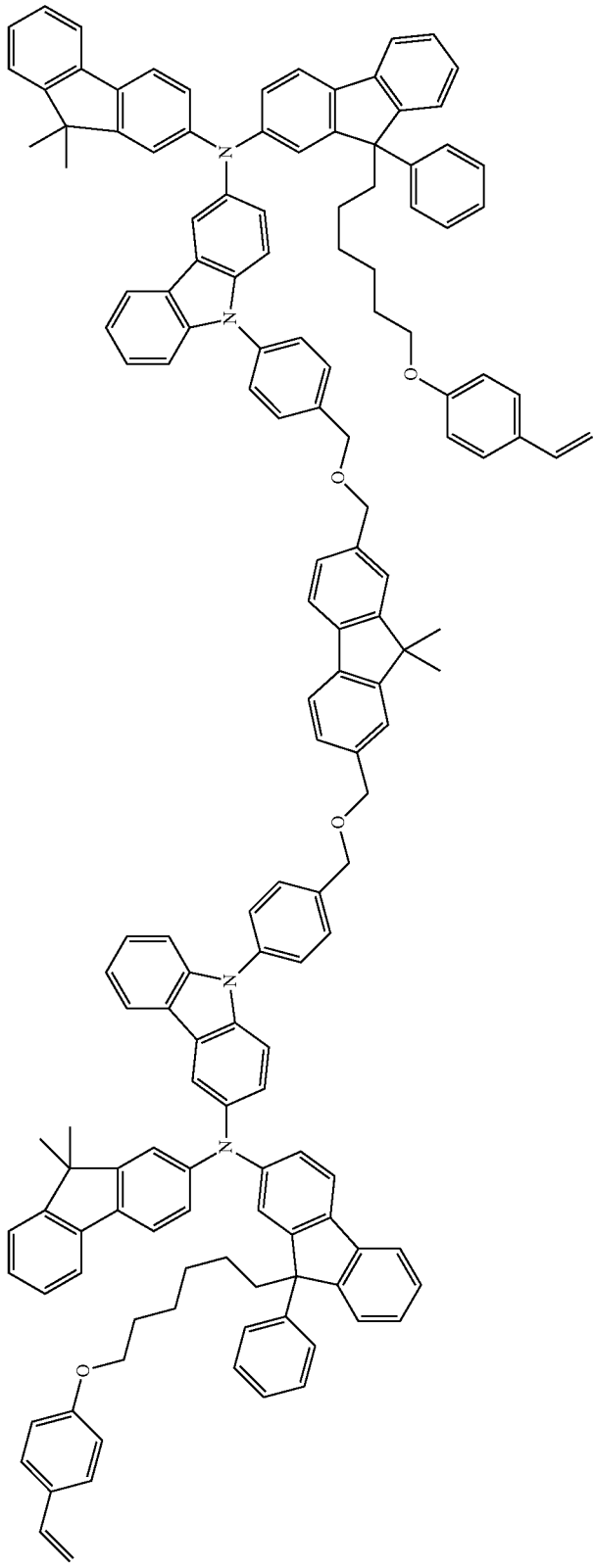
[Compound 86]
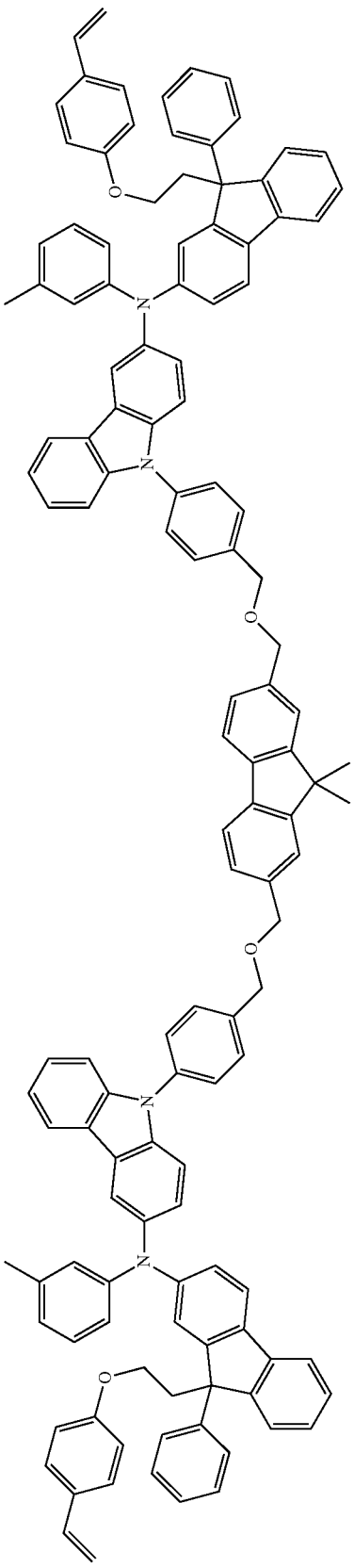

[Compound 87]
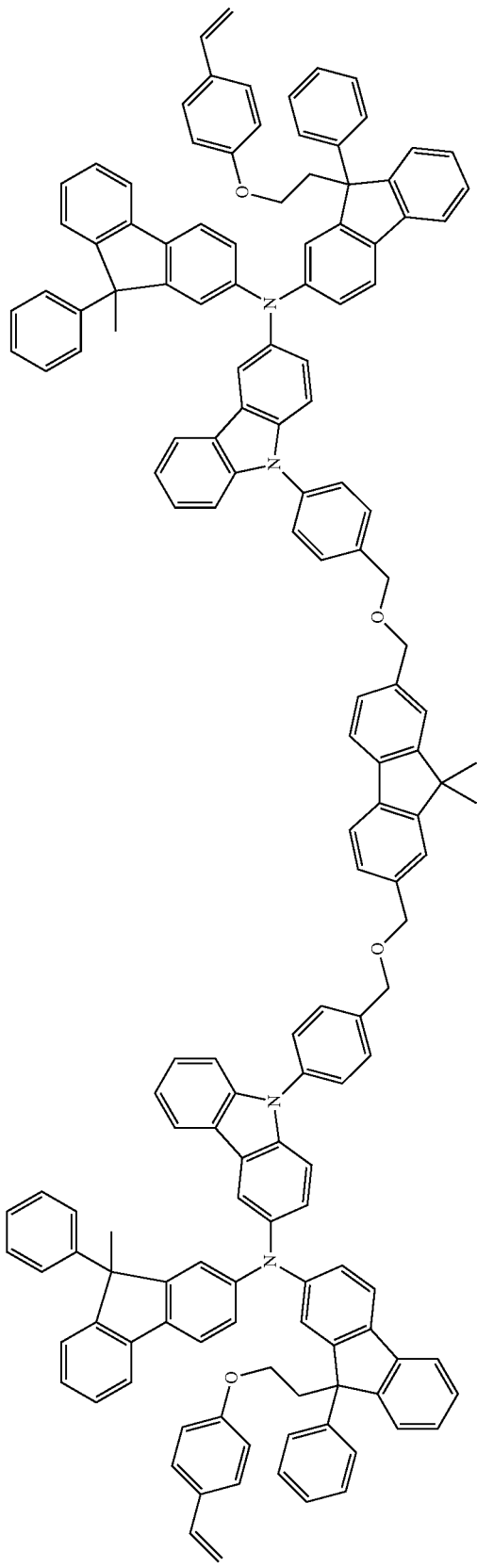
[Compound 88]
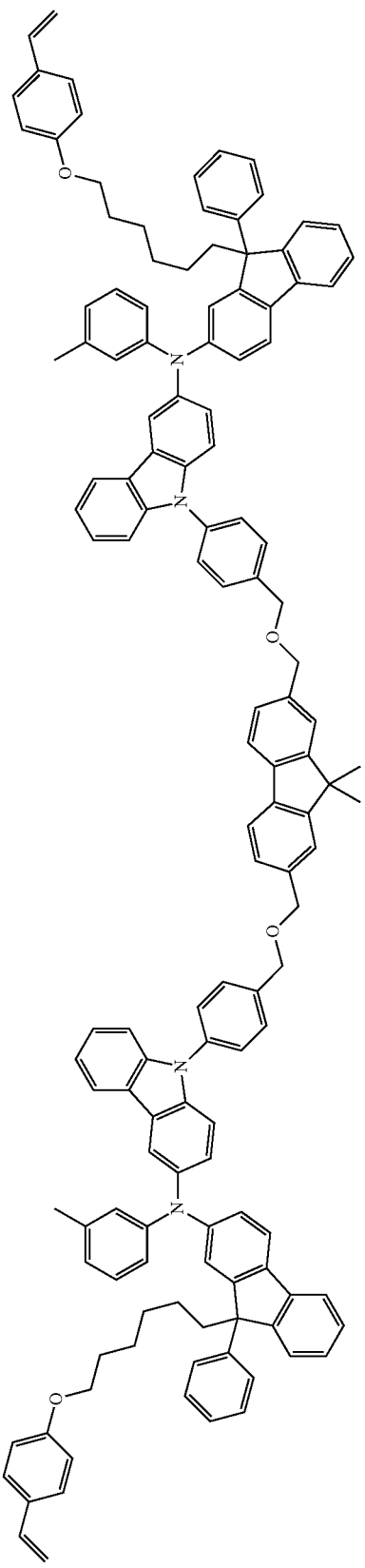

[Compound 89]
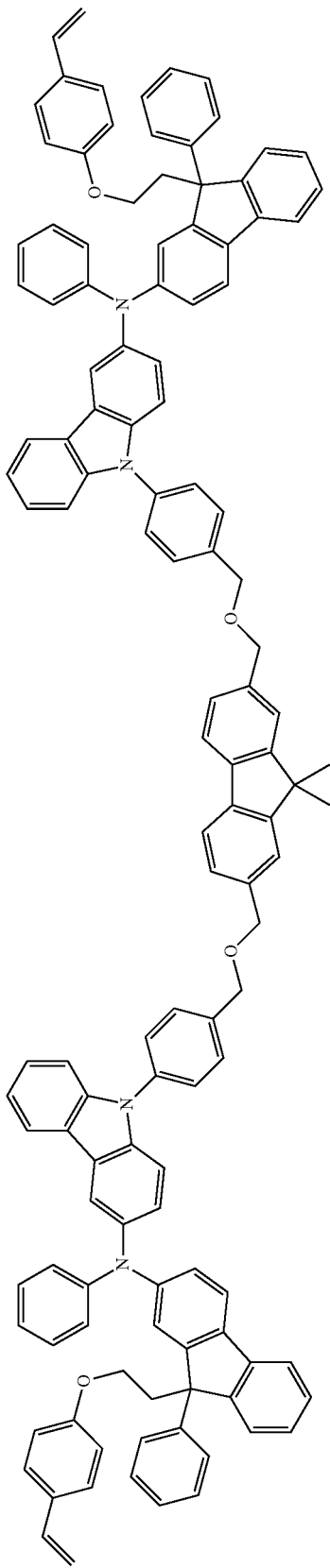
[Compound 90]
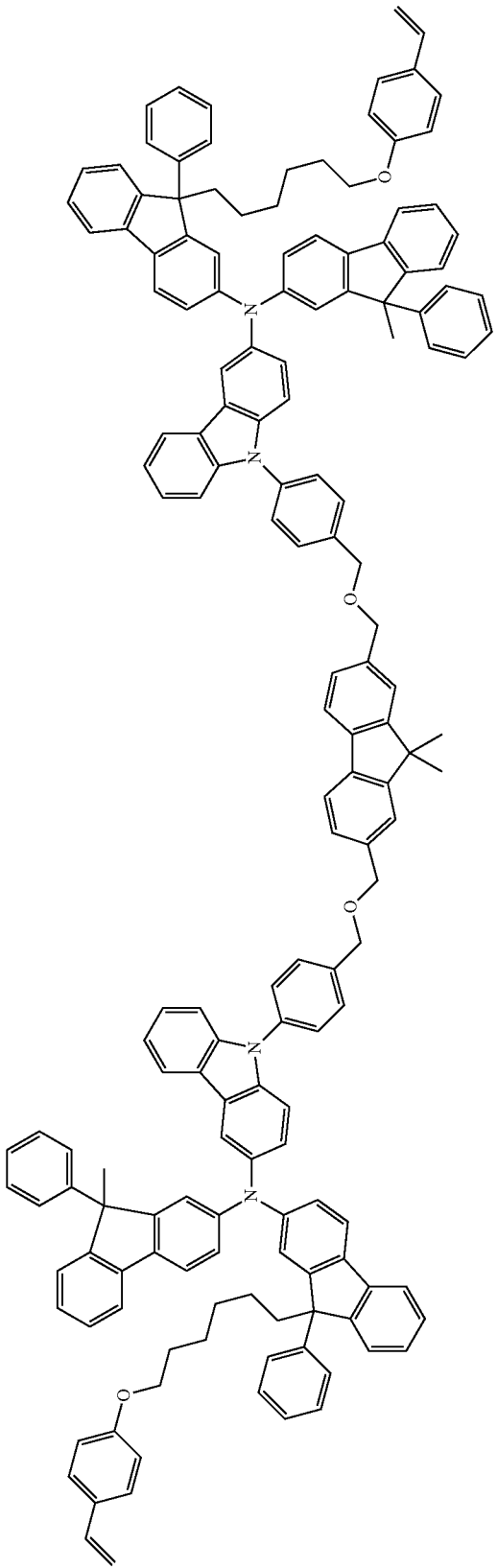

329
[Compound 91]
330
[Compound 92]
-continued
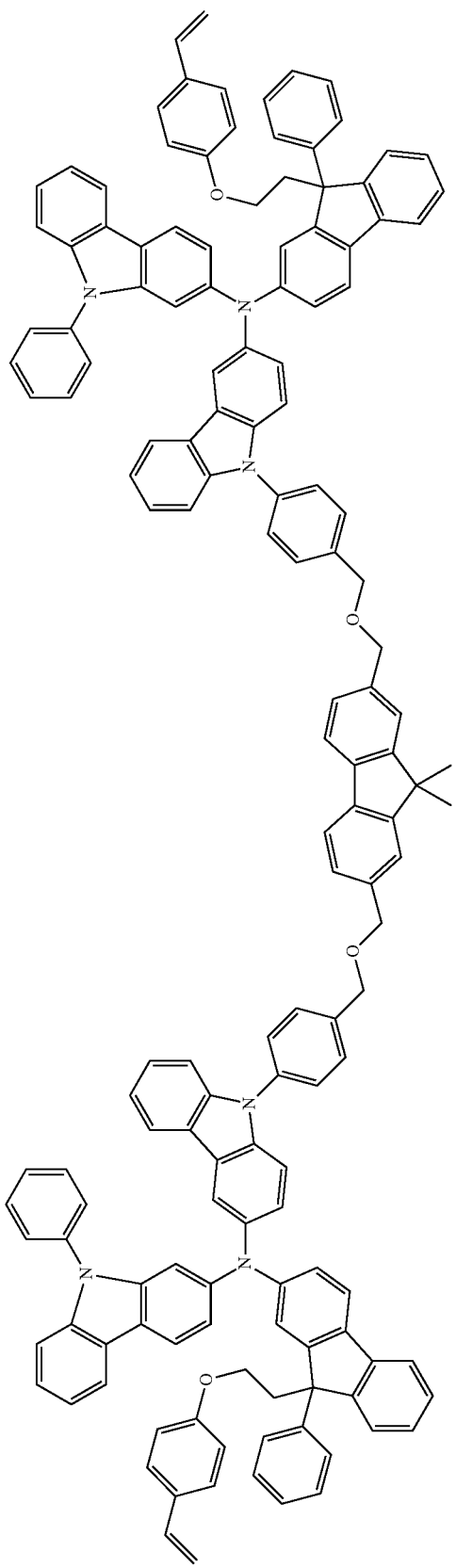
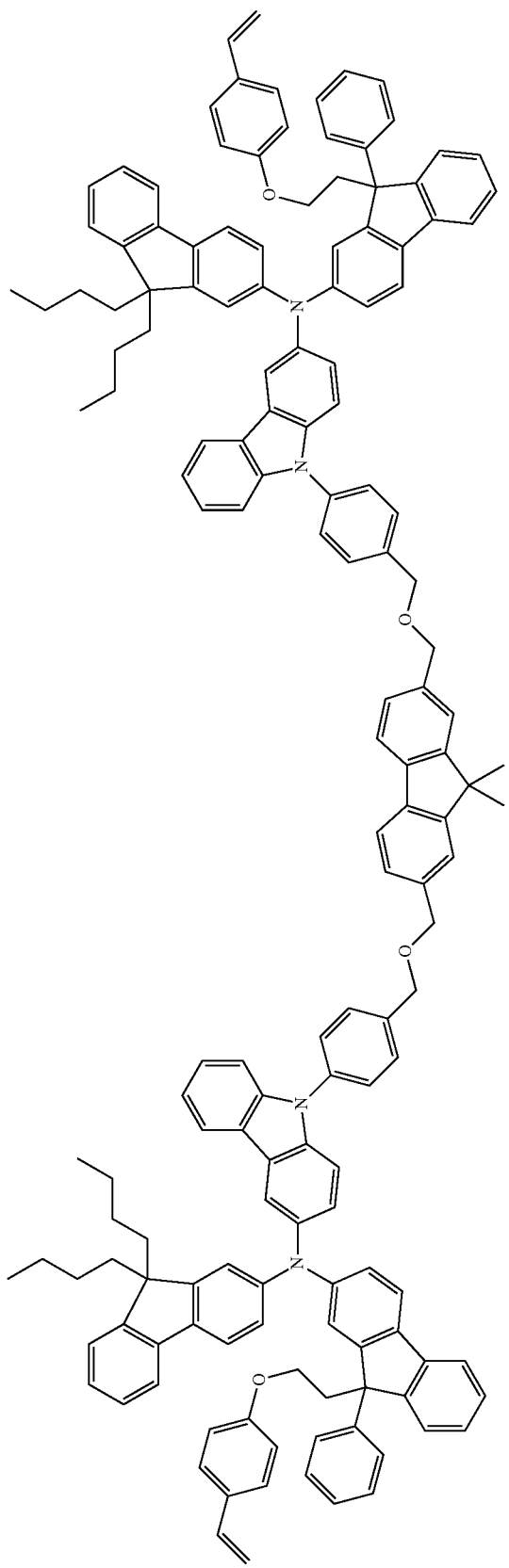

331
[Compound 93]
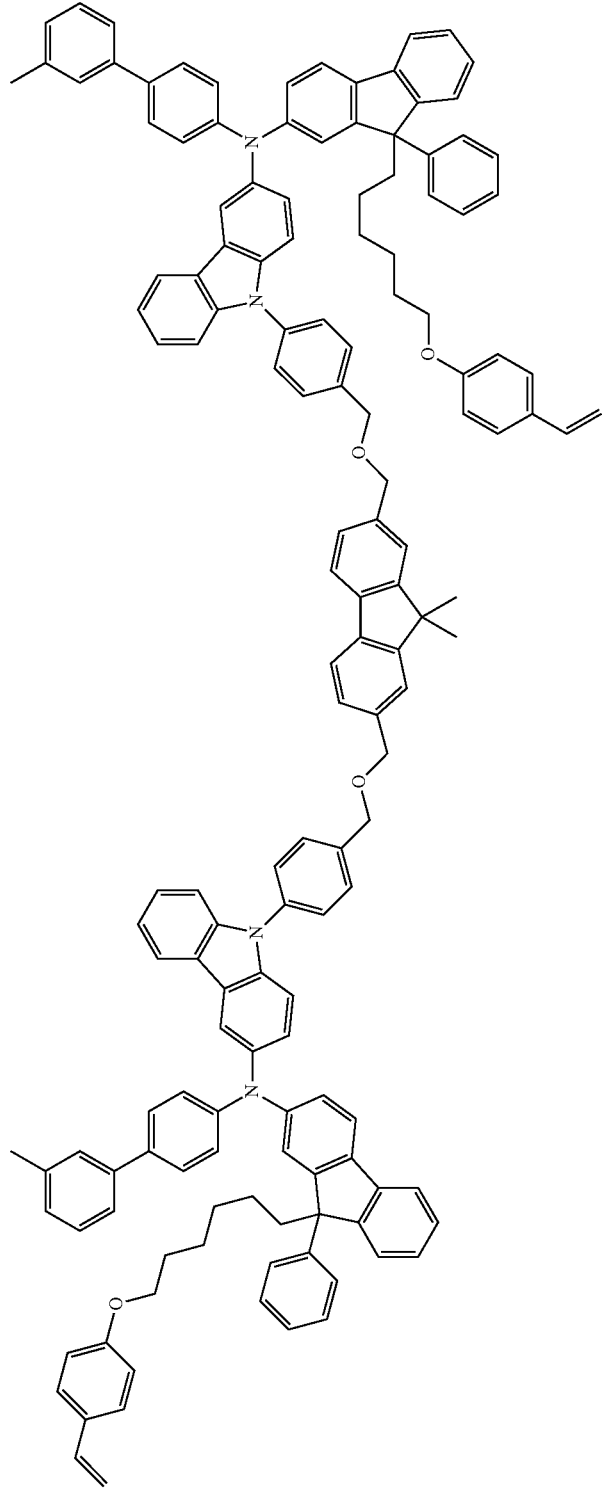
332
[Compound 94]
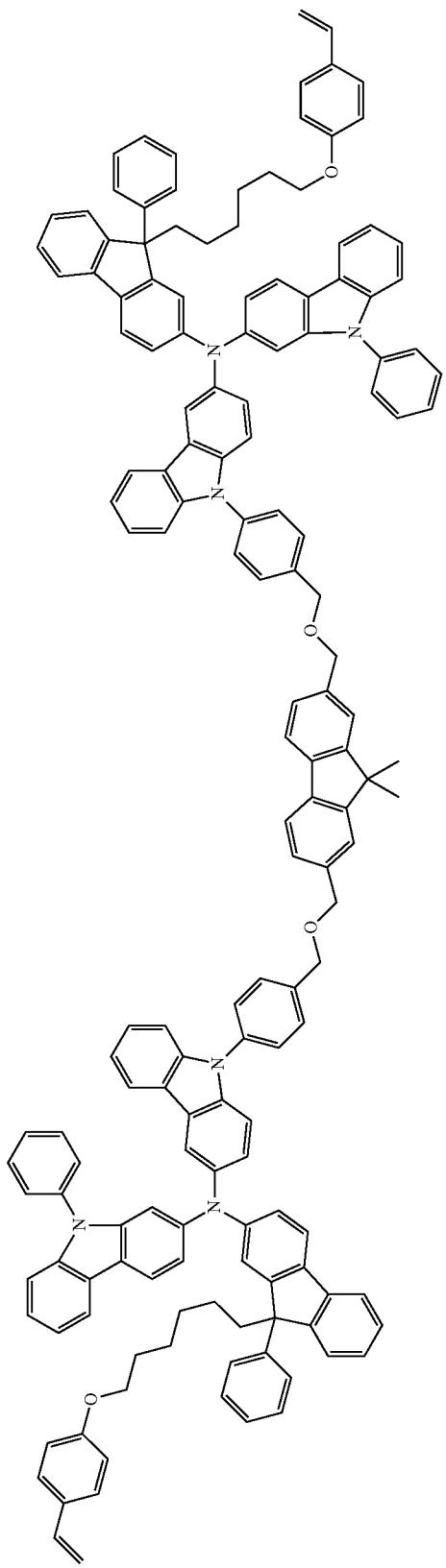

333
[Compound 95]
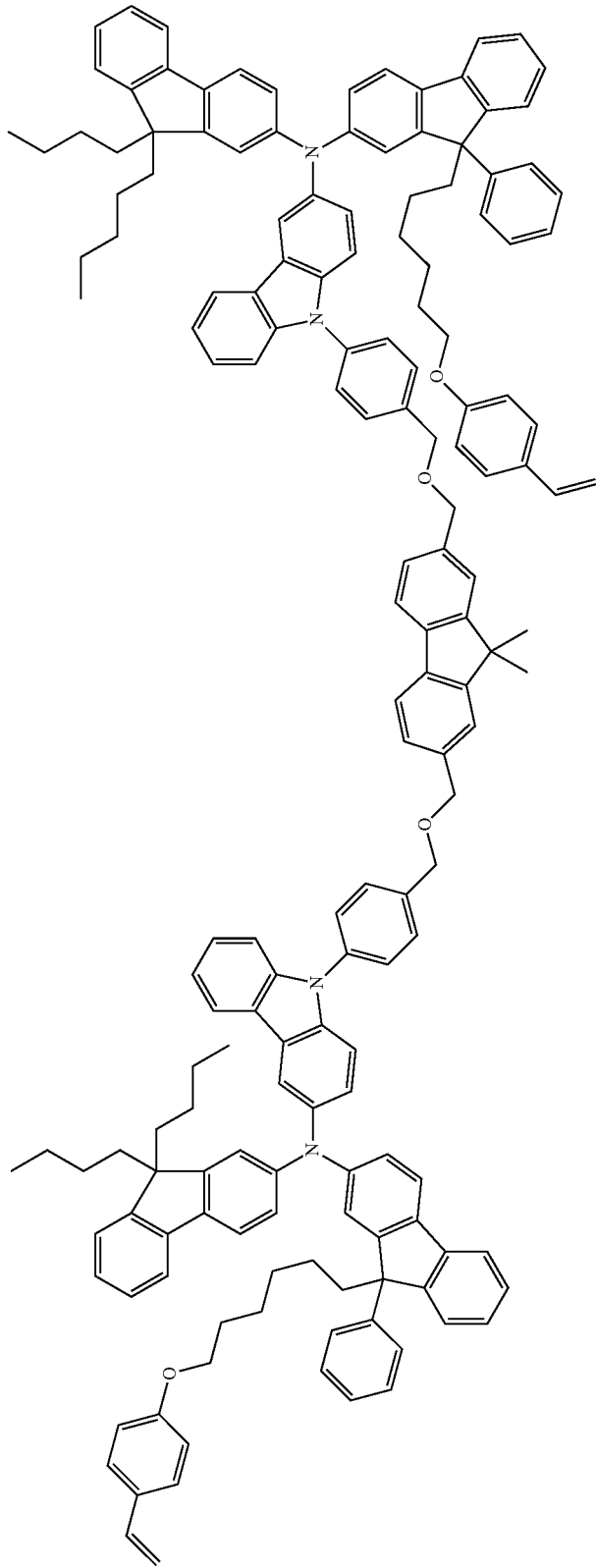
334
[Compound 96]
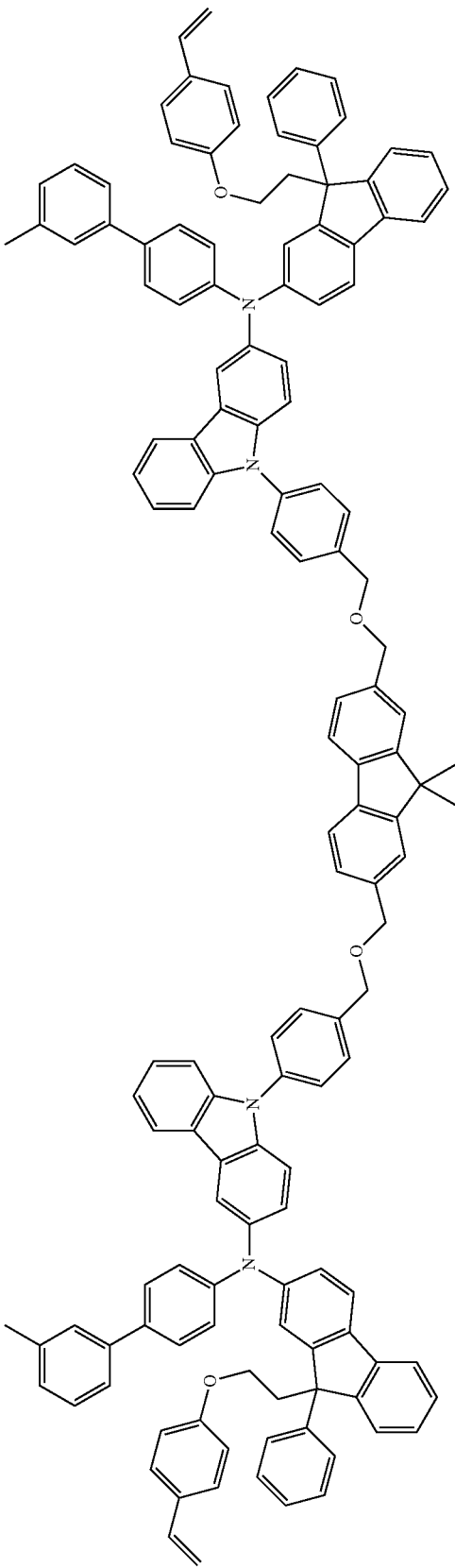

[Compound 97]
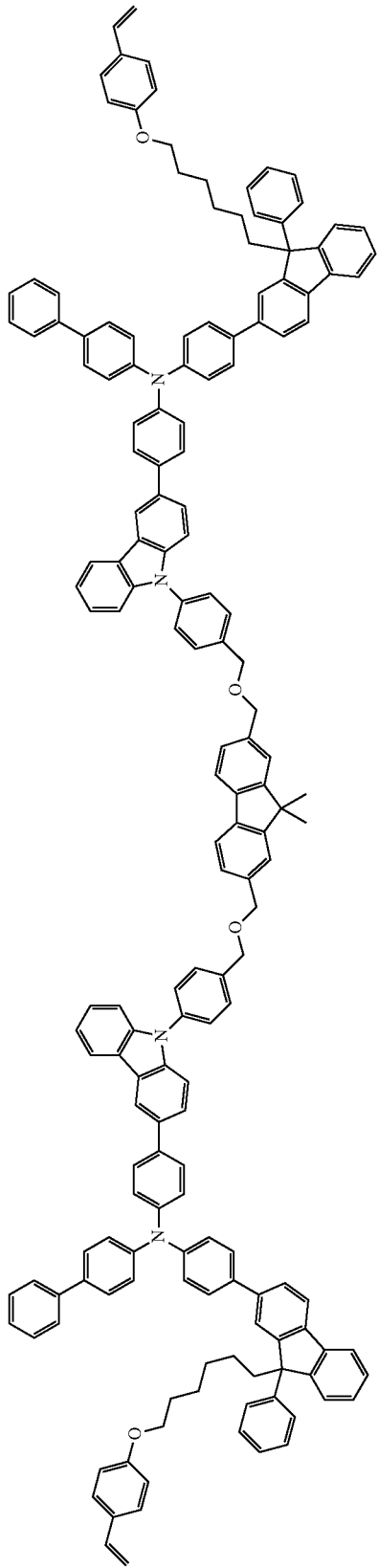
[Compound 98]
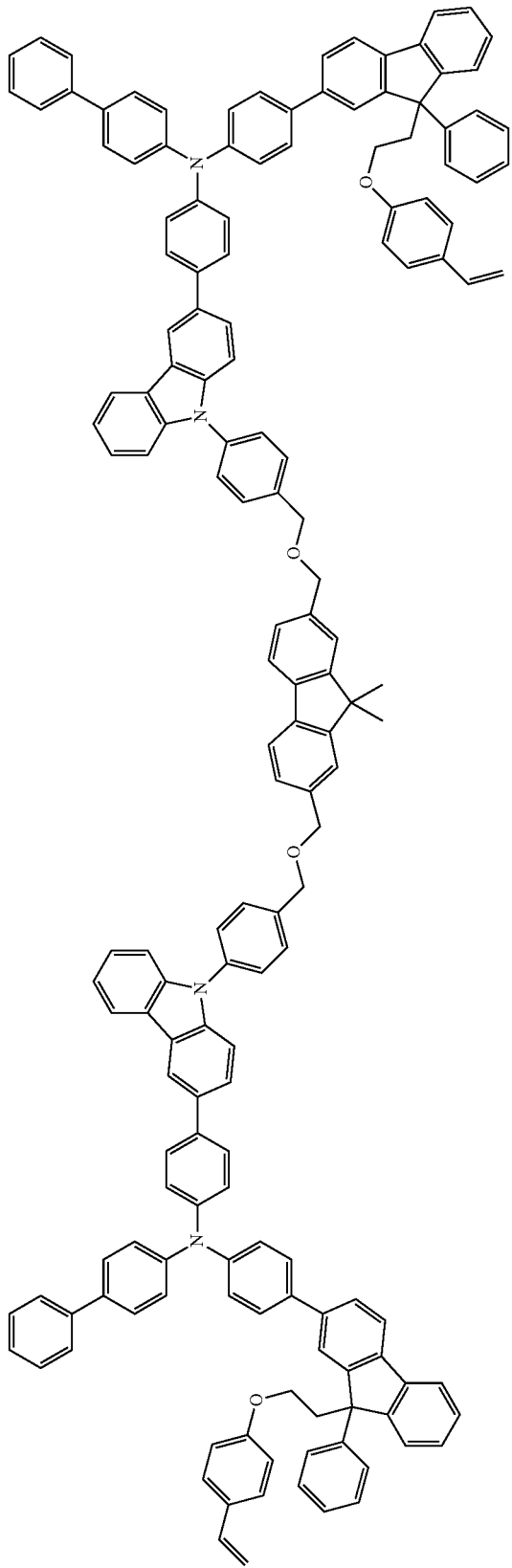

[Compound 99]
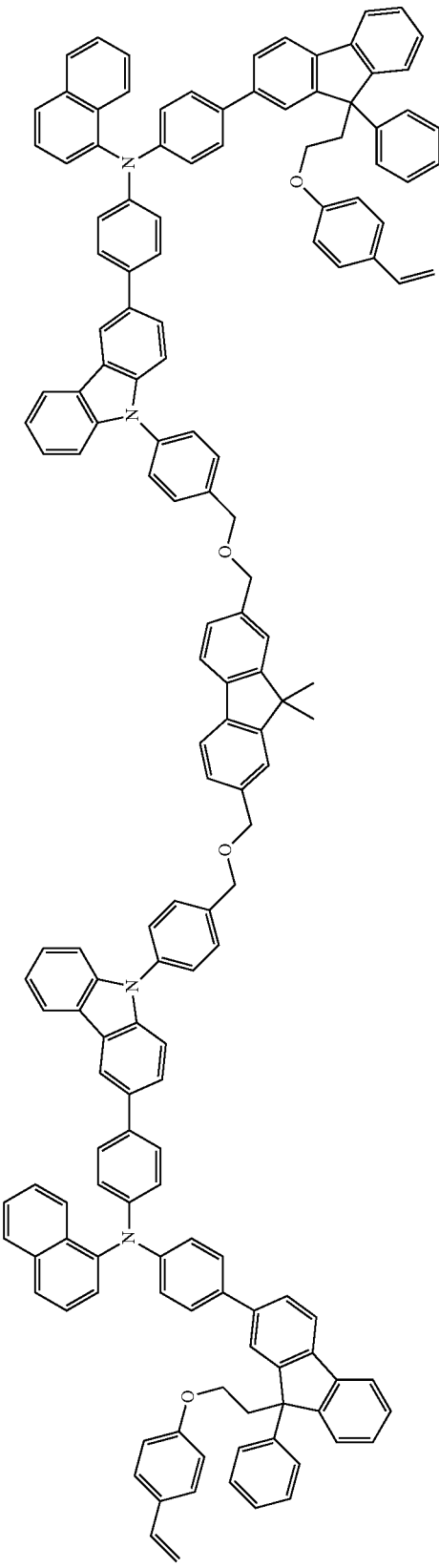
[Compound 100]
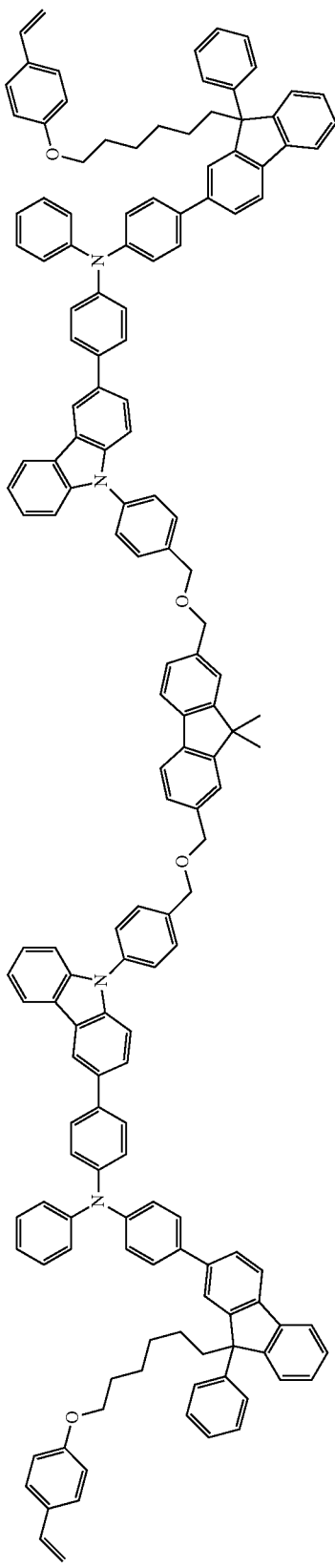

[Compound 101]
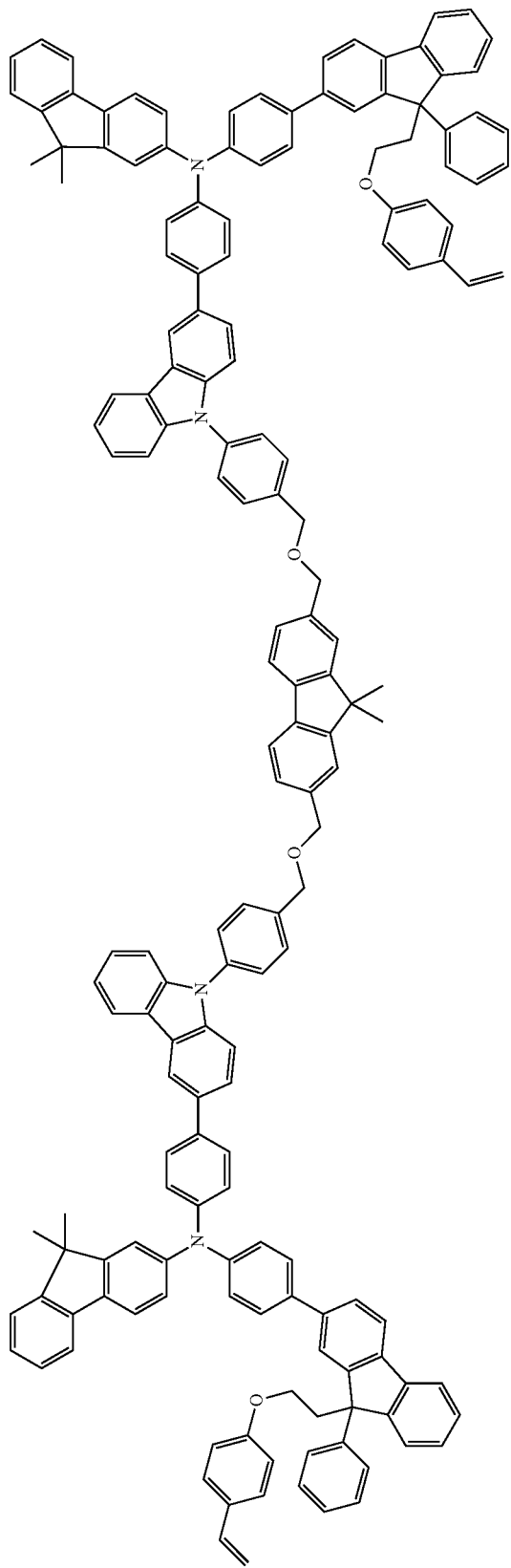

[Compound 102]
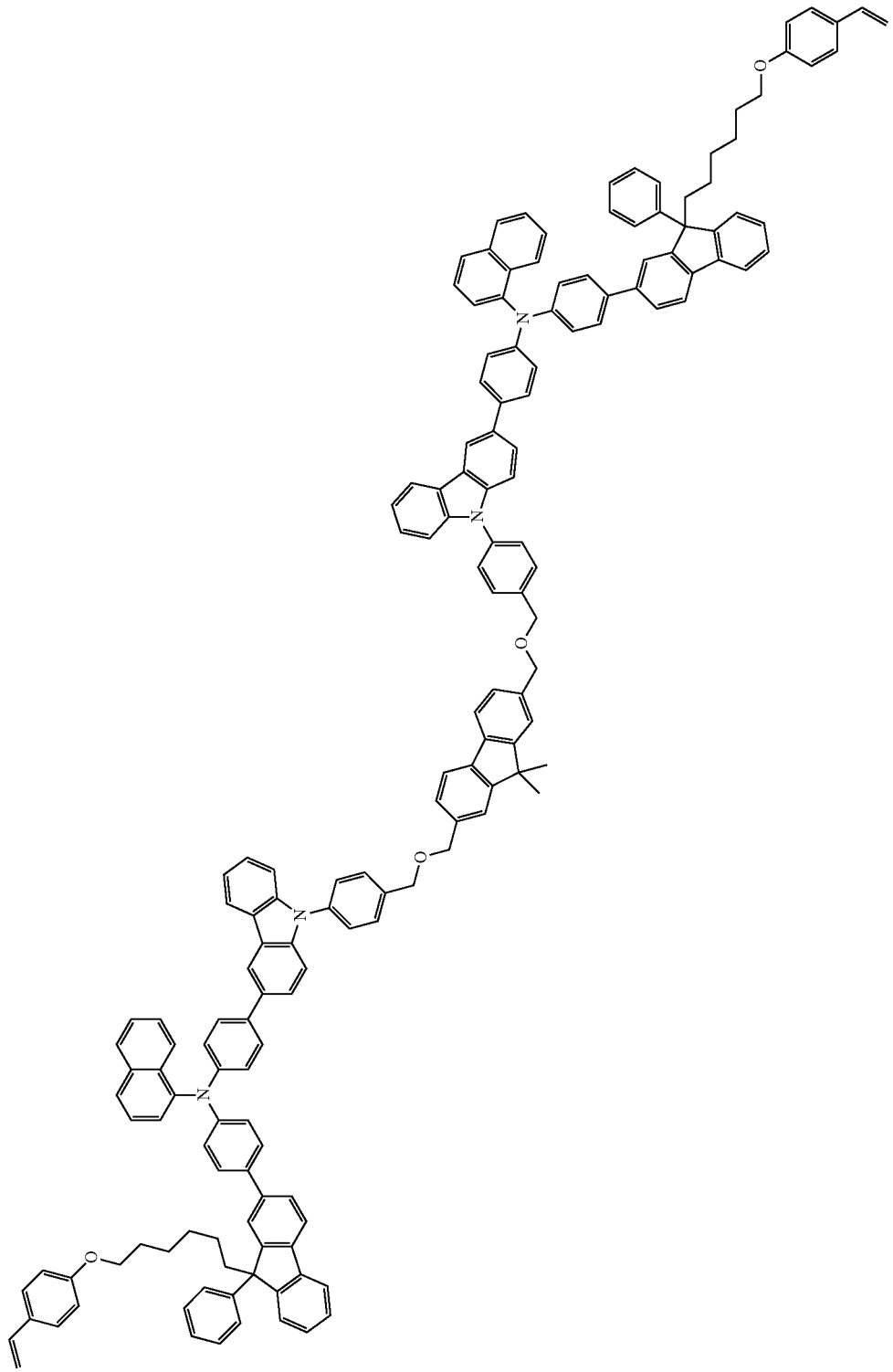

[Compound 103]
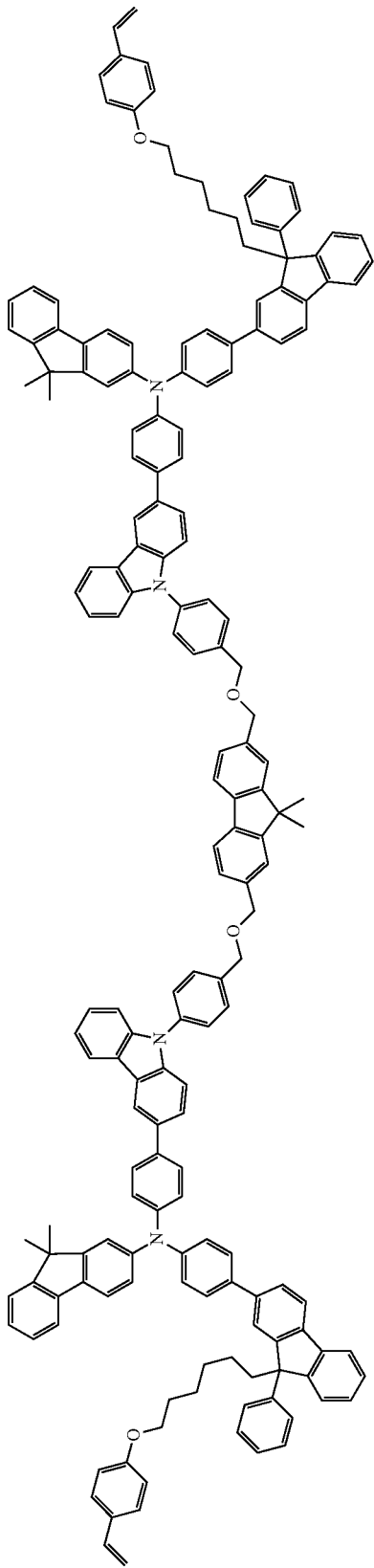
[Compound 104]
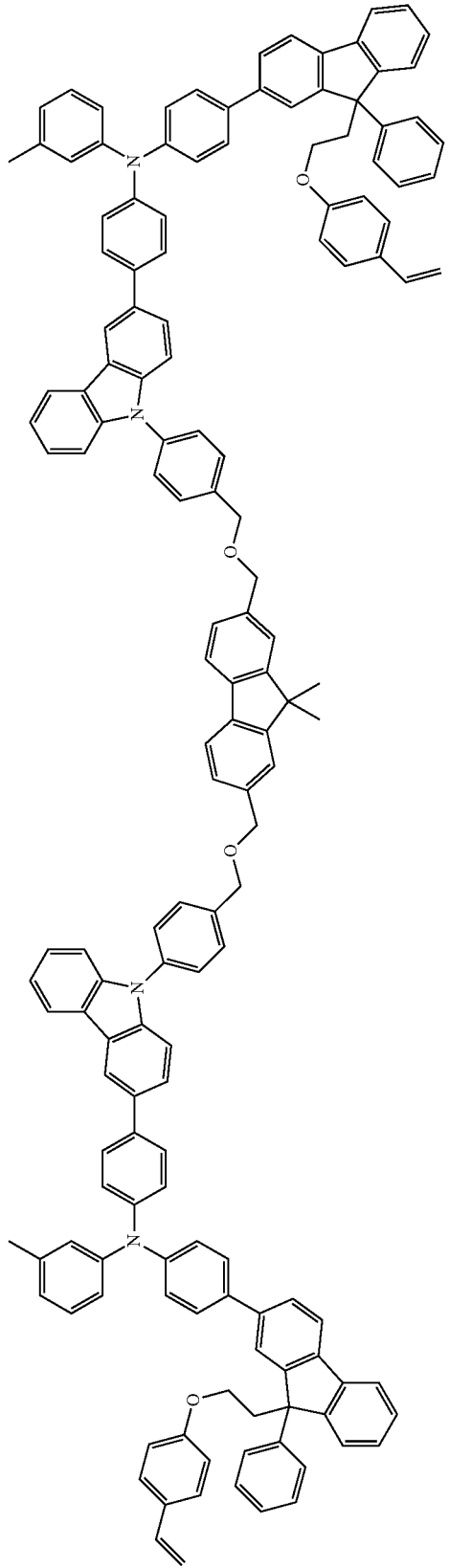

-continued
[Compound 105]
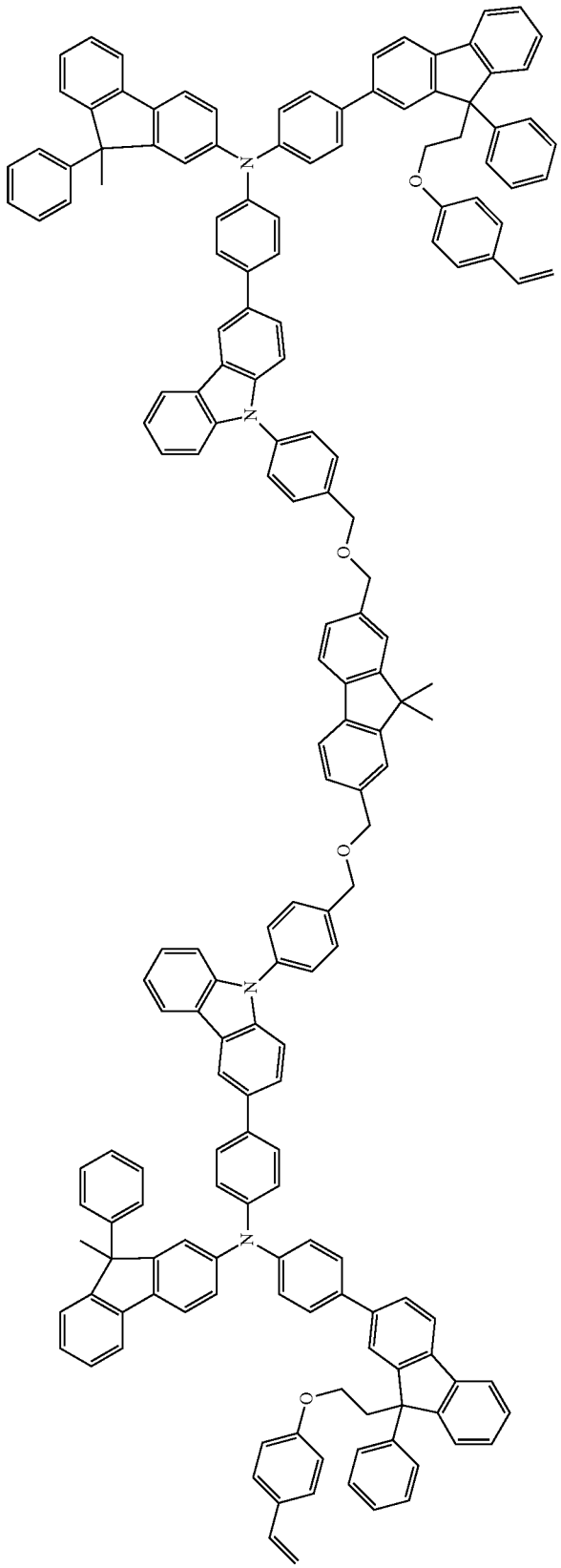
[Compound 106]
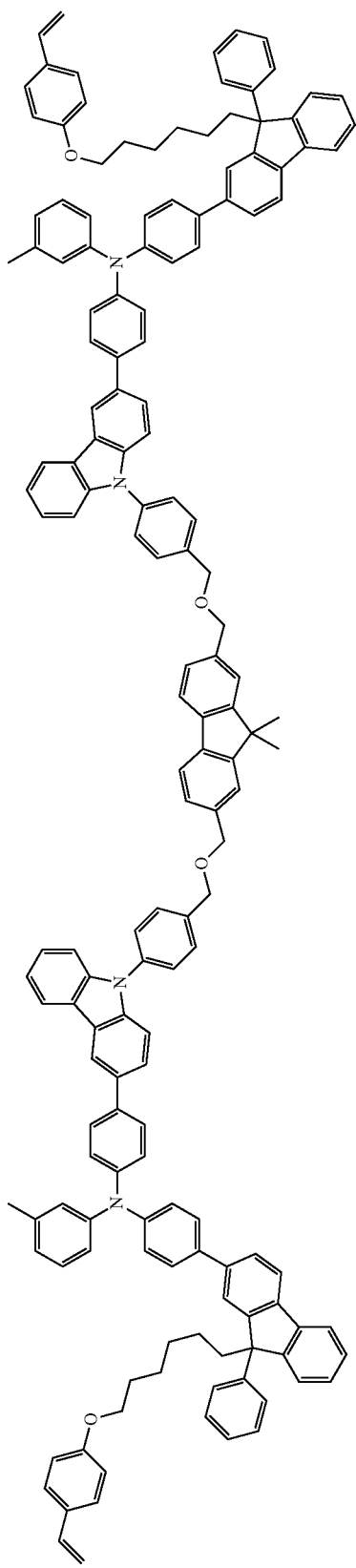

-continued
[Compound 107]
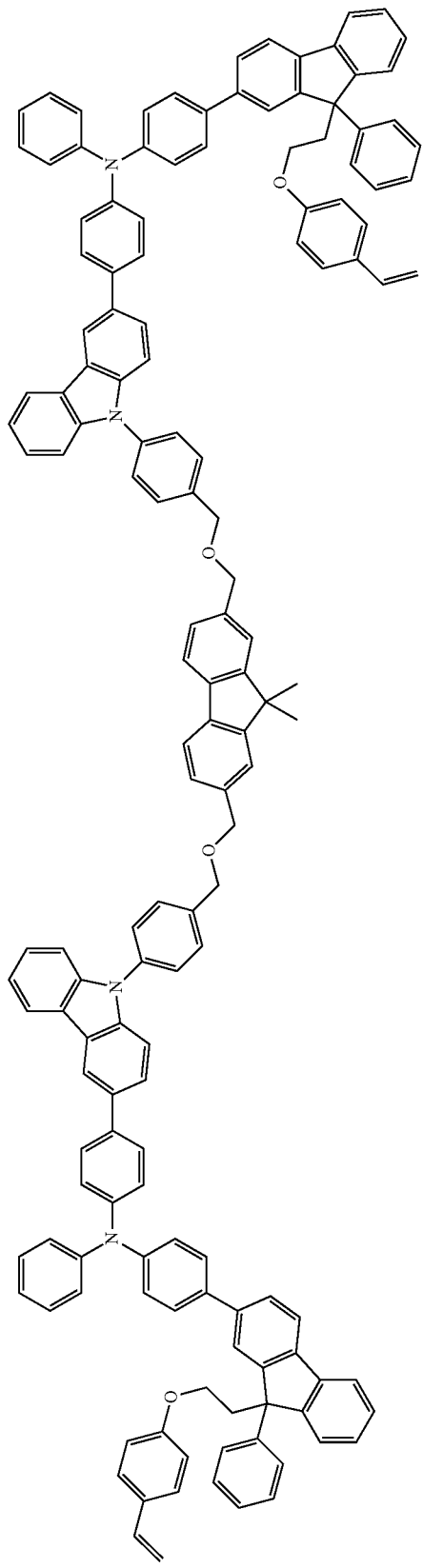
[Compound 108]
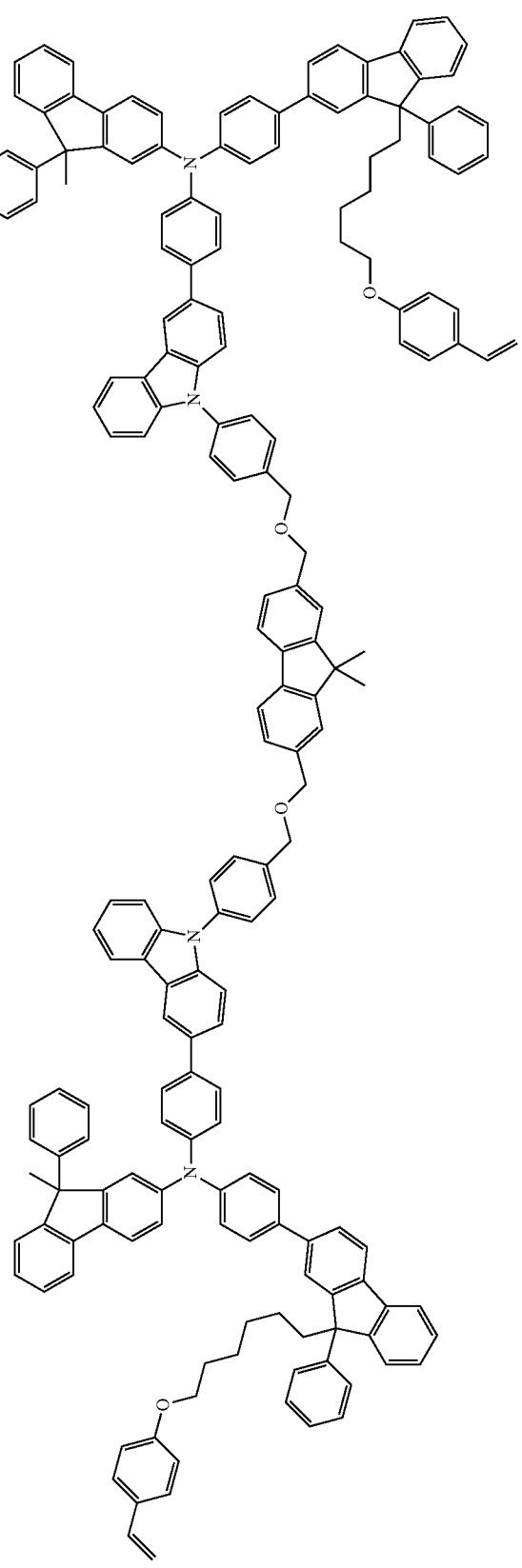

[Compound 109]
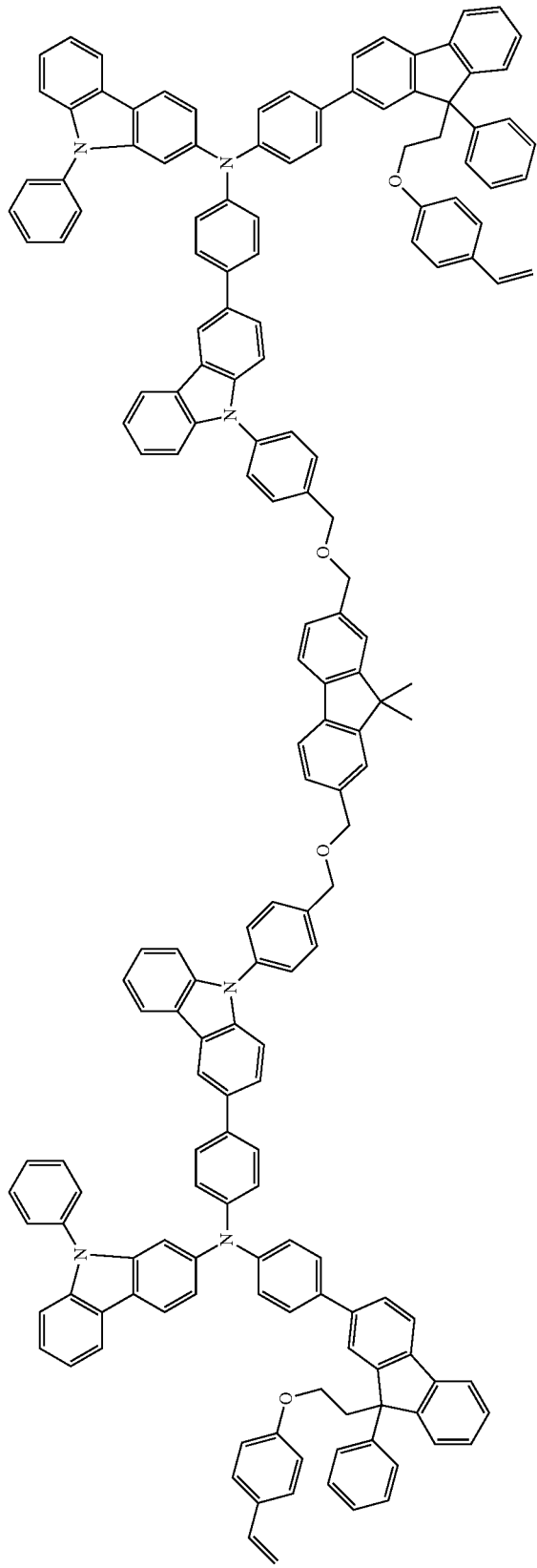

-continued
[Compound 110]
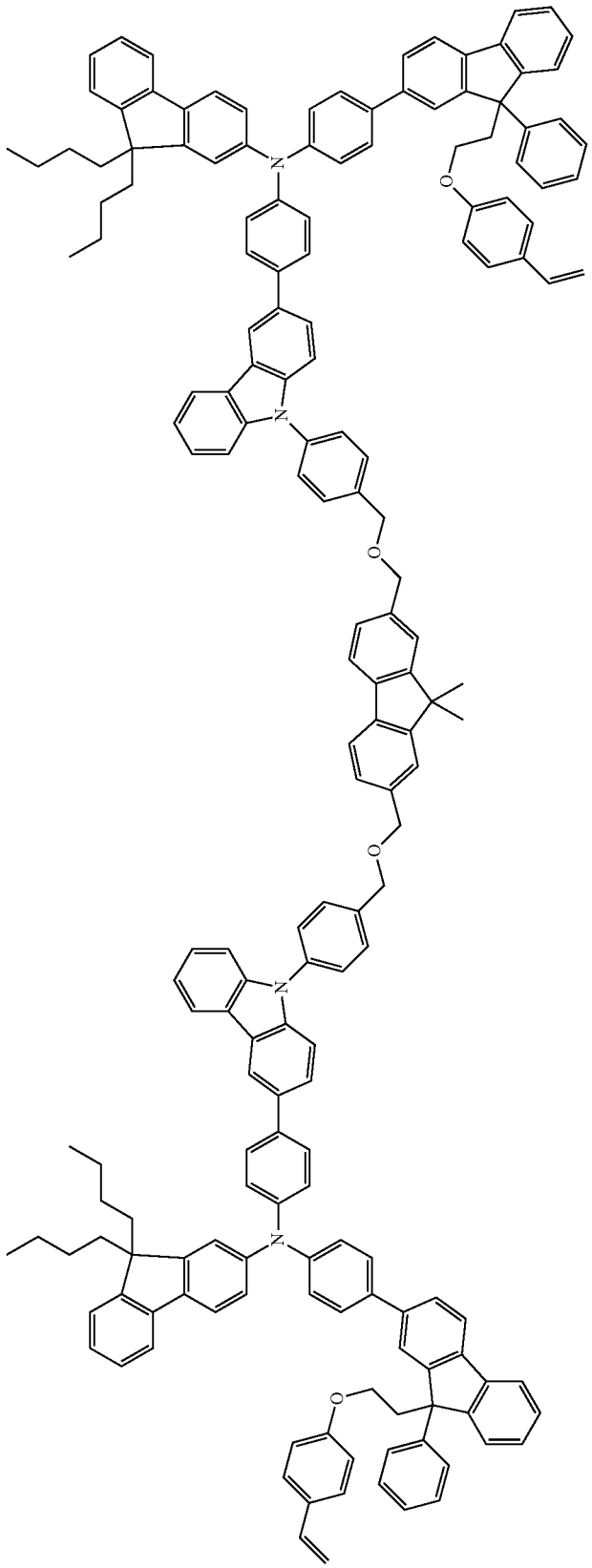
[Compound 111]
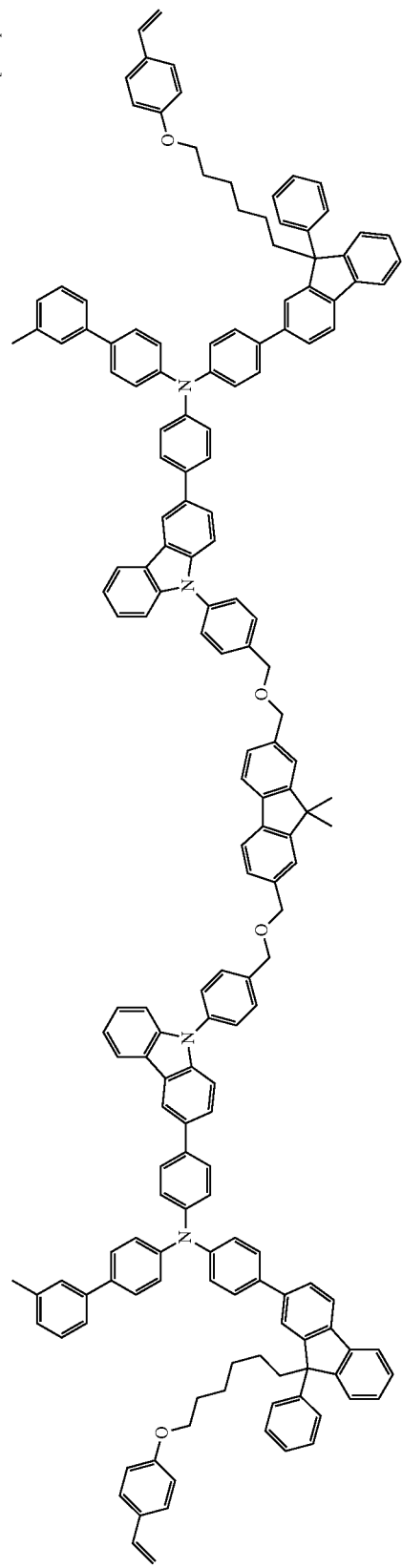

-continued
[Compound 112]
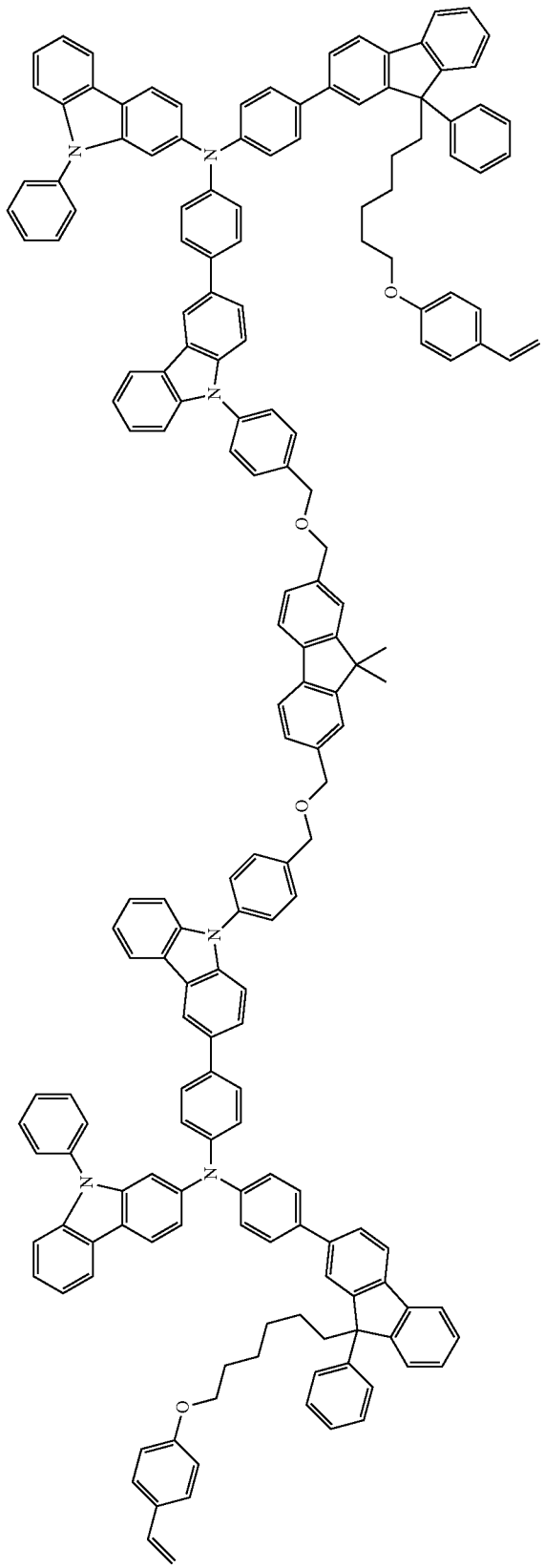
[Compound 113]
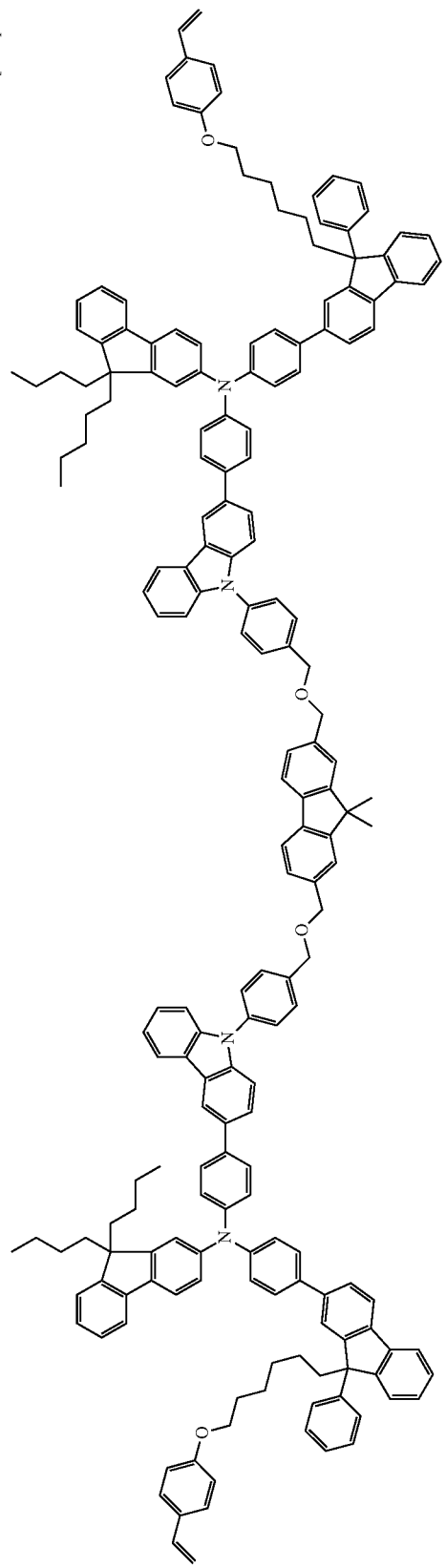

-continued
[Compound 114]
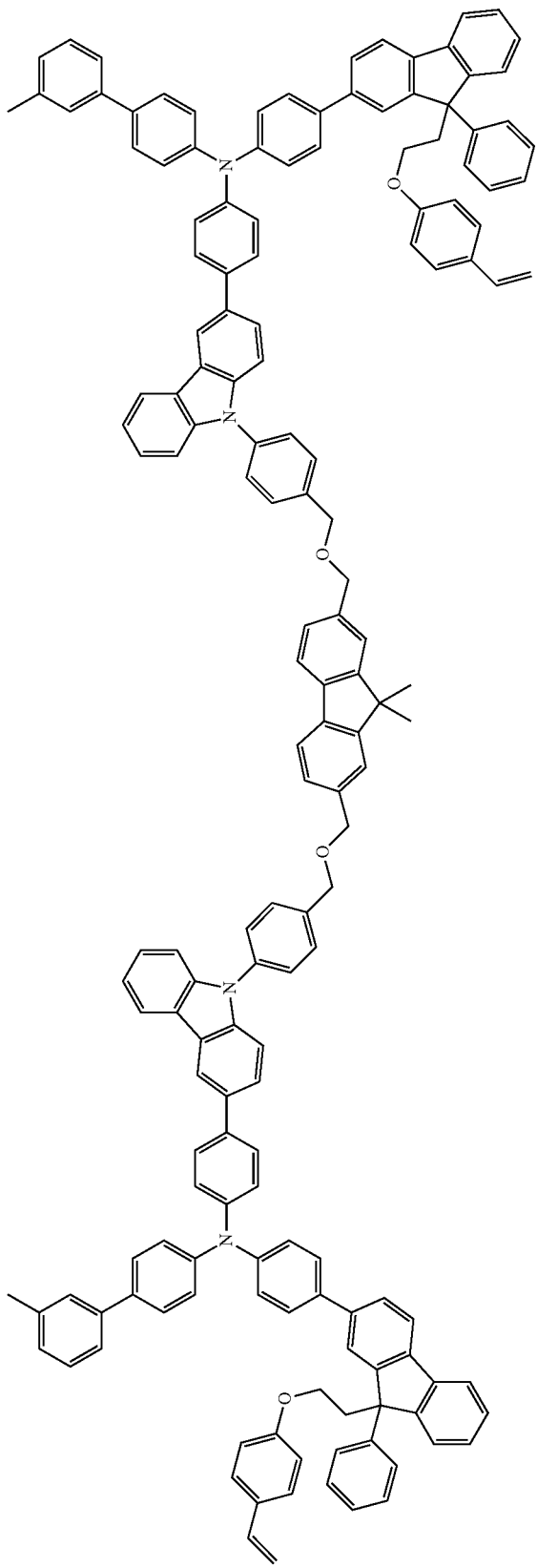

[Compound 115]
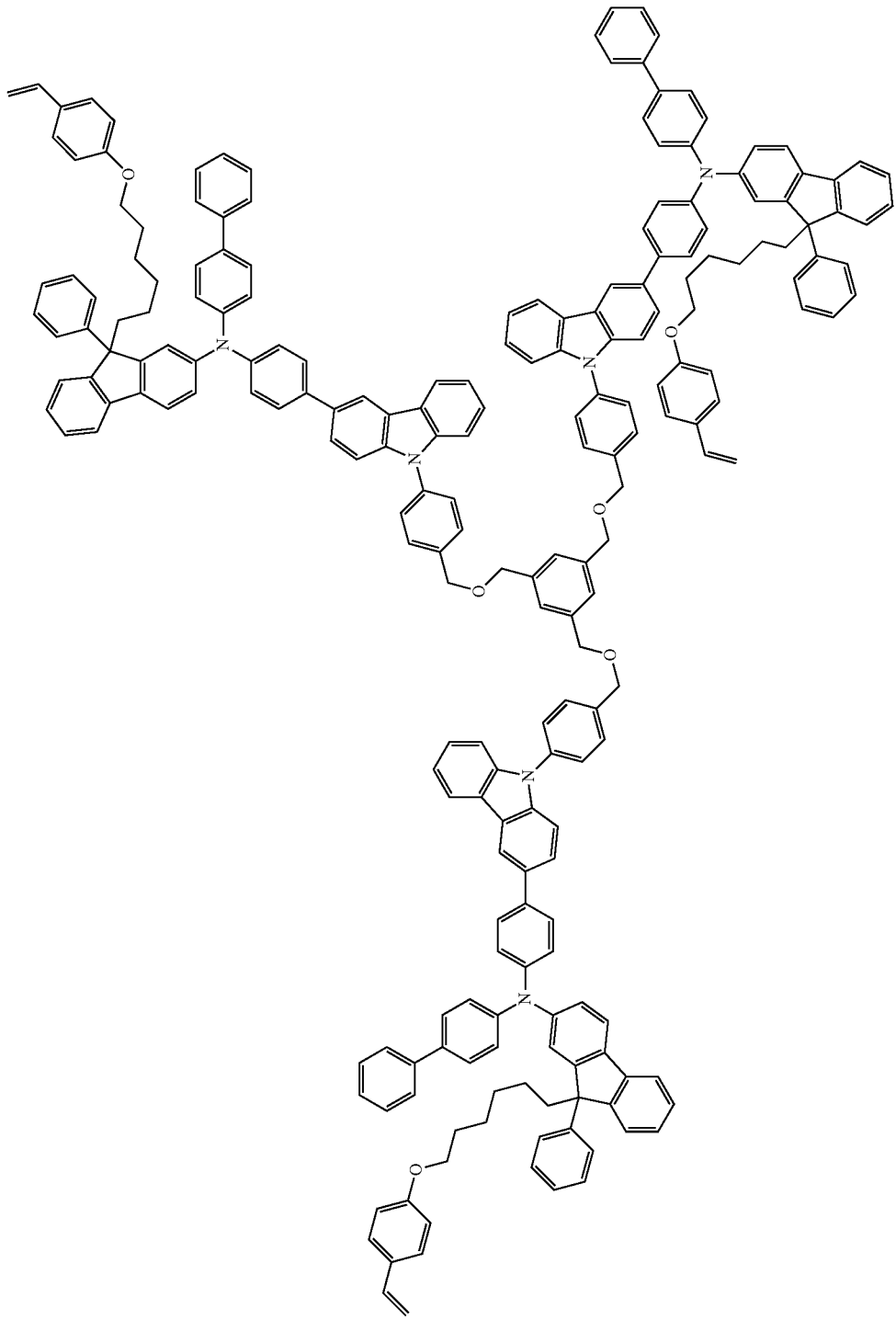

[Compound 116]
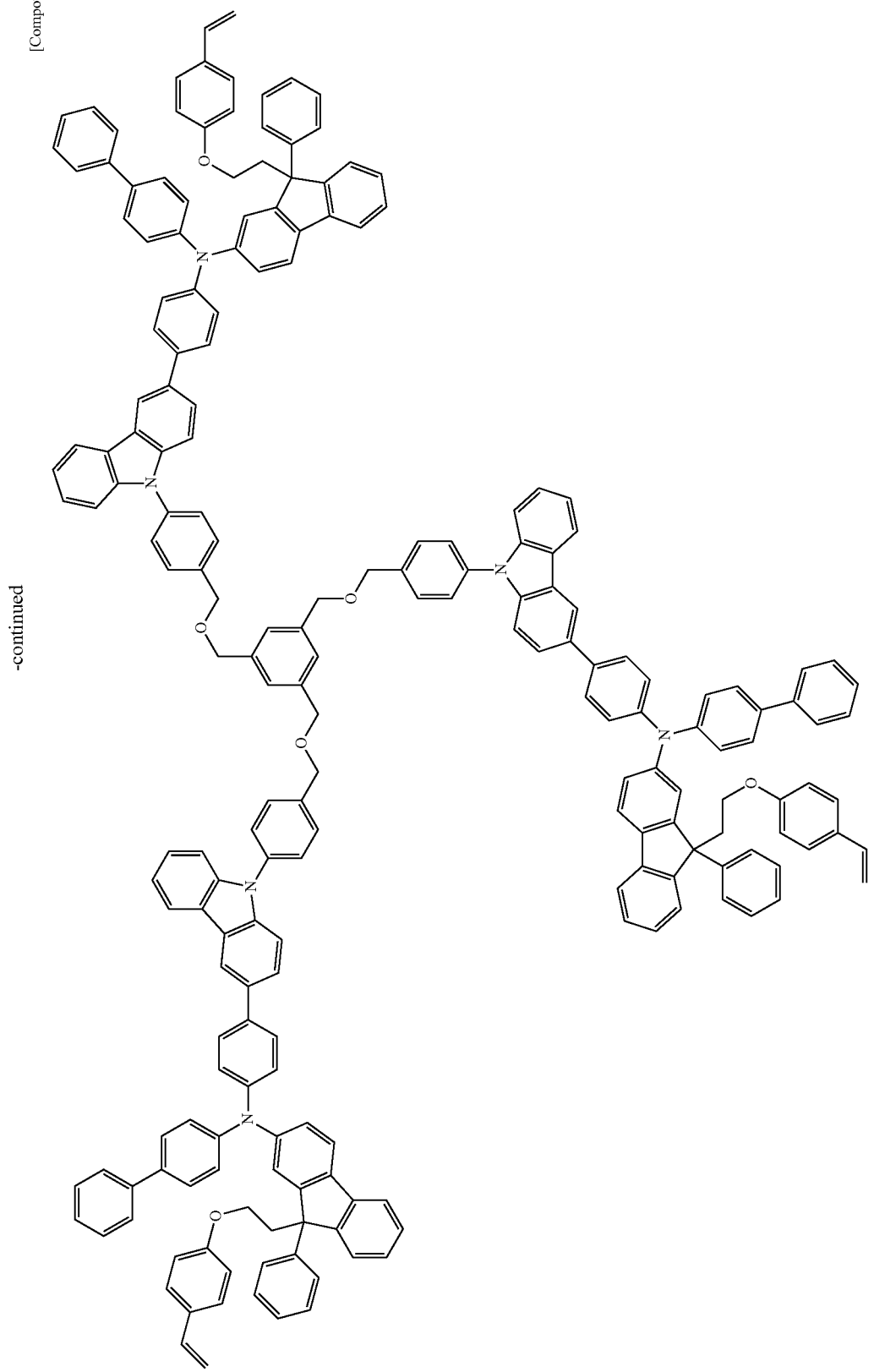

[Compound 117]
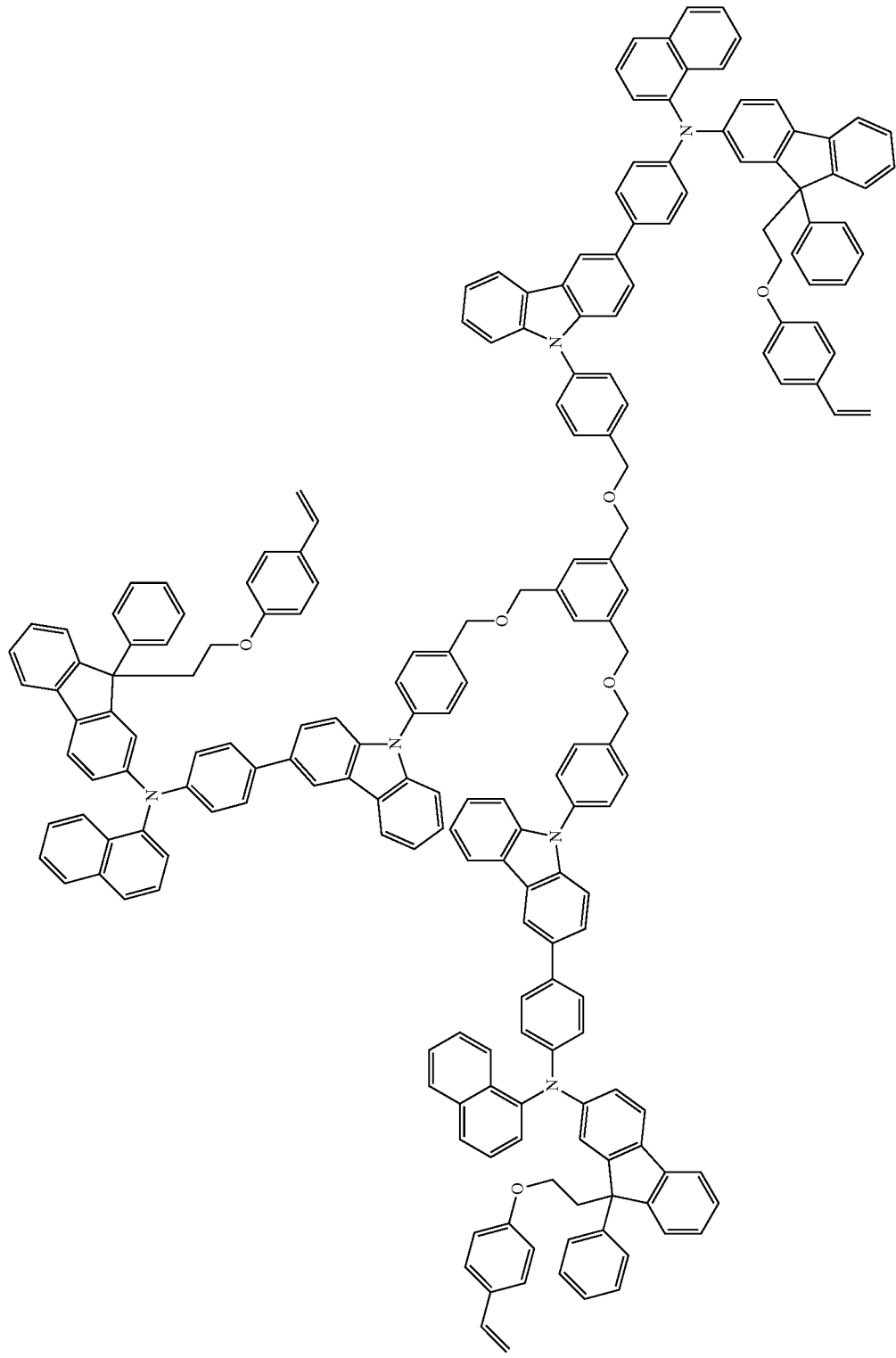

[Compound 118]
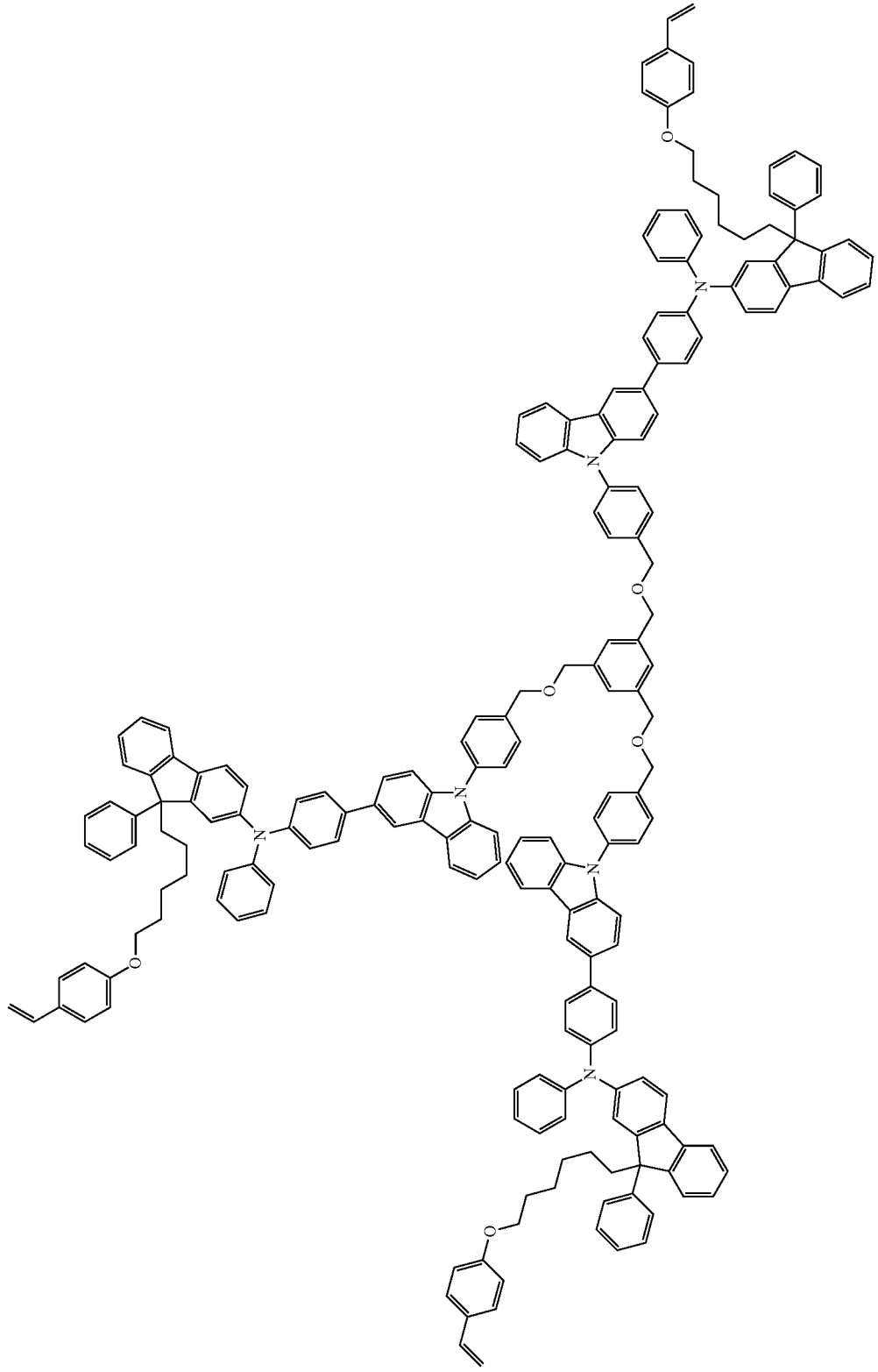

[Compound 119]
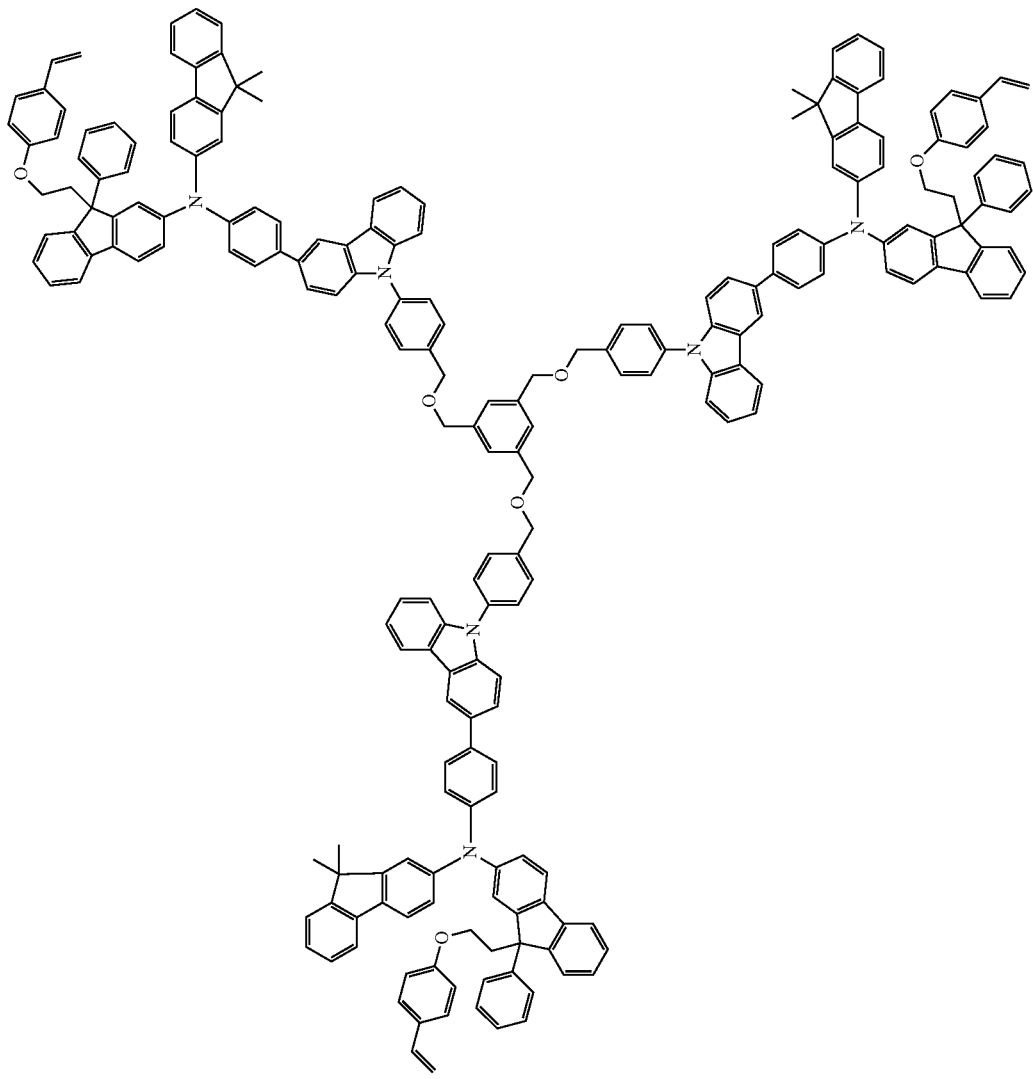

[Compound 120]
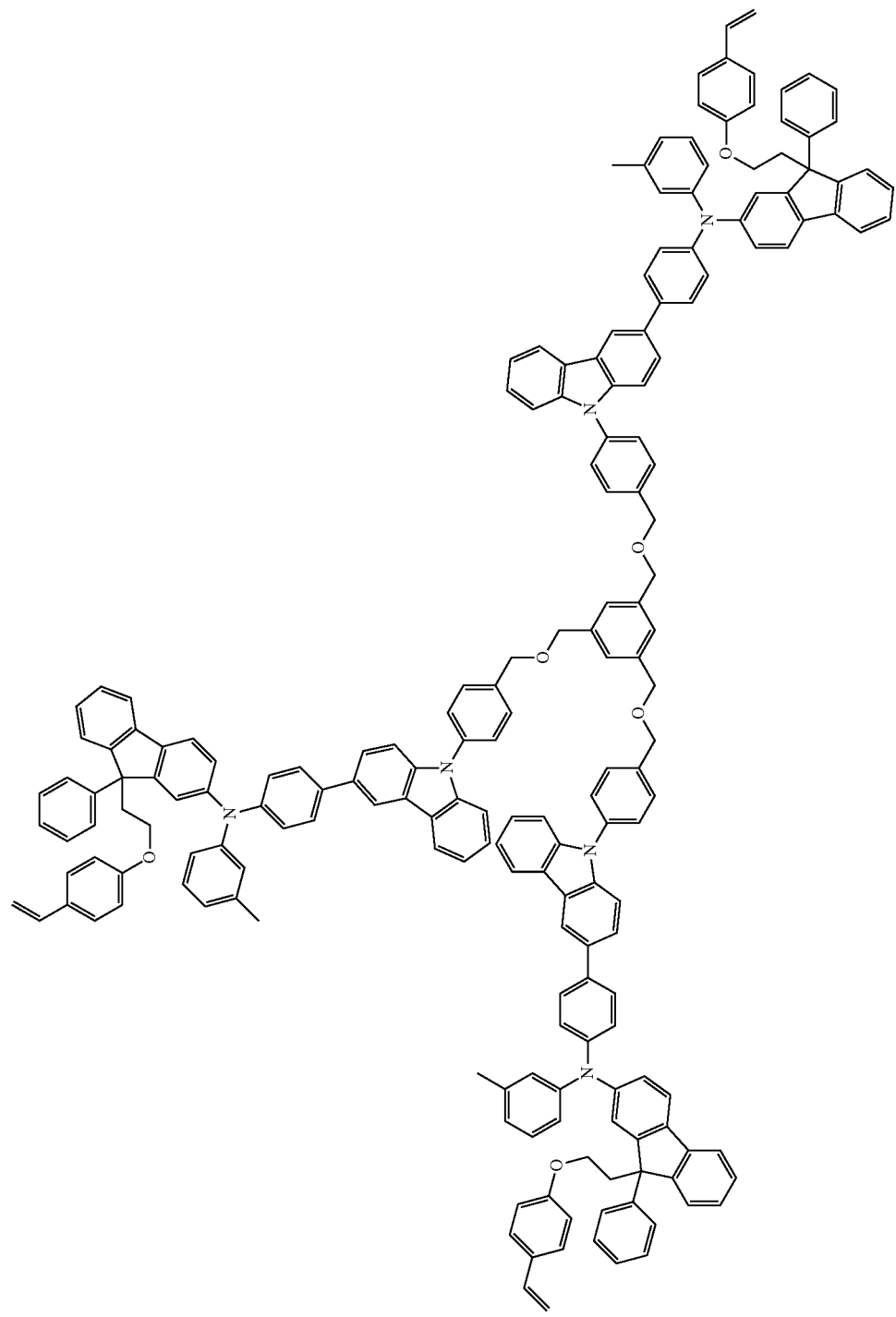

[Compound 121]
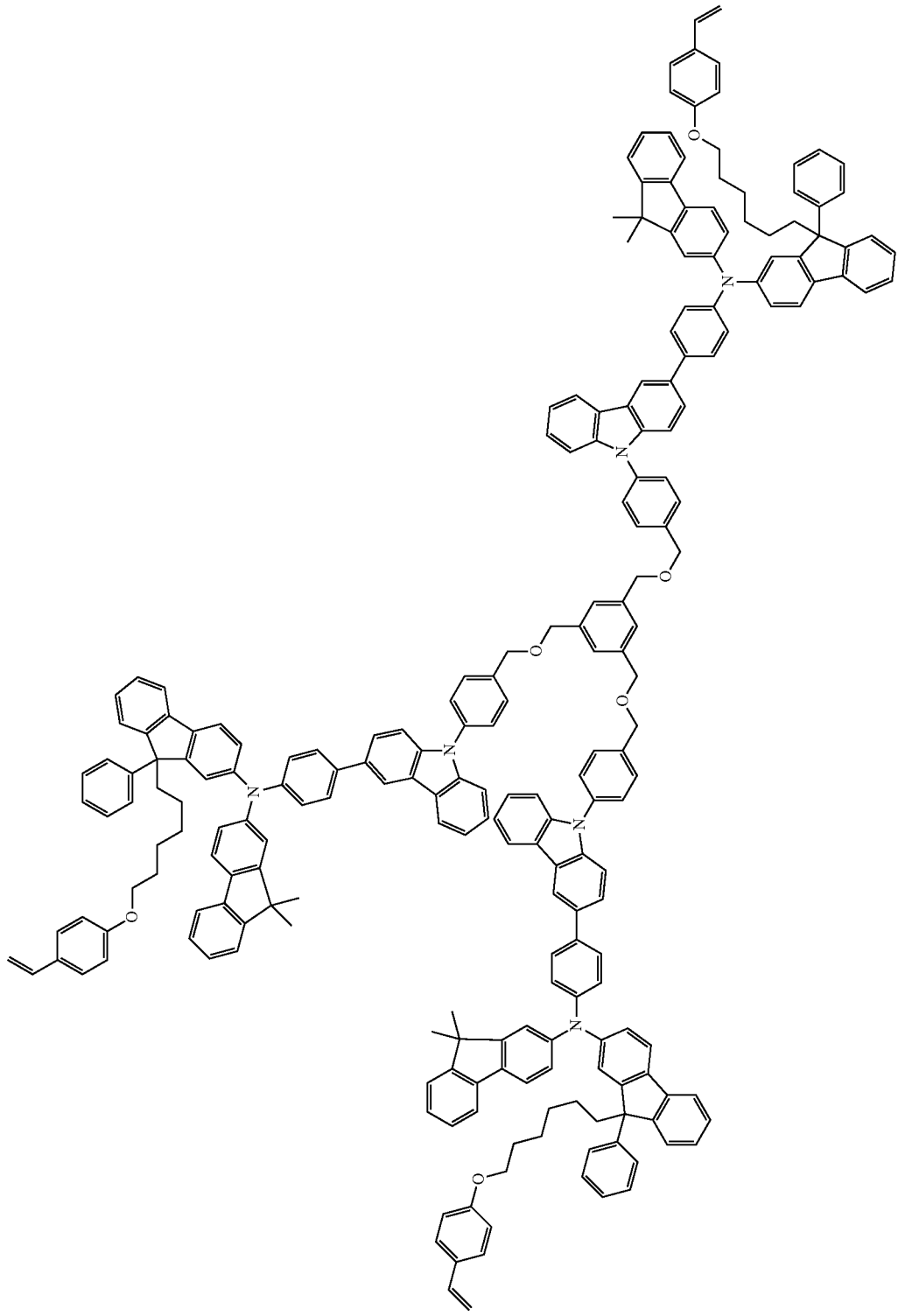

[Compound 122]
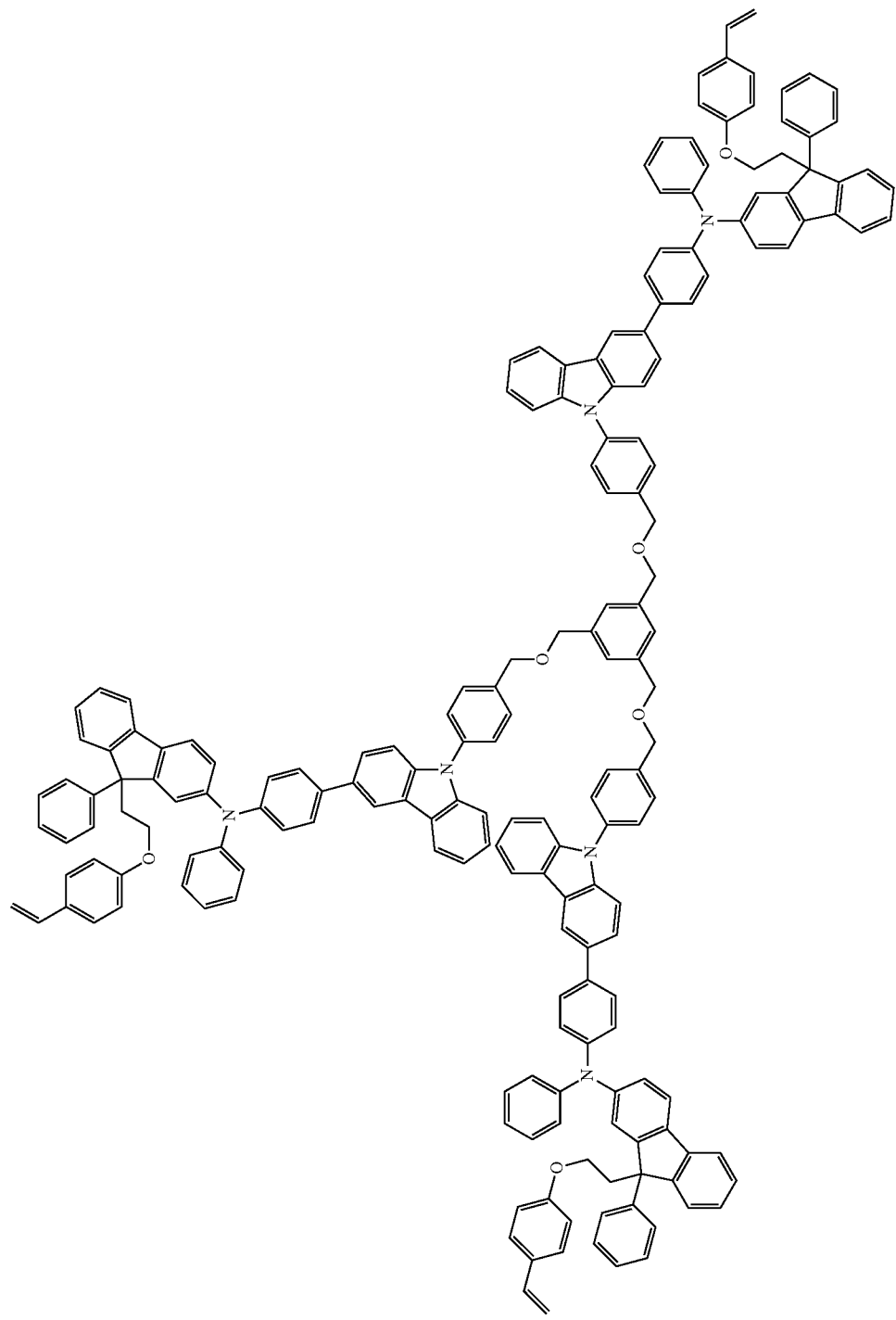

[Compound 123]
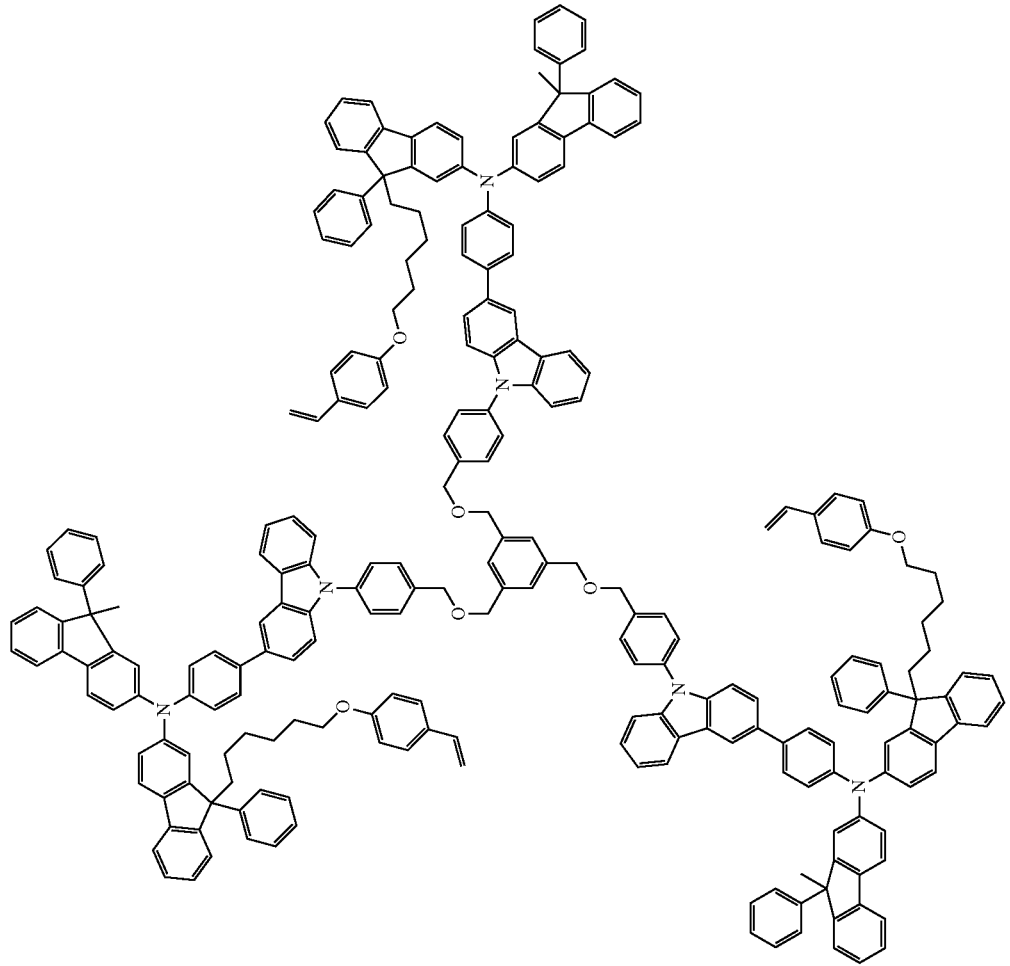

[Compound 124]
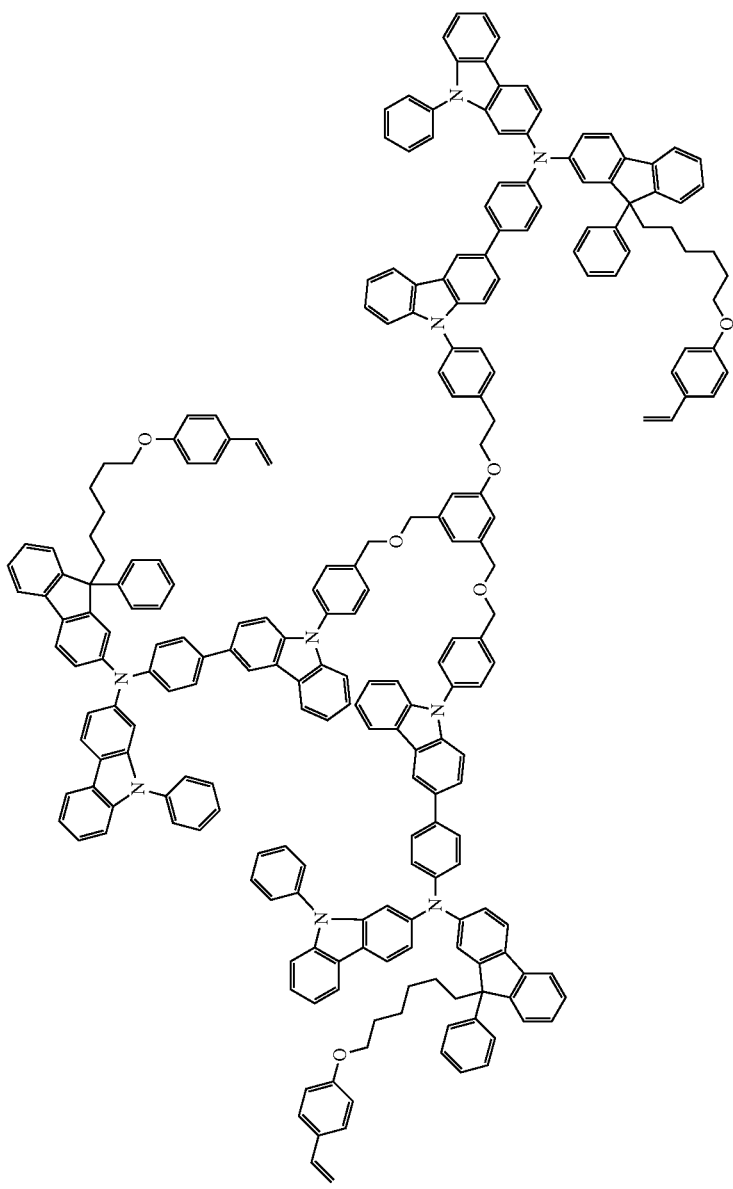

[Compound 125]
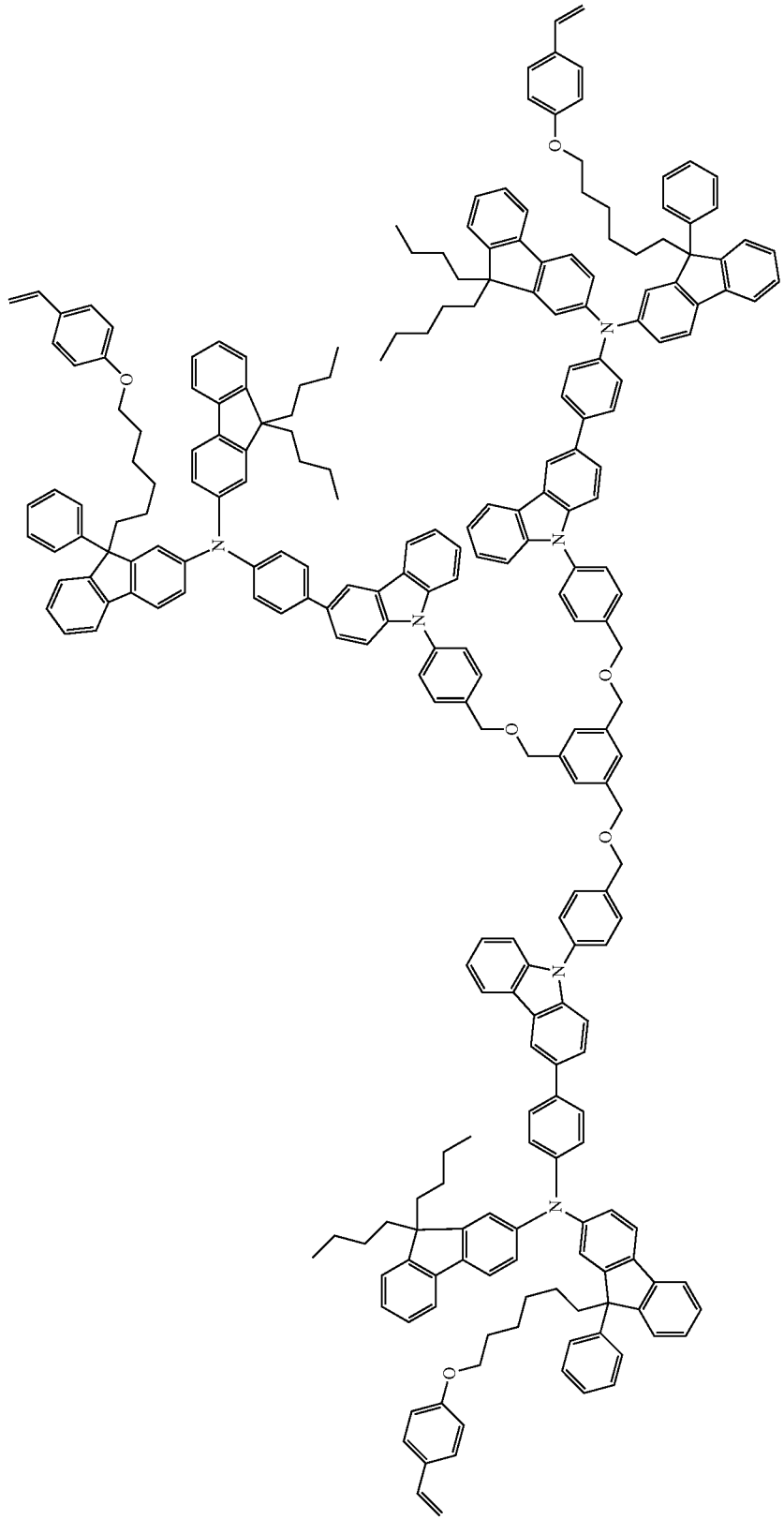

[Compound 126]

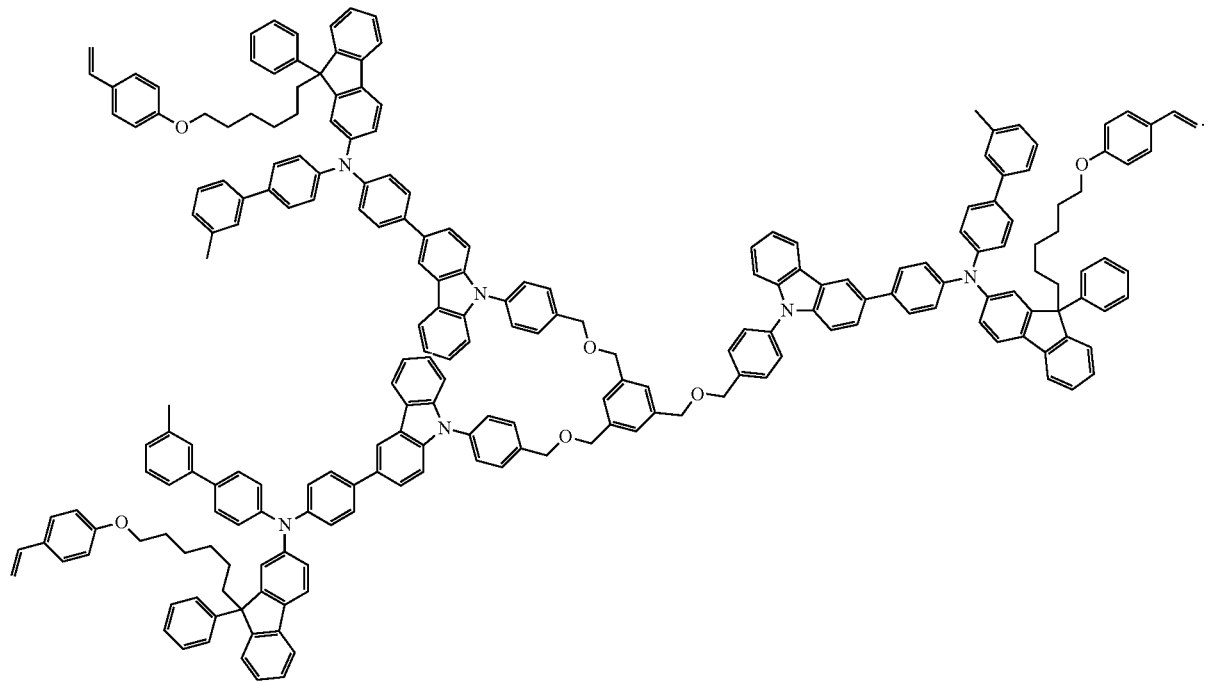

4. A coating composition comprising the compound of claim 1.

5. The coating composition of claim 4, further comprising a p-doping material.

6. An organic light emitting device comprising:
a first electrode;
a second electrode; and
one or more organic material layers provided between the first electrode and the second electrode,
wherein one or more layers of the organic material layers comprise a cured material of the coating composition of claim 4, and
the cured material of the coating composition is in a cured state by heat treating or light treating the coating composition.

7. The organic light emitting device of claim 6, wherein the organic material layer comprising the cured material of the coating composition is a hole transfer layer or a hole injection layer.

8. A method for manufacturing an organic light emitting device comprising:
preparing a substrate;
forming a first electrode on the substrate;
forming one or more organic material layers on the first electrode; and
forming a second electrode on the organic material layer,
wherein the forming of organic material layers comprises forming one or more organic material layers using the coating composition of claim 4.

9. The method for manufacturing an organic light emitting device of claim 8, wherein the forming of one or more organic material layers using the coating composition uses a spin coating method.

10. The method for manufacturing an organic light emitting device of claim 8, wherein the forming of one or more organic material layers using the coating composition comprises coating the coating composition on the first electrode; and heat treating or light treating the coated coating composition.

11. The compound of claim 2, wherein in Chemical Formula 2, L3 to L10 are the same as or different from each other, and each independently a direct bond; a substituted or unsubstituted divalent alkyl group having 1 to 60 carbon atoms; a substituted or unsubstituted divalent aryl group having 6 to 60 carbon atoms; or a substituted or unsubstituted divalent heteroaryl group having 2 to 60 carbon atoms.

12. The compound of claim 2, wherein in Chemical Formula 2, L3, L5, L8 and L10 are a divalent phenyl group, L4 and L9 are a divalent carbazole group, and L6 and L7 are a divalent methyl group.

13. The compound of claim 1, wherein in Chemical Formula 1, Ar1 and Ar2 are the same as or different from each other, and each independently hydrogen; deuterium; a substituted or unsubstituted aryl group having 6 to 60 carbon atoms; or a substituted or unsubstituted heterocyclic group having 2 to 60 carbon atoms.

14. The compound of claim 1, wherein in Chemical Formula 1, L is any one of the following structures that are optionally further substituted:

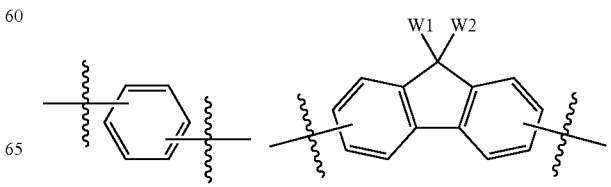

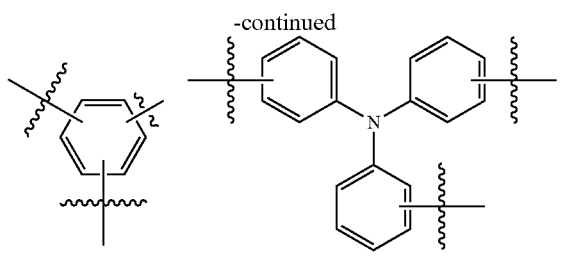

in the structures,

W1 and W2 are the same as or different from each other, and each independently hydrogen; or a substituted or unsubstituted alkyl group.

15. The compound of claim 14, wherein W' and W" are the same as or different from each other, and each independently hydrogen; or a substituted or unsubstituted alkyl group having 1 to 20 carbon atoms.

16. The compound of claim 1, wherein Chemical Formula 1 is any one of the following Chemical Formula 3 to chemical Formula 6:

[Chemical Formula 3]

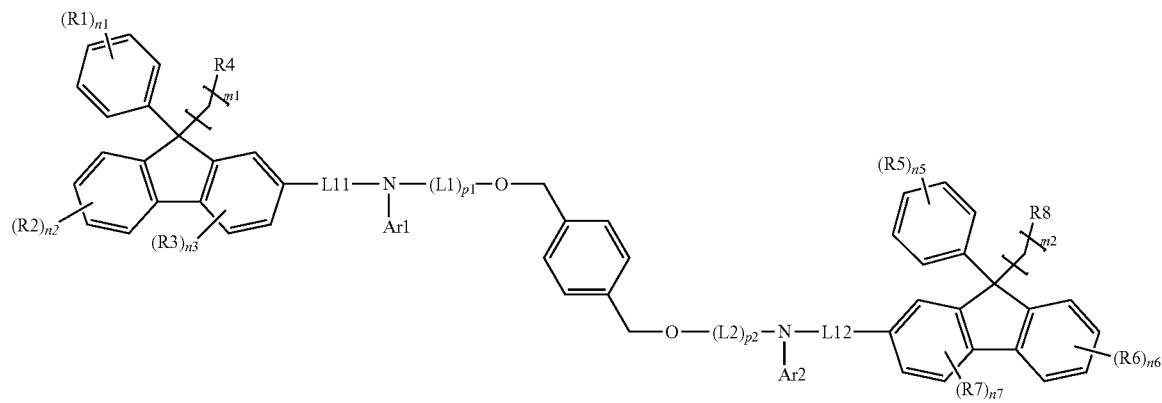

[Chemical Formula 4]

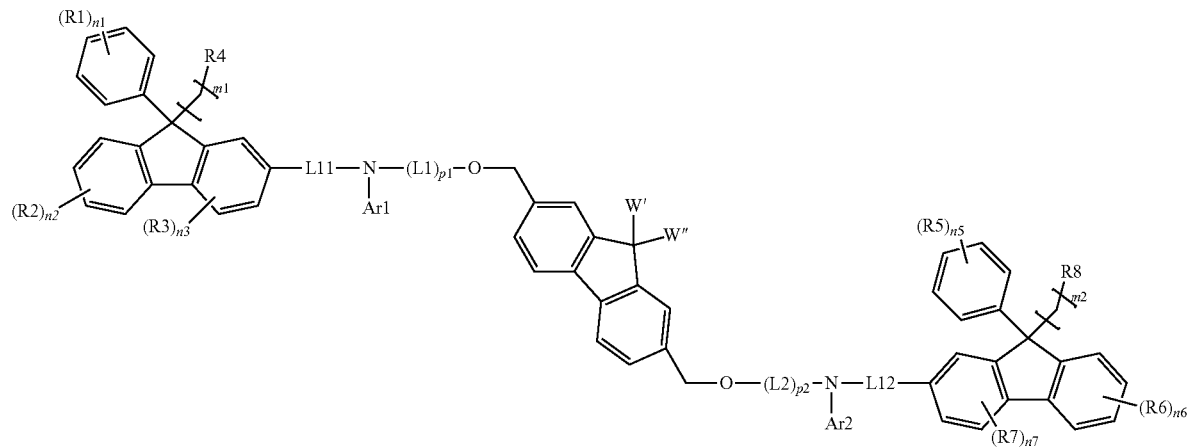

[Chemical Formula 5]
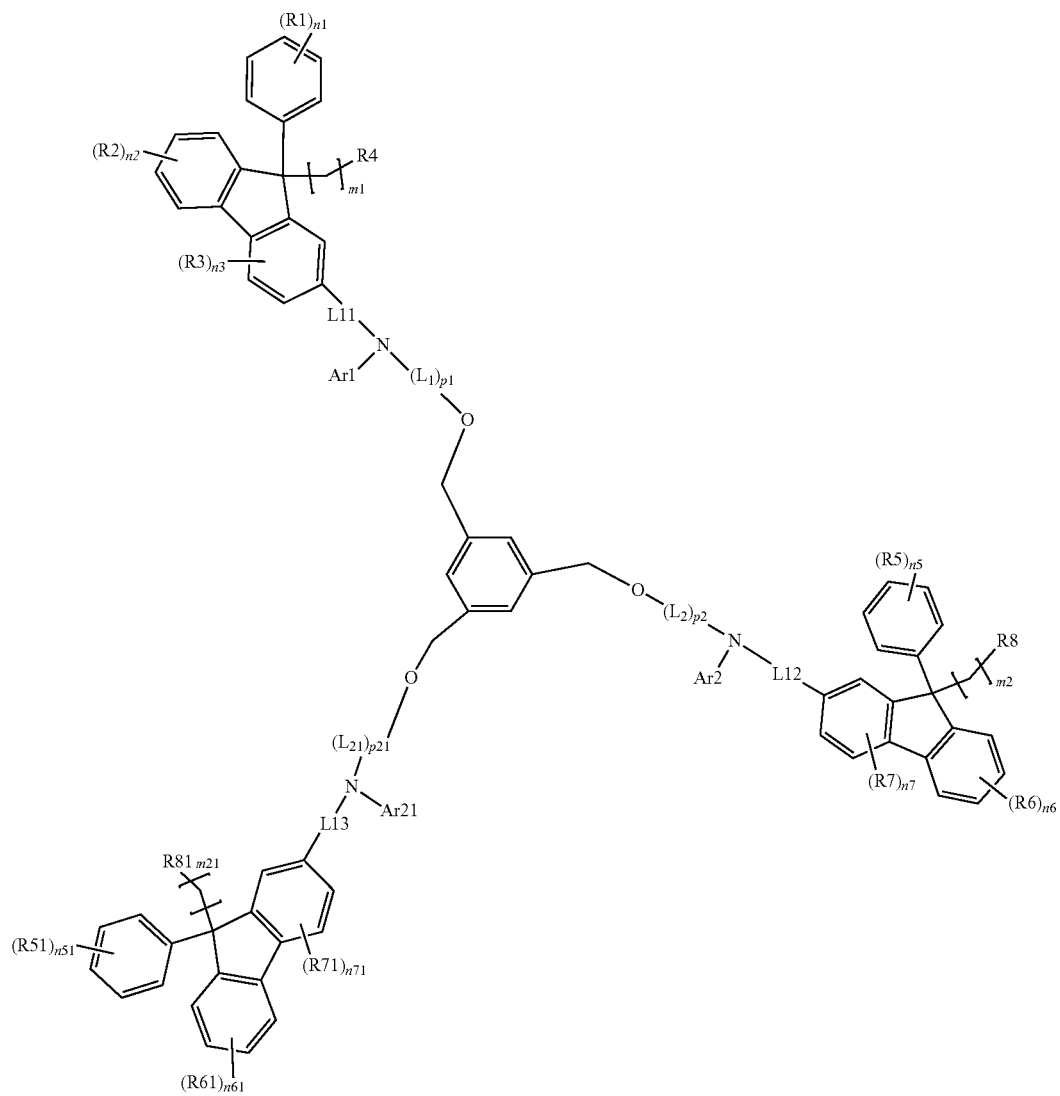

[Chemical Formula 6]

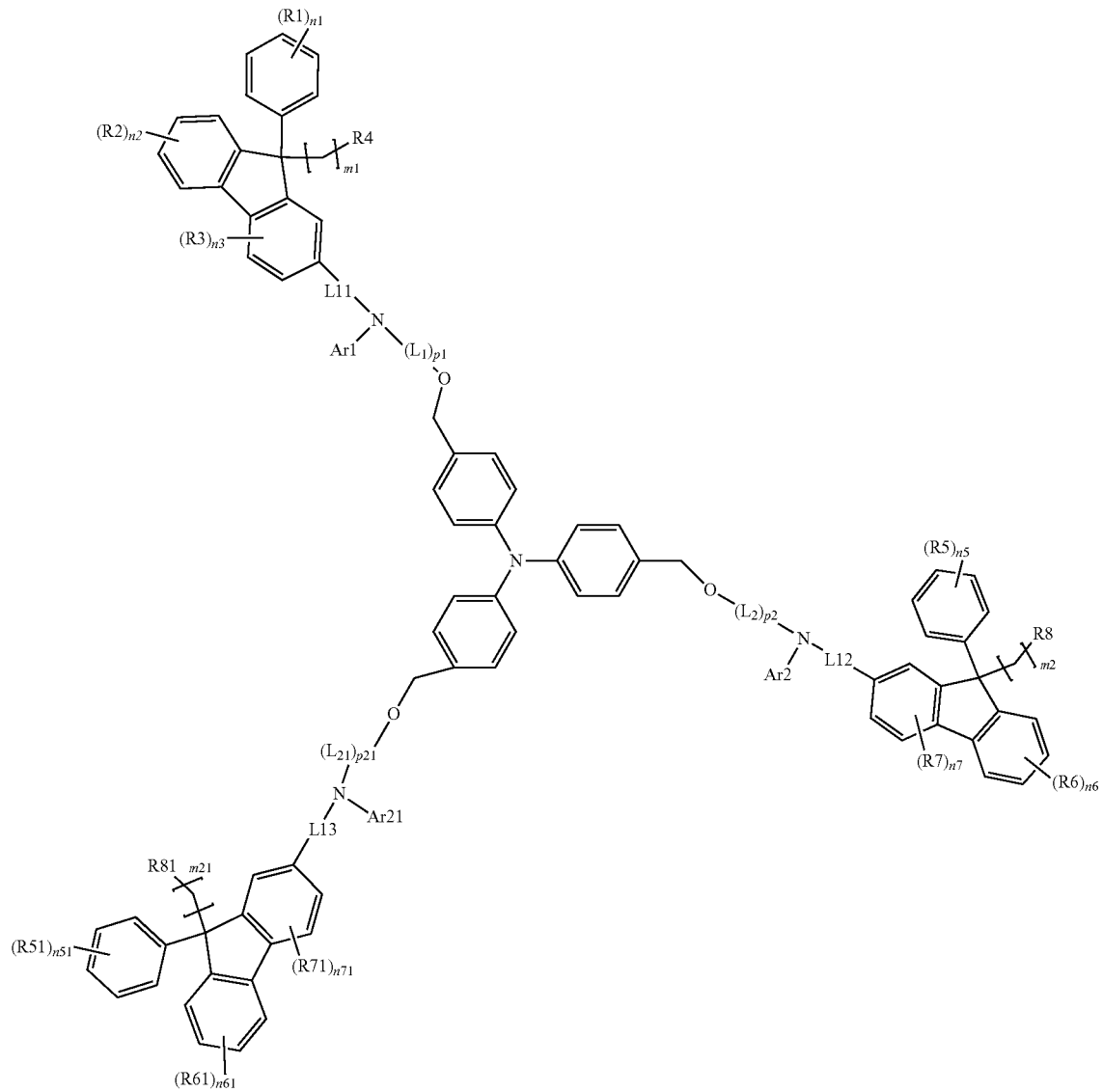

in Chemical Formulae 3 to 6,

R1 to R8, m1, m2, n1 to n3, n5 to n7, L1, L2, L11, L12, p1, p2, Ar1 and Ar2 have the same definitions as in Chemical Formula 1, L13 is a direct bond; or a substituted or unsubstituted divalent aryl group, L21 is a direct bond; a substituted or unsubstituted divalent alkyl group; a substituted or unsubstituted divalent aryl group; or a substituted or unsubstituted divalent heteroaryl group, Ar21 is hydrogen; deuterium; a substituted or unsubstituted alkyl group; a substituted or unsubstituted cycloalkyl group; a substituted or unsubstituted aryl group; or a substituted or unsubstituted heterocyclic group, R51, R61 and R71 are the same as or different from each other, and each independently hydrogen; deuterium; a halogen group; a nitrile group; —SiRaRbRc; —BRdRe; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, wherein Ra, Rb, Rc Rd and Re are each independently hydrogen; a substituted or unsubstituted alkyl group; or a substituted or unsubstituted aryl group, R81 is a functional group crosslinkable by heat or light, m21 is an integer of 0 to 12, p21 is an integer of 1 to 4, n51 is an integer of 0 to 5, n61 is an integer of 0 to 4, n71 is an integer of 0 to 3, and when p21, n51, n61 and n71 are each 2 or greater, L21s, R51s, R61 s and R71 s are each independently the same as or different from each other.

17. The coating composition of claim 5, wherein the p-doping material comprises at least one compound represented by the following Chemical Formula A or B:

[Chemical Formula A]
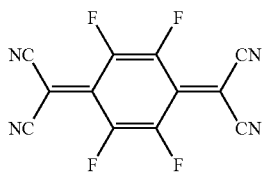
[Chemical Formula B]
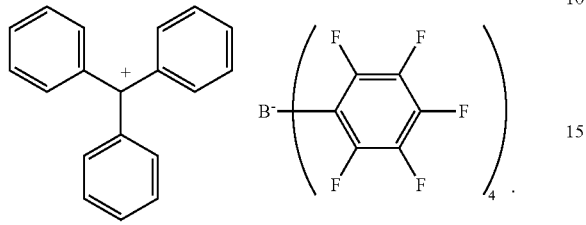
18. The coating composition of claim 5, wherein the p-doping material is present in an amount of 0% by weight to 50% by weight based on the compound of Chemical Formula 1.
* * * * *